US010144922B2

(12) United States Patent
Svendsen et al.

(10) Patent No.: US 10,144,922 B2
(45) Date of Patent: Dec. 4, 2018

(54) SUBTILASE VARIANTS AND COMPOSITIONS COMPRISING THE SAME

(71) Applicant: Novozymes A/S, Bagsvaerd (DK)

(72) Inventors: Allan Svendsen, Horsholm (DK); Henriette Draborg, Alleroed (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/280,387

(22) Filed: Sep. 29, 2016

(65) Prior Publication Data

US 2017/0233709 A1    Aug. 17, 2017

Related U.S. Application Data

(63) Continuation of application No. 14/863,058, filed on Sep. 23, 2015, now Pat. No. 9,493,758, which is a continuation of application No. 14/013,231, filed on Aug. 29, 2013, now Pat. No. 9,169,475, which is a continuation of application No. 13/743,839, filed on Jan. 17, 2013, now Pat. No. 8,546,122, which is a continuation of application No. 13/304,880, filed on Nov. 28, 2011, now Pat. No. 8,383,387, which is a continuation of application No. 12/879,410, filed on Sep. 10, 2010, now Pat. No. 8,084,241, which is a continuation of application No. 11/928,576, filed on Oct. 30, 2007, now abandoned, which is a continuation of application No. 10/786,850, filed on Feb. 24, 2004, now Pat. No. 7,294,499, which is a continuation of application No. PCT/DK2004/000066, filed on Jan. 30, 2004.

(60) Provisional application No. 60/468,574, filed on May 7, 2003, provisional application No. 60/445,300, filed on Feb. 5, 2003.

(30) Foreign Application Priority Data

Jan. 30, 2003 (DK) .................. 2003 00119
May 7, 2003 (DK) .................. 2003 00689

(51) Int. Cl.
*C12N 9/54* (2006.01)
*C11D 3/386* (2006.01)

(52) U.S. Cl.
CPC ............... *C12N 9/54* (2013.01); *C11D 3/386* (2013.01); *C12Y 304/21062* (2013.01)

(58) Field of Classification Search
None
See application file for complete search history.

(56) References Cited

U.S. PATENT DOCUMENTS

| | | | |
|---|---|---|---|
| 4,914,031 A | 4/1990 | Zukowski | |
| 4,990,452 A | 2/1991 | Bryan et al. | |
| 5,118,623 A | 6/1992 | Boguslowski | |
| 5,260,207 A | 11/1993 | Pantoliano et al. | |
| 5,362,414 A | 11/1994 | Outtrup et al. | |
| 5,389,307 A | 2/1995 | Lindegaard | |
| 5,397,705 A | 3/1995 | Zukowski | |
| 5,470,733 A | 11/1995 | Bryan et al. | |
| 5,482,849 A | 1/1996 | Branner et al. | |
| 5,567,601 A | 10/1996 | Bryan et al. | |
| 5,665,587 A | 9/1997 | Aaslyng | |
| 5,700,676 A | 12/1997 | Bott et al. | |
| 5,707,848 A | 1/1998 | Bryan et al. | |
| 5,741,694 A | 4/1998 | Hastrup | |
| 5,891,701 A | 4/1999 | Sloma et al. | |
| 5,972,683 A | 10/1999 | Tsai | |
| 6,190,900 B1 | 2/2001 | Sierkstra | |
| 6,376,450 B1 | 4/2002 | Ghosh | |
| 6,440,717 B1 | 8/2002 | Brode | |
| 6,451,574 B1 | 9/2002 | Brode | |
| 6,455,295 B1 | 9/2002 | Brode | |
| 6,475,765 B1 | 11/2002 | Brode | |
| 6,511,371 B2 | 1/2003 | Outtrup | |
| 6,541,234 B1 | 4/2003 | Bryan | |
| 6,541,235 B1 | 4/2003 | Bryan | |
| 6,599,730 B1 | 7/2003 | Brode | |
| 7,294,499 B2 | 11/2007 | Svendsen | |
| 7,306,937 B2 | 12/2007 | Poulose | |
| 7,727,756 B2 | 6/2010 | Svendsen | |
| 8,008,057 B2 | 8/2011 | Svendsen | |
| 8,084,241 B2 | 12/2011 | Svendsen | |
| 8,383,387 B2 | 2/2013 | Svendsen | |
| 8,546,122 B2 | 10/2013 | Svendsen | |
| 2002/0103100 A1 | 8/2002 | Outtrup | |
| 2005/0054843 A1 | 3/2005 | Estell et al. | |
| 2005/0148059 A1 | 7/2005 | Estell et al. | |
| 2005/0181446 A1 | 8/2005 | Roggen et al. | |
| 2012/0088288 A1 | 4/2012 | Svendsen | |

(Continued)

FOREIGN PATENT DOCUMENTS

| | | |
|---|---|---|
| WO | 92/17577 A1 | 10/1992 |
| WO | 92/29024 A1 | 4/2002 |
| WO | 2004/083362 A2 | 9/2004 |

OTHER PUBLICATIONS

Gjermansen et al, 2017, U.S. Pat. No. 2017/0029796 SEQ ID No. 9. Alignment with SEQ ID No: 1 herein.*
Royal Society of Chemistry, Surfactants: the ubiquitous amphiphiles. Downloaded Mar. 13, 2014.*
Ecological Surfactants, Saponins. Downloaded Mar. 13, 2014.*
USPTO in-house search results EAST and patent sequence databases. Performed Jan. 22, 2018.*
Almog et al, J. Mol. Biol., vol. 332, pp. 1071-1082 (2003).
Davail et al., "Purification, Characterization, and Sequence of the Heat-Labile Subtilisin from the Antarctic Psychrophile Bacillus TA41", The Journal of Biological Chemistry, vol. 269, No. 26, pp. 1748-1753 (1994).

(Continued)

Primary Examiner — Sheridan Swope
(74) Attorney, Agent, or Firm — David Fazzolare

(57) ABSTRACT

The present invention relates to methods for producing variants of a parent TY145 subtilase and of a parent BPN' subtilase and to TY145 and BPN' variants having altered properties as compared to the parent TY145/BPN' subtilase.

7 Claims, 3 Drawing Sheets

Specification includes a Sequence Listing.

(56) References Cited

U.S. PATENT DOCUMENTS

2017/0029796 A1* 2/2017 Gjermansen ..... C12Y 304/2106

OTHER PUBLICATIONS

Miyazaki et al, "Directed Evolution Study of Temperature Adaptation in a Psychrophilic Enzyme", J. Mol. Biol., vol. 297, pp. 1015-1026 (2000).
Narinx et al., "Subtilisin from psychrophilic antarctic bacteria: characterization and site-directed mutagenesis of residues possibly involved in the adaptation to cold", Protein Engineering, vol. 10, No. 11, pp. 1271-1279 (1997).
Pantoliano et al, Biochemstry, vol. 28, pp. 7205-7213 (1989).
Rost et al., J. Mol. Biol., vol. 232, pp. 584-599 (1993).
Servant et al. "Production of CryIIa and CryIIBa toxins in Bacillus Sphaericus Confers Toxicity towards Aedes aegypti and resistant Cutex populations", Applied and Environmental Microbiology, vol. 65, pp. 3021-3026 (1999).
Servant et al., "Production of Crylla and CryllBa toxins in Bacillus Sphaericus Confers Toxicity towards Aedes aegypti and resistant Cutex populations", UniProt Accession No. Q9S3L6 (May 1, 2000).
Siezen et al., The superfamily of sibtilisin-like serine proteases, Protein Science, vol. 6, pp. 501-523 (1997).
Toma et al., Biochemistry, vol. 30, pp. 97-107 (1991).
Wati et al., "Toxin degrading protease of Bacillus sphaericus, 4343 amino acid precursor protease", UniProt Accession No. 054327 (Jun. 1, 1998).
Wintrode et al., Cold Adaptation of a Mesophilic Subtilisin-like Protease by Laboratory Evolution, The Journal of Biological Chemistry, vol. 275, No. 41, pp. 31635-31640 (2000).
Wintrode et al., Biochimica et Biophysica Acta, vol. 1549, pp. 1-8 (2001).

* cited by examiner

Figure 1

```
*RASQQIPWG IKAIYNNDTL TSTTGGSGIN IAVLDTGVNT SHPDLVNNVE  49  B.sphaericus (SEQ ID NO: 4)
AVPSTQTPWG IKSIYNDQSI TKTTGGSGIK VAVLDTGVYT SHLDLAGSAE  50  TY145 (SEQ ID NO: 1)
 AASQSTPWG IKAIYNNSNL TSTSGGAGIN IAVLDTGVNT NHPDLSNNVE  49  TA41 (SEQ ID NO: 3)
 AASQSTPWG IKAIYNNSSI TQTSGGGGIN IAVLDTGVNT NHPDLRNNVE  49  TA39 (SEQ ID NO: 2)

***AQSVPWG ISRVQAPAAH NRGLTGSGVK VAVLDTGIS* THPDL**NIR  44  Savinase (SEQ ID NO: 6)

QCKDFTGATT PINNSCTDRN GHGTHVAGTA LADGGSDQAG IYGVAPDADL  99
QCKDFTQSNP LVDGSCTDRQ GHGTHVAGTV LAHGGSNGQG VYGVAPQAKL 100
QCKDFTVGTN FTDNSCTDRQ GHGTHVAGSA LANGGT*GSG VYGVAPEADL  98
QCKDFTVGTT YTNNSCTDRQ GHGTHVAGSA LADGGT*GNG VYGVAPDADL  98

GGASFVPGEP ****STQDGN GHGTHVAGTI AALNN**SIG VLGVAPSAEL  88

WAYKVLLDSG SGYSDDIAAA IRHAADQATA TGTKTIISMS LGSSANNSLI 149
WAYKVLGDNG SGYSDDIAAA IRHVADEASR TGSKVVINMS LGSSAKDSLI 150
WAYKVLGDDG SGYADDIAEA IRHAGDQATA LNTKVVINMS LGSSGESSLI 148
WAYKVLGDDG SGYADDIAAA IRHAGDQATA LNTKVVINMS LGSSGESSLI 148

YAVKVLGASG SGSVSSIAQG LEWAGNNG** ****MHVANLS LGSPSPSATL 133

SSAVNYAYSK GVLIVAAAGN SGYSQGTIGY PGALPNAIAV AALENVQQNG 199
ASAVDYAYGK GVLIVAAAGN SGSGSNTIGF PGGLVNAVAV AALENVQQNG 200
TNAVDYAYDK GVLIIAAAGN SGPKPGSIGY PGALVNAVAV AALENTIQNG 198
TNAVNYSYNK GVLIIAAAGN SGPYQGSIGY PGALVNAVAV AALENKVENG 198

EQAVNSATSR GVLVVAASGN SGAGSISY PARYANAMAV GATDQN** 177

TYRVADYSSR GYISTAGDYV IQEGDIEISA PGSSVYSTWY NGGYNTISGT 249
TYRVADFSSR GNPATAGDYI IQERDIEVSA PGASVESTWY TGGYNTISGT 250
TYRVADFSSR GHKRTAGDYV IQKGDVEISA PGAAVYSTWF DGGYATISGT 248
TYRVADFSSR GYSWTDGDYA IQKGDVEISA PGAAIYSTWF DGGYATISGT 248

*NNRASFSQY GA******** ****GLDIVA PGVNVQSTYP GSTYASLNGT 214

SMATPHVSGL AAKIWAENPS LSNTQLRSNL QERAKSVDIK GGYGAAIGDD 299
SMATPHVAGL AAKIWSANTS LSHSQLRTEL QNRAKVYDIK GGIGAGTGDD 300
SMASPHAAGL AAKIWAQSPA ASNVDVRGEL QTRASVNDIL SGNSAGSGDD 298
SMASPHAAGL AAKIWAQYPS ASNVDVRGEL QYPAYENDIL SGYYAGYGDD 298

SMATPHVAGA AALVKQRNPS WSNVQIRNHL KNTA**TSLG *******ST  254

YASGFGFARV Q                                          310
YASGFGYPRV K                                          311
IASGFGFAKV Q                                          309
FASGFGFATV Q                                          309

NLYGSGLVNA EAATR                                      269
```

No:         275
a)  Q-A-A-A-Q
b)  E-A-A-T-R a) = BPN' (SEQ ID NO: 5)

b) = Savinase (SEQ ID NO: 6)
```

SUBTILASE VARIANTS AND COMPOSITIONS COMPRISING THE SAME

CROSS-REFERENCE TO RELATED APPLICATIONS

This application is a continuation of U.S. application Ser. No. 14/863,058 filed Sep. 23, 2015, now U.S. Pat. No. 9,493,758, which is a continuation of U.S. application Ser. No. 14/013,231 filed Aug. 29, 2013, now U.S. Pat. No. 9,169,475, which is a continuation of U.S. application Ser. No. 13/743,839 filed Jan. 17, 2013, now U.S. Pat. No. 8,546,122, which is a continuation of U.S. application Ser. No. 13/304,880 filed Nov. 28, 2011, now U.S. Pat. No. 8,383,387, which is a continuation of U.S. Ser. No. 12/879,410 filed Sep. 10, 2010, now U.S. Pat. No. 8,084,241, which is a continuation of U.S. application Ser. No. 11/928,576 filed Oct. 30, 2007, now abandoned, which is a continuation of U.S. application Ser. No. 10/786,850 filed Feb. 24, 2004, now U.S. Pat. No. 7,294,499, which is a continuation of international application no. PCT/DK2004/000066 filed Jan. 30, 2004, which claims priority or the benefit under 35 U.S.C. 119 of Danish application nos. PA 2003 00119 and PA 2003 00689 filed Jan. 30, 2003 and May 7, 2003, respectively, and U.S. provisional application Nos. 60/445,300 and 60/468,574 filed Feb. 5, 2003 and May 7, 2003, respectively. The content of these application is fully incorporated herein by reference.

REFERENCE TO SEQUENCE LISTING

The present application contains a computer readable form of a sequence listing, which is fully incorporated herein by reference.

BACKGROUND OF THE INVENTION

Field of the Invention

The present invention relates to variants of TY145 subtilases and BPN' subtilases and to methods of construction such variants with altered properties, such as stability (e.g., thermostability or storage stability), $Ca^{2+}$ dependency, pH dependent activity.

Description of Related Art

Enzymes have been used within the detergent industry as part of washing formulations for more than 30 years. Proteases are from a commercial perspective the most relevant enzyme in such formulations, but other enzymes including lipases, amylases, cellulases, hemicellulases or mixtures of enzymes are also often used.

To improve the cost and/or the performance of proteases there is an ongoing search for proteases with altered properties, such as increased activity at low temperatures, increased thermostability, increased specific activity at a given pH, altered $Ca^{2+}$ dependency, increased stability in the presence of other detergent ingredients (e.g., bleach, surfactants etc.) etc.

The search for proteases with altered properties include both discovery of naturally occurring proteases, i.e., so called wild-type proteases but also alteration of well-known proteases by, e.g., genetic manipulation of the nucleic acid sequence encoding said proteases. Knowledge of the relationship between the three-dimensional structure and the function of a protein has improved the ability to evaluate which areas of a protein to alter to affect a specific characteristic of the protein.

One family of proteases, which are often used in detergents, are the subtilases. This family has previously been further grouped into 6 different sub-groups by Siezen R J and Leunissen J A M, 1997, Protein Science, 6, 501-523. One of these sub-groups is the Subtilisin family which includes subtilases such as BPN', subtilisin 309 (SAVINASE®, Novozymes A/S), subtilisin Carlsberg (ALCALASE®, Novozymes A/S), subtilisin S41 (a subtilase from the psychrophilic Antarctic *Bacillus* TA41, Davail et al., 1994, *Journal of Biological Chemistry* 269(26): 17448-17453), subtilisin S39 (a subtilase from the psychrophilic Antarctic *Bacillus* TA39, Narinx et al., 1997, *Protein Engineering* 10(11): 1271-1279) and TY145 (a subtilase from *Bacillus* sp. TY145, NCIMB 40339 described in WO 92/17577).

However, despite the sequence homology between the subtilases belonging to the Subtilisin subgroup of subtilases, modelling of the three-dimensional structure of one subtilase on the basis of the three-dimensional structure of another subtilase may result in an incorrect three-dimensional structure because of structural differences.

The inventors of the present invention have elucidated the three-dimensional structure of the TY145 subtilase and found that there are several differences between this and the three-dimensional structure of BPN' also belonging to the Subtilisin subgroup of subtilases. This surprising difference in structure makes it advantageous to use the TY145 structure as basis for homology modelling of TY145 like subtilisins, which, in turn, will improve the ability to obtain desired changes in functionality by protein engineering.

Two studies have used protein engineering to alter functionality of TY145 like subtilisins: Miyazaki et al., 2000, *J. Mol. Biol.* 297:1015-1026 discloses enhancement of the thermostability and activity of the psychrophilic protease subtilisin S41 by methods of directed evolution.

Wintrode et al., 2000, *Journal of Biological Chemistry* 275(41): 31635-31640 discloses conversion of a mesophilic subtilisin-like protease from *Bacillus sphaericus* SSII into its psychrophilic counterpart by methods of directed evolution. Wintrode et al. constructed the three-dimensional structural model of the SSII subtilase on basis of its homology with subtilisins Carlsberg, Savinase, BPN' and Thermitase. However, according to the present invention the SSII subtilase pertain to the new group of TY145 like subtilases and thus the modelling of SSII based on the 3D structure of the BPN' like subtilases will likely give an inaccurate result.

The differences between the three-dimensional structures of TY145 and BPN' are confirmed by the recently published three-dimensional structure of the subtilase "sphericase" from *Bacillus sphaericus* (PDB NO:1EA7, Protein Data Bank). The overall structure and many details of this subtilase are very homologous to the TY145 subtilase structure.

BRIEF DESCRIPTION OF THE INVENTION

The inventors have modified the amino acid sequence of a subtilase to obtain variants with improved properties, based on the three-dimensional structure of the subtilases TY145 and BPN'. The variants have altered properties, such as increased activity at low temperatures, increased thermostability, increased specific activity at a given pH, altered $Ca^{2+}$ dependency, increased stability in the presence of other detergent ingredients (e.g., bleach, surfactants, etc.) etc.

Accordingly, the object of the present invention is to provide a method for constructing subtilases having altered properties, in particular to provide a method for constructing subtilases having altered properties as described above.

Thus, in its broadest aspect, the present invention relates to a method for constructing a variant of a parent subtilase, wherein the variant has at least one altered property as compared to said parent subtilase, which method comprises:

i) analyzing the three-dimensional structure of the subtilase to identify, on the basis of an evaluation of structural considerations, at least one amino acid residue or at least one structural region of the subtilase, which is of relevance for altering said property;

ii) constructing a variant of the subtilase, which as compared to the parent subtilase, has been modified in the amino acid residue or structural part identified in i) so as to alter said property; and iii) testing the resulting subtilase variant for said property.

Although it has been described in the following that modification of the parent subtilase in certain regions and/or positions is expected to confer a particular effect to the thus produced subtilase variant, it should be noted that modification of the parent subtilase in any of such regions may also give rise to any other of the above-mentioned effects. For example, any of the regions and/or positions mentioned as being of particular interest with respect to, e.g., improved thermostability, may also give rise to, e.g., higher activity at a lower pH, an altered pH optimum, or increased specific activity, such as increased peptidase activity.

Further aspects of the present invention relates to variants of a subtilase, the DNA encoding such variants and methods of preparing the variants. Still further aspects of the present invention relates to the use of the variants for various industrial purposes, in particular as an additive in detergent compositions. Other aspects of the present invention will be apparent from the below description as well as from the appended claims.

BRIEF DESCRIPTION OF APPENDIX

Appendix 1 shows the structural coordinates for the solved crystal 3D structure of the TY145 subtilase (SEQ ID NO: 1).

BRIEF DESCRIPTION OF DRAWINGS

FIG. 1 shows a multiple alignment of 3D sequences of subtilases from TY145 (SEQ ID NO: 1), TA39 (SEQ ID NO: 2), TA41 (SEQ ID NO: 3), *Bacillus sphaericus* (SEQ ID NO: 4) and Savinase (SEQ ID NO: 6).

FIG. 2 shows an alignment between the amino acid sequences of subtilisin BPN' (SEQ ID NO: 5) and Savinase (SEQ ID NO: 6) in order to define the BPN' numbering of Savinase.

DEFINITIONS

Figure 3:
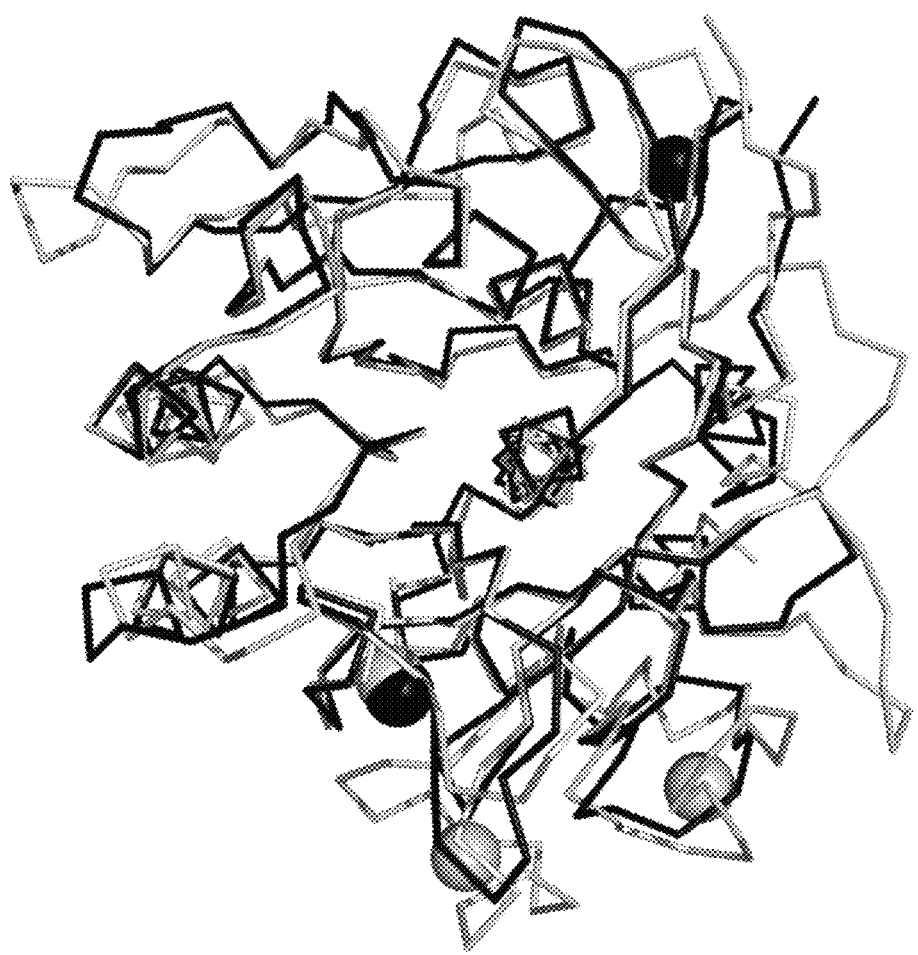
FIG. 3 shows a superposition of TY145 subtilase (SEQ ID NO: 1) (light) and BPN' structures (SEQ ID NO: 5) (dark), with spheres indicating ion-binding sites. The TY145 ion-binding sites are light and the BPN' ion-binding sites are dark.

Prior to discussing this invention in further detail, the following terms and conventions will first be defined.

For a detailed description of the nomenclature of amino acids and nucleic acids, we refer to WO 00/71691, page 5, hereby incorporated by reference. A description of the nomenclature of modifications introduced in a polypeptide by genetic manipulation can be found in WO 00/71691 page 7-12, hereby incorporated by reference.

The term "subtilases" refer to a sub-group of serine protease according to Siezen et al., 1991, *Protein Engng.* 4: 719-737 and Siezen et al. 1997, *Protein Science* 6: 501-523. Serine proteases or serine peptidases is a subgroup of proteases characterized by having a serine in the active site, which forms a covalent adduct with the substrate. Further the subtilases (and the serine proteases) are characterized by having two active site amino acid residues apart from the serine, namely a histidine and an aspartic acid residue.

Subtilases are defined by homology analysis of more than 170 amino acid sequences of serine proteases previously referred to as subtilisin-like proteases. The subtilases may be divided into 6 sub-divisions, i.e., the Subtilisin family, the Thermitase family, the Proteinase K family, the Lantibiotic peptidase family, the Kexin family and the Pyrolysin family.

The Subtilisin family (EC 3.4.21.62) may be further divided into 3 sub-groups, i.e., I-S1 ("true" subtilisins), I-S2 (highly alkaline proteases) and intracellular subtilisins. Definitions or grouping of enzymes may vary or change, however, in the context of the present invention the above division of subtilases into sub-division or sub-groups shall be understood as those described by Siezen et al., 1991, *Protein Engng.* 4: 719-737 and Siezen et al., 1997, *Protein Science* 6: 501-523.

The term "parent" is in the context of the present invention to be understood as a protein, which is modified to create a protein variant. The parent protein may be a naturally occurring (wild-type) polypeptide or it may be a variant thereof prepared by any suitable means. For instance, the parent protein may be a variant of a naturally occurring protein which has been modified by substitution, chemical modification, deletion or truncation of one or more amino acid residues, or by addition or insertion of one or more amino acid residues to the amino acid sequence, of a naturally-occurring polypeptide. Thus the term "parent subtilase" refers to a subtilase which is modified to create a subtilase variant.

The term "variant" is in the context of the present invention to be understood as a protein which has been modified as compared to a parent protein at one or more amino acid residues.

The term "modification(s)" or "modified" is in the context of the present invention to be understood as to include chemical modification of a protein as well as genetic manipulation of the DNA encoding a protein. The modification(s) may be replacement(s) of the amino acid side chain(s), substitution(s), deletion(s) and/or insertions in or at the amino acid(s) of interest. Thus the term "modified protein", e.g., "modified subtilase", is to be understood as a protein which contains modification(s) compared to a parent protein, e.g., subtilase.

The term "(a) TY145 subtilase" or "(a) TY145 like subtilase" should in the context of the present invention be understood as a subtilase belonging to the Subtilisin group according to Siezen et al., 1997, *Protein Science* 6: 501-523 and which has at least 63% homology to TY145, SEQ ID NO: 1. In the context of the present invention a TY145 subtilase has three ion-binding sites.

The term "(a) BPN' subtilase" or "(a) BPN' like subtilase" should in the context of the present invention be understood as a subtilase belonging to the Subtilisin group according Siezen et al., 1997, *Protein Science* 6: 501-523 and which has at least 61% homology to BPN' SEQ ID NO: 5. Such a BPN' like subtilase is for example Savinase. In the context of the present invention a BPN' subtilase has two, three or five ion-binding sites. A BPN' like subtilase may, in the context of the present invention, belong to branch I-S of the subtilisins, i.e., to branch I-S1, the "true" subtilisins or I-S2, the highly alkaline proteases (Siezen et al., 1991, *Protein Engng.* 4: 719-737).

"Homology" or "homologous to" is in the context of the present invention to be understood in its conventional meaning and the "homology" between two amino acid sequences should be determined by use of the "Similarity" defined by the GAP program from the University of Wisconsin Genetics Computer Group (UWGCG) package using default settings for alignment parameters, comparison matrix, gap and gap extension penalties. Default values for GAP penalties, i.e., GAP creation penalty of 3.0 and GAP extension penalty of 0.1 (Program Manual for the Wisconsin Package, Version 8, August 1994, Genetics Computer Group, 575 Science Drive, Madison, Wis., USA 53711). The method is also described in Needleman and Wunsch, 1970, *Journal of Molecular Biology* 48: 443-445. Identities can be extracted from the same calculation. The homology between two amino acid sequences can also be determined by "identity" or "similarity" using the GAP routine of the UWGCG package version 9.1 with default setting for alignment parameters, comparison matrix, gap and gap extension penalties can also be applied using the following parameters: gap creation penalty=8 and gap extension penalty=8 and all other parameters kept at their default values. The output from the routine is besides the amino acid alignment the calculation of the "Percent Identity" and the "Similarity" between the two sequences. The numbers calculated using UWGCG package version 9.1 is slightly different from the version 8.

The term "position" is in the context of the present invention to be understood as the number of an amino acid in a peptide or polypeptide when counting from the N-terminal end of said peptide/polypeptide. The position numbers used in the present invention refer to different subtilases depending on which subgroup the subtilase belongs to.

The four known subtilases belonging to the TY145 subgroup, i.e., subtilases obtained from TY145, TA39, TA41 and *Bacillus sphaericus* are numbered individually according to each of SEQ ID NOS: 1, 2, 3 and 4.

Likewise other subtilases belonging to the TY145 subgroup are numbered individually according to their own sequence. However in order to determine homologous positions in such other subtilases an alignment with each of SEQ ID NOS: 1, 2, 3 and 4 is conducted according to the GAP procedure described above. Subsequently the homologous positions are determined with reference to the most homologous of SEQ ID NOS: 1, 2, 3 and 4.

Alternatively subtilases belonging to the TY145 subgroup can be numbered by reference to the positions of TY145 subtilase (SEQ ID NO: 1).

Subtilases belonging to the BPN' subgroup refers to the positions of Subtilisin Novo (BPN') from *B. amyloliquefaciens* (SEQ ID NO: 5).

DETAILED DESCRIPTION OF THE INVENTION

Despite the great homology of the subtilases described above the inventors of the present invention have elucidated the three-dimensional structure of TY145, SEQ ID NO: 1 by X-ray crystallography and found that there are several substantial differences between the three dimensional structures of TY145 and BPN'. The inventors of the present invention have further compared the sequence homology of a representative number of subtilases belonging to the Subtilisin subgroup. This is shown in the homology matrix in Table 1 below.

TABLE 1

| No. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | *100* | 93 | 76 | 51 | 50 | 51 | 55 | 52 | 54 | 58 | 58 | 59 | 57 | 60 | 60 |
| 2 |  | *100* | 75 | 52 | 52 | 52 | 56 | 53 | 55 | 58 | 58 | 61 | 58 | 62 | 61 |
| 3 |  |  | *100* | 60 | 60 | 60 | 58 | 60 | 62 | 58 | 57 | 59 | 59 | 62 | 59 |
| 4 |  |  |  | *100* | 99 | 99 | 97 | 91 | 76 | 63 | 69 | 74 | 66 | 74 | 74 |
| 5 |  |  |  |  | *100* | 99 | 97 | 90 | 76 | 69 | 74 | 66 | 74 | 74 | 56 |
| 6 |  |  |  |  |  | *100* | 98 | 91 | 77 | 63 | 69 | 74 | 66 | 74 | 74 |
| 7 |  |  |  |  |  |  | *100* | 88 | 79 | 69 | 67 | 74 | 74 | 74 | 74 |
| 8 |  |  |  |  |  |  |  | *100* | 77 | 66 | 71 | 74 | 67 | 74 | 74 |
| 9 |  |  |  |  |  |  |  |  | *100* | 64 | 69 | 74 | 67 | 73 | 73 |
| 10 |  |  |  |  |  |  |  |  |  | *100* | 99 | 76 | 72 | 76 | 76 |
| 11 |  |  |  |  |  |  |  |  |  |  | *100* | 76 | 76 | 76 | 76 |
| 12 |  |  |  |  |  |  |  |  |  |  |  | *100* | 99 | 99 | 99 |
| 13 |  |  |  |  |  |  |  |  |  |  |  |  | *100* | 99 | 99 |
| 14 |  |  |  |  |  |  |  |  |  |  |  |  |  | *100* | 98 |
| 15 |  |  |  |  |  |  |  |  |  |  |  |  |  |  | *100* |

Legend to Table 1
TY145 like subtilases:
1: q45681; Subtilase derived from *B. subtilis* (BSTA41)
2: p28842; Psychrophilic subtilisin derived from Antarctic *Bacillus* strain (BSTA39)
3: abb77095; Subtilase derived from *Bacillus* sp. (TY145) BPN' like subtilases, I-S1:
4: p00783; Subtilase derived from *Bacillus subtilis* var. *amylosaccharticus* (BSAMY)
5: p29142; Subtilase derived from *Bacillus stearothermophilus* (BSSJ)
6: p35835; Subtilase derived from *Bacillus subtilis* var. natto. (BSNAT)
7: p07518; Subtilase derived from *Bacillus pumilus* (*B. mesentericus*) (BPMES)
8: p00782; Subtilase derived from *Bacillus amyloliquefaciens* (BPN')
9: p00780; Subtilase derived from *Bacillus licheniformis* (BLSCAR) BPN' like subtilases, I-S2
10: p41363; Subtilase derived from *Bacillus halodurans* (BHSAH)
11: aaw62222; Subtilase derived from *Bacillus lentus* (BLS147)
12: p29600; Subtilase derived from *Bacillus lentus* (BLSAVI, BLS309)
13: p27693; Subtilase derived from *Bacillus alcalophilus* (BAALKP)
14: q99405; Subtilase derived from *Bacillus* sp. strain KSM-K16 (BSKSMK)
15: p29599; Subtilase derived from *Bacillus lentus* (BLSUBL).

On the basis of the 3D structure comparison and protein sequence the inventors of the present invention find that the subgroup of TY145 subtilases are different from BPN' subtilases based on the 3D structure comparison of the enclosed 3D structure of TY145 and the BPN' 3D structure but also indicated from the sequence homology between TY145 and BPN'.

TY145 Subtilases

As described above a TY145 subtilase is in the context of the present invention to be understood as a subtilase which has at least 63% homology to SEQ ID NO: 1. In particular said TY145 subtilase may have at least 65%, such as at least 70%, at least 74%, at least 80%, at least 83%, at least 90%, at least 91%, at least 92%, at least 93%, at least 94%, at least 95%, at least 96%, at least 97%, at least 98% or at least 99% homology to TY145, i.e., to SEQ ID NO: 1.

In a first embodiment of the present invention a TY145 subtilase suitable for the purpose described herein may be a subtilase homologous to the three-dimensional structure of TY145, i.e., it may be homologous to the three-dimensional structure defined by the structure coordinates in Appendix 1.

As it is well-known to a person skilled in the art that a set of structure coordinates for a protein or a portion thereof is a relative set of points that define a shape in three dimensions, it is possible that an entirely different set of coordinates could define an identical or a similar shape. Moreover, slight variations in the individual coordinates may have little or no effect on the overall shape.

These variations in coordinates may be generated because of mathematical manipulations of the structure coordinates. For example, the structure coordinates of Appendix 1 (TY145 structure) may be manipulated by crystallographic permutations of the structure coordinates, fractionalization of the structure coordinates, integer additions or subtractions to sets of the structure coordinates, inversion of the structure coordinates or any combination of the above. Alternatively, said variations may be due to differences in the primary amino acid sequence.

If such variations are within an acceptable standard error as compared to the structure coordinates of Appendix 1 said three-dimensional structure is within the context of the present invention to be understood as being homologous to the structure of Appendix 1. The standard error may typically be measured as the root mean square deviation of, e.g., conserved backbone residues, where the term "root mean square deviation" (RMS) means the square root of the arithmetic mean of the squares of the deviations from the mean.

As it is also well-known to a person skilled in the art that within a group of proteins which have a homologous structure there may be variations in the three-dimensional structure in certain areas or domains of the structure, e.g., loops, which are not or at least only of a small importance to the functional domains of the structure, but which may result in a big root mean square deviation of the conserved residue backbone atoms between said structures.

Thus it is well known that a set of structure coordinates is unique to the crystallized protein. No other three dimensional structure will have the exact same set of coordinates, be it a homologous structure or even the same protein crystallized in different manner. There are natural fluctuations in the coordinates. The overall structure and the inter-atomic relationship can be found to be similar. The similarity can be discussed in terms of root mean square deviation of each atom of a structure from each "homologous" atom of another structure. However, only identical proteins have the exact same number of atoms. Therefore, proteins having a similarity below 100% will normally have a different number of atoms, and thus the root mean square deviation can not be calculated on all atoms, but only the ones that are considered "homologous". A precise description of the similarity based on the coordinates is thus difficult to describe and difficult to compute for homologous proteins. Regarding the present invention, similarities in 3D structure of different subtilases can be described by the content of homologous structural elements, and/or the similarity in amino acid or DNA sequence. For sequences having no deletions or insertions a RMS for the calcium atoms can be calculated.

Examples of TY145 like subtilases include the psychrophilic subtilisin protease S41 derived from the Antarctic *Bacillus* TA41, herein also called TA41 subtilase (Davail et al., 1994, *J. Biol. Chem.* 269: 17448-17453), and the psychrophilic subtilisin protease S39 derived from the Antarctic *Bacillus* TA39, herein also called TA39 subtilase (Narinx et al., 1997, *Protein Engineering* 10(11): 1271-1279). Recently a three-dimensional structure of a subtilisin homologous with the TY145 subtilisins was published in the Protein Data Bank (Accession No:1EA7). The overall structure and many details of this *Bacillus sphaericus* "sphericase" subtilase are very homologous with the TY145 subtilase structure; however the structure of the sphericase revealed as much as five ion-binding sites. The number of ion-binding sites may vary in similar structures depending on the medium used for crystallization. Thus it appears that the two extra ion-binding sites of *Bacillus sphaericus* "sphericase" are due to a calcium containing crystallization medium.

Accordingly, a preferred embodiment of the present invention is a parent subtilase or a subtilase variant which is at least 63% homologous to the sequence of SEQ ID NO: 1, preferably at least 65%, at least 70%, at least 74%, at least 80%, at least 83%, at least 90%, at least 91%, at least 92%, at least 93%, at least 94%, at least 95%, at least 96%, at least 97%, at least 98% or at least 99% homologous to the sequence of SEQ ID NO: 1, and optionally said subtilase further comprises the following structural characteristics:

a) a twisted beta-sheet with 7 strands,
b) six alpha helices,
c) at least three ion-binding sites and wherein the Strong ion-binding site of the BPN' like subtilases is not present, and with the exception of the TY145 subtilase, the TA39 subtilase, the TA41 subtilase, and the *Bacillus sphaericus* "sphericase".

The TY145 subtilase of the present invention is encoded by an isolated nucleic acid sequence, which nucleic acid sequence has at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% homology with the nucleic acid sequence shown in SEQ ID NO: 20.

Further the isolated nucleic acid sequence encoding a TY145 subtilase of the invention hybridizes with a complementary strand of the nucleic acid sequence shown in SEQ ID NO: 20 preferably under low stringency conditions, at least under medium stringency conditions, at least under medium/high stringency conditions, at least under high stringency conditions, at least under very high stringency conditions.

Suitable experimental conditions for determining hybridization at low, medium, or high stringency between a nucleotide probe and a homologous DNA or RNA sequence involves presoaking of the filter containing the DNA fragments or RNA to hybridize in 5×SSC (Sodium chloride/

Sodium citrate, Sambrook et al., 1989) for 10 min, and prehybridization of the filter in a solution of 5×SSC, 5×Denhardt's solution (Sambrook et al., 1989), 0.5% SDS and 100 micrograms/ml of denatured sonicated salmon sperm DNA (Sambrook et al., 1989), followed by hybridization in the same solution containing a concentration of 10 ng/ml of a random-primed (Feinberg and Vogelstein, 1983, *Anal. Biochem.* 132: 6-13), $^{32}$P-dCTP-labeled (specific activity >1×10$^9$ cpm/μg) probe for 12 hours at ca. 45° C. The filter is then washed twice for 30 minutes in 2×SSC, 0.5% SDS at at least 55° C. (low stringency), more preferably at least 60° C. (medium stringency), still more preferably at least 65° C. (medium/high stringency), even more preferably at least 70° C. (high stringency), and even more preferably at least 75° C. (very high stringency).

BPN' Subtilases

As described above a BPN' subtilase is in the context of the present invention to be understood as a subtilase which has at least 61% homology to SEQ ID NO: 5. In particular said BPN' subtilase may have at least 70%, such as at least 75%, at least 80%, at least 85%, at least 90%, at least 91%, at least 92%, at least 93%, at least 94%, at least 95%, at least 96%, at least 97%, at least 98% or at least 99% homology to BPN', i.e., to SEQ ID NO: 5.

In one embodiment of the present invention a BPN' subtilase suitable for the purpose described herein may be a subtilase homologous to the three-dimensional structure of BPN' as defined by the structure coordinates given in PDB Nos. 1SBT and 1GNS (Protein Data Bank), or one of the several other structures of BPN' that are accessible from the Protein Data Bank. Variations between homologous structures may occur for several reasons as described above. Thus a BPN' subtilase within the context of the present invention is to be understood as any subtilase having the structural characteristics pertaining to the BPN' subtilases as described above, and in addition such subtilases does preferably not have further structural characteristics which are not present in the BPN' subtilases as described herein. Further a BPN' subtilase of the present invention may have the necessary percentage of similarity with SEQ ID NO: 5.

Examples of BPN' like subtilases include the subtilisin 309 (PDB NO:1SVN SAVINASE®, Novozymes A/S) and subtilisin Carlsberg (ALCALASE®, Novozymes A/S), among others.

In FIG. 1 of Siezen and Leunissen, 1997, *Protein Science* 6(3): 501-523, a structure of subtilases is described. A subtilase consists of 6-8 helices, 11 strands of which 7 are central in a twisted beta-sheet. Two ion-binding sites are mentioned, one of which is the so called "Weak" calcium-binding site. It was later discovered that for some structures (subtilisin DY PDB no. 1BH6, 1998), this calcium-binding site was shown to be a Na (sodium) binding site when the calcium concentration in the crystallization medium was low. Thus, in the following we refer to ion-binding sites instead of calcium-binding sites.

The BPN' subtilase of the present invention is encoded by an isolated nucleic acid sequence, which nucleic acid sequence has at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% homology with the nucleic acid sequence shown in SEQ ID NO: 21.

Further the isolated nucleic acid sequence encoding a BPN' subtilase of the invention hybridizes with a complementary strand of the nucleic acid sequence shown in SEQ ID NO: 21 preferably under low stringency conditions, but at least under medium stringency conditions, at least under medium/high stringency conditions, at least under high stringency conditions, at least under very high stringency conditions.

Three-Dimensional Structure of TY145 Subtilases

The TY145 subtilase was used to elucidate the three-dimensional structure forming the basis for the present invention.

The structure of TY145 was solved in accordance with the principle for x-ray crystallographic methods, for example, as given in X-Ray Structure Determination, Stout, G. K. and Jensen, L. H., John Wiley & Sons, Inc. NY, 1989.

The structural coordinates for the solved crystal structure of TY145 are given in standard PDB format (Protein Data Bank, Brookhaven National Laboratory, Brookhaven, Conn.) as set forth in Appendix 1. It is to be understood that Appendix 1 forms part of the present application. In the context of Appendix 1, the following abbreviations are used: CA refers to c-alpha (carbon atoms) or to calcium ions, (however to avoid misunderstandings we use the full names "c-alpha atoms" and "calcium" or "ion" in the present specification). Amino acid residues are given in their standard three-letter code. The attached structural coordinates contain the protease structure, and an inhibitor structure CI2 as well as water molecules. The protease coordinates has a chain identification called A, whereas the CI2 inhibitor is called B, the calcium ions are called C, and the water is W. In the following the positions of the mentioned residues refer to the sequence of TY145 as disclosed in SEQ ID NO: 1.

The structure of TY145 shows the same "overall" fold as found in the S8 family of subtilisins. The structure comprises a twisted beta-sheet with 7 strands arranged in the following sequential order S2, S3, S1, S4, S5, S6, S7. There are six alpha helices in the structure of which number H1 contains residues 9-15, H2 contains residues 72-81, H3 contains residues 114-131, H4 contains residues 148-158, H5 contains residues 250-267 and H6 contains residues 273-286.

The TY145 like subtilases are shown to lack the well-known Strong ion-binding site of the BPN' subtilases. However, in addition to the Weak calcium or ion-binding site also known from the BPN' subtilases, the TY145 subtilases have two ion-binding sites which are not present in the BPN' subtilisin structures. This can be seen in the structural alignment presented in FIG. 3. These additional ion-binding sites are hereinafter referred to as "Near" and "Far" according to their distance to the Weak ion-binding site. Thus in relation to the atomic coordinates disclosed in Appendix 1, the ion-binding sites of TY145 are located at:

Weak—calcium atom named C 314,
Near—calcium atom named C 312, and
Far—calcium atom named C 313 in the PDB table (Appendix 1).

The position of an ion-binding site can be defined by the distance to four specific atoms in the core structure. The distance from the ion-binding site to the c-alpha atoms of the three active site residues has been chosen. Throughout the subtilases the residues Ser, His and Asp in the active site are highly conserved. In TY145 they are Asp35, His72 and Ser251. The fourth distance chosen is the distance to the c-alpha atom of the amino acid residue coming first after the active site serine residue in the sequence (herein after called "next to Ser"); in the 3D structure of TY145 it is Met252.

In a preferred embodiment of the present invention, the distance between:

a) the Weak ion-binding site and i) Asp c-alpha atom is 17.50-19.50 Å, ii) His c-alpha atom is 21-23 Å, iii) Ser c-alpha atom is 13.80-15.80 Å, iv) next to Ser c-alpha atom is 15.80-17.80 Å, b) the Far ion-binding site and i) Asp c-alpha atom is 28.70-30.70 Å, ii) His c-alpha atom is 28-30 Å, iii) Ser c-alpha atom is 20-22 Å, iv) next to Ser c-alpha atom is 19.50-21.50 Å, c) the Near ion-binding site and i) Asp c-alpha atom is 27-29 Å, ii) His c-alpha atom is 29.50-31.50 Å, iii) Ser c-alpha atom is 21.40-23.40 Å, iv) next to Ser c-alpha atom is 22.50-24.50 Å.

Below are the specific distances between the four chosen c-alpha atoms and the three ion binding sites of the TY145 subtilase given in Å:

|  | Weak ion-binding site | Far ion-binding site | Near ion-binding site |
| --- | --- | --- | --- |
| Met252 c-alpha atom | 16.75 | 20.35 | 23.58 |
| His72 c-alpha atom | 21.98 | 29.10 | 30.43 |
| Asp35 c-alpha atom | 18.55 | 29.68 | 28.04 |
| Ser251 c-alpha atom | 14.71 | 20.96 | 22.28 |
| Weak ion-binding site | 0 | 16.62 | 9.79 |
| Far ion-binding site | 16.62 | 0 | 12.48 |
| Near ion-binding site | 9.79 | 12.48 | 0 |

However these distances may vary from one subtilase to the other, and as described above, the Weak ion binding site may also bind to a sodium ion. The present distances are given with a calcium ion in the structure. If a sodium ion was bound instead the distances would be shifted a little bit. Generally the distances can vary ±0.8 Å, preferably ±0.7 Å, ±0.6 Å, ±0.5 Å, ±0.4 Å, or most preferably ±0.3 Å.

Further, in the TY145 like subtilases, the peptide structure circumscribing the Weak ion-binding site is composed of the amino acid residues placed in positions 182-189 and 221-227 with the coordinating atoms being the backbone carbonyl oxygen atom of residues G182, A187, L184 and two water molecules.

The peptide structure circumscribing the Near ion-binding site is composed of residues 212-225 with the coordinating atoms being the backbone carbonyl oxygen atom of residues I220 and T215, the oxygens from the carboxylic acids of residues D225 and D218 and the amid group of residue Q222.

The peptide structure circumscribing the Far ion-binding site is composed of residues 288-306 with the coordinating atoms being the backbone carbonyl oxygen atom of residues G298, G296 and I289, the oxygens from the carboxylic acids of residues D300 and D288, and two water molecules.

In comparison with the BPN' like subtilase structures the structure of the TY145 like subtilase can be divided into a "common subtilase-like" region, an "intermediate" region and a "nonhomolo-gous" region.

The active site can be found in the common subtilase-like region, which is structurally closely related to the BPN' structures. The common subtilase-like region is composed of residues 88-128 and 225-284, and contains the alpha-helix H3 and the central alpha-helix H5 in which the active site serine residue is situated in the N-terminal part. The common subtilase-like region has an RMS lower than 1.2.

Outside the common subtilase-like region the structure of the TY145 like subtilase differs from the BPN' structures to a greater extent.

The intermediate region consist of residues 24-45, 48-58, 65-66, 67-85, 134-174, 175-196, 202-212 and 287-290. The intermediate region has an RMS higher than 1.2 and lower than 1.8. The relationships between the three-dimensional structure and functionality are potentially difficult to predict in this region of the TY145 like subtilases.

The nonhomologous region consists of residues 5-15, 16-23, 86-87, 129-133, 197-201, 213-124, 285-286, 291-298 and 299-311. The nonhomologous region has a RMS higher than 1.5, which also pertains to residues 65-66 from the intermediate region. The group comprising residues 5-15 and 299-311 has an RMS between 2.1-2.2. The relationships between the three-dimensional structure and functionality are very difficult to predict in this region of the TY145 like subtilases.

The regions in areas A1-T5, N16-T24, A46-Q51, S58-C66, G84-G90, S129-K134, S129-K134, S173-S175, V196-T201, N212-R224, A284-V286, K290-D299 and V310-K311 in the TY145 structure differs significantly from the other S8 family subtilisins (including the BPN' type subtilisins) in c-alpha atom coordinates. An RMS cannot be calculated for these last residues as there are no homologous c-alpha atoms in the compared subtilases.

Homology Building of TY145 and BPN' Like Subtilases

A model structure of a TY145 like subtilase or a BPN' like subtilase can be built using the Homology program or a comparable program, e.g., Modeller (both from Molecular Simulations, Inc., San Diego, Calif.). The principle is to align the amino acid sequence of a protein for which the 3D structure is known with the amino acid sequence of a protein for which a model 3D structure has to be constructed. The structurally conserved regions can then be built on the basis of consensus sequences. In areas lacking homology, loop structures can be inserted, or sequences can be deleted with subsequent bonding of the necessary residues using, e.g., the program Homology. Subsequent relaxing and optimization of the structure should be done using either Homology or another molecular simulation program, e.g., CHARMm from Molecular Simulations.

Methods for Designing TY145 and Subtilisin Family Subtilase Variants

Comparisons of the molecular dynamics of different proteins can give a hint as to which domains are important or connected to certain properties pertained by each protein.

The present invention comprises a method of producing a variant of a parent TY145 like subtilase, the variant having at least one altered property as compared to the parent TY145 like subtilase, the method comprising:

a) modelling the parent TY145 subtilase on the three-dimensional structure of a TY145 subtilase to produce a three-dimensional structure of the parent TY145 subtilase;

b) comparing the three-dimensional structure obtained in step a) to the three-dimensional structure of a TY145 subtilase;

c) identifying on the basis of the comparison in step b) at least one structural part of the parent TY145 subtilase, wherein an alteration in said structural part is predicted to result in an altered property;

d) modifying the nucleic acid sequence encoding the parent TY145 subtilase to produce a nucleic acid sequence encoding deletion or substitution of one or more amino acids at a position corresponding to said structural part, or an insertion of one or more amino acid residues in positions corresponding to said structural part;

e) expressing the modified nucleic acid sequence in a host cell to produce the variant TY145 subtilase;

f) isolating the produced subtilase;
g) purifying the isolated subtilase; and
h) recovering the purified subtilase.

Further the present invention comprises a method of producing a variant of a parent Subtilisin family subtilase, such as a BPN' like subtilase, the variant having at least one altered property as compared to the parent Subtilisin family subtilase, the method comprising:

a) modelling the parent Subtilisin family subtilase on the three-dimensional structure of a Subtilisin family subtilase to produce a three-dimensional structure of the parent Subtilisin family subtilase;

b) comparing the three-dimensional structure obtained in step a) to the three-dimensional structure of a TY145 like subtilase;

c) identifying on the basis of the comparison in step b) at least one structural part of the parent Subtilisin family subtilase, wherein an alteration in said structural part is predicted to result in an altered property;

d) modifying the nucleic acid sequence encoding the parent Subtilisin family subtilase to produce a nucleic acid sequence encoding deletion or substitution of one or more amino acids at a position corresponding to said structural part, or an insertion of one or more amino acid residues in positions corresponding to said structural part;

e) expressing the modified nucleic acid sequence in a host cell to produce the variant Subtilisin family subtilase, f) isolating the produced subtilase,
g) purifying the isolated subtilase, and
h) recovering the purified subtilase.

Further the present invention comprises a method of producing a variant of a parent TY145 like subtilase, the variant having at least one altered property as compared to the parent TY145 like subtilase, the method comprising:

a) modelling the parent TY145 like subtilase on the three-dimensional structure of a TY145 like subtilase to produce a three-dimensional structure of the parent TY145 like subtilase;

b) comparing the three-dimensional structure obtained in step a) to the three-dimensional structure of a Subtilisin family subtilase;

c) identifying on the basis of the comparison in step b) at least one structural part of the parent TY145 like subtilase, wherein an alteration in said structural part is predicted to result in an altered property;

d) modifying the nucleic acid sequence encoding the parent TY145 like subtilase to produce a nucleic acid sequence encoding deletion or substitution of one or more amino acids at a position corresponding to said structural part, or an insertion of one or more amino acid residues in positions corresponding to said structural part;

e) expressing the modified nucleic acid sequence in a host cell to produce the variant TY145 like subtilase;

f) isolating the produced subtilase;
g) purifying the isolated subtilase; and
h) recovering the purified subtilase.

Stability—Alteration of Ion-Binding Sites

As described above the TY145 subtilases has two new ion-binding sites not present in the BPN' subtilisin structures but lacks the Strong ion-binding site of the BPN' subtilases. Stability of the ion-binding site is of crucial importance for the functionality of the enzyme. Therefore alterations of the amino acid residues close to the ion-binding sites are likely to result in alterations of the stability of the enzyme.

The positions which may be modified are located:
Weak: at a distance of 10 Å or less around calcium atom named C 314,
Near: at a distance of 10 Å or less around calcium atom named C 312, and
Far: at a distance of 10 Å or less around calcium atom named C 313 in the PDB table (Appendix 1).

Improved Stability

Stabilization of the ion-binding sites of TY145 may possibly be obtained by alterations in the positions close to the sites. Positions located at a distance of 10 Å or less to the ion-binding sites of TY145 (SEQ ID NO: 1) are:
Weak: 154, 155, 158, 164, 165, 166, 167, 168, 178-191 (i.e., 178, 179, 180, 181, 182, 183, 184, 185, 186, 187, 188, 189, 190, 191), 211, 220-228 (i.e., 220, 221, 222, 223, 224, 225, 226, 227, 228), 277, 281 and 305.
Near: 185, 211-227 (i.e., 211, 212, 213, 214, 215, 216, 217, 218, 219, 220, 221, 222, 223, 224, 225, 226, 227), 277, 281, 299, 300, 301, 304, 305.
Far: 193, 198, 199, 201, 202, 204, 216, 217, 219, 226, 227, 228, 229 and 284-307 (i.e., 284, 285, 286, 287, 288, 289, 290, 291, 292, 293, 294, 295, 296, 297, 298, 299, 300, 301, 302, 303, 304, 305, 306, 307).

In detergent compositions calcium chelaters contribute to removal of calcium from the subtilases with subsequent inactivation of the enzyme as the result. To decrease the inactivation due to calcium removal of, e.g., calcium chelaters, variants with improved calcium stability can be constructed.

Variants with alterations close to the Near ion-binding site are I220S,T and T215S, variants with alterations close to the Far ion-binding site are G298A,S,T and G296A,S,T, and variants with alterations close to the Weak ion-binding site are V185T and I221N,D,T.

TY145 with Extra Ion-Binding Site

The Strong ion-binding site from the BPN' subtilases can be transplanted into TY145 (or other subtilases in TY145 subgroup) by deletion(s) of or in the region H83-G90 (of SEQ ID NO: 1) and subsequent insertion of one or more amino acid residues. A preferred variant has the whole region deleted and a subsequent insertion between A82 and V91 of the sequence LNNSIG.

Removal of Ion-Binding Site in TY145

By removing a ion-binding site it is possible to alter the enzymes dependency of calcium or other ions in the solution. The Far and Near ion-binding sites in TY145 (or others from TY145 group) can be removed with guidance from the three-dimensional structure of BPN' and Savinase (or others in BPN' group).

Removal of the Far site can be done by deletion(s) of or in the region K290-D300 (of SEQ ID NO: 1) and subsequent insertion of one or more amino acid residues. A preferred variant has the whole region deleted and a subsequent insertion between I289 and Y301 of the sequence GDS or DST. Preferably, but not mandatory the substitution S303Y is further added.

Removal of the Near site can be done by deletion(s) of or in the region N212-R224 (of SEQ ID NO: 1) and subsequent insertion of one or more amino acid residues. A preferred variant has the whole region deleted and a subsequent insertion of a proline or alanine residue between G211 and D225.

Removal of Strong Ion-Binding Site in BPN' Subtilases

The Strong ion-binding site in BPN' like subtilases can be removed. Exemplified in Savinase, the removal can be done by deletion of or in the region L75-G80 (BPN' numbering) and subsequent insertion of one or more amino acid residues. A preferred variant has the whole region deleted and a subsequent insertion of residues 84-88 from TY145. In addition the substitutions L82Y and Q2A,N can be applied.

Alteration of Thermostability

A variant with improved stability (typically increased thermostability) may be obtained by substitution with proline, introduction of a disulfide bond, altering a hydrogen bond contact, altering charge distribution, introduction of a salt bridge, filling in an internal structural cavity with one or more amino acids with bulkier side groups (in, e.g., regions which are structurally mobile), substitution of histidine residues with other amino acids, removal of a deamidation site, or by helix capping.

Regions with Increased Mobility:

The following regions of TY145 have an increased mobility in the crystal structure of the enzyme, and it is presently believed that these regions can be responsible for stability or activity of TY145. Especially thermostabilization may possibly be obtained by altering the highly mobile regions. Improvements of the enzyme can be obtained by mutation in the below regions and positions. Introducing, e.g., larger residues or residues having more atoms in the side chain could increase the stability, or, e.g., introduction of residues having fewer atoms in the side chain could be important for the mobility and thus the activity profile of the enzyme. The regions can be found by analysing the B-factors taken from the coordinate file in Appendix 1, and/or from molecular dynamics calculations of the isotropic fluctuations. These can be obtained by using the program CHARMm from MSI (Molecular Simulations Inc.).

Molecular dynamics simulation at 300K of TY145 reveals the following highly mobile regions:

| | |
|---|---|
| 84-89 | (i.e., 84, 85, 86, 87, 88, 89) |
| 108-117 | (i.e., 108, 109, 110, 111, 112, 113, 114, 115, 116, 117) |
| 141-146 | (i.e., 141, 142, 143, 144, 145, 146) |
| 150-152 | (i.e., 150, 151, 152) |
| 169-171 | (i.e., 169, 170, 171) |
| 200-201 | |
| 211-220 | (i.e., 211, 212, 213, 214, 215, 216, 217, 218, 219, 220) |
| 242-243 | |
| 268-270 | (i.e., 268, 269, 270). |

Also B-factors (see "in X-Ray Structure Determination, Stout, G. K. and Jensen, L. H., John Wiley & Sons, Inc. NY, 1989") from crystallographic data indicates the following more mobile regions in the TY145 structure:

| | |
|---|---|
| 1-7 | (i.e., 1, 2, 3, 4, 5, 6, 7), |
| 17-23 | (i.e., 17, 18, 19, 20, 21, 22, 23), |
| 38-50 | (i.e., 38, 39, 40, 41, 42, 43, 44, 45, 46, 47, 48, 49, 50), |
| 57-69 | (i.e., 57, 58, 59, 60, 61, 62, 63, 64, 65, 66, 67, 68, 69), |
| 84-92 | (i.e., 84, 85, 86, 87, 88, 89, 90, 91, 92), |
| 107-110 | (i.e., 107, 108, 109, 110), |
| 239-243 | (i.e., 239, 240, 241, 242, 243) and |
| 265-266. | |

Preferably the regions 57-69 and 84-92.

Disulfide Bonds:

A TY145 variant of the present invention with improved stability, e.g., thermostability, as compared to the parent TY145 may be obtained by introducing new inter-domain or intra-domain bonds, such as by establishing inter- or intra-domain disulfide bridges.

Thus a further aspect of the present invention relates to a method for producing a variant of a parent TY145 comprising the methods described in the paragraph "Methods of preparing TY145 like or BPN' like subtilase variants" herein.

According to the guidelines mentioned above the below mentioned amino acid residues identified in the amino acid sequence of SEQ ID NO: 1 are suitable for cysteine replacement. With one or more of these substitutions with cysteine, disulfide bridges may possibly form in a variant of TY145. The substitutions are: G26C+A95C; A167C+T254C; R203C+G292C and V228C+A284C.

Similar residues suitable for cysteine replacement in homologous subtilases such as TA39, TA41 can be elucidated by finding the homologous positions in the alignment of FIG. 1. Concerning another TY145 like sequence the homologous positions suitable for cysteine replacement can be selected by aligning said TY145 like sequence with all of the sequences of FIG. 1 using the GAP analysis method as described above. The suitable residues can then be selected in accordance with the homologous positions in the most homologous of SEQ ID NOS: 1, 2, 3 and 4 which are the sequences of the subtilases aligned in FIG. 1.

Surface Charge Distribution

A variant with improved stability (typically improved thermostability) as compared to the parent subtilase may be obtained by changing the surface charge distribution of the subtilase. For example, when the pH is lowered to about 5 or below histidine residues typically become positively charged and, consequently, unfavorable electrostatic interactions on the protein surface may occur. By engineering the surface charge of the subtilase one may avoid such unfavorable electrostatic interactions that in turn lead to a higher stability of the subtilase.

Therefore, a further aspect of the present invention relates to a method for constructing a variant of a parent subtilase, the method comprising:

a) identifying, on the surface of the parent subtilase, preferably a TY145 like or a BPN' like subtilase, at least one amino acid residue selected from the group consisting of Asp, Glu, Arg, Lys and His;

b) substituting, on the surface of the parent subtilase, at least one amino acid residue selected from the group consisting of Asp, Glu, Arg, Lys and His with an uncharged amino acid residue;

c) optionally repeating steps a) and b) recursively;

d) optionally, making alterations each of which is an insertion, a deletion or a substitution of an amino acid residue at one or more positions other than b);

e) preparing the variant resulting from steps a)-d);

f) testing the stability of said variant; and g) optionally repeating steps a)-f) recursively; and h) selecting a subtilase variant having increased stability as compared to the parent subtilase.

As it will be understood by the skilled person it may also, in some cases, be advantageous to substitute an uncharged amino acid residue with an amino acid residue bearing a charge or, alternatively, it may in some cases be advantageous to substitute an amino acid residue bearing a charge with an amino acid residue bearing a charge of opposite sign. Thus, the above-mentioned method may easily be employed by the skilled person also for these purposes. In the case of substituting an uncharged amino acid residue with an amino acid residue bearing a charge the above-mentioned method may be employed the only difference being steps a) and b) which will then read:

a) identifying, on the surface of the parent subtilase, at least one uncharged amino acid residue;

b) substituting, on the surface of the parent subtilase, at least one uncharged amino acid residue with a charged amino acid residue selected from the group consisting of Asp, Glu, Arg, Lys and His.

Also in the case of changing the sign of an amino acid residue present on the surface of the subtilase the above method may be employed. Again, compared to the above method, the only difference being steps a) and b) which, in this case, read:

a) identifying, on the surface of the parent subtilase, at least one charged amino acid residue selected from the group consisting of Asp, Glu, Arg, Lys and His;

b) substituting, on the surface of the parent subtilase, at least one charged amino acid residue identified in step a) with an amino acid residue having an opposite charge.

Thus, Asp may be substituted with Arg, Lys or His; Glu may be substituted with Arg, Lys or His; Arg may be substituted with Asp or Glu; Lys may be substituted with Asp or Glu; and His may be substituted with Asp or Glu.

In order to determine the amino acid residues of a subtilase, which are present on the surface of the enzyme, the surface accessible area are measured using the DSSP program (Kabsch and Sander, 1983, *Biopolymers* 22: 2577-2637). All residues having a surface accessibility higher than 0 is regarded a surface residue.

An amino acid residue found on the surface of TY145 using the above method is D116 and it is contemplated that the substitutions D116H,K,R are of particular interest.

Similar substitutions may be introduced in equivalent positions of other TY145 like subtilases.

Substitution with Proline Residues

Improved thermostability of a subtilase can be obtained by subjecting the subtilase in question to analysis for secondary structure, identifying residues in the subtilase having dihedral angles φ (phi) and ψ (psi) confined to the intervals [$-90°<\phi<-40°$ and $-180°<\psi<180°$], preferably the intervals [$-90°<\phi<-40°$ and $120°<\psi<180°$] or [$-90°<\phi<-40°$ and $-50°<\psi<10°$] and excluding residues located in regions in which the subtilase is characterized by possessing α-helical or β-sheet structure.

After the dihedral angles φ (phi) and ψ (psi) for the amino acids have been calculated, based on the atomic structure in the crystalline subtilases, it is possible to select position(s) which has/have dihedral phi and psi angles favourable for substitution with a proline residue. The aliphatic side chain of proline residues is bonded covalently to the nitrogen atom of the peptide group. The resulting cyclic five-membered ring consequently imposes a rigid constraint on the rotation about the N—$C_\alpha$ bond of the peptide backbone and simultaneously prevents the formation of hydrogen bonding to the backbone N-atom. For these structural reasons, proline residues are generally not compatible with α-helical and β-sheet secondary conformations.

If a proline residue is not already at the identified position(s), the naturally occurring amino acid residue is substituted with a proline residue, preferably by site directed mutagenesis applied on a gene encoding the subtilase in question.

In the group of TY145 like subtilases proline residues can be introduced at positions 18, 115, 185, 269 and 293. Accordingly, a preferred TY145 variant has one or more of the substitutions: Q18P, D115P, V185P, T269P and I293P.

Alteration of Activity
Introduction of Activity at Low Temperature in TY145 and Savinase A comparison of the molecular dynamics at 300K of TY145 (a mesophilic-derived enzyme obtained from crystal structure) and TA41 (a psychrophilic derived enzyme obtained from modelling) was conducted.

The comparison was directed to low temperature activity and revealed a difference in dynamical behaviour of TY145 and TA41. The theory derived from the comparison is that the difference in dynamics, especially around the active site, are important for the low temperature functionality of the psychrophilic enzyme. The necessary dynamics are needed for the enzyme to have activity at low temperature and thus the activity drops if the enzymes dynamics are lowered.

The higher mobility regions in TA41 compared to TY145 measured by molecular dynamics simulation indicates important regions for the low temperature activity, of the enzyme TA41 which can be transferred to TY145.

The regions in TA41 are:

16-22 (i.e., 16, 17, 18, 19, 20, 21, 22),
40-73 (i.e., 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73),
118-131 (i.e., 118, 119, 120, 121, 122, 123, 124, 125, 126, 127, 128, 129, 130, 131)
140-161 (i.e., 140, 141, 142, 143, 144, 145, 146, 147, 148, 149, 150, 151, 152, 153, 154, 155, 156, 157, 158, 159, 160, 161) and
275-294 (i.e., 275, 276, 277, 278, 279, 280, 281, 282, 283, 284, 285, 286, 287, 288, 289, 290, 291, 292, 293, 294).

Regions closest to the active site and the substrate binding site are regarded as preferred in relation to making higher activity at low temperature for TY145: 40-73 and 140-161, preferably 65-73 and 140-150. The regions in TY145 should be modified to be more mobile for example by substitution with small less rigid residues, i.e., residues with smaller side chains (such as Gly, Ala, Ser, Thr or Val), into the TY145 backbone.

The other regions in TA41 are most interesting for stabilization of the psychrophilic enzyme. These regions can easily be found in TA39 as well or in other homologous enzymes, also non psychrophilics.

The regions around the active site and the substrate binding site are the regions most likely involved in the low temperature functionality.

Below are suggestions for transferring the low temperature activity of TA41 and homologous sequences to TY145-like sequences and the BPN'-like sequences:

| TA41 | TY145 | Savinase |
| --- | --- | --- |
| I31 | V31I, A, L | V28I, A, L |
| V38 | V38A, L | I35V, A, L |
| S79 | T79S | T71S |
| A80 | V80A, G, V | I72A, G, V |
| L81 | L81G | A73L, G |
| V187 | V188A | M175V, A |
| T253 | T254S, A | T224S, A |

The numbering is according to SEQ ID NOS: 3, 1 and 5, respectively. Savinase is numbered according to subtilisin BPN'.

Preferred Savinase variants are V28I, I35V, T71S, I72A, A73L, M175V and T224S.

Examples of core variants of TY145 are: V31I, V80A, T79S.

The alterations of the TY145-like sequences and the BPN'-like sequences can be single mutations or combinations of the suggested mutations.

Substrate Bindings Site

The substrate binding site is identified by the residues in contact with a substrate model, such as the CI2 inhibitor. The 3D structure coordinates of the TY145 subtilase with CI2 bound in the active site can be found in Appendix 1. Without being limited to any theory, it is presently believed that binding between a substrate and an enzyme is supported by favorable interactions found within a sphere 10 Å from the substrate molecule, in particular within a sphere of 6 Å from the substrate molecule. Examples of such favorable bonds are hydrogen bonds, strong electrostatic interaction and/or hydrophobic interactions.

The following residues of the TY145 subtilase (SEQ ID NO: 1), are within a distance of 6 Å from the Cl2 inhibitor and thus believed to be involved in interactions with said substrate:
35, 36, 70, 72, 106, 109, 110, 111, 112, 113, 114, 117, 139, 140, 141, 142, 143, 144, 145, 147, 150, 167, 168, 169, 170, 171, 172, 173, 174, 177, 180, 207, 239, 247, 248, 249, 250, 251 and 252.

Stabilization by Modification of Asn-Gly Pairs

It is known that at alkaline pH, the side chain of Asn may interact with the NH group of a sequential neighbouring amino acid to form an isoAsp residue where the backbone goes through the Asp side chain. This will leave the backbone more vulnerable to proteolysis. The deamidation is much more likely to occur if the residue that follows is a Gly. Changing the Asn in front of the Gly or the Gly will prevent this from happening and thus improve the stability, especially as concerns thermo- and storage stability.

The invention consequently further relates to a subtilase, in which either or both residues of any of the Asn-Gly sequence appearing in the amino acid sequence of the parent RP-II protease is/are deleted or substituted with a residue of a different amino acid.

The Asn and/or Gly residue may, for instance, be substituted with a residue of an amino acid selected from the group consisting of A, Q, S, P, T and Y.

Asn-Gly sequences can be found in the following positions:
B. sphaericus: 198-199, 240-241
TY145: 87-88, 109-110, 199-200
TA41: 83-84, 198-199
TA39: 88-89, 198-199

The present invention in this respect thus relates to modifications, such as deletions and substitutions in one or more of these positions in accordance with the principles given above.

Modification of Tyrosine Residues

In relation to wash performance it has been found that the modification of certain tyrosine residues to phenylalanine provides an improved wash performance. Without being bound by any specific theory, it is believed that titration of these Tyr residues in the alkaline wash liquor has negative effects that are alleviated by replacing the Tyr residues with other residues, especially Phe or Trp, particularly Phe.

Tyrosines can be found in the following positions:
B. sphaericus: 14, 91, 102, 112, 155, 157, 172, 179, 201, 206, 211, 218, 235, 239, 243, 292, 300,
TY145: 15, 39, 92, 103, 113, 156, 158, 202, 219, 240, 244, 287, 301, 307,
TA41: 15, 91, 102, 112, 155, 157, 179, 201, 218, 235, 243,
TA39: 15, 61, 91, 102, 112, 155, 157, 173, 179, 201, 211, 218, 235, 243, 267, 281, 284, 292, 293, 296

The present invention in this respect thus relates to modifications, such as deletions and substitutions in one or more of these positions in accordance with the principles given above.

Modification of Methionine Residues

In order to improve the oxidation stability of proteins it has been found that the substitution or even deletion of methionine residues is beneficial, Especially modification of the methionine residue normally found next to the active serine residue may provide a significant improvement of the oxidation stability. Modifications to Ser or Ala are the most preferred substitutions for this Met.

Methionines can be found in the following positions:
B. sphaericus: 138, 251,
TY145: 139, 252,
TA41: 1, 138, 251,
TA39: 1, 138, 251.

The present invention in this respect thus relates to modifications, such as deletions and substitutions in one or more of these positions in accordance with the principles given above.

Combined Modifications

The present invention also encompasses any of the above mentioned subtilase variants in combination with any other modification to the amino acid sequence thereof. Especially combinations with other modifications known in the art to provide improved properties to the enzyme are envisaged.

Such combinations comprise the positions: 222 (improves oxidation stability), 218 (improves thermal stability), substitutions in the $Ca^{2+}$-binding sites stabilizing the enzyme, e.g., position 76, and many other apparent from the prior art (all positions according to BPN' numbering).

In further embodiments a subtilase variant described herein may advantageously be combined with one or more modification(s) in any of the positions:
27, 36, 56, 76, 87, 95, 96, 97, 98, 99, 100, 101, 102, 103, 104, 120, 123, 159, 167, 170, 206, 218, 222, 224, 232, 235, 236, 245, 248, 252 and 274 (BPN' numbering).

Specifically, the following BLSAVI, BLSUBL, BSKSMK, and BAALKP modifications are considered appropriate for combination:
K27R, *36D, S56P, N76D, S87N, G97N, S101G, S103A, V104A, V104I, V104N, V104Y, H120D, N123S, G159D, Y167A, R170S, R170L, Q206E, N218S, M222S, M222A, T224S, A232V, K235L, Q236H, Q245R, N248D, N252K and T274A (BPN' numbering).

Furthermore variants comprising any of the modifications S101G+V104N, S87N+S101G+V104N, K27R+V104Y+N123S+T274A, N76D+S103A+V104I or N76D+V104A, or other combinations of the modifications K27R, N76D, S101G, S103A, V104N, V104Y, V104I, V104A, N123S, G159D, A232V, Q236H, Q245R, N248D, N252K, T274A in combination with any one or more of the modification(s) mentioned above exhibit improved properties.

A particular interesting variant is a variant, which, in addition to modifications according to the invention, contains the following substitutions:
S101G+S103A+V104I+G159D+A232V+Q236H+Q245R+N248D+N252K.

Moreover, subtilase variants of the main aspect(s) of the invention are preferably combined with one or more modification(s) in any of the positions 129, 131 and 194, preferably as 129K, 131H and 194P modifications, and most preferably as P129K, P131H and A194P modifications. Any of those modification(s) are expected to provide a higher expression level of the subtilase variant in the production thereof.

Methods of Preparing TY145 Like or BPN' Like Subtilase Variants

The subtilase variants, i.e., the TY145 and BPN' variants of the present invention may be produced by any known method within the art and the present invention also relates to nucleic acid encoding a subtilase variant of the present invention, a DNA construct comprising said nucleic acid and a host cell comprising said nucleic acid sequence.

In general natural occurring proteins may be produced by culturing the organism expressing the protein and subsequently purifying the protein or it may be produced by cloning a nucleic acid, e.g., genomic DNA or cDNA, encoding the protein into an expression vector, introducing said expression vector into a host cell, culturing the host cell and purifying the expressed protein.

Typically protein variants may be produced by site-directed mutagenesis of a parent protein, introduction into expression vector, host cell etc. The parent protein may be cloned from a strain producing the polypeptide or from an expression library, i.e., it may be isolated from genomic DNA or prepared from cDNA, or a combination thereof.

In general standard procedures for cloning of genes and/or introducing mutations (random and/or site directed) into said genes may be used in order to obtain a parent subtilase, or subtilase or subtilase variant of the invention. For further description of suitable techniques reference is made to Molecular cloning: A laboratory manual (Sambrook et al. (1989), Cold Spring Harbor lab., Cold Spring Harbor, N.Y.; Ausubel, F. M. et al. (eds.)); Current protocols in Molecular Biology (John Wiley and Sons, 1995; Harwood, C. R., and Cutting, S. M. (eds.)); Molecular Biological Methods for *Bacillus* (John Wiley and Sons, 1990); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); A Practical Guide To Molecular Cloning (B. Perbal, (1984)) and WO 96/34946.

Further, variants could be constructed by:

Random Mutagenesis

Random mutagenesis is suitably performed either as localized or region-specific random mutagenesis in at least three parts of the gene translating to the amino acid sequence shown in question, or within the whole gene.

The random mutagenesis of a DNA sequence encoding a parent subtilase may be conveniently performed by use of any method known in the art.

In relation to the above, a further aspect of the present invention relates to a method for generating a variant of a parent subtilase, wherein the variant exhibits an altered property, such as increased thermostability, increased stability at low pH and at low calcium concentration, relative to the parent subtilase, the method comprising:

(a) subjecting a DNA sequence encoding the parent subtilase to random mutagenesis, (b) expressing the mutated DNA sequence obtained in step (a) in a host cell, and (c) screening for host cells expressing a subtilase variant which has an altered property relative to the parent subtilase.

Step (a) of the above method of the invention is preferably performed using doped primers.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents. The mutagenizing agent may, e.g., be one which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions that are to be changed. The doping or spiking may be done so that codons for unwanted amino acids are avoided. The doped or spiked oligonucleotide can be incorporated into the DNA encoding the subtilase enzyme by any published technique, using, e.g., PCR, LCR or any DNA polymerase and ligase as deemed appropriate.

Preferably, the doping is carried out using "constant random doping", in which the percentage of wild-type and modification in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% modifications in each position. An additional consideration in the choice of a doping scheme is based on genetic as well as protein-structural constraints. The doping scheme may be made by using the DOPE program which, inter alia, ensures that introduction of stop codons is avoided (Jensen et al., 1998, *Nucleic Acid Research* 26: 697-702.

When PCR-generated mutagenesis is used, either a chemically treated or non-treated gene encoding a parent subtilase enzyme is subjected to PCR under conditions that increase the misincorporation of nucleotides (Deshler, 1992; Leung et al., 1989, *Technique* 1: 11-15).

A mutator strain of *E. coli* (Fowler et al., 1974, *Molec. Gen. Genet.* 133: 179-191), *S. cereviseae* or any other microbial organism may be used for the random mutagenesis of the DNA encoding the subtilase by, e.g., transforming a plasmid containing the parent enzyme into the mutator strain, growing the mutator strain with the plasmid and isolating the mutated plasmid from the mutator strain. The mutated plasmid may be subsequently transformed into the expression organism.

The DNA sequence to be mutagenized may conveniently be present in a genomic or cDNA library prepared from an organism expressing the parent subtilase. Alternatively, the DNA sequence may be present on a suitable vector such as a plasmid or a bacteriophage, which as such may be incubated with or otherwise exposed to the mutagenising agent. The DNA to be mutagenized may also be present in a host cell either by being integrated in the genome of said cell or by being present on a vector harbored in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to performing the expression step b) or the screening step c). Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenising agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are the following: gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans* or *Streptomyces murinus*; and gram negative bacteria such as *E. coli*.

The mutated DNA sequence may further comprise a DNA sequence encoding functions permitting expression of the mutated DNA sequence.

Localized Random Mutagenesis

The random mutagenesis may be advantageously localized to a part of the parent subtilase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

General Method for Random Mutagenesis by Use of the DOPE Program

The random mutagenesis may be carried out by the following steps:
1. Select regions of interest for modification in the parent enzyme
2. Decide on mutation sites and non-mutated sites in the selected region
3. Decide on which kind of mutations should be carried out, e.g., with respect to the desired stability and/or performance of the variant to be constructed
4. Select structurally reasonable mutations
5. Adjust the residues selected by step 3 with regard to step 4.
6. Analyse by use of a suitable dope algorithm the nucleotide distribution.
7. If necessary, adjust the wanted residues to genetic code realism, e.g., taking into account constraints resulting from the genetic code, e.g., in order to avoid introduction of stop codons; the skilled person will be aware that some codon combinations cannot be used in practice and will need to be adapted
8. Make primers
9. Perform random mutagenesis by use of the primers
10. Select resulting subtilase variants by screening for the desired improved properties.

Suitable dope algorithms for use in step 6 are well known in the art. One such algorithm is described by Tomandl et al., 1997, *Journal of Computer-Aided Molecular Design* 11: 29-38. Another algorithm is DOPE (Jensen et al., 1998, *Nucleic Acids Research* 26: 697-702).

Expression Vectors

A recombinant expression vector comprising a nucleic acid sequence encoding a subtilase variant of the invention may be any vector that may conveniently be subjected to recombinant DNA procedures and which may bring about the expression of the nucleic acid sequence.

The choice of vector will often depend on the host cell into which it is to be introduced. Examples of a suitable vector include a linear or closed circular plasmid or a virus. The vector may be an autonomously replicating vector, i.e., a vector which exists as an extra-chromosomal entity, the replication of which is independent of chromosomal replication, e.g., a plasmid, an extra-chromosomal element, a mini chromosome, or an artificial chromosome. The vector may contain any means for assuring self-replication. Examples of bacterial origins of replication are the origins of replication of plasmids pBR322, pUC19, pACYC177, pACYC184, pUB110, pE194, pTA1060, and pAMβ1. Examples of origin of replications for use in a yeast host cell are the 2 micron origin of replication, the combination of CEN6 and ARS4, and the combination of CEN3 and ARS1. The origin of replication may be one having a mutation which makes it function as temperature-sensitive in the host cell (see, e.g., Ehrlich, 1978, *Proceedings of the National Academy of Sciences USA* 75:1433).

Alternatively, the vector may be one which, when introduced into the host cell, is integrated into the genome and replicated together with the chromosome(s) into which it has been integrated. Vectors which are integrated into the genome of the host cell may contain any nucleic acid sequence enabling integration into the genome, in particular it may contain nucleic acid sequences facilitating integration into the genome by homologous or non-homologous recombination. The vector system may be a single vector, e.g., plasmid or virus, or two or more vectors, e.g., plasmids or virus', which together contain the total DNA to be introduced into the genome of the host cell, or a transposon.

The vector may in particular be an expression vector in which the DNA sequence encoding the subtilase variant of the invention is operably linked to additional segments or control sequences required for transcription of the DNA. The term, "operably linked" indicates that the segments are arranged so that they function in concert for their intended purposes, e.g., transcription initiates in a promoter and proceeds through the DNA sequence encoding the subtilase variant. Additional segments or control sequences include a promoter, a leader, a polyadenylation sequence, a propeptide sequence, a signal sequence and a transcription terminator. At a minimum the control sequences include a promoter and transcriptional and translational stop signals.

The promoter may be any DNA sequence that shows transcriptional activity in the host cell of choice and may be derived from genes encoding proteins either homologous or heterologous to the host cell.

Examples of suitable promoters for use in bacterial host cells include the promoter of the *Bacillus subtilis* levansucrase gene (sacB), the *Bacillus stearothermophilus* maltogenic amylase gene (amyM), the *Bacillus licheniformis* alpha-amylase gene (amyL), the *Bacillus amyloliquefaciens* alpha-amylase gene (amyQ), the *Bacillus subtilis* alkaline protease gene, or the *Bacillus pumilus* xylosidase gene, the *Bacillus amyloliquefaciens* BAN amylase gene, the *Bacillus licheniformis* penicillinase gene (penP), the *Bacillus subtilis* xylA and xylB genes, and the prokaryotic beta-lactamase gene (Villa-Kamaroff et al., 1978, Proceedings of the National Academy of Sciences USA 75:3727-3731). Other examples include the phage Lambda $P_R$ or $P_L$ promoters or the *E. coli* lac, trp or tac promoters or the *Streptomyces*

*coelicolor* agarase gene (dagA). Further promoters are described in "Useful proteins from recombinant bacteria" in *Scientific American* 242: 74-94 (1980); and in Sambrook et al., 1989, supra.

Examples of suitable promoters for use in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (as described in U.S. Pat. No. 4,288,627, which is incorporated herein by reference), and hybrids thereof. Particularly preferred promoters for use in filamentous fungal host cells are the TAKA amylase, NA2-tpi (a hybrid of the promoters from the genes encoding *Aspergillus niger* neutral (-amylase and *Aspergillus oryzae* triose phosphate isomerase), and glaA promoters. Further suitable promoters for use in filamentous fungus host cells are the ADH3 promoter (McKnight et al., 1985, *The EMBO J.* 4: 2093-2099) or the tpiA promoter.

Examples of suitable promoters for use in yeast host cells include promoters from yeast glycolytic genes (Hitzeman et al., 1980, *J. Biol. Chem.* 255: 12073-12080; Alber and Kawasaki, 1982, *J. Mol. Appl. Gen.* 1: 419-434) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4c (Russell et al., 1983, *Nature* 304: 652-654) promoters.

Further useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8: 423-488. In a mammalian host cell, useful promoters include viral promoters such as those from Simian Virus 40 (SV40), Rous sarcoma virus (RSV), adenovirus, and bovine papilloma virus (BPV).

Examples of suitable promoters for use in mammalian cells are the SV40 promoter (Subramani et al., 1981, *Mol. Cell Biol.* 1: 854-864), the MT-1 (metallothionein gene) promoter (Palmiter et al., 1983, *Science* 222: 809-814) or the adenovirus 2 major late promoter.

An example of a suitable promoter for use in insect cells is the polyhedrin promoter (U.S. Pat. No. 4,745,051; Vasuvedan et al., 1992, *FEBS Lett.* 311: 7-11), the P10 promoter (Vlak et al., 1988, *J. Gen. Virology* 69: 765-776), the *Autographa californica* polyhedrosis virus basic protein promoter (EP 397 485), the baculovirus immediate early gene 1 promoter (U.S. Pat. No. 5,155,037; U.S. Pat. No. 5,162,222), or the baculovirus 39K delayed-early gene promoter (U.S. Pat. No. 5,155,037; U.S. Pat. No. 5,162,222).

The DNA sequence encoding a subtilase variant of the invention may also, if necessary, be operably connected to a suitable terminator.

The recombinant vector of the invention may further comprise a DNA sequence enabling the vector to replicate in the host cell in question.

The vector may also comprise a selectable marker, e.g., a gene the product of which complements a defect in the host cell, or a gene encoding resistance to, e.g., antibiotics like ampicillin, kanamycin, chloramphenicol, erythromycin, tetracycline, spectinomycine, neomycin, hygromycin, methotrexate, or resistance to heavy metals, virus or herbicides, or which provides for prototrophy or auxotrophs. Examples of bacterial selectable markers are the dal genes from *Bacillus subtilis* or *Bacillus licheniformis*, resistance. A frequently used mammalian marker is the dihydrofolate reductase gene (DHFR). Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), and glufosinate resistance markers, as well as equivalents from other species. Particularly, for use in an *Aspergillus* cell are the amdS and pyrG markers of *Aspergillus nidulans* or *Aspergillus oryzae* and the bar marker of *Streptomyces hygroscopicus*. Furthermore, selection may be accomplished by co-transformation, e.g., as described in WO 91/17243, where the selectable marker is on a separate vector.

To direct a subtilase variant of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al.).

More than one copy of a nucleic acid sequence encoding an enzyme of the present invention may be inserted into the host cell to amplify expression of the nucleic acid sequence. Stable amplification of the nucleic acid sequence can be obtained by integrating at least one additional copy of the sequence into the host cell genome using methods well known in the art and selecting for transformants.

The nucleic acid constructs of the present invention may also comprise one or more nucleic acid sequences which encode one or more factors that are advantageous in the expression of the polypeptide, e.g., an activator (e.g., a trans-acting factor), a chaperone, and a processing protease. Any factor that is functional in the host cell of choice may be used in the present invention. The nucleic acids encoding one or more of these factors are not necessarily in tandem with the nucleic acid sequence encoding the polypeptide.

Host Cells

The DNA sequence encoding a subtilase variant of the present invention may be either homologous or heterologous to the host cell into which it is introduced. If homologous to the host cell, i.e., produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell that is capable of producing the present subtilase variants, such as prokaryotes, e.g., bacteria or eukaryotes, such as fungal cells, e.g., yeasts or filamentous fungi, insect cells, plant cells or mammalian cells.

Examples of bacterial host cells which, on cultivation, are capable of producing the subtilase variants of the invention are gram-positive bacteria such as strains of *Bacillus*, e.g., strains of *B. subtilis*, *B. licheniformis*, *B. lentus*, *B. brevis*, *B. stearothermophilus*, *B. alkalophilus*, *B. amyloliquefaciens*, *B. coagulans*, *B. circulans*, *B. lautus*, *B. megaterium* or *B. thuringiensis*, or strains of *Streptomyces*, such as *S. lividans* or *S. murinus*, or gram-negative bacteria such as *Escherichia coli* or *Pseudomonas* sp.

The transformation of the bacteria may be effected by protoplast transformation, electroporation, conjugation, or by using competent cells in a manner known per se (cf. Sambrook et al., supra).

When expressing the subtilase variant in bacteria such as *E. coli*, the enzyme may be retained in the cytoplasm, typically as insoluble granules (known as inclusion bodies), or it may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g., by sonication or osmotic shock, to release the contents of the periplasmic space and recovering the enzyme.

When expressing the subtilase variant in gram-positive bacteria such as *Bacillus* or *Streptomyces* strains, the enzyme may be retained in the cytoplasm, or it may be directed to the extracellular medium by a bacterial secretion sequence. In the latter case, the enzyme may be recovered from the medium as described below.

Examples of host yeast cells include cells of a species of *Candida*, *Kluyveromyces*, *Saccharomyces*, *Schizosaccharomyces*, *Pichia*, *Hansehula*, or *Yarrowia*. In a particular embodiment, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. Other useful yeast host cells are a *Kluyveromyces lactis*, *Kluyveromyces fragilis*, *Hansehula polymorpha*, *Pichia pastoris*, *Yarrowia lipolytica*, *Schizosaccharomyces pombe*, *Ustilgo maylis*, *Candida maltose*, *Pichia guillermondii* and *Pichia methanolio* cell (cf. Gleeson et al., 1986, *J. Gen. Microbiol.* 132: 3459-3465; U.S. Pat. No. 4,882,279 and U.S. Pat. No. 4,879,231). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., Biochemistry and Genetics of Yeast, Bacil, M., Horecker, B. J., and Stopani, A. O. M., editors, 2nd edition, 1987; The Yeasts, Rose, A. H., and Harrison, J. S., editors, 2nd edition, 1987; and The Molecular Biology of the Yeast *Saccharomyces*, Strathern et al., editors, 1981). Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Examples of filamentous fungal cells include filamentous forms of the subdivision Eumycota and Oomycota (as defined by Hawksworth et al., 1995, supra), in particular it may of the a cell of a species of *Acremonium*, such as *A. chrysogenum*, *Aspergillus*, such as *A. awamori*, *A. foetidus*, *A. japonicus*, *A. niger*, *A. nidulans* or *A. oryzae*, *Fusarium*, such as *F. bactridioides*, *F. cerealis*, *F. crookwellense*, *F. culmorum*, *F. graminearum*, *F. graminum*, *F. heterosporum*, *F. negundi*, *F. reticulatum*, *F. roseum*, *F. sambucinum*, *F. sarcochroum*, *F. sulphureum*, *F. trichothecioides* or *F. oxysporum*, *Humicola*, such as *H. insolens* or *H. lanuginose*, *Mucor*, such as *M. miehei*, *Myceliophthora*, such as *M. thermophilum*, *Neurospora*, such as *N. crassa*, *Penicillium*, such as *P. purpurogenum*, *Thielavia*, such as *T. terrestris*, *Tolypocladium*, or *Trichoderma*, such as *T. harzianum*, *T. koningii*, *T. longibrachiatum*, *T. reesei* or *T. viride*, or a teleomorph or synonym thereof. The use of *Aspergillus* spp. for the expression of proteins is described in, e.g., EP 272 277, EP 230 023.

Examples of insect cells include a *Lepidoptera* cell line, such as *Spodoptera frugiperda* cells or *Trichoplusia ni* cells (cf. U.S. Pat. No. 5,077,214). Culture conditions may suitably be as described in WO 89/01029 or WO 89/01028. Transformation of insect cells and production of heterologous polypeptides therein may be performed as described in U.S. Pat. No. 4,745,051; U.S. Pat. No. 4,775,624; U.S. Pat. No. 4,879,236; U.S. Pat. No. 5,155,037; U.S. Pat. No. 5,162,222; EP 397,485).

Examples of mammalian cells include Chinese hamster ovary (CHO) cells, HeLa cells, baby hamster kidney (BHK) cells, COS cells, or any number of other immortalized cell lines available, e.g., from the American Type Culture Collection. Methods of transfecting mammalian cells and expressing DNA sequences introduced in the cells are described in, e.g., Kaufman and Sharp, 1982, *J. Mol. Biol.* 159: 601-621; Southern and Berg, 1982, *J. Mol. Appl. Genet.* 1: 327-341; Loyter et al., 1982, *Proc. Natl. Acad. Sci. USA* 79: 422-426; Wigler et al., 1978, *Cell* 14: 725; Corsaro and Pearson, 1981, *Somatic Cell Genetics* 7: 603, Ausubel et al., Current Protocols in Molecular Biology, John Wiley and Sons, Inc., N.Y., 1987, Hawley-Nelson et al., 1993, *Focus* 15: 73; Ciccarone et al., 1993, *Focus* 15: 80; Graham and van der Eb, 1973, *Virology* 52: 456; and Neumann et al., 1982, *EMBO J.* 1: 841-845. Mammalian cells may be transfected by direct uptake using the calcium phosphate precipitation method of Graham and Van der Eb, 1978, *Virology* 52: 546).

Methods for Expression and Isolation of Proteins

To express an enzyme of the present invention the above mentioned host cells transformed or transfected with a vector comprising a nucleic acid sequence encoding an enzyme of the present invention are typically cultured in a suitable nutrient medium under conditions permitting the production of the desired molecules, after which these are recovered from the cells, or the culture broth.

The medium used to culture the host cells may be any conventional medium suitable for growing the host cells, such as minimal or complex media containing appropriate supplements. Suitable media are available from commercial suppliers or may be prepared according to published recipes (e.g., in catalogues of the American Type Culture Collection). The media may be prepared using procedures known in the art (see, e.g., references for bacteria and yeast; Bennett, J. W. and LaSure, L., editors, More Gene Manipulations in Fungi, Academic Press, CA, 1991).

If the enzymes of the present invention are secreted into the nutrient medium, they may be recovered directly from the medium. If they are not secreted, they may be recovered from cell lysates. The enzymes of the present invention may be recovered from the culture medium by conventional procedures including separating the host cells from the medium by centrifugation or filtration, precipitating the proteinaceous components of the supernatant or filtrate by means of a salt, e.g., ammonium sulphate, purification by a variety of chromatographic procedures, e.g., ion exchange chromatography, gelfiltration chromatography, affinity chromatography, or the like, dependent on the enzyme in question.

The enzymes of the invention may be detected using methods known in the art that are specific for these proteins. These detection methods include use of specific antibodies, formation of a product, or disappearance of a substrate. For example, an enzyme assay may be used to determine the activity of the molecule. Procedures for determining various kinds of activity are known in the art.

The enzymes of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J-C Janson and Lars Ryden, editors, VCH Publishers, New York, 1989).

When an expression vector comprising a DNA sequence encoding an enzyme of the present invention is transformed/transfected into a heterologous host cell it is possible to enable heterologous recombinant production of the enzyme. An advantage of using a heterologous host cell is that it is possible to make a highly purified enzyme composition, characterized in being free from homologous impurities, which are often present when a protein or peptide is expressed in a homologous host cell. In this context homologous impurities mean any impurity (e.g., other polypeptides than the enzyme of the invention) which originates from the homologous cell where the enzyme of the invention is originally obtained from.

Detergent Applications

The enzyme of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases:

Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase®, Savinase®, Primase®, Duralase®, Esperase®, Ovozyme® and Kannase® (Novozymes A/S), Maxatase™, Maxacal™, Maxapem™, Properase™, Purafect™, Purafect OxP™, FN2™ FN3™ and FN4™ (Genencor International Inc.).

Lipases:

Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta* 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipex®, Lipolase® and Lipolase Ultra® (Novozymes A/S).

Amylases:

Suitable amylases (α and/or β) include those of bacterial or fungal origin. Chemically modified or protein engineered mutants are included. Amylases include, for example, α-amylases obtained from *Bacillus*, e.g., a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novozymes A/S), Rapidase™ and Purastar™ (from Genencor International Inc.).

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme® and Carezyme® (Novozymes A/S), Clazinase™, and Puradax HA™ (Genencor International Inc.), and KAC-500 (B)™ (Kao Corporation).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme® (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose, poly(vinylpyrrolidone), poly (ethylene glycol), poly(vinyl alcohol), poly (vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, e.g., the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-200 mg of enzyme protein per liter of wash liquor, preferably 0.05-50 mg of enzyme protein per liter of wash liquor, in particular 0.1-10 mg of enzyme protein per liter of wash liquor.

The enzyme of the invention may additionally be incorporated in the detergent formulations disclosed in WO 97/07202 which is hereby incorporated as reference.

Materials and Methods

Textiles

Standard textile pieces are obtained from EMPA St. Gallen, Lerchfeldstrasse 5, CH-9014 St. Gallen, Switzerland. Especially type EMPA 116 (cotton textile stained with blood, milk and ink) and EMPA 117 (polyester/cotton textile stained with blood, milk and ink).

Method for Producing a Subtilase Variant

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

When an expression vector comprising a DNA sequence encoding the enzyme is transformed into a heterologous host cell it is possible to enable heterologous recombinant production of the enzyme of the invention. Thereby it is possible to make a highly purified subtilase composition, characterized in being free from homologous impurities.

The medium used to culture the transformed host cells may be any conventional medium suitable for growing the host cells in question. The expressed subtilase may conveniently be secreted into the culture medium and may be recovered there-from by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

Example 1

Construction of Library of Savinase Variants

A library, based on Savinase positions V28, I35, T71, I72, A73, M175 and T224 (BPN' numbering) was synthesized. The library contains exclusively TY145-suggested alterations and covers the introduced mutations V28I,A,L; I35V,A,L; T71S; I72A,G,V; A73L,G; M175V,A; T224S,A introduced in oligopeptides, some of which were doped. Doping of nucleotide bases from a desired doping of individual amino acid residues, which is used for the example below, can be calculated as described above.

In the attached sequence listing, the doped nucleotides below have been given the nucleotide symbols recommended by the WIPO Standard ST25.

The constructed oligopeptide primers are listed below. The primers are named after which positions are subject to modifications, thus 28-35-CN has alterations in positions 28 and 35, 71-72-73-NC has alterations in positions 71, 72 and 73, and so forth.

28-35-CN,
SEQ ID NO: 7
5'-TAG ATC TGG ATG AGT GGA (50%T/50%A)(80%A/10%G/

10%C)(75%T/25%C) CCC TGT ATC GAG GAC AGC (75%A/

25%T)(90%A/10%G)(80%C/10%T/10%G) TTT TAC ACC AGA

ACC TGT-3'

28-35-NC,
SEQ ID NO: 8
5'-TCC ACT CAT CCA GAT CTA-3'

(I) 71-72-73-CN,
SEQ ID NO: 9
5'-AAT CGA ATT GTT TAA AGC AGC (65%T/35%A)(80%A/

10%C/10%G)(75%T/25%C)(90%C/10%T)G(90%T/10%A) CCC

GGC CAC ATG CGT GCC-3'

(II) 71-72-73-CN,
SEQ ID NO: 10
5'-AAT CGA ATT GTT TAA AGC AAG (65%T/35%A)(80%A/

10%C/10%G)(75%T/25%C)(90%C/10%T)G(90%T/10%A) CCC

GGC CAC ATG CGT GCC-3'

(III) 71-72-73-CN,
SEQ ID NO: 11
5'-AAT CGA ATT GTT TAA AGC GCC (65%T/35%A)(80%A/

10%C/10%G)(75%T/25%C)(90%C/10%T)G(90%T/10%A) CCC

GGC CAC ATG CGT GCC-3'

71-72-73-NC,
SEQ ID NO: 12
5'GCT TTA AAC AAT TCG ATT 3'

139,
SEQ ID NO: 13
5'-GAT TAA CGC GTT GCC GCT TCT GCG-3'

(I) 175-CN (90%),
SEQ ID NO: 14
5'-ATC AGT AGC TCC GAC TGC CA(90%T/10%C) TGC GTT

CGC ATA GCG CGC-3'

(II) 175-CN (10%),
SEQ ID NO: 15
5'-ATC AGT AGC TCC GAC TGC CGC TGC GTT CGC ATA GCG

CGC-3'

175-NC,
SEQ ID NO: 16
5'-GCA GTC GGA GCT ACT GAT-3'

224-CN,
SEQ ID NO: 17
5'-CGC ACC TGC AAC ATG AGG CG(80%T/10%C/10%A) AGC

CAT CGA TGT ACC GTT-3'

224-NC,
SEQ ID NO: 18
5'-CCT CAT GTT GCA GGT GCG-3'

317,
SEQ ID NO: 19
5'-TGG CGC AAT CGG TAC CAT GGG G-3'

The Savinase gene was used as template for five individual PCR reactions under standard PCR conditions (Sambrook et al., Molecular Cloning: A Laboratory Manual, 2nd Ed., Cold Spring Harbor, 1989) where the oligos were combined as follows:

317 with 28-35-CN, 28-35-NC with 71-72-73-CN (a mixture of 80% (I) 71-72-73-CN, 10% (II) 71-72-73-CN and 10% (III) 71-72-73-CN), 71-72-73-NC with 175-CN (a mixture of 90% (I) 175-CN and 10% (II) 175-CN), 175-NC with 224-CN, 224-NC with 139, giving PCR products of 125 bp, 126 bp, 312 bp, 165 bp and 158 bp respectively.

The library was assembled by an additional PCR reaction where the five PCR products were mixed in equal molar amounts. Thereby the library contained a large number of different Savinase variants altered in one or more of the mentioned positions. The PCR reaction was assembled using a PTC-200 DNA Engine (MJ Research, Watertown, Mass.) and the following cycling parameters: 1 cycle of 2 min at 94° C. followed by 25 cycles of 30 sec at 94° C., 30 sec at 55° C. and 1 min at 68° C., and 1 cycle of 2 min at 68° C. The library was cloned by PCR multimerization (Shafikhani et al. 1997) into Savinase expression vector psx222 and transformed into a B. subtilis host for expression. Subsequently Savinase variants were isolated from the library, purified and characterized.

Likewise, properties from a BPN' like subtilase could be transferred to TY145 like subtilase by applying a similar procedure.

Example 2

Transfer of Regions from TY145 to BPN' Subtilases

The below mentioned highly mobile regions in TY145 were selected for transfer from TY145 to Savinase. The Savinase regions (BPN' numbering) were deleted and the TY145 regions (SEQ ID NO: 1) inserted instead. In addition regions can be selected for transfer between the psychrophiles TA41/TA39 and BPN' type protease like Savinase, or from TA39/TA41 to TY145 type non-psychrophilic subtilases.

```
SEGMENT I
                                                  (SEQ ID NO: 22)
TY145         SAKDSLIASAVD, positions 144-155

(SEQ ID NO: 23)
Savinase      PSPSATLEQAVN, positions 129-140

SEGMENT II
                                                  (SEQ ID NO: 24)
TY145         AGNSGSGSNTIGFPGGLV, positions 168-185

(SEQ ID NO: 25)
Savinase      SGNSGAGSISYPARYA, positions 153-172

SEGMENT IV
                                                  (SEQ ID NO: 26)
TY145         ASVESTWYTGGYNTIS, positions 233-248

(SEQ ID NO: 27)
Savinase      VNVQSTYPGSTYASLN, positions 203-218
```

Savinase variants modified by receiving respectively segments II (Hybrid II), IV (Hybrid IV) or I+II (Hybrid I+II) from TY145 were observed to exhibit subtilase activity as determined by the formation of clearing zones on skim milk powder plates.

Example 3

Transfer of Regions from S39 and S41 to BPN' Subtilases

The below mentioned highly mobile regions in the TA39 subtilase S39 and the TA41 subtilase S41, determined by the previous described homology building programs, were selected for transfer to Savinase. The Savinase regions (BPN' numbering) were deleted and the S39 regions or S41 regions were inserted instead. Below, the S39 and S41 regions are numbered according to FIG. 1. In addition regions can be selected for transfer between the psychrophiles TA41/TA39 and TY145 type non-psychrophilic subtilases. Savinase variant V104S was used as acceptor for the S39 segment II.

```
SEGMENT I
                                                  (SEQ ID NO: 28)
S39                 MSLGSSG, positions 137-143

(SEQ ID NO: 29)
Savinase2           LSLGSPS, positions 124-130

SEGMENT II
                                                  (SEQ ID NO: 30)
S39                 MSLGSSGESSLI, positions 137-148

(SEQ ID NO: 31)
Savinase variant    LSLGSPSPSATL, positions
V104S               124-135

SEGMENT III
                                                  (SEQ ID NO: 32)
S39                 NNSSITQT, positions 15-22

(SEQ ID NO: 33)
Savinase            VQAPAAHN, positions 11-18

SEGMENT IV
                                                  (SEQ ID NO: 34)
S39                 TVGTTYTN, positions 55-62

(SEQ ID NO: 35)
Savinase2           VPG*EPST, positions 51*-58

SEGMENT V
S39                 RQ, positions 68-69

Savinase            GN, positions 61-62

SEGMENT VI
                                                  (SEQ ID NO: 36)
S39                 SGESSLI, positions 142-148

(SEQ ID NO: 37)
Savinase            PSPSATL, positions 129-135

SEGMENT VII
                                                  (SEQ ID NO: 38)
S39                 WFDGGYATI, positions 237-245

(SEQ ID NO: 39)
Savinase            YPGSTYASL, positions 209-217
```

Savinase variants modified by receiving respectively segments I or II from S39 were observed to have subtilase activity against the substrate suc-AAPF-pNA (Suc-Ala-Ala-Pro-Phe-pNA). The subtilase activity was determined in a temperature profile assay where specific activities, i.e., micromole substrate per minute per mg enzyme against before mentioned substrates, were determined at every 5 degrees Celsius. The measurements were done in a Tris-base buffer pH 9.

To measure subtilase activity in suc-AAPF-pNA: 100 uL 1.56 mM Suc-Ala-Ala-Pro-Phe-pNA in 0.1 M Tris was added to 100 uL Tris-base, pH 9.0 buffer and 20 uL enzyme. The development of the degradation product pNA (paranitrophenol) was measured as initial velocities at 405 nm on an Elisa Reader for 1 minute.

The Savinase variant with segment I substituted had less specific activity against suc-AAPF-pNA compared to Savinase, whereas the Savinase variant with segment II substituted had more than 2 times higher specific activity against suc-AAPF-pNA than Savinase. In an AMSA-test (performed like described in Example 5 herein) the wash performance was shown to be preserved in Savinase variant with segment II compared to Savinase.

Further, four Savinase variants were constructed with the following combinations of segments from S39:

Segments III, V and VII; Segments III and V; Segments III, V, VI and Segments III and IV. All four Savinase variants showed subtilase activity on skim milk plates.

Segments from the S41 subtilase suggested for transfer to Savinase are:

```
SEGMENT VIII
                                                  (SEQ ID NO: 40)
S41             TVGTNFTD, positions 55-62

(SEQ ID NO: 41)
Savinase        VPG*EPST, positions 51-58
```

-continued

```
SEGMENT IX
                              (SEQ ID NO: 42)
S41          NGGTGS, positions 82-87

(SEQ ID NO: 43)
Savinase     ALNNSI, positions 74-79

SEGMENT X
                              (SEQ ID NO: 44)
S41          DDGSGYA, positions 106-112

(SEQ ID NO: 45)
Savinase     ASGSGSV, positions 98-104

SEGMENT XI
                              (SEQ ID NO: 46)
S41          WAQSPAA, positions 263-269

(SEQ ID NO: 47)
Savinase     KQKNPSW, positions 235-241
```

Four Savinase variants were constructed with the following segments from S41: Segment X; Segments IX and X; Segments VIII and X; and Segments X and XI. All four Savinase variants showed subtilase activity on skim milk plates.

AMSA wash tests were performed on variants with Segment X and Segments X and XI like described in Example 5 herein.

The assay was conducted under the experimental conditions specified below:

| | |
|---|---|
| Detergent base | Omo Acao |
| Detergent dosage | 2.5 g/l |
| Test solution volume | 160 micro l |
| pH | 10-10.5 adjusted with $NaHCO_3$ |
| Wash time | 14 minutes |
| Temperature | 15° C. |
| Water hardness | 9°dH |
| Enzyme concentration in test solution | 5 nM, 10 nM and 30 nM |
| Test material | EMPA 117 |

The wash performance score (described in Example 5 herein) of the Savinase variants with Segment X and Segments X and XI was S (1) indicating an improved wash performance compared to Savinase.

Example 4

Purification and Assessment of Enzyme Concentration

After fermentation, purification of subtilisin variants was accomplished using Hydrophobic Charge Induction Chromatography (HCIC) and subsequent vacuum filtration.

To capture the enzyme, the HCIC uses a cellulose matrix to which 4-Mercapto-Ethyl-Pyridine (4-MEP) is bound.

Beads of the cellulose matrix sized 80-100 µm were mixed with a media containing yeast and the transformed *B. subtilis* capable of secreting the subtilisin variants and incubated at pH 9.5 in Unifilter® microplates.

As 4-MEP is hydrophobic at pH>7 and the subtilisin variants are hydrophobic at pH 9.5 a hydrophobic association was made between the secreted enzyme and the 4-MEP on the beads. After incubation the media and cell debris were removed by vacuum filtration while the beads and enzyme were kept on the filter.

To elute the enzyme from the beads the pH was lowered by washing the filter with an elution buffer (pH 5) resulting in the enzyme parting from the beads. The enzyme was then retrieved from the buffer.

The concentration of the purified subtilisin enzyme variants was assessed by active site titration (AST).

The purified enzyme was incubated with the high affinity inhibitor CI-2A at different concentrations to inhibit a varying amount of the active sites. The protease and inhibitor binds to each other at a 1:1 ratio and accordingly the enzyme concentration can be directly related to the concentration of inhibitor, at which all protease is inactive. To measure the residual protease activity, a substrate suc-AAPF-pNA (0.6 mM Suc-Ala-Ala-Pro-Phe-pNA in Tris/HCl buffer) was added after the incubation with inhibitor and during the following 4 minutes the development of the degradation product pNA (paranitrophenol) was measured periodically at 405 nm on an Elisa Reader.

Example 5

Wash Performance of Detergent Compositions Comprising Modified Enzymes

Wash performance of detergent compositions comprising enzyme hybrids or enzyme variants of the present invention was tested at low washing temperature.

The Savinase variant Hybrid IV of Example 2 was tested for washing performance in two different assays; a microliter scale assay (AMSA) and a milliliter scale assay (Mini wash).

AMSA

The enzyme variants of the present application were tested using the Automatic Mechanical Stress Assay (AMSA). With the AMSA test the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid were vigorously shaken to bring the test solution in contact with the textile and apply mechanical stress. For further description see WO 02/42740 especially the paragraph "Special method embodiments" at page 23-24.

The assay was conducted under the experimental conditions specified below:

| | |
|---|---|
| Detergent base | Omo Acao |
| Detergent dosage | 1.5 g/l |
| Test solution volume | 160 micro l |
| pH | 10-10.5 adjusted with $NaHCO_3$ |
| Wash time | 12 minutes |
| Temperature | 20° C. |
| Water hardness | 9°dH |
| Enzyme concentration in test solution | 5 nM, 10 nM and 30 nM |
| Test material | EMPA 117 |

After washing the textile pieces were flushed in tap water and air-dried.

The performance of the enzyme variant was measured as the brightness of the color of the textile samples washed with that specific enzyme variant. Brightness can also be expressed as the intensity of the light reflected from the textile sample when luminated with white light. When the textile is stained the intensity of the reflected light is lower, than that of a clean textile. Therefore the intensity of the reflected light can be used to measure wash performance of an enzyme variant.

Color measurements were made with a professional flatbed scanner (PFU DL2400pro), which was used to capture an image of the washed textile samples. The scans were made with a resolution of 200 dpi and with an output color dept of 24 bits. In order to get accurate results, the scanner was frequently calibrated with a Kodak reflective IT8 target.

To extract a value for the light intensity from the scanned images, a special designed software application was used (Novozymes Color Vector Analyzer). The program retrieves the 24 bit pixel values from the image and converts them into values for red, green and blue (RGB). The intensity value (Int) is calculated by adding the RGB values together as vectors and then taking the length of the resulting vector:

$$Int = \sqrt{r^2 + g^2 + b^2}.$$

The wash performance (P) of the variants was calculated in accordance with the below formula:

$$P = Int(v) - Int(r)$$

where

Int(v) is the light intensity value of textile surface washed with enzyme variant and Int(r) is the light intensity value of textile surface washed with the reference enzyme subtilisin 309 (BLSAVI).

The result of the AMSA wash of Hybrid IV was a Performance Score of S (2) in accordance with the definition:

Performance Scores (S) are summing up the performances (P) of the tested enzyme variants as:

S (2) which indicates that the variant performs better than the reference at all three concentrations (5, 10 and 30 nM) and S (1) which indicates that the variant performs better than the reference at one or two concentrations.

Mini Wash Assay

The milliliter scale wash performance assay was conducted under the following conditions:

| | |
|---|---|
| Detergent base | Omo Acao detergent powder |
| Detergent dose | 1.5 g/l |
| pH | "as is" in the current detergent solution and is not adjusted. |
| Wash time | 14 min. |
| Temperature | 20° C. |
| Water hardness | 9°dH, adjusted by adding $CaCl_2 \cdot 2H_2O$; $MgCl_2 \cdot 6H_2O$; $NaHCO_3$ ($Ca^{2+}:Mg^{2+}:HCO^{3-}$ = 2:1:6) to milli-Q water. |
| Enzymes | Hybrid IV, Savinase |
| Enzyme conc. | 5 nM, 10 nM |
| Test system | 125 ml glass beakers. Textile dipped in test solution. Continuously up and down, 50 times per minute |
| Textile/volume | 1 textile piece (13 × 3 cm) in 50 ml test solution |
| Test material | EMPA 117 textile swatches |

After wash the measurement of remission from the test material was done at 460 nm using a Zeiss MCS 521 VIS spectrophotometer. The measurements were done according to the manufacturer's protocol.

As shown in Table 1 the textile washed with the Savinase variant Hybrid IV at 20° C. in Omo Acao has a higher remission than the textile washed with the parent. This result indicates that this variant has better wash performance at low temperature than the parent Savinase. Table 1. Wash performance results of the subtilase variant in Omo Acao for a dosage of 5 nM and 10 nM enzyme.

| Enzyme | Remission, 5 nM enzyme | Remission, 10 nM enzyme |
|---|---|---|
| Blank (no enzyme) | 12.0 | 12.3 |
| Savinase | 15.8 | 17.4 |
| Hybrid IV | 17.0 | 18.3 |

As it can be concluded from Table 1 the modified subtilases of the invention exhibits an improvement in wash performance.

Example 6

Wash performance of detergent compositions comprising enzyme variants of the present invention was tested at low washing temperature using the Automatic Mechanical Stress Assay (AMSA) as described in Example 5 herein.

TABLE 2

AMSA wash results of subtilase variants.

| Enzyme variant | Performance score |
|---|---|
| V28I + *98aD + T224S | 2 |
| *98aS + P131F + M175V + T224A | 1 |

APPENDIX 1

```
REMARK   3
REMARK   3   REFINEMENT.
REMARK   3     PROGRAM      : REFMAC 5.0
REMARK   3     AUTHORS      : MURSHUDOV, VAGIN, DODSON
REMARK   3
REMARK   3    REFINEMENT TARGET : MAXIMUM LIKELIHOOD
REMARK   3
REMARK   3   DATA USED IN REFINEMENT.
REMARK   3    RESOLUTION RANGE HIGH    (ANGSTROMS) :  1.80
REMARK   3    RESOLUTION RANGE LOW     (ANGSTROMS) : 56.80
REMARK   3    DATA CUTOFF              (SIGMA(F))  : NONE
REMARK   3    COMPLETENESS FOR RANGE        (%) : 99.88
REMARK   3    NUMBER OF REFLECTIONS            :  38045
REMARK   3
REMARK   3   FIT TO DATA USED IN REFINEMENT.
REMARK   3    CROSS-VALIDATION METHOD          : THROUGHOUT
REMARK   3    FREE R VALUE TEST SET SELECTION  : RANDOM
REMARK   3    R VALUE     (WORKING + TEST SET) : 0.15648
REMARK   3    R VALUE              (WORKING SET) : 0.15487
REMARK   3    FREE R VALUE                     : 0.18707
REMARK   3    FREE R VALUE TEST SET SIZE  (%)  : 5.0
REMARK   3    FREE R VALUE TEST SET COUNT      : 2009
REMARK   3
```

APPENDIX 1-continued

```
REMARK 3    FIT IN THE HIGHEST RESOLUTION BIN.
REMARK 3      TOTAL NUMBER OF BINS USED            :     20
REMARK 3      BIN RESOLUTION RANGE HIGH            :     1.796
REMARK 3      BIN RESOLUTION RANGE LOW             :     1.842
REMARK 3      REFLECTION IN BIN     (WORKING SET) :     2738
REMARK 3      BIN R VALUE           (WORKING SET) :     0.191
REMARK 3      BIN FREE R VALUE SET COUNT           :     138
REMARK 3      BIN FREE R VALUE                     :     0.234
REMARK 3
REMARK 3    NUMBER OF NON-HYDROGEN ATOMS USED IN REFINEMENT.
REMARK 3      ALL ATOMS           :          3156
REMARK 3
REMARK 3    B VALUES.
REMARK 3      FROM WILSON PLOT            (A**2) : NULL
REMARK 3      MEAN B VALUE        (OVERALL, A**2) : 14.804
REMARK 3      OVERALL ANISOTROPIC B VALUE.
REMARK 3       B11 (A**2) :       0.28
REMARK 3       B22 (A**2) :      -0.86
REMARK 3       B33 (A**2) :       0.58
REMARK 3       B12 (A**2) :       0.00
REMARK 3       B13 (A**2) :       0.00
REMARK 3       B23 (A**2) :       0.00
REMARK 3
REMARK 3    ESTIMATED OVERALL COORDINATE ERROR.
REMARK 3      ESU BASED ON R VALUE                          (A):  0.100
REMARK 3      ESU BASED ON FREE R VALUE                     (A):  0.098
REMARK 3      ESU BASED ON MAXIMUM LIKELIHOOD               (A):  0.093
REMARK 3      ESU FOR B VALUES BASED ON MAXIMUM LIKELIHOOD  (A**2): 2.910
REMARK 3
REMARK 3    CORRELATION COEFFICIENTS.
REMARK 3      CORRELATION COEFFICIENT FO-FC       :  0.963
REMARK 3      CORRELATION COEFFICIENT FO-FC FREE  :  0.952
REMARK 3    RMS DEVIATIONS FROM IDEAL VALUES              COUNT    RMS    WEIGHT
REMARK 3      BOND LENGTHS REFINED ATOMS         (A):     2798 ;  0.021 ;  0.021
REMARK 3      BOND LENGTHS OTHERS                (A):     2500 ;  0.001 ;  0.020
REMARK 3      BOND ANGLES REFINED ATOMS     (DEGREES):    3805 ;  1.859 ;  1.943
REMARK 3      BOND ANGLES OTHERS            (DEGREES):    5821 ;  0.854 ;  3.000
REMARK 3      TORSION ANGLES, PERIOD 1      (DEGREES):     372 ;  5.125 ;  3.000
REMARK 3      TORSION ANGLES, PERIOD 3      (DEGREES):     462 ; 16.877 ; 15.000
REMARK 3      CHIRAL-CENTER RESTRAINTS       (A**3):       437 ;  0.119 ;  0.200
REMARK 3      GENERAL PLANES REFINED ATOMS       (A):     3201 ;  0.009 ;  0.020
REMARK 3      GENERAL PLANES OTHERS              (A):      535 ;  0.004 ;  0.020
REMARK 3      NON-BONDED CONTACTS REFINED ATOMS  (A):      610 ;  0.228 ;  0.300
REMARK 3      NON-BONDED CONTACTS OTHERS         (A):     2548 ;  0.203 ;  0.300
REMARK 3      H-BOND (X . . . Y) REFINED ATOMS   (A):      374 ;  0.184 ;  0.500
REMARK 3      H-BOND (X . . . Y) OTHERS          (A):        3 ;  0.279 ;  0.500
REMARK 3      POTENTIAL METAL-ION REFINED ATOMS  (A):       16 ;  0.119 ;  0.500
REMARK 3      SYMMETRY VDW REFINED ATOMS         (A):        7 ;  0.127 ;  0.300
REMARK 3      SYMMETRY VDW OTHERS                (A):       27 ;  0.152 ;  0.300
REMARK 3      SYMMETRY H-BOND REFINED ATOMS      (A):       37 ;  0.278 ;  0.500
REMARK 3
REMARK 3    ISOTROPIC THERMAL FACTOR RESTRAINTS.           COUNT    RMS    WEIGHT
REMARK 3      MAIN-CHAIN BOND REFINED ATOMS      (A**2):   1840 ;  1.131 ;  1.500
REMARK 3      MAIN-CHAIN ANGLE REFINED ATOMS     (A**2):   2941 ;  1.781 ;  2.000
REMARK 3      SIDE-CHAIN BOND REFINED ATOMS      (A**2):    958 ;  2.873 ;  3.000
REMARK 3      SIDE-CHAIN ANGLE REFINED ATOMS     (A**2):    864 ;  4.300 ;  4.500
REMARK 3
REMARK 3    NCS RESTRAINTS STATISTICS
REMARK 3      NUMBER OF NCS GROUPS : NULL
REMARK 3
REMARK 3
REMARK 3    TLS DETAILS
REMARK 3      NUMBER OF TLS GROUPS : NULL
REMARK 3
REMARK 3
REMARK 3    BULK SOLVENT MODELLING.
REMARK 3      METHOD USED: BABINET MODEL WITH MASK
REMARK 3      PARAMETERS FOR MASK CALCULATION
REMARK 3      VDW PROBE RADIUS     :     1.40
REMARK 3      ION PROBE RADIUS     :     0.80
REMARK 3      SHRINKAGE RADIUS     :     0.80
REMARK 3
REMARK 3    OTHER REFINEMENT REMARKS:
REMARK 3      HYDROGENS HAVE BEEN ADDED IN THE RIDING POSITIONS
REMARK 3
CISPEP   1 GLY A  172    SER A  173         0.00
CISPEP   2 PHE A  180    PRO A  181         0.00
SSBOND   1 CYS A   52    CYS A   66
CRYST1   58.753   66.838  107.082  90.00  90.00  90.00 P 21 21 21
SCALE1      0.017020  0.000000  0.000000        0.00000
```

APPENDIX 1-continued

| | | | | | | | | | | | |
|---|---|---|---|---|---|---|---|---|---|---|---|
| SCALE2 | | 0.000000 | 0.014962 | 0.000000 | | 0.00000 | | | | | |
| SCALE3 | | 0.000000 | 0.000000 | 0.009339 | | 0.00000 | | | | | |
| ATOM | 1 | N | ALA | A | 1 | 2.336 | 20.870 | 1.027 | 1.00 | 27.48 | N |
| ATOM | 3 | CA | ALA | A | 1 | 1.951 | 20.940 | 2.465 | 1.00 | 29.42 | C |
| ATOM | 5 | CB | ALA | A | 1 | 2.391 | 19.637 | 3.197 | 1.00 | 29.45 | C |
| ATOM | 9 | C | ALA | A | 1 | 2.665 | 22.149 | 3.096 | 1.00 | 28.87 | C |
| ATOM | 10 | O | ALA | A | 1 | 3.696 | 22.577 | 2.627 | 1.00 | 30.49 | O |
| ATOM | 13 | N | VAL | A | 2 | 2.014 | 22.747 | 4.052 | 1.00 | 30.31 | N |
| ATOM | 15 | CA | VAL | A | 2 | 2.658 | 23.754 | 4.877 | 1.00 | 30.69 | C |
| ATOM | 17 | CB | VAL | A | 2 | 2.068 | 25.139 | 4.604 | 1.00 | 30.94 | C |
| ATOM | 19 | CG1 | VAL | A | 2 | 2.611 | 25.702 | 3.252 | 1.00 | 32.62 | C |
| ATOM | 23 | CG2 | VAL | A | 2 | 0.577 | 25.086 | 4.667 | 1.00 | 30.84 | C |
| ATOM | 27 | C | VAL | A | 2 | 2.494 | 23.346 | 6.347 | 1.00 | 29.48 | C |
| ATOM | 28 | O | VAL | A | 2 | 1.580 | 22.610 | 6.743 | 1.00 | 29.33 | O |
| ATOM | 29 | N | PRO | A | 3 | 3.412 | 23.788 | 7.186 | 1.00 | 28.10 | N |
| ATOM | 30 | CA | PRO | A | 3 | 3.298 | 23.380 | 8.581 | 1.00 | 27.90 | C |
| ATOM | 32 | CB | PRO | A | 3 | 4.645 | 23.830 | 9.185 | 1.00 | 26.48 | C |
| ATOM | 35 | CG | PRO | A | 3 | 5.116 | 24.998 | 8.340 | 1.00 | 26.57 | C |
| ATOM | 38 | CD | PRO | A | 3 | 4.530 | 24.697 | 6.933 | 1.00 | 27.60 | C |
| ATOM | 41 | C | PRO | A | 3 | 2.129 | 24.112 | 9.216 | 1.00 | 27.01 | C |
| ATOM | 42 | O | PRO | A | 3 | 1.602 | 25.037 | 8.600 | 1.00 | 28.48 | O |
| ATOM | 43 | N | SER | A | 4 | 1.767 | 23.774 | 10.434 | 1.00 | 26.37 | N |
| ATOM | 45 | CA | SER | A | 4 | 0.718 | 24.505 | 11.159 | 1.00 | 25.29 | C |
| ATOM | 47 | CB | SER | A | 4 | 0.279 | 23.780 | 12.444 | 1.00 | 26.52 | C |
| ATOM | 50 | OG | SER | A | 4 | 1.173 | 23.913 | 13.554 | 1.00 | 25.41 | O |
| ATOM | 52 | C | SER | A | 4 | 1.105 | 25.956 | 11.445 | 1.00 | 26.09 | C |
| ATOM | 53 | O | SER | A | 4 | 0.212 | 26.810 | 11.603 | 1.00 | 25.32 | O |
| ATOM | 54 | N | THR | A | 5 | 2.415 | 26.233 | 11.497 | 1.00 | 24.12 | N |
| ATOM | 56 | CA | THR | A | 5 | 3.023 | 27.567 | 11.741 | 1.00 | 22.81 | C |
| ATOM | 58 | CB | THR | A | 5 | 3.009 | 28.007 | 13.237 | 1.00 | 24.21 | C |
| ATOM | 60 | OG1 | THR | A | 5 | 3.793 | 29.191 | 13.386 | 1.00 | 23.29 | O |
| ATOM | 62 | CG2 | THR | A | 5 | 3.727 | 26.999 | 14.151 | 1.00 | 22.71 | C |
| ATOM | 66 | C | THR | A | 5 | 4.413 | 27.436 | 11.219 | 1.00 | 23.10 | C |
| ATOM | 67 | O | THR | A | 5 | 5.012 | 26.322 | 11.267 | 1.00 | 21.48 | O |
| ATOM | 68 | N | GLN | A | 6 | 4.959 | 28.518 | 10.692 | 1.00 | 21.30 | N |
| ATOM | 70 | CA | GLN | A | 6 | 6.260 | 28.438 | 10.102 | 1.00 | 21.50 | C |
| ATOM | 72 | CB | GLN | A | 6 | 6.512 | 29.634 | 9.209 | 1.00 | 22.77 | C |
| ATOM | 75 | CG | GLN | A | 6 | 5.626 | 29.570 | 7.926 | 1.00 | 23.15 | C |
| ATOM | 78 | CD | GLN | A | 6 | 5.999 | 30.579 | 6.911 | 1.00 | 28.40 | C |
| ATOM | 79 | OE1 | GLN | A | 6 | 5.356 | 31.619 | 6.822 | 1.00 | 30.34 | O |
| ATOM | 80 | NE2 | GLN | A | 6 | 7.016 | 30.300 | 6.133 | 1.00 | 24.59 | N |
| ATOM | 83 | C | GLN | A | 6 | 7.295 | 28.389 | 11.185 | 1.00 | 20.24 | C |
| ATOM | 84 | O | GLN | A | 6 | 8.438 | 28.017 | 10.927 | 1.00 | 18.46 | O |
| ATOM | 85 | N | THR | A | 7 | 6.870 | 28.777 | 12.378 | 1.00 | 18.84 | N |
| ATOM | 87 | CA | THR | A | 7 | 7.752 | 28.808 | 13.565 | 1.00 | 19.27 | C |
| ATOM | 89 | CB | THR | A | 7 | 8.135 | 30.238 | 13.914 | 1.00 | 19.55 | C |
| ATOM | 91 | OG1 | THR | A | 7 | 6.958 | 31.041 | 14.091 | 1.00 | 23.00 | O |
| ATOM | 93 | CG2 | THR | A | 7 | 8.910 | 30.878 | 12.842 | 1.00 | 19.61 | C |
| ATOM | 97 | C | THR | A | 7 | 7.111 | 28.128 | 14.755 | 1.00 | 18.28 | C |
| ATOM | 98 | O | THR | A | 7 | 6.436 | 28.735 | 15.547 | 1.00 | 18.57 | O |
| ATOM | 99 | N | PRO | A | 8 | 7.288 | 26.803 | 14.834 | 1.00 | 17.34 | N |
| ATOM | 100 | CA | PRO | A | 8 | 6.795 | 26.000 | 15.922 | 1.00 | 17.79 | C |
| ATOM | 102 | CB | PRO | A | 8 | 7.459 | 24.615 | 15.659 | 1.00 | 17.18 | C |
| ATOM | 105 | CG | PRO | A | 8 | 7.556 | 24.570 | 14.138 | 1.00 | 18.32 | C |
| ATOM | 108 | CD | PRO | A | 8 | 7.961 | 25.984 | 13.814 | 1.00 | 16.59 | C |
| ATOM | 111 | C | PRO | A | 8 | 7.162 | 26.584 | 17.273 | 1.00 | 16.99 | C |
| ATOM | 112 | O | PRO | A | 8 | 8.105 | 27.339 | 17.369 | 1.00 | 18.02 | O |
| ATOM | 113 | N | TRP | A | 9 | 6.426 | 26.203 | 18.280 | 1.00 | 18.21 | N |
| ATOM | 115 | CA | TRP | A | 9 | 6.613 | 26.750 | 19.611 | 1.00 | 17.56 | C |
| ATOM | 117 | CB | TRP | A | 9 | 5.723 | 26.059 | 20.603 | 1.00 | 17.84 | C |
| ATOM | 120 | CG | TRP | A | 9 | 6.129 | 24.806 | 21.197 | 1.00 | 14.36 | C |
| ATOM | 121 | CD1 | TRP | A | 9 | 5.772 | 23.569 | 20.796 | 1.00 | 15.37 | C |
| ATOM | 123 | NE1 | TRP | A | 9 | 6.278 | 22.630 | 21.658 | 1.00 | 15.66 | N |
| ATOM | 125 | CE2 | TRP | A | 9 | 7.033 | 23.276 | 22.609 | 1.00 | 16.83 | C |
| ATOM | 126 | CD2 | TRP | A | 9 | 6.952 | 24.642 | 22.345 | 1.00 | 14.81 | C |
| ATOM | 127 | CE3 | TRP | A | 9 | 7.642 | 25.531 | 23.186 | 1.00 | 14.62 | C |
| ATOM | 129 | CZ3 | TRP | A | 9 | 8.362 | 24.982 | 24.301 | 1.00 | 11.92 | C |
| ATOM | 131 | CH2 | TRP | A | 9 | 8.393 | 23.626 | 24.526 | 1.00 | 15.97 | C |
| ATOM | 133 | CZ2 | TRP | A | 9 | 7.757 | 22.750 | 23.677 | 1.00 | 14.67 | C |
| ATOM | 135 | C | TRP | A | 9 | 8.073 | 26.760 | 20.083 | 1.00 | 18.17 | C |
| ATOM | 136 | O | TRP | A | 9 | 8.531 | 27.737 | 20.662 | 1.00 | 15.91 | O |
| ATOM | 137 | N | GLY | A | 10 | 8.780 | 25.675 | 19.859 | 1.00 | 16.36 | N |
| ATOM | 139 | CA | GLY | A | 10 | 10.180 | 25.618 | 20.307 | 1.00 | 15.48 | C |
| ATOM | 142 | C | GLY | A | 10 | 11.108 | 26.619 | 19.663 | 1.00 | 15.80 | C |
| ATOM | 143 | O | GLY | A | 10 | 12.089 | 27.060 | 20.254 | 1.00 | 14.71 | O |
| ATOM | 144 | N | ILE | A | 11 | 10.801 | 26.939 | 18.410 | 1.00 | 15.18 | N |
| ATOM | 146 | CA | ILE | A | 11 | 11.599 | 27.866 | 17.642 | 1.00 | 15.64 | C |
| ATOM | 148 | CB | ILE | A | 11 | 11.303 | 27.768 | 16.151 | 1.00 | 14.65 | C |
| ATOM | 150 | CG1 | ILE | A | 11 | 11.479 | 26.328 | 15.653 | 1.00 | 15.91 | C |
| ATOM | 153 | CD1 | ILE | A | 11 | 12.945 | 25.811 | 15.725 | 1.00 | 16.96 | C |

APPENDIX 1-continued

| | | | | | | | | | | | |
|---|---|---|---|---|---|---|---|---|---|---|---|
| ATOM | 157 | CG2 | ILE | A | 11 | 12.204 | 28.704 | 15.385 | 1.00 | 16.09 | C |
| ATOM | 161 | C | ILE | A | 11 | 11.291 | 29.225 | 18.193 | 1.00 | 15.73 | C |
| ATOM | 162 | O | ILE | A | 11 | 12.197 | 29.995 | 18.438 | 1.00 | 15.02 | O |
| ATOM | 163 | N | LYS | A | 12 | 10.005 | 29.552 | 18.352 | 1.00 | 16.62 | N |
| ATOM | 165 | CA | LYS | A | 12 | 9.649 | 30.832 | 18.949 | 1.00 | 16.28 | C |
| ATOM | 167 | CB | LYS | A | 12 | 8.147 | 30.926 | 19.078 | 1.00 | 17.21 | C |
| ATOM | 170 | CG | LYS | A | 12 | 7.419 | 31.148 | 17.707 | 1.00 | 20.12 | C |
| ATOM | 173 | CD | LYS | A | 12 | 5.874 | 31.303 | 17.997 | 1.00 | 20.50 | C |
| ATOM | 176 | CE | LYS | A | 12 | 5.137 | 31.855 | 16.795 | 1.00 | 28.93 | C |
| ATOM | 179 | NZ | LYS | A | 12 | 4.564 | 30.819 | 15.858 | 1.00 | 19.42 | N |
| ATOM | 183 | C | LYS | A | 12 | 10.242 | 30.956 | 20.345 | 1.00 | 15.82 | C |
| ATOM | 184 | O | LYS | A | 12 | 10.790 | 32.014 | 20.745 | 1.00 | 15.87 | O |
| ATOM | 185 | N | SER | A | 13 | 10.172 | 29.865 | 21.075 | 1.00 | 13.09 | N |
| ATOM | 187 | CA | SER | A | 13 | 10.655 | 29.893 | 22.450 | 1.00 | 13.64 | C |
| ATOM | 189 | CB | SER | A | 13 | 10.284 | 28.586 | 23.149 | 1.00 | 12.46 | C |
| ATOM | 192 | OG | SER | A | 13 | 10.790 | 28.548 | 24.491 | 1.00 | 14.12 | O |
| ATOM | 194 | C | SER | A | 13 | 12.167 | 30.131 | 22.519 | 1.00 | 12.81 | C |
| ATOM | 195 | O | SER | A | 13 | 12.650 | 30.959 | 23.323 | 1.00 | 11.51 | O |
| ATOM | 196 | N | ILE | A | 14 | 12.931 | 29.371 | 21.752 | 1.00 | 12.90 | N |
| ATOM | 198 | CA | ILE | A | 14 | 14.391 | 29.521 | 21.839 | 1.00 | 13.05 | C |
| ATOM | 200 | CB | ILE | A | 14 | 15.108 | 28.318 | 21.206 | 1.00 | 12.73 | C |
| ATOM | 202 | CG1 | ILE | A | 14 | 16.498 | 28.183 | 21.810 | 1.00 | 13.73 | C |
| ATOM | 205 | CD1 | ILE | A | 14 | 17.265 | 26.959 | 21.415 | 1.00 | 17.32 | C |
| ATOM | 209 | CG2 | ILE | A | 14 | 15.161 | 28.394 | 19.753 | 1.00 | 14.13 | C |
| ATOM | 213 | C | ILE | A | 14 | 14.869 | 30.861 | 21.299 | 1.00 | 14.41 | C |
| ATOM | 214 | O | ILE | A | 14 | 15.907 | 31.367 | 21.680 | 1.00 | 15.23 | O |
| ATOM | 215 | N | TYR | A | 15 | 14.094 | 31.423 | 20.389 | 1.00 | 15.25 | N |
| ATOM | 217 | CA | TYR | A | 15 | 14.392 | 32.753 | 19.877 | 1.00 | 16.87 | C |
| ATOM | 219 | CB | TYR | A | 15 | 13.742 | 32.965 | 18.490 | 1.00 | 15.13 | C |
| ATOM | 222 | CG | TYR | A | 15 | 14.683 | 32.629 | 17.348 | 1.00 | 16.40 | C |
| ATOM | 223 | CD1 | TYR | A | 15 | 14.956 | 31.303 | 17.008 | 1.00 | 14.01 | C |
| ATOM | 225 | CE1 | TYR | A | 15 | 15.834 | 30.998 | 16.024 | 1.00 | 16.36 | C |
| ATOM | 227 | CZ | TYR | A | 15 | 16.453 | 31.993 | 15.321 | 1.00 | 16.82 | C |
| ATOM | 228 | OH | TYR | A | 15 | 17.364 | 31.738 | 14.329 | 1.00 | 15.20 | O |
| ATOM | 230 | CE2 | TYR | A | 15 | 16.182 | 33.303 | 15.621 | 1.00 | 17.27 | C |
| ATOM | 232 | CD2 | TYR | A | 15 | 15.320 | 33.610 | 16.628 | 1.00 | 16.64 | C |
| ATOM | 234 | C | TYR | A | 15 | 13.925 | 33.826 | 20.856 | 1.00 | 16.27 | C |
| ATOM | 235 | O | TYR | A | 15 | 14.311 | 35.008 | 20.744 | 1.00 | 17.84 | O |
| ATOM | 236 | N | ASN | A | 16 | 13.075 | 33.432 | 21.780 | 1.00 | 17.21 | N |
| ATOM | 238 | CA | ASN | A | 16 | 12.534 | 34.334 | 22.811 | 1.00 | 17.53 | C |
| ATOM | 240 | CB | ASN | A | 16 | 13.628 | 34.860 | 23.743 | 1.00 | 16.83 | C |
| ATOM | 243 | CG | ASN | A | 16 | 13.098 | 35.265 | 25.103 | 1.00 | 18.27 | C |
| ATOM | 244 | OD1 | ASN | A | 16 | 11.901 | 35.461 | 25.288 | 1.00 | 21.90 | O |
| ATOM | 245 | ND2 | ASN | A | 16 | 13.987 | 35.324 | 26.075 | 1.00 | 17.31 | N |
| ATOM | 248 | C | ASN | A | 16 | 11.788 | 35.480 | 22.114 | 1.00 | 19.04 | C |
| ATOM | 249 | O | ASN | A | 16 | 11.940 | 36.642 | 22.463 | 1.00 | 18.19 | O |
| ATOM | 250 | N | ASP | A | 17 | 10.972 | 35.107 | 21.135 | 1.00 | 18.56 | N |
| ATOM | 252 | CA | ASP | A | 17 | 10.176 | 36.069 | 20.372 | 1.00 | 19.69 | C |
| ATOM | 254 | CB | ASP | A | 17 | 11.019 | 36.634 | 19.287 | 1.00 | 19.45 | C |
| ATOM | 257 | CG | ASP | A | 17 | 10.362 | 37.812 | 18.579 | 1.00 | 20.65 | C |
| ATOM | 258 | OD1 | ASP | A | 17 | 9.160 | 38.017 | 18.745 | 1.00 | 24.61 | O |
| ATOM | 259 | OD2 | ASP | A | 17 | 11.034 | 38.547 | 17.849 | 1.00 | 19.73 | O |
| ATOM | 260 | C | ASP | A | 17 | 8.937 | 35.412 | 19.778 | 1.00 | 19.80 | C |
| ATOM | 261 | O | ASP | A | 17 | 9.032 | 34.693 | 18.834 | 1.00 | 22.05 | O |
| ATOM | 262 | N | GLN | A | 18 | 7.791 | 35.647 | 20.369 | 1.00 | 20.51 | N |
| ATOM | 264 | CA | GLN | A | 18 | 6.593 | 34.957 | 19.960 | 1.00 | 21.49 | C |
| ATOM | 266 | CB | GLN | A | 18 | 5.549 | 35.062 | 21.054 | 1.00 | 22.51 | C |
| ATOM | 269 | CG | GLN | A | 18 | 5.917 | 34.348 | 22.318 | 1.00 | 24.55 | C |
| ATOM | 272 | CD | GLN | A | 18 | 6.243 | 32.907 | 22.041 | 1.00 | 29.84 | C |
| ATOM | 273 | OE1 | GLN | A | 18 | 7.347 | 32.450 | 22.314 | 1.00 | 31.44 | O |
| ATOM | 274 | NE2 | GLN | A | 18 | 5.301 | 32.204 | 21.457 | 1.00 | 28.00 | N |
| ATOM | 277 | C | GLN | A | 18 | 6.076 | 35.511 | 18.658 | 1.00 | 21.92 | C |
| ATOM | 278 | O | GLN | A | 18 | 5.213 | 34.911 | 18.021 | 1.00 | 22.98 | O |
| ATOM | 279 | N | SER | A | 19 | 6.697 | 36.572 | 18.185 | 1.00 | 22.89 | N |
| ATOM | 281 | CA | SER | A | 19 | 6.231 | 37.202 | 16.951 | 1.00 | 23.92 | C |
| ATOM | 283 | CB | SER | A | 19 | 6.338 | 38.715 | 17.096 | 1.00 | 23.69 | C |
| ATOM | 286 | OG | SER | A | 19 | 7.627 | 39.225 | 16.746 | 1.00 | 25.66 | O |
| ATOM | 288 | C | SER | A | 19 | 6.947 | 36.728 | 15.670 | 1.00 | 24.30 | C |
| ATOM | 289 | O | SER | A | 19 | 6.454 | 36.972 | 14.566 | 1.00 | 25.69 | O |
| ATOM | 290 | N | ILE | A | 20 | 8.079 | 36.029 | 15.764 | 1.00 | 23.62 | N |
| ATOM | 292 | CA | ILE | A | 20 | 8.791 | 35.673 | 14.529 | 1.00 | 23.92 | C |
| ATOM | 294 | CB | ILE | A | 20 | 10.104 | 34.965 | 14.836 | 1.00 | 24.53 | C |
| ATOM | 296 | CG1 | ILE | A | 20 | 9.858 | 33.755 | 15.727 | 1.00 | 22.48 | C |
| ATOM | 299 | CD1 | ILE | A | 20 | 11.041 | 32.826 | 15.641 | 1.00 | 23.83 | C |
| ATOM | 303 | CG2 | ILE | A | 20 | 11.127 | 35.902 | 15.477 | 1.00 | 27.13 | C |
| ATOM | 307 | C | ILE | A | 20 | 8.011 | 34.784 | 13.573 | 1.00 | 23.40 | C |
| ATOM | 308 | O | ILE | A | 20 | 7.241 | 33.913 | 13.999 | 1.00 | 24.30 | O |
| ATOM | 309 | N | THR | A | 21 | 8.295 | 34.963 | 12.296 | 1.00 | 23.97 | N |
| ATOM | 311 | CA | THR | A | 21 | 7.686 | 34.184 | 11.215 | 1.00 | 24.95 | C |
| ATOM | 313 | CB | THR | A | 21 | 6.856 | 35.107 | 10.283 | 1.00 | 24.97 | C |

APPENDIX 1-continued

| | | | | | | | | | | | |
|---|---|---|---|---|---|---|---|---|---|---|---|
| ATOM | 315 | OG1 | THR | A | 21 | 7.690 | 36.186 | 9.842 | 1.00 | 27.61 | O |
| ATOM | 317 | CG2 | THR | A | 21 | 5.771 | 35.794 | 11.039 | 1.00 | 28.02 | C |
| ATOM | 321 | C | THR | A | 21 | 8.799 | 33.570 | 10.392 | 1.00 | 23.92 | C |
| ATOM | 322 | O | THR | A | 21 | 8.544 | 32.865 | 9.419 | 1.00 | 23.90 | O |
| ATOM | 323 | N | LYS | A | 22 | 10.044 | 33.862 | 10.735 | 1.00 | 23.93 | N |
| ATOM | 325 | CA | LYS | A | 22 | 11.148 | 33.239 | 10.041 | 1.00 | 24.18 | C |
| ATOM | 327 | CB | LYS | A | 22 | 11.386 | 33.880 | 8.675 | 1.00 | 25.22 | C |
| ATOM | 330 | CG | LYS | A | 22 | 11.830 | 35.314 | 8.724 | 1.00 | 28.95 | C |
| ATOM | 333 | CD | LYS | A | 22 | 12.397 | 35.808 | 7.348 | 1.00 | 32.55 | C |
| ATOM | 336 | CE | LYS | A | 22 | 13.701 | 35.129 | 6.988 | 0.10 | 31.56 | C |
| ATOM | 339 | NZ | LYS | A | 22 | 14.274 | 35.671 | 5.722 | 0.10 | 31.66 | N |
| ATOM | 343 | C | LYS | A | 22 | 12.406 | 33.333 | 10.903 | 1.00 | 23.63 | C |
| ATOM | 344 | O | LYS | A | 22 | 12.471 | 34.145 | 11.823 | 1.00 | 24.17 | O |
| ATOM | 345 | N | THR | A | 23 | 13.395 | 32.491 | 10.628 | 1.00 | 21.41 | N |
| ATOM | 347 | CA | THR | A | 23 | 14.661 | 32.526 | 11.342 | 1.00 | 20.21 | C |
| ATOM | 349 | CB | THR | A | 23 | 14.914 | 31.202 | 12.030 | 1.00 | 20.28 | C |
| ATOM | 351 | OG1 | THR | A | 23 | 14.859 | 30.158 | 11.034 | 1.00 | 19.28 | O |
| ATOM | 353 | CG2 | THR | A | 23 | 13.846 | 30.915 | 13.074 | 1.00 | 21.44 | C |
| ATOM | 357 | C | THR | A | 23 | 15.785 | 32.791 | 10.384 | 1.00 | 20.28 | C |
| ATOM | 358 | O | THR | A | 23 | 15.565 | 32.740 | 9.182 | 1.00 | 19.80 | O |
| ATOM | 359 | N | THR | A | 24 | 16.996 | 33.027 | 10.908 | 1.00 | 19.65 | N |
| ATOM | 361 | CA | THR | A | 24 | 18.201 | 33.246 | 10.130 | 1.00 | 19.91 | C |
| ATOM | 363 | CB | THR | A | 24 | 18.532 | 34.784 | 9.840 | 1.00 | 21.93 | C |
| ATOM | 365 | OG1 | THR | A | 24 | 18.685 | 35.435 | 11.102 | 1.00 | 25.69 | O |
| ATOM | 367 | CG2 | THR | A | 24 | 17.402 | 35.514 | 9.229 | 1.00 | 25.02 | C |
| ATOM | 371 | C | THR | A | 24 | 19.407 | 32.743 | 10.928 | 1.00 | 19.55 | C |
| ATOM | 372 | O | THR | A | 24 | 19.372 | 32.551 | 12.149 | 1.00 | 19.70 | O |
| ATOM | 373 | N | GLY | A | 25 | 20.473 | 32.497 | 10.225 | 1.00 | 17.41 | N |
| ATOM | 375 | CA | GLY | A | 25 | 21.716 | 32.187 | 10.893 | 1.00 | 17.64 | C |
| ATOM | 378 | C | GLY | A | 25 | 22.286 | 30.799 | 10.641 | 1.00 | 16.16 | C |
| ATOM | 379 | O | GLY | A | 25 | 21.583 | 29.936 | 10.124 | 1.00 | 15.92 | O |
| ATOM | 380 | N | GLY | A | 26 | 23.548 | 30.620 | 11.068 | 1.00 | 15.49 | N |
| ATOM | 382 | CA | GLY | A | 26 | 24.296 | 29.380 | 10.938 | 1.00 | 15.44 | C |
| ATOM | 385 | C | GLY | A | 26 | 25.166 | 29.220 | 9.692 | 1.00 | 15.61 | C |
| ATOM | 386 | O | GLY | A | 26 | 25.782 | 28.199 | 9.493 | 1.00 | 15.36 | O |
| ATOM | 387 | N | SER | A | 27 | 25.264 | 30.249 | 8.861 | 1.00 | 17.72 | N |
| ATOM | 389 | CA | SER | A | 27 | 26.108 | 30.182 | 7.691 | 1.00 | 18.45 | C |
| ATOM | 391 | CB | SER | A | 27 | 25.990 | 31.500 | 6.837 | 1.00 | 20.08 | C |
| ATOM | 394 | OG | SER | A | 27 | 26.686 | 32.496 | 7.490 | 1.00 | 26.34 | O |
| ATOM | 396 | C | SER | A | 27 | 27.534 | 29.838 | 8.029 | 1.00 | 17.45 | C |
| ATOM | 397 | O | SER | A | 27 | 28.166 | 30.341 | 8.969 | 1.00 | 17.59 | O |
| ATOM | 398 | N | GLY | A | 28 | 28.071 | 28.913 | 7.241 | 1.00 | 16.01 | N |
| ATOM | 400 | CA | GLY | A | 28 | 29.421 | 28.494 | 7.385 | 1.00 | 16.46 | C |
| ATOM | 403 | C | GLY | A | 28 | 29.615 | 27.360 | 8.377 | 1.00 | 15.36 | C |
| ATOM | 404 | O | GLY | A | 28 | 30.739 | 26.917 | 8.527 | 1.00 | 16.82 | O |
| ATOM | 405 | N | ILE | A | 29 | 28.587 | 26.931 | 9.076 | 1.00 | 14.25 | N |
| ATOM | 407 | CA | ILE | A | 29 | 28.782 | 25.832 | 10.044 | 1.00 | 13.92 | C |
| ATOM | 409 | CB | ILE | A | 29 | 28.057 | 26.170 | 11.335 | 1.00 | 14.10 | C |
| ATOM | 411 | CG1 | ILE | A | 29 | 28.482 | 27.563 | 11.856 | 1.00 | 13.61 | C |
| ATOM | 414 | CD1 | ILE | A | 29 | 29.986 | 27.710 | 12.081 | 1.00 | 15.86 | C |
| ATOM | 418 | CG2 | ILE | A | 29 | 28.269 | 25.076 | 12.417 | 1.00 | 14.40 | C |
| ATOM | 422 | C | ILE | A | 29 | 28.143 | 24.586 | 9.459 | 1.00 | 14.30 | C |
| ATOM | 423 | O | ILE | A | 29 | 27.190 | 24.708 | 8.690 | 1.00 | 14.55 | O |
| ATOM | 424 | N | LYS | A | 30 | 28.614 | 23.402 | 9.853 | 1.00 | 13.73 | N |
| ATOM | 426 | CA | LYS | A | 30 | 28.008 | 22.173 | 9.422 | 1.00 | 13.73 | C |
| ATOM | 428 | CB | LYS | A | 30 | 29.019 | 21.204 | 8.860 | 1.00 | 14.64 | C |
| ATOM | 431 | CG | LYS | A | 30 | 30.072 | 21.822 | 7.951 | 1.00 | 15.03 | C |
| ATOM | 434 | CD | LYS | A | 30 | 29.438 | 22.566 | 6.745 | 1.00 | 16.42 | C |
| ATOM | 437 | CE | LYS | A | 30 | 30.497 | 23.364 | 5.987 | 1.00 | 19.44 | C |
| ATOM | 440 | NZ | LYS | A | 30 | 29.865 | 24.009 | 4.752 | 1.00 | 17.01 | N |
| ATOM | 444 | C | LYS | A | 30 | 27.354 | 21.482 | 10.655 | 1.00 | 13.57 | C |
| ATOM | 445 | O | LYS | A | 30 | 27.978 | 21.473 | 11.716 | 1.00 | 14.48 | O |
| ATOM | 446 | N | VAL | A | 31 | 26.163 | 20.941 | 10.498 | 1.00 | 13.11 | N |
| ATOM | 448 | CA | VAL | A | 31 | 25.572 | 20.118 | 11.583 | 1.00 | 13.65 | C |
| ATOM | 450 | CB | VAL | A | 31 | 24.249 | 20.639 | 12.061 | 1.00 | 13.16 | C |
| ATOM | 452 | CG1 | VAL | A | 31 | 23.726 | 19.743 | 13.173 | 1.00 | 15.78 | C |
| ATOM | 456 | CG2 | VAL | A | 31 | 24.401 | 22.058 | 12.573 | 1.00 | 12.55 | C |
| ATOM | 460 | C | VAL | A | 31 | 25.470 | 18.708 | 11.047 | 1.00 | 14.30 | C |
| ATOM | 461 | O | VAL | A | 31 | 24.828 | 18.458 | 10.003 | 1.00 | 14.74 | O |
| ATOM | 462 | N | ALA | A | 32 | 26.129 | 17.789 | 11.737 | 1.00 | 14.62 | N |
| ATOM | 464 | CA | ALA | A | 32 | 26.092 | 16.387 | 11.366 | 1.00 | 13.46 | C |
| ATOM | 466 | CB | ALA | A | 32 | 27.419 | 15.728 | 11.606 | 1.00 | 11.29 | C |
| ATOM | 470 | C | ALA | A | 32 | 24.972 | 15.696 | 12.149 | 1.00 | 13.08 | C |
| ATOM | 471 | O | ALA | A | 32 | 25.056 | 15.556 | 13.393 | 1.00 | 12.55 | O |
| ATOM | 472 | N | VAL | A | 33 | 23.916 | 15.340 | 11.435 | 1.00 | 10.76 | N |
| ATOM | 474 | CA | VAL | A | 33 | 22.778 | 14.654 | 12.038 | 1.00 | 11.75 | C |
| ATOM | 476 | CB | VAL | A | 33 | 21.468 | 15.152 | 11.453 | 1.00 | 11.00 | C |
| ATOM | 478 | CG1 | VAL | A | 33 | 20.317 | 14.313 | 11.935 | 1.00 | 13.80 | C |
| ATOM | 482 | CG2 | VAL | A | 33 | 21.268 | 16.618 | 11.738 | 1.00 | 12.19 | C |
| ATOM | 486 | C | VAL | A | 33 | 22.959 | 13.155 | 11.847 | 1.00 | 12.72 | C |

APPENDIX 1-continued

| | | | | | | | | | | | |
|---|---|---|---|---|---|---|---|---|---|---|---|
| ATOM | 487 | O | VAL | A | 33 | 22.830 | 12.623 | 10.715 | 1.00 | 11.99 | O |
| ATOM | 488 | N | LEU | A | 34 | 23.290 | 12.466 | 12.932 | 1.00 | 12.34 | N |
| ATOM | 490 | CA | LEU | A | 34 | 23.599 | 11.022 | 12.949 | 1.00 | 11.72 | C |
| ATOM | 492 | CB | LEU | A | 34 | 24.811 | 10.744 | 13.878 | 1.00 | 11.57 | C |
| ATOM | 495 | CG | LEU | A | 34 | 26.190 | 10.819 | 13.262 | 1.00 | 11.59 | C |
| ATOM | 497 | CD1 | LEU | A | 34 | 26.515 | 12.228 | 12.621 | 1.00 | 10.38 | C |
| ATOM | 501 | CD2 | LEU | A | 34 | 27.275 | 10.414 | 14.265 | 1.00 | 12.17 | C |
| ATOM | 505 | C | LEU | A | 34 | 22.303 | 10.366 | 13.416 | 1.00 | 12.33 | C |
| ATOM | 506 | O | LEU | A | 34 | 21.964 | 10.409 | 14.581 | 1.00 | 11.53 | O |
| ATOM | 507 | N | ASP | A | 35 | 21.571 | 9.765 | 12.490 | 1.00 | 11.34 | N |
| ATOM | 509 | CA | ASP | A | 35 | 20.224 | 9.416 | 12.794 | 1.00 | 11.07 | C |
| ATOM | 511 | CB | ASP | A | 35 | 19.397 | 10.677 | 12.779 | 1.00 | 12.91 | C |
| ATOM | 514 | CG | ASP | A | 35 | 18.231 | 10.611 | 13.697 | 1.00 | 11.93 | C |
| ATOM | 515 | OD1 | ASP | A | 35 | 17.334 | 9.791 | 13.472 | 1.00 | 12.81 | O |
| ATOM | 516 | OD2 | ASP | A | 35 | 18.166 | 11.390 | 14.700 | 1.00 | 15.59 | O |
| ATOM | 517 | C | ASP | A | 35 | 19.687 | 8.393 | 11.816 | 1.00 | 12.34 | C |
| ATOM | 518 | O | ASP | A | 35 | 20.470 | 7.623 | 11.250 | 1.00 | 12.33 | O |
| ATOM | 519 | N | THR | A | 36 | 18.376 | 8.385 | 11.604 | 1.00 | 12.33 | N |
| ATOM | 521 | CA | THR | A | 36 | 17.783 | 7.395 | 10.702 | 1.00 | 13.86 | C |
| ATOM | 523 | CB | THR | A | 36 | 16.312 | 7.198 | 10.972 | 1.00 | 13.36 | C |
| ATOM | 525 | OG1 | THR | A | 36 | 15.603 | 8.446 | 10.753 | 1.00 | 14.42 | O |
| ATOM | 527 | CG2 | THR | A | 36 | 16.058 | 6.781 | 12.383 | 1.00 | 11.98 | C |
| ATOM | 531 | C | THR | A | 36 | 17.933 | 7.710 | 9.199 | 1.00 | 14.93 | C |
| ATOM | 532 | O | THR | A | 36 | 17.341 | 7.023 | 8.379 | 1.00 | 15.02 | O |
| ATOM | 533 | N | GLY | A | 37 | 18.699 | 8.735 | 8.885 | 1.00 | 15.27 | N |
| ATOM | 535 | CA | GLY | A | 37 | 18.838 | 9.282 | 7.530 | 1.00 | 15.54 | C |
| ATOM | 538 | C | GLY | A | 37 | 18.041 | 10.594 | 7.487 | 1.00 | 16.06 | C |
| ATOM | 539 | O | GLY | A | 37 | 17.413 | 10.973 | 8.482 | 1.00 | 14.08 | O |
| ATOM | 540 | N | VAL | A | 38 | 18.065 | 11.292 | 6.337 | 1.00 | 16.27 | N |
| ATOM | 542 | CA | VAL | A | 38 | 17.315 | 12.547 | 6.177 | 1.00 | 15.20 | C |
| ATOM | 544 | CB | VAL | A | 38 | 18.214 | 13.784 | 6.447 | 1.00 | 15.83 | C |
| ATOM | 546 | CG1 | VAL | A | 38 | 17.501 | 15.075 | 6.182 | 1.00 | 16.87 | C |
| ATOM | 550 | CG2 | VAL | A | 38 | 18.774 | 13.766 | 7.839 | 1.00 | 17.47 | C |
| ATOM | 554 | C | VAL | A | 38 | 16.863 | 12.628 | 4.695 | 1.00 | 16.04 | C |
| ATOM | 555 | O | VAL | A | 38 | 17.622 | 12.277 | 3.793 | 1.00 | 14.66 | O |
| ATOM | 556 | N | TYR | A | 39 | 15.623 | 13.008 | 4.532 | 1.00 | 18.21 | N |
| ATOM | 558 | CA | TYR | A | 39 | 15.046 | 13.247 | 3.214 | 1.00 | 19.90 | C |
| ATOM | 560 | CB | TYR | A | 39 | 13.564 | 13.150 | 3.366 | 1.00 | 18.60 | C |
| ATOM | 563 | CG | TYR | A | 39 | 12.795 | 13.480 | 2.082 | 1.00 | 23.59 | C |
| ATOM | 564 | CD1 | TYR | A | 39 | 13.278 | 13.110 | 0.833 | 1.00 | 27.19 | C |
| ATOM | 566 | CE1 | TYR | A | 39 | 12.555 | 13.413 | −0.309 | 1.00 | 30.38 | C |
| ATOM | 568 | CZ | TYR | A | 39 | 11.391 | 14.129 | −0.226 | 1.00 | 31.18 | C |
| ATOM | 569 | OH | TYR | A | 39 | 10.734 | 14.412 | −1.434 | 1.00 | 30.34 | O |
| ATOM | 571 | CE2 | TYR | A | 39 | 10.912 | 14.528 | 1.005 | 1.00 | 29.74 | C |
| ATOM | 573 | CD2 | TYR | A | 39 | 11.623 | 14.208 | 2.144 | 1.00 | 23.70 | C |
| ATOM | 575 | C | TYR | A | 39 | 15.495 | 14.623 | 2.786 | 1.00 | 19.47 | C |
| ATOM | 576 | O | TYR | A | 39 | 14.795 | 15.631 | 2.992 | 1.00 | 22.39 | O |
| ATOM | 577 | N | THR | A | 40 | 16.675 | 14.659 | 2.240 | 1.00 | 22.23 | N |
| ATOM | 579 | CA | THR | A | 40 | 17.366 | 15.869 | 1.904 | 1.00 | 23.84 | C |
| ATOM | 581 | CB | THR | A | 40 | 18.797 | 15.520 | 1.499 | 1.00 | 25.17 | C |
| ATOM | 583 | OG1 | THR | A | 40 | 18.841 | 14.473 | 0.518 | 1.00 | 27.20 | O |
| ATOM | 585 | CG2 | THR | A | 40 | 19.633 | 14.890 | 2.687 | 1.00 | 23.66 | C |
| ATOM | 589 | C | THR | A | 40 | 16.650 | 16.659 | 0.804 | 1.00 | 25.31 | C |
| ATOM | 590 | O | THR | A | 40 | 17.008 | 17.803 | 0.566 | 1.00 | 25.93 | O |
| ATOM | 591 | N | SER | A | 41 | 15.671 | 16.051 | 0.147 | 1.00 | 25.63 | N |
| ATOM | 593 | CA | SER | A | 41 | 14.953 | 16.703 | −0.942 | 1.00 | 26.05 | C |
| ATOM | 595 | CB | SER | A | 41 | 14.662 | 15.676 | −2.047 | 1.00 | 25.60 | C |
| ATOM | 598 | OG | SER | A | 41 | 15.836 | 15.411 | −2.759 | 1.00 | 26.14 | O |
| ATOM | 600 | C | SER | A | 41 | 13.669 | 17.317 | −0.445 | 1.00 | 26.09 | C |
| ATOM | 601 | O | SER | A | 41 | 12.896 | 17.889 | −1.232 | 1.00 | 26.66 | O |
| ATOM | 602 | N | HIS | A | 42 | 13.366 | 17.179 | 0.857 | 1.00 | 22.90 | N |
| ATOM | 604 | CA | HIS | A | 42 | 12.245 | 17.917 | 1.419 | 1.00 | 21.28 | C |
| ATOM | 606 | CB | HIS | A | 42 | 12.224 | 17.792 | 2.927 | 1.00 | 21.28 | C |
| ATOM | 609 | CG | HIS | A | 42 | 10.988 | 18.267 | 3.562 | 1.00 | 18.79 | C |
| ATOM | 610 | ND1 | HIS | A | 42 | 10.616 | 19.591 | 3.556 | 1.00 | 17.72 | N |
| ATOM | 612 | CE1 | HIS | A | 42 | 9.482 | 19.706 | 4.197 | 1.00 | 14.42 | C |
| ATOM | 614 | NE2 | HIS | A | 42 | 9.124 | 18.516 | 4.654 | 1.00 | 18.07 | N |
| ATOM | 616 | CD2 | HIS | A | 42 | 10.028 | 17.601 | 4.230 | 1.00 | 15.85 | C |
| ATOM | 618 | C | HIS | A | 42 | 12.427 | 19.379 | 1.036 | 1.00 | 20.43 | C |
| ATOM | 619 | O | HIS | A | 42 | 13.543 | 19.890 | 1.077 | 1.00 | 19.85 | O |
| ATOM | 620 | N | LEU | A | 43 | 11.326 | 20.044 | 0.686 | 1.00 | 21.20 | N |
| ATOM | 622 | CA | LEU | A | 43 | 11.380 | 21.409 | 0.210 | 1.00 | 21.25 | C |
| ATOM | 624 | CB | LEU | A | 43 | 10.030 | 21.945 | −0.087 | 1.00 | 22.55 | C |
| ATOM | 627 | CG | LEU | A | 43 | 9.448 | 21.512 | −1.433 | 1.00 | 25.81 | C |
| ATOM | 629 | CD1 | LEU | A | 43 | 8.021 | 21.976 | −1.464 | 1.00 | 27.58 | C |
| ATOM | 633 | CD2 | LEU | A | 43 | 10.234 | 22.108 | −2.559 | 1.00 | 27.86 | C |
| ATOM | 637 | C | LEU | A | 43 | 12.023 | 22.311 | 1.227 | 1.00 | 21.05 | C |
| ATOM | 638 | O | LEU | A | 43 | 12.699 | 23.255 | 0.879 | 1.00 | 18.87 | O |
| ATOM | 639 | N | ASP | A | 44 | 11.847 | 22.042 | 2.500 | 1.00 | 21.71 | N |
| ATOM | 641 | CA | ASP | A | 44 | 12.514 | 22.885 | 3.487 | 1.00 | 20.87 | C |

APPENDIX 1-continued

| ATOM | 643 | CB | ASP | A | 44 | 11.642 | 22.917 | 4.719 | 1.00 | 21.17 | C |
| --- | --- | --- | --- | --- | --- | --- | --- | --- | --- | --- | --- |
| ATOM | 646 | CG | ASP | A | 44 | 10.262 | 23.417 | 4.441 | 1.00 | 23.00 | C |
| ATOM | 647 | OD1 | ASP | A | 44 | 10.060 | 24.154 | 3.406 | 1.00 | 21.93 | O |
| ATOM | 648 | OD2 | ASP | A | 44 | 9.325 | 23.156 | 5.206 | 1.00 | 16.28 | O |
| ATOM | 649 | C | ASP | A | 44 | 13.962 | 22.528 | 3.812 | 1.00 | 21.02 | C |
| ATOM | 650 | O | ASP | A | 44 | 14.593 | 23.214 | 4.604 | 1.00 | 18.05 | O |
| ATOM | 651 | N | LEU | A | 45 | 14.488 | 21.431 | 3.252 | 1.00 | 18.30 | N |
| ATOM | 653 | CA | LEU | A | 45 | 15.868 | 21.070 | 3.445 | 1.00 | 19.90 | C |
| ATOM | 655 | CB | LEU | A | 45 | 15.922 | 19.624 | 4.024 | 1.00 | 18.80 | C |
| ATOM | 658 | CG | LEU | A | 45 | 15.174 | 19.394 | 5.300 | 1.00 | 18.65 | C |
| ATOM | 660 | CD1 | LEU | A | 45 | 15.424 | 17.925 | 5.756 | 1.00 | 18.05 | C |
| ATOM | 664 | CD2 | LEU | A | 45 | 15.714 | 20.351 | 6.357 | 1.00 | 20.33 | C |
| ATOM | 668 | C | LEU | A | 45 | 16.750 | 21.110 | 2.197 | 1.00 | 20.37 | C |
| ATOM | 669 | O | LEU | A | 45 | 17.960 | 20.890 | 2.251 | 1.00 | 22.13 | O |
| ATOM | 670 | N | ALA | A | 46 | 16.104 | 21.400 | 1.079 | 1.00 | 22.51 | N |
| ATOM | 672 | CA | ALA | A | 46 | 16.728 | 21.327 | −0.210 | 1.00 | 21.13 | C |
| ATOM | 674 | CB | ALA | A | 46 | 15.738 | 21.695 | −1.365 | 1.00 | 21.15 | C |
| ATOM | 678 | C | ALA | A | 46 | 17.880 | 22.199 | −0.244 | 1.00 | 20.28 | C |
| ATOM | 679 | O | ALA | A | 46 | 17.806 | 23.344 | 0.177 | 1.00 | 22.66 | O |
| ATOM | 680 | N | GLY | A | 47 | 18.959 | 21.639 | −0.759 | 1.00 | 20.67 | N |
| ATOM | 682 | CA | GLY | A | 47 | 20.217 | 22.320 | −0.968 | 1.00 | 21.84 | C |
| ATOM | 685 | C | GLY | A | 47 | 21.042 | 22.419 | 0.291 | 1.00 | 21.53 | C |
| ATOM | 686 | O | GLY | A | 47 | 22.226 | 22.881 | 0.280 | 1.00 | 24.34 | O |
| ATOM | 687 | N | SER | A | 48 | 20.522 | 21.910 | 1.392 | 1.00 | 22.52 | N |
| ATOM | 689 | CA | SER | A | 48 | 21.310 | 21.980 | 2.610 | 1.00 | 21.98 | C |
| ATOM | 691 | CB | ASER | A | 48 | 20.384 | 22.083 | 3.833 | 0.50 | 22.54 | C |
| ATOM | 692 | CB | BSER | A | 48 | 20.408 | 22.073 | 3.814 | 0.50 | 22.26 | C |
| ATOM | 697 | OG | ASER | A | 48 | 19.449 | 21.001 | 3.944 | 0.50 | 23.88 | O |
| ATOM | 698 | OG | BSER | A | 48 | 19.660 | 23.258 | 3.738 | 0.50 | 21.10 | O |
| ATOM | 701 | C | SER | A | 48 | 22.295 | 20.852 | 2.826 | 1.00 | 21.47 | C |
| ATOM | 702 | O | SER | A | 48 | 23.317 | 21.066 | 3.466 | 1.00 | 21.64 | O |
| ATOM | 703 | N | ALA | A | 49 | 22.035 | 19.670 | 2.285 | 1.00 | 20.96 | N |
| ATOM | 705 | CA | ALA | A | 49 | 22.951 | 18.532 | 2.483 | 1.00 | 22.38 | C |
| ATOM | 707 | CB | ALA | A | 49 | 22.192 | 17.247 | 2.068 | 1.00 | 22.64 | C |
| ATOM | 711 | C | ALA | A | 49 | 24.233 | 18.644 | 1.718 | 1.00 | 23.21 | C |
| ATOM | 712 | O | ALA | A | 49 | 24.228 | 18.551 | 0.500 | 1.00 | 26.19 | O |
| ATOM | 713 | N | GLU | A | 50 | 25.328 | 18.866 | 2.426 | 1.00 | 20.40 | N |
| ATOM | 715 | CA | GLU | A | 50 | 26.598 | 18.826 | 1.753 | 1.00 | 21.76 | C |
| ATOM | 717 | CB | GLU | A | 50 | 27.625 | 19.892 | 2.250 | 1.00 | 22.32 | C |
| ATOM | 720 | CG | GLU | A | 50 | 27.374 | 21.244 | 1.591 | 1.00 | 26.62 | C |
| ATOM | 723 | CD | GLU | A | 50 | 28.046 | 22.421 | 2.279 | 1.00 | 30.59 | C |
| ATOM | 724 | OE1 | GLU | A | 50 | 28.886 | 22.227 | 3.181 | 1.00 | 24.43 | O |
| ATOM | 725 | OE2 | GLU | A | 50 | 27.683 | 23.561 | 1.918 | 1.00 | 35.88 | O |
| ATOM | 726 | C | GLU | A | 50 | 27.208 | 17.435 | 1.866 | 1.00 | 20.83 | C |
| ATOM | 727 | O | GLU | A | 50 | 28.257 | 17.188 | 1.220 | 1.00 | 21.81 | O |
| ATOM | 728 | N | GLN | A | 51 | 26.761 | 16.586 | 2.783 | 1.00 | 19.08 | N |
| ATOM | 730 | CA | GLN | A | 51 | 27.273 | 15.186 | 2.847 | 1.00 | 18.38 | C |
| ATOM | 732 | CB | GLN | A | 51 | 28.416 | 14.936 | 3.863 | 1.00 | 18.98 | C |
| ATOM | 735 | CG | GLN | A | 51 | 29.720 | 15.707 | 3.698 | 1.00 | 16.56 | C |
| ATOM | 738 | CD | GLN | A | 51 | 30.864 | 15.082 | 4.418 | 1.00 | 18.35 | C |
| ATOM | 739 | OE1 | GLN | A | 51 | 30.728 | 14.001 | 4.993 | 1.00 | 16.59 | O |
| ATOM | 740 | NE2 | GLN | A | 51 | 32.021 | 15.746 | 4.421 | 1.00 | 18.88 | N |
| ATOM | 743 | C | GLN | A | 51 | 26.048 | 14.303 | 3.122 | 1.00 | 18.15 | C |
| ATOM | 744 | O | GLN | A | 51 | 25.088 | 14.739 | 3.753 | 1.00 | 17.95 | O |
| ATOM | 745 | N | CYS | A | 52 | 26.032 | 13.097 | 2.549 | 1.00 | 19.15 | N |
| ATOM | 747 | CA | CYS | A | 52 | 24.933 | 12.197 | 2.657 | 1.00 | 19.58 | C |
| ATOM | 749 | CB | CYS | A | 52 | 23.994 | 12.383 | 1.463 | 1.00 | 20.58 | C |
| ATOM | 752 | SG | CYS | A | 52 | 22.757 | 11.113 | 1.313 | 1.00 | 23.23 | S |
| ATOM | 753 | C | CYS | A | 52 | 25.609 | 10.827 | 2.666 | 1.00 | 19.62 | C |
| ATOM | 754 | O | CYS | A | 52 | 26.112 | 10.376 | 1.630 | 1.00 | 17.75 | O |
| ATOM | 755 | N | LYS | A | 53 | 25.706 | 10.188 | 3.841 | 1.00 | 18.28 | N |
| ATOM | 757 | CA | LYS | A | 53 | 26.435 | 8.938 | 3.934 | 1.00 | 17.30 | C |
| ATOM | 759 | CB | LYS | A | 53 | 27.835 | 9.165 | 4.542 | 1.00 | 17.03 | C |
| ATOM | 762 | CG | LYS | A | 53 | 28.733 | 10.042 | 3.720 | 1.00 | 16.05 | C |
| ATOM | 765 | CD | LYS | A | 53 | 30.097 | 10.281 | 4.325 | 1.00 | 17.76 | C |
| ATOM | 768 | CE | LYS | A | 53 | 31.031 | 11.033 | 3.333 | 1.00 | 17.09 | C |
| ATOM | 771 | NZ | LYS | A | 53 | 32.138 | 11.733 | 3.893 | 1.00 | 19.33 | N |
| ATOM | 775 | C | LYS | A | 53 | 25.698 | 7.913 | 4.801 | 1.00 | 18.20 | C |
| ATOM | 776 | O | LYS | A | 53 | 24.966 | 8.299 | 5.712 | 1.00 | 15.09 | O |
| ATOM | 777 | N | ASP | A | 54 | 25.905 | 6.619 | 4.518 | 1.00 | 15.90 | N |
| ATOM | 779 | CA | ASP | A | 54 | 25.186 | 5.563 | 5.218 | 1.00 | 17.38 | C |
| ATOM | 781 | CB | ASP | A | 54 | 24.244 | 4.911 | 4.223 | 1.00 | 17.91 | C |
| ATOM | 784 | CG | ASP | A | 54 | 23.222 | 3.960 | 4.825 | 1.00 | 20.51 | C |
| ATOM | 785 | OD1 | ASP | A | 54 | 23.261 | 3.554 | 6.029 | 1.00 | 15.70 | O |
| ATOM | 786 | OD2 | ASP | A | 54 | 22.292 | 3.563 | 4.088 | 1.00 | 19.49 | O |
| ATOM | 787 | C | ASP | A | 54 | 26.131 | 4.552 | 5.807 | 1.00 | 17.88 | C |
| ATOM | 788 | O | ASP | A | 54 | 26.969 | 3.968 | 5.093 | 1.00 | 17.08 | O |
| ATOM | 789 | N | PHE | A | 55 | 25.998 | 4.356 | 7.135 | 1.00 | 15.74 | N |
| ATOM | 791 | CA | PHE | A | 55 | 26.865 | 3.464 | 7.867 | 1.00 | 15.03 | C |
| ATOM | 793 | CB | PHE | A | 55 | 27.359 | 4.168 | 9.131 | 1.00 | 13.99 | C |

APPENDIX 1-continued

| | | | | | | | | | | | |
|---|---|---|---|---|---|---|---|---|---|---|---|
| ATOM | 796 | CG | PHE | A | 55 | 28.268 | 5.336 | 8.844 | 1.00 | 15.45 | C |
| ATOM | 797 | CD1 | PHE | A | 55 | 27.753 | 6.544 | 8.432 | 1.00 | 15.76 | C |
| ATOM | 799 | CE1 | PHE | A | 55 | 28.616 | 7.657 | 8.155 | 1.00 | 14.10 | C |
| ATOM | 801 | CZ | PHE | A | 55 | 29.907 | 7.536 | 8.256 | 1.00 | 13.98 | C |
| ATOM | 803 | CE2 | PHE | A | 55 | 30.431 | 6.303 | 8.656 | 1.00 | 15.61 | C |
| ATOM | 805 | CD2 | PHE | A | 55 | 29.594 | 5.232 | 8.950 | 1.00 | 14.62 | C |
| ATOM | 807 | C | PHE | A | 55 | 26.160 | 2.191 | 8.265 | 1.00 | 15.07 | C |
| ATOM | 808 | O | PHE | A | 55 | 26.732 | 1.387 | 9.025 | 1.00 | 15.44 | O |
| ATOM | 809 | N | THR | A | 56 | 24.962 | 1.994 | 7.769 | 1.00 | 15.31 | N |
| ATOM | 811 | CA | THR | A | 56 | 24.149 | 0.858 | 8.159 | 1.00 | 16.77 | C |
| ATOM | 813 | CB | THR | A | 56 | 22.724 | 1.253 | 8.463 | 1.00 | 17.17 | C |
| ATOM | 815 | OG1 | THR | A | 56 | 22.006 | 1.623 | 7.272 | 1.00 | 15.48 | O |
| ATOM | 817 | CG2 | THR | A | 56 | 22.628 | 2.535 | 9.443 | 1.00 | 13.67 | C |
| ATOM | 821 | C | THR | A | 56 | 24.134 | −0.328 | 7.166 | 1.00 | 20.28 | C |
| ATOM | 822 | O | THR | A | 56 | 23.451 | −1.319 | 7.407 | 1.00 | 21.69 | O |
| ATOM | 823 | N | GLN | A | 57 | 24.852 | −0.239 | 6.069 | 1.00 | 22.81 | N |
| ATOM | 825 | CA | GLN | A | 57 | 24.736 | −1.314 | 5.061 | 1.00 | 25.52 | C |
| ATOM | 827 | CB | GLN | A | 57 | 24.681 | −0.724 | 3.646 | 1.00 | 25.67 | C |
| ATOM | 830 | CG | GLN | A | 57 | 23.521 | 0.217 | 3.502 | 1.00 | 27.65 | C |
| ATOM | 833 | CD | GLN | A | 57 | 23.366 | 0.800 | 2.117 | 1.00 | 36.31 | C |
| ATOM | 834 | OE1 | GLN | A | 57 | 23.871 | 0.240 | 1.156 | 1.00 | 35.97 | O |
| ATOM | 835 | NE2 | GLN | A | 57 | 22.686 | 1.938 | 2.016 | 1.00 | 30.80 | N |
| ATOM | 838 | C | GLN | A | 57 | 25.848 | −2.331 | 5.196 | 1.00 | 28.75 | C |
| ATOM | 839 | O | GLN | A | 57 | 26.735 | −2.182 | 6.034 | 1.00 | 28.60 | O |
| ATOM | 840 | N | SER | A | 58 | 25.792 | −3.388 | 4.363 | 1.00 | 32.27 | N |
| ATOM | 842 | CA | SER | A | 58 | 26.798 | −4.440 | 4.371 | 1.00 | 34.96 | C |
| ATOM | 844 | CB | SER | A | 58 | 26.488 | −5.494 | 3.291 | 1.00 | 35.23 | C |
| ATOM | 847 | OG | SER | A | 58 | 25.088 | −5.548 | 3.041 | 1.00 | 37.60 | O |
| ATOM | 849 | C | SER | A | 58 | 28.149 | −3.762 | 4.140 | 1.00 | 35.56 | C |
| ATOM | 850 | O | SER | A | 58 | 29.096 | −3.989 | 4.843 | 1.00 | 36.58 | O |
| ATOM | 851 | N | ASN | A | 59 | 28.224 | −2.889 | 3.147 | 1.00 | 37.91 | N |
| ATOM | 853 | CA | ASN | A | 59 | 29.409 | −2.054 | 3.003 | 1.00 | 38.41 | C |
| ATOM | 855 | CB | ASN | A | 59 | 29.288 | −1.232 | 1.739 | 1.00 | 39.92 | C |
| ATOM | 858 | CG | ASN | A | 59 | 30.172 | −1.727 | 0.636 | 1.00 | 44.62 | C |
| ATOM | 859 | OD1 | ASN | A | 59 | 31.413 | −1.752 | 0.759 | 1.00 | 52.42 | O |
| ATOM | 860 | ND2 | ASN | A | 59 | 29.547 | −2.121 | −0.468 | 1.00 | 50.97 | N |
| ATOM | 863 | C | ASN | A | 59 | 29.421 | −1.061 | 4.156 | 1.00 | 37.64 | C |
| ATOM | 864 | O | ASN | A | 59 | 28.436 | −0.360 | 4.338 | 1.00 | 37.26 | O |
| ATOM | 865 | N | PRO | A | 60 | 30.474 | −1.028 | 4.961 | 1.00 | 37.50 | N |
| ATOM | 866 | CA | PRO | A | 60 | 30.591 | −0.066 | 6.064 | 1.00 | 36.81 | C |
| ATOM | 868 | CB | PRO | A | 60 | 32.016 | −0.315 | 6.585 | 1.00 | 37.80 | C |
| ATOM | 871 | CG | PRO | A | 60 | 32.661 | −1.116 | 5.519 | 1.00 | 38.85 | C |
| ATOM | 874 | CD | PRO | A | 60 | 31.589 | −1.986 | 4.997 | 1.00 | 38.04 | C |
| ATOM | 877 | C | PRO | A | 60 | 30.421 | 1.431 | 5.770 | 1.00 | 35.74 | C |
| ATOM | 878 | O | PRO | A | 60 | 30.266 | 2.188 | 6.749 | 1.00 | 34.22 | O |
| ATOM | 879 | N | LEU | A | 61 | 30.478 | 1.876 | 4.517 | 1.00 | 33.77 | N |
| ATOM | 881 | CA | LEU | A | 61 | 30.183 | 3.278 | 4.258 | 1.00 | 33.86 | C |
| ATOM | 883 | CB | LEU | A | 61 | 31.403 | 4.170 | 4.541 | 1.00 | 34.63 | C |
| ATOM | 886 | CG | LEU | A | 61 | 31.122 | 5.691 | 4.652 | 1.00 | 38.34 | C |
| ATOM | 888 | CD1 | LEU | A | 61 | 32.418 | 6.454 | 4.765 | 1.00 | 41.14 | C |
| ATOM | 892 | CD2 | LEU | A | 61 | 30.383 | 6.236 | 3.501 | 1.00 | 40.32 | C |
| ATOM | 896 | C | LEU | A | 61 | 29.681 | 3.440 | 2.838 | 1.00 | 31.90 | C |
| ATOM | 897 | O | LEU | A | 61 | 30.371 | 3.109 | 1.887 | 1.00 | 32.30 | O |
| ATOM | 898 | N | VAL | A | 62 | 28.452 | 3.862 | 2.682 | 1.00 | 29.42 | N |
| ATOM | 900 | CA | VAL | A | 62 | 27.944 | 4.129 | 1.363 | 1.00 | 29.40 | C |
| ATOM | 902 | CB | VAL | A | 62 | 26.721 | 3.365 | 1.091 | 1.00 | 28.97 | C |
| ATOM | 904 | CG1 | VAL | A | 62 | 26.082 | 3.877 | −0.187 | 1.00 | 30.81 | C |
| ATOM | 908 | CG2 | VAL | A | 62 | 27.060 | 1.874 | 1.015 | 1.00 | 31.48 | C |
| ATOM | 912 | C | VAL | A | 62 | 27.768 | 5.625 | 1.255 | 1.00 | 27.76 | C |
| ATOM | 913 | O | VAL | A | 62 | 27.015 | 6.233 | 1.970 | 1.00 | 26.96 | O |
| ATOM | 914 | N | ASP | A | 63 | 28.646 | 6.224 | 0.470 | 1.00 | 28.18 | N |
| ATOM | 916 | CA | ASP | A | 63 | 28.600 | 7.643 | 0.235 | 1.00 | 26.20 | C |
| ATOM | 918 | CB | ASP | A | 63 | 29.993 | 8.062 | −0.215 | 1.00 | 26.90 | C |
| ATOM | 921 | CG | ASP | A | 63 | 30.222 | 9.517 | −0.099 | 1.00 | 25.49 | C |
| ATOM | 922 | OD1 | ASP | A | 63 | 29.290 | 10.281 | −0.017 | 1.00 | 26.02 | O |
| ATOM | 923 | OD2 | ASP | A | 63 | 31.318 | 10.031 | −0.150 | 1.00 | 28.08 | O |
| ATOM | 924 | C | ASP | A | 63 | 27.571 | 7.929 | −0.826 | 1.00 | 27.79 | C |
| ATOM | 925 | O | ASP | A | 63 | 27.455 | 7.199 | −1.812 | 1.00 | 27.28 | O |
| ATOM | 926 | N | GLY | A | 64 | 26.753 | 8.936 | −0.581 | 1.00 | 26.48 | N |
| ATOM | 928 | CA | GLY | A | 64 | 25.703 | 9.316 | −1.502 | 1.00 | 25.76 | C |
| ATOM | 931 | C | GLY | A | 64 | 24.357 | 8.742 | −1.234 | 1.00 | 25.62 | C |
| ATOM | 932 | O | GLY | A | 64 | 23.474 | 8.881 | −2.053 | 1.00 | 28.14 | O |
| ATOM | 933 | N | SER | A | 65 | 24.184 | 8.096 | −0.080 | 1.00 | 22.83 | N |
| ATOM | 935 | CA | SER | A | 65 | 22.953 | 7.499 | 0.304 | 1.00 | 22.85 | C |
| ATOM | 937 | CB | SER | A | 65 | 23.003 | 6.005 | 0.117 | 1.00 | 23.23 | C |
| ATOM | 940 | OG | SER | A | 65 | 21.699 | 5.584 | 0.027 | 1.00 | 29.80 | O |
| ATOM | 942 | C | SER | A | 65 | 22.705 | 7.773 | 1.749 | 1.00 | 21.08 | C |
| ATOM | 943 | O | SER | A | 65 | 23.671 | 7.638 | 2.504 | 1.00 | 19.41 | O |
| ATOM | 944 | N | CYS | A | 66 | 21.521 | 8.181 | 2.140 | 1.00 | 20.00 | N |
| ATOM | 946 | CA | CYS | A | 66 | 21.278 | 8.539 | 3.546 | 1.00 | 20.11 | C |

APPENDIX 1-continued

| ATOM | 948 | CB | CYS | A | 66 | 22.034 | 9.822 | 3.885 | 1.00 | 19.63 | C |
|---|---|---|---|---|---|---|---|---|---|---|---|
| ATOM | 951 | SG | CYS | A | 66 | 21.484 | 11.254 | 2.900 | 1.00 | 19.95 | S |
| ATOM | 952 | C | CYS | A | 66 | 19.803 | 8.601 | 3.712 | 1.00 | 18.81 | C |
| ATOM | 953 | O | CYS | A | 66 | 19.168 | 9.468 | 4.308 | 1.00 | 17.95 | O |
| ATOM | 954 | N | THR | A | 67 | 19.180 | 7.568 | 3.214 | 1.00 | 19.39 | N |
| ATOM | 956 | CA | THR | A | 67 | 17.768 | 7.596 | 3.075 | 1.00 | 19.72 | C |
| ATOM | 958 | CB | THR | A | 67 | 17.481 | 6.628 | 1.924 | 1.00 | 20.77 | C |
| ATOM | 960 | OG1 | THR | A | 67 | 18.082 | 7.189 | 0.735 | 1.00 | 26.00 | O |
| ATOM | 962 | CG2 | THR | A | 67 | 16.113 | 6.443 | 1.665 | 1.00 | 23.79 | C |
| ATOM | 966 | C | THR | A | 67 | 16.941 | 7.325 | 4.315 | 1.00 | 18.14 | C |
| ATOM | 967 | O | THR | A | 67 | 17.066 | 6.297 | 4.990 | 1.00 | 16.62 | O |
| ATOM | 968 | N | ASP | A | 68 | 16.070 | 8.278 | 4.623 | 1.00 | 17.54 | N |
| ATOM | 970 | CA | ASP | A | 68 | 15.191 | 8.149 | 5.786 | 1.00 | 17.68 | C |
| ATOM | 972 | CB | ASP | A | 68 | 14.877 | 9.530 | 6.360 | 1.00 | 16.82 | C |
| ATOM | 975 | CG | ASP | A | 68 | 14.131 | 9.480 | 7.697 | 1.00 | 17.49 | C |
| ATOM | 976 | OD1 | ASP | A | 68 | 13.988 | 8.380 | 8.314 | 1.00 | 14.56 | O |
| ATOM | 977 | OD2 | ASP | A | 68 | 13.610 | 10.516 | 8.221 | 1.00 | 16.31 | O |
| ATOM | 978 | C | ASP | A | 68 | 13.909 | 7.425 | 5.423 | 1.00 | 19.14 | C |
| ATOM | 979 | O | ASP | A | 68 | 13.100 | 7.936 | 4.626 | 1.00 | 19.83 | O |
| ATOM | 980 | N | ARG | A | 69 | 13.688 | 6.262 | 6.023 | 1.00 | 19.38 | N |
| ATOM | 982 | CA | ARG | A | 69 | 12.427 | 5.549 | 5.858 | 1.00 | 20.20 | C |
| ATOM | 984 | CB | ARG | A | 69 | 12.665 | 4.106 | 5.357 | 1.00 | 20.57 | C |
| ATOM | 987 | CG | ARG | A | 69 | 13.461 | 4.061 | 4.081 | 1.00 | 23.84 | C |
| ATOM | 990 | CD | ARG | A | 69 | 13.499 | 2.688 | 3.401 | 1.00 | 28.11 | C |
| ATOM | 993 | NE | ARG | A | 69 | 14.384 | 2.688 | 2.239 | 1.00 | 31.97 | N |
| ATOM | 995 | CZ | ARG | A | 69 | 15.683 | 2.433 | 2.284 | 1.00 | 34.34 | C |
| ATOM | 996 | NH1 | ARG | A | 69 | 16.288 | 2.155 | 3.437 | 1.00 | 33.57 | N |
| ATOM | 999 | NH2 | ARG | A | 69 | 16.416 | 2.464 | 1.173 | 1.00 | 37.78 | N |
| ATOM | 1002 | C | ARG | A | 69 | 11.615 | 5.543 | 7.120 | 1.00 | 20.20 | C |
| ATOM | 1003 | O | ARG | A | 69 | 10.605 | 4.861 | 7.222 | 1.00 | 19.58 | O |
| ATOM | 1004 | N | GLN | A | 70 | 12.022 | 6.341 | 8.120 | 1.00 | 18.56 | N |
| ATOM | 1006 | CA | GLN | A | 70 | 11.359 | 6.330 | 9.404 | 1.00 | 18.67 | C |
| ATOM | 1008 | CB | GLN | A | 70 | 12.459 | 6.087 | 10.480 | 1.00 | 17.38 | C |
| ATOM | 1011 | CG | GLN | A | 70 | 11.887 | 5.512 | 11.734 | 1.00 | 24.45 | C |
| ATOM | 1014 | CD | GLN | A | 70 | 11.094 | 6.496 | 12.618 | 1.00 | 29.69 | C |
| ATOM | 1015 | OE1 | GLN | A | 70 | 11.259 | 7.719 | 12.568 | 1.00 | 28.81 | O |
| ATOM | 1016 | NE2 | GLN | A | 70 | 10.180 | 5.934 | 13.390 | 1.00 | 36.98 | N |
| ATOM | 1019 | C | GLN | A | 70 | 10.678 | 7.677 | 9.729 | 1.00 | 16.99 | C |
| ATOM | 1020 | O | GLN | A | 70 | 9.502 | 7.745 | 10.177 | 1.00 | 18.53 | O |
| ATOM | 1021 | N | GLY | A | 71 | 11.448 | 8.740 | 9.546 | 1.00 | 17.00 | N |
| ATOM | 1023 | CA | GLY | A | 71 | 10.936 | 10.086 | 9.792 | 1.00 | 16.91 | C |
| ATOM | 1026 | C | GLY | A | 71 | 11.766 | 10.862 | 10.826 | 1.00 | 16.73 | C |
| ATOM | 1027 | O | GLY | A | 71 | 12.023 | 12.040 | 10.683 | 1.00 | 16.08 | O |
| ATOM | 1028 | N | HIS | A | 72 | 12.190 | 10.148 | 11.848 | 1.00 | 15.53 | N |
| ATOM | 1030 | CA | HIS | A | 72 | 12.902 | 10.764 | 12.965 | 1.00 | 14.82 | C |
| ATOM | 1032 | CB | HIS | A | 72 | 13.305 | 9.625 | 13.926 | 1.00 | 14.91 | C |
| ATOM | 1035 | CG | HIS | A | 72 | 13.996 | 10.088 | 15.170 | 1.00 | 11.42 | C |
| ATOM | 1036 | ND1 | HIS | A | 72 | 15.356 | 10.264 | 15.228 | 1.00 | 11.65 | N |
| ATOM | 1038 | CE1 | HIS | A | 72 | 15.690 | 10.620 | 16.456 | 1.00 | 15.57 | C |
| ATOM | 1040 | NE2 | HIS | A | 72 | 14.603 | 10.660 | 17.194 | 1.00 | 12.24 | N |
| ATOM | 1042 | CD2 | HIS | A | 72 | 13.527 | 10.309 | 16.414 | 1.00 | 15.18 | C |
| ATOM | 1044 | C | HIS | A | 72 | 14.077 | 11.632 | 12.515 | 1.00 | 14.31 | C |
| ATOM | 1045 | O | HIS | A | 72 | 14.157 | 12.811 | 12.906 | 1.00 | 14.46 | O |
| ATOM | 1046 | N | GLY | A | 73 | 14.993 | 11.101 | 11.686 | 1.00 | 13.23 | N |
| ATOM | 1048 | CA | GLY | A | 73 | 16.140 | 11.851 | 11.227 | 1.00 | 13.67 | C |
| ATOM | 1051 | C | GLY | A | 73 | 15.743 | 13.097 | 10.452 | 1.00 | 14.47 | C |
| ATOM | 1052 | O | GLY | A | 73 | 16.388 | 14.147 | 10.556 | 1.00 | 14.58 | O |
| ATOM | 1053 | N | THR | A | 74 | 14.691 | 12.976 | 9.638 | 1.00 | 14.43 | N |
| ATOM | 1055 | CA | THR | A | 74 | 14.223 | 14.163 | 8.902 | 1.00 | 14.75 | C |
| ATOM | 1057 | CB | THR | A | 74 | 13.166 | 13.722 | 7.889 | 1.00 | 15.14 | C |
| ATOM | 1059 | OG1 | THR | A | 74 | 13.832 | 12.851 | 6.979 | 1.00 | 14.14 | O |
| ATOM | 1061 | CG2 | THR | A | 74 | 12.703 | 14.949 | 7.052 | 1.00 | 17.07 | C |
| ATOM | 1065 | C | THR | A | 74 | 13.672 | 15.256 | 9.779 | 1.00 | 13.89 | C |
| ATOM | 1066 | O | THR | A | 74 | 13.964 | 16.449 | 9.549 | 1.00 | 14.36 | O |
| ATOM | 1067 | N | HIS | A | 75 | 12.985 | 14.834 | 10.823 | 1.00 | 13.97 | N |
| ATOM | 1069 | CA | HIS | A | 75 | 12.345 | 15.653 | 11.803 | 1.00 | 13.53 | C |
| ATOM | 1071 | CB | HIS | A | 75 | 11.464 | 14.793 | 12.693 | 1.00 | 14.00 | C |
| ATOM | 1074 | CG | HIS | A | 75 | 10.525 | 15.543 | 13.566 | 1.00 | 13.88 | C |
| ATOM | 1075 | ND1 | HIS | A | 75 | 10.923 | 16.209 | 14.706 | 1.00 | 13.19 | N |
| ATOM | 1077 | CE1 | HIS | A | 75 | 9.888 | 16.830 | 15.235 | 1.00 | 15.22 | C |
| ATOM | 1079 | NE2 | HIS | A | 75 | 8.826 | 16.616 | 14.465 | 1.00 | 15.33 | N |
| ATOM | 1081 | CD2 | HIS | A | 75 | 9.203 | 15.822 | 13.415 | 1.00 | 14.61 | C |
| ATOM | 1083 | C | HIS | A | 75 | 13.464 | 16.423 | 12.565 | 1.00 | 14.20 | C |
| ATOM | 1084 | O | HIS | A | 75 | 13.447 | 17.650 | 12.685 | 1.00 | 11.71 | O |
| ATOM | 1085 | N | VAL | A | 76 | 14.436 | 15.685 | 13.031 | 1.00 | 13.61 | N |
| ATOM | 1087 | CA | VAL | A | 76 | 15.543 | 16.273 | 13.761 | 1.00 | 13.90 | C |
| ATOM | 1089 | CB | VAL | A | 76 | 16.471 | 15.117 | 14.276 | 1.00 | 12.59 | C |
| ATOM | 1091 | CG1 | VAL | A | 76 | 17.771 | 15.657 | 14.716 | 1.00 | 13.85 | C |
| ATOM | 1095 | CG2 | VAL | A | 76 | 15.788 | 14.354 | 15.381 | 1.00 | 13.36 | C |
| ATOM | 1099 | C | VAL | A | 76 | 16.280 | 17.319 | 12.925 | 1.00 | 13.76 | C |

APPENDIX 1-continued

| ATOM | 1100 | O | VAL | A | 76 | 16.549 | 18.419 | 13.362 | 1.00 | 13.81 | O |
|---|---|---|---|---|---|---|---|---|---|---|---|
| ATOM | 1101 | N | ALA | A | 77 | 16.598 | 16.976 | 11.693 | 1.00 | 13.31 | N |
| ATOM | 1103 | CA | ALA | A | 77 | 17.316 | 17.850 | 10.844 | 1.00 | 13.43 | C |
| ATOM | 1105 | CB | ALA | A | 77 | 17.586 | 17.164 | 9.553 | 1.00 | 12.82 | C |
| ATOM | 1109 | C | ALA | A | 77 | 16.538 | 19.154 | 10.631 | 1.00 | 13.42 | C |
| ATOM | 1110 | O | ALA | A | 77 | 17.137 | 20.256 | 10.595 | 1.00 | 16.51 | O |
| ATOM | 1111 | N | GLY | A | 78 | 15.223 | 19.047 | 10.501 | 1.00 | 13.22 | N |
| ATOM | 1113 | CA | GLY | A | 78 | 14.413 | 20.237 | 10.270 | 1.00 | 14.59 | C |
| ATOM | 1116 | C | GLY | A | 78 | 14.431 | 21.221 | 11.448 | 1.00 | 14.40 | C |
| ATOM | 1117 | O | GLY | A | 78 | 14.427 | 22.440 | 11.294 | 1.00 | 14.85 | O |
| ATOM | 1118 | N | THR | A | 79 | 14.537 | 20.673 | 12.643 | 1.00 | 12.64 | N |
| ATOM | 1120 | CA | THR | A | 79 | 14.546 | 21.535 | 13.817 | 1.00 | 11.83 | C |
| ATOM | 1122 | CB | THR | A | 79 | 14.350 | 20.656 | 15.063 | 1.00 | 11.71 | C |
| ATOM | 1124 | OG1 | THR | A | 79 | 12.990 | 20.162 | 15.166 | 1.00 | 12.60 | O |
| ATOM | 1126 | CG2 | THR | A | 79 | 14.569 | 21.491 | 16.347 | 1.00 | 11.10 | C |
| ATOM | 1130 | C | THR | A | 79 | 15.842 | 22.248 | 13.795 | 1.00 | 12.20 | C |
| ATOM | 1131 | O | THR | A | 79 | 15.917 | 23.440 | 14.122 | 1.00 | 12.14 | O |
| ATOM | 1132 | N | VAL | A | 80 | 16.917 | 21.568 | 13.358 | 1.00 | 11.44 | N |
| ATOM | 1134 | CA | VAL | A | 80 | 18.195 | 22.225 | 13.293 | 1.00 | 11.80 | C |
| ATOM | 1136 | CB | VAL | A | 80 | 19.299 | 21.273 | 12.865 | 1.00 | 11.91 | C |
| ATOM | 1138 | CG1 | VAL | A | 80 | 20.637 | 21.963 | 12.687 | 1.00 | 13.34 | C |
| ATOM | 1142 | CG2 | VAL | A | 80 | 19.520 | 20.158 | 13.884 | 1.00 | 12.77 | C |
| ATOM | 1146 | C | VAL | A | 80 | 18.216 | 23.369 | 12.266 | 1.00 | 13.39 | C |
| ATOM | 1147 | O | VAL | A | 80 | 18.646 | 24.514 | 12.553 | 1.00 | 12.65 | O |
| ATOM | 1148 | N | LEU | A | 81 | 17.751 | 23.054 | 11.069 | 1.00 | 13.69 | N |
| ATOM | 1150 | CA | LEU | A | 81 | 18.057 | 23.946 | 9.965 | 1.00 | 14.13 | C |
| ATOM | 1152 | CB | LEU | A | 81 | 19.454 | 23.675 | 9.439 | 1.00 | 14.13 | C |
| ATOM | 1155 | CG | LEU | A | 81 | 19.893 | 22.189 | 9.225 | 1.00 | 11.54 | C |
| ATOM | 1157 | CD1 | LEU | A | 81 | 19.058 | 21.552 | 8.105 | 1.00 | 15.65 | C |
| ATOM | 1161 | CD2 | LEU | A | 81 | 21.308 | 22.059 | 8.854 | 1.00 | 14.83 | C |
| ATOM | 1165 | C | LEU | A | 81 | 17.043 | 24.065 | 8.827 | 1.00 | 15.14 | C |
| ATOM | 1166 | O | LEU | A | 81 | 17.442 | 24.518 | 7.766 | 1.00 | 17.76 | O |
| ATOM | 1167 | N | ALA | A | 82 | 15.791 | 23.694 | 9.035 | 1.00 | 15.38 | N |
| ATOM | 1169 | CA | ALA | A | 82 | 14.830 | 23.894 | 7.920 | 1.00 | 16.54 | C |
| ATOM | 1171 | CB | ALA | A | 82 | 13.485 | 23.412 | 8.253 | 1.00 | 16.56 | C |
| ATOM | 1175 | C | ALA | A | 82 | 14.807 | 25.381 | 7.616 | 1.00 | 17.73 | C |
| ATOM | 1176 | O | ALA | A | 82 | 14.873 | 26.246 | 8.522 | 1.00 | 16.11 | O |
| ATOM | 1177 | N | HIS | A | 83 | 14.637 | 25.678 | 6.321 | 1.00 | 18.61 | N |
| ATOM | 1179 | CA | HIS | A | 83 | 14.802 | 27.048 | 5.845 | 1.00 | 17.82 | C |
| ATOM | 1181 | CB | HIS | A | 83 | 16.057 | 27.116 | 4.996 | 1.00 | 18.66 | C |
| ATOM | 1184 | CG | HIS | A | 83 | 16.040 | 26.187 | 3.831 | 1.00 | 19.55 | C |
| ATOM | 1185 | ND1 | HIS | A | 83 | 14.935 | 26.066 | 3.023 | 1.00 | 23.39 | N |
| ATOM | 1187 | CE1 | HIS | A | 83 | 15.196 | 25.205 | 2.056 | 1.00 | 24.12 | C |
| ATOM | 1189 | NE2 | HIS | A | 83 | 16.395 | 24.706 | 2.259 | 1.00 | 24.21 | N |
| ATOM | 1191 | CD2 | HIS | A | 83 | 16.960 | 25.326 | 3.349 | 1.00 | 22.73 | C |
| ATOM | 1193 | C | HIS | A | 83 | 13.606 | 27.689 | 5.119 | 1.00 | 19.24 | C |
| ATOM | 1194 | O | HIS | A | 83 | 13.802 | 28.694 | 4.468 | 1.00 | 20.21 | O |
| ATOM | 1195 | N | GLY | A | 84 | 12.433 | 27.158 | 5.342 | 1.00 | 19.88 | N |
| ATOM | 1197 | CA | GLY | A | 84 | 11.151 | 27.653 | 4.874 | 1.00 | 23.01 | C |
| ATOM | 1200 | C | GLY | A | 84 | 10.891 | 27.373 | 3.388 | 1.00 | 23.83 | C |
| ATOM | 1201 | O | GLY | A | 84 | 9.816 | 27.693 | 2.873 | 1.00 | 25.88 | O |
| ATOM | 1202 | N | GLY | A | 85 | 11.891 | 26.852 | 2.716 | 1.00 | 25.14 | N |
| ATOM | 1204 | CA | GLY | A | 85 | 11.754 | 26.452 | 1.333 | 1.00 | 28.31 | C |
| ATOM | 1207 | C | GLY | A | 85 | 11.845 | 27.607 | 0.361 | 1.00 | 30.82 | C |
| ATOM | 1208 | O | GLY | A | 85 | 11.704 | 28.777 | 0.750 | 1.00 | 32.32 | O |
| ATOM | 1209 | N | SER | A | 86 | 12.066 | 27.253 | −0.910 | 1.00 | 33.23 | N |
| ATOM | 1211 | CA | SER | A | 86 | 12.332 | 28.220 | −1.982 | 1.00 | 35.37 | C |
| ATOM | 1213 | CB | SER | A | 86 | 12.287 | 27.551 | −3.374 | 1.00 | 35.51 | C |
| ATOM | 1216 | OG | SER | A | 86 | 11.022 | 26.920 | −3.531 | 1.00 | 36.16 | O |
| ATOM | 1218 | C | SER | A | 86 | 11.323 | 29.323 | −1.984 | 1.00 | 35.85 | C |
| ATOM | 1219 | O | SER | A | 86 | 11.673 | 30.481 | −2.155 | 1.00 | 37.71 | O |
| ATOM | 1220 | N | ASN | A | 87 | 10.066 | 28.993 | −1.784 | 1.00 | 36.18 | N |
| ATOM | 1222 | CA | ASN | A | 87 | 9.060 | 30.024 | −1.844 | 1.00 | 37.05 | C |
| ATOM | 1224 | CB | ASN | A | 87 | 7.842 | 29.472 | −2.589 | 1.00 | 37.33 | C |
| ATOM | 1227 | CG | ASN | A | 87 | 6.943 | 28.626 | −1.702 | 1.00 | 40.53 | C |
| ATOM | 1228 | OD1 | ASN | A | 87 | 7.323 | 28.240 | −0.581 | 1.00 | 40.83 | O |
| ATOM | 1229 | ND2 | ASN | A | 87 | 5.732 | 28.329 | −2.205 | 1.00 | 39.22 | N |
| ATOM | 1232 | C | ASN | A | 87 | 8.678 | 30.600 | −0.469 | 1.00 | 35.97 | C |
| ATOM | 1233 | O | ASN | A | 87 | 7.564 | 31.143 | −0.295 | 1.00 | 36.81 | O |
| ATOM | 1234 | N | GLY | A | 88 | 9.554 | 30.402 | 0.526 | 1.00 | 34.13 | N |
| ATOM | 1236 | CA | GLY | A | 88 | 9.307 | 30.979 | 1.841 | 1.00 | 32.36 | C |
| ATOM | 1239 | C | GLY | A | 88 | 8.149 | 30.556 | 2.701 | 1.00 | 30.27 | C |
| ATOM | 1240 | O | GLY | A | 88 | 7.882 | 31.189 | 3.728 | 1.00 | 30.72 | O |
| ATOM | 1241 | N | GLN | A | 89 | 7.375 | 29.545 | 2.305 | 1.00 | 28.00 | N |
| ATOM | 1243 | CA | GLN | A | 89 | 6.212 | 29.190 | 3.117 | 1.00 | 27.11 | C |
| ATOM | 1245 | CB | GLN | A | 89 | 4.898 | 29.091 | 2.269 | 1.00 | 28.51 | C |
| ATOM | 1248 | CG | GLN | A | 89 | 3.596 | 28.969 | 3.114 | 0.10 | 26.48 | C |
| ATOM | 1251 | CD | GLN | A | 89 | 2.269 | 28.881 | 2.318 | 0.10 | 25.84 | C |
| ATOM | 1252 | OE1 | GLN | A | 89 | 2.243 | 28.873 | 1.085 | 0.10 | 20.77 | O |
| ATOM | 1253 | NE2 | GLN | A | 89 | 1.164 | 28.811 | 3.052 | 0.10 | 23.86 | N |

APPENDIX 1-continued

| | | | | | | | | | | | |
|---|---|---|---|---|---|---|---|---|---|---|---|
| ATOM | 1256 | C | GLN | A | 89 | 6.384 | 27.908 | 3.974 | 1.00 | 26.64 | C |
| ATOM | 1257 | O | GLN | A | 89 | 5.463 | 27.490 | 4.638 | 1.00 | 25.73 | O |
| ATOM | 1258 | N | GLY | A | 90 | 7.572 | 27.312 | 3.967 | 1.00 | 26.19 | N |
| ATOM | 1260 | CA | GLY | A | 90 | 7.781 | 26.104 | 4.760 | 1.00 | 24.89 | C |
| ATOM | 1263 | C | GLY | A | 90 | 8.133 | 26.372 | 6.223 | 1.00 | 25.02 | C |
| ATOM | 1264 | O | GLY | A | 90 | 7.940 | 27.492 | 6.751 | 1.00 | 25.06 | O |
| ATOM | 1265 | N | VAL | A | 91 | 8.598 | 25.330 | 6.888 | 1.00 | 22.83 | N |
| ATOM | 1267 | CA | VAL | A | 91 | 8.942 | 25.462 | 8.304 | 1.00 | 20.77 | C |
| ATOM | 1269 | CB | VAL | A | 91 | 8.681 | 24.116 | 9.045 | 1.00 | 19.91 | C |
| ATOM | 1271 | CG1 | VAL | A | 91 | 9.781 | 23.160 | 8.797 | 1.00 | 21.25 | C |
| ATOM | 1275 | CG2 | VAL | A | 91 | 8.463 | 24.309 | 10.528 | 1.00 | 21.36 | C |
| ATOM | 1279 | C | VAL | A | 91 | 10.344 | 25.938 | 8.411 | 1.00 | 18.60 | C |
| ATOM | 1280 | O | VAL | A | 91 | 11.184 | 25.738 | 7.532 | 1.00 | 19.96 | O |
| ATOM | 1281 | N | TYR | A | 92 | 10.632 | 26.589 | 9.547 | 1.00 | 18.11 | N |
| ATOM | 1283 | CA | TYR | A | 92 | 11.941 | 27.076 | 9.868 | 1.00 | 17.39 | C |
| ATOM | 1285 | CB | TYR | A | 92 | 11.880 | 28.546 | 10.256 | 1.00 | 16.87 | C |
| ATOM | 1288 | CG | TYR | A | 92 | 11.827 | 29.420 | 9.027 | 1.00 | 17.86 | C |
| ATOM | 1289 | CD1 | TYR | A | 92 | 12.989 | 29.758 | 8.379 | 1.00 | 16.53 | C |
| ATOM | 1291 | CE1 | TYR | A | 92 | 12.993 | 30.516 | 7.233 | 1.00 | 20.55 | C |
| ATOM | 1293 | CZ | TYR | A | 92 | 11.793 | 30.963 | 6.717 | 1.00 | 23.54 | C |
| ATOM | 1294 | OH | TYR | A | 92 | 11.862 | 31.737 | 5.549 | 1.00 | 25.77 | O |
| ATOM | 1296 | CE2 | TYR | A | 92 | 10.619 | 30.672 | 7.325 | 1.00 | 19.89 | C |
| ATOM | 1298 | CD2 | TYR | A | 92 | 10.626 | 29.840 | 8.507 | 1.00 | 20.04 | C |
| ATOM | 1300 | C | TYR | A | 92 | 12.542 | 26.375 | 11.099 | 1.00 | 14.56 | C |
| ATOM | 1301 | O | TYR | A | 92 | 11.856 | 26.154 | 12.042 | 1.00 | 14.48 | O |
| ATOM | 1302 | N | GLY | A | 93 | 13.824 | 26.133 | 11.058 | 1.00 | 13.49 | N |
| ATOM | 1304 | CA | GLY | A | 93 | 14.547 | 25.546 | 12.182 | 1.00 | 15.74 | C |
| ATOM | 1307 | C | GLY | A | 93 | 15.350 | 26.635 | 12.819 | 1.00 | 14.86 | C |
| ATOM | 1308 | O | GLY | A | 93 | 15.203 | 27.819 | 12.473 | 1.00 | 17.02 | O |
| ATOM | 1309 | N | VAL | A | 94 | 16.231 | 26.278 | 13.759 | 1.00 | 14.32 | N |
| ATOM | 1311 | CA | VAL | A | 94 | 16.981 | 27.306 | 14.421 | 1.00 | 14.34 | C |
| ATOM | 1313 | CB | VAL | A | 94 | 17.654 | 26.753 | 15.712 | 1.00 | 13.59 | C |
| ATOM | 1315 | CG1 | VAL | A | 94 | 18.263 | 27.876 | 16.515 | 1.00 | 13.33 | C |
| ATOM | 1319 | CG2 | VAL | A | 94 | 16.633 | 26.043 | 16.538 | 1.00 | 13.90 | C |
| ATOM | 1323 | C | VAL | A | 94 | 18.010 | 28.055 | 13.577 | 1.00 | 14.53 | C |
| ATOM | 1324 | O | VAL | A | 94 | 18.196 | 29.258 | 13.779 | 1.00 | 16.71 | O |
| ATOM | 1325 | N | ALA | A | 95 | 18.724 | 27.356 | 12.692 | 1.00 | 14.24 | N |
| ATOM | 1327 | CA | ALA | A | 95 | 19.859 | 27.839 | 11.990 | 1.00 | 14.00 | C |
| ATOM | 1329 | CB | ALA | A | 95 | 21.100 | 27.227 | 12.574 | 1.00 | 14.43 | C |
| ATOM | 1333 | C | ALA | A | 95 | 19.757 | 27.491 | 10.498 | 1.00 | 15.52 | C |
| ATOM | 1334 | O | ALA | A | 95 | 20.476 | 26.644 | 9.954 | 1.00 | 13.66 | O |
| ATOM | 1335 | N | PRO | A | 96 | 18.847 | 28.184 | 9.840 | 1.00 | 15.59 | N |
| ATOM | 1336 | CA | PRO | A | 96 | 18.487 | 27.876 | 8.443 | 1.00 | 16.93 | C |
| ATOM | 1338 | CB | PRO | A | 96 | 17.330 | 28.851 | 8.170 | 1.00 | 17.23 | C |
| ATOM | 1341 | CG | PRO | A | 96 | 17.628 | 29.986 | 9.086 | 1.00 | 16.22 | C |
| ATOM | 1344 | CD | PRO | A | 96 | 18.078 | 29.307 | 10.383 | 1.00 | 13.71 | C |
| ATOM | 1347 | C | PRO | A | 96 | 19.598 | 28.049 | 7.403 | 1.00 | 17.82 | C |
| ATOM | 1348 | O | PRO | A | 96 | 19.478 | 27.477 | 6.306 | 1.00 | 16.77 | O |
| ATOM | 1349 | N | GLN | A | 97 | 20.664 | 28.772 | 7.719 | 1.00 | 17.73 | N |
| ATOM | 1351 | CA | GLN | A | 97 | 21.812 | 28.891 | 6.826 | 1.00 | 18.02 | C |
| ATOM | 1353 | CB | GLN | A | 97 | 22.374 | 30.341 | 6.726 | 1.00 | 18.03 | C |
| ATOM | 1356 | CG | GLN | A | 97 | 21.509 | 31.218 | 5.783 | 1.00 | 22.97 | C |
| ATOM | 1359 | CD | GLN | A | 97 | 20.220 | 31.715 | 6.401 | 1.00 | 23.17 | C |
| ATOM | 1360 | OE1 | GLN | A | 97 | 20.303 | 32.467 | 7.345 | 1.00 | 27.41 | O |
| ATOM | 1361 | NE2 | GLN | A | 97 | 19.016 | 31.311 | 5.865 | 1.00 | 26.08 | N |
| ATOM | 1364 | C | GLN | A | 97 | 22.901 | 27.903 | 7.080 | 1.00 | 17.35 | C |
| ATOM | 1365 | O | GLN | A | 97 | 23.900 | 27.913 | 6.351 | 1.00 | 17.54 | O |
| ATOM | 1366 | N | ALA | A | 98 | 22.763 | 27.057 | 8.125 | 1.00 | 15.56 | N |
| ATOM | 1368 | CA | ALA | A | 98 | 23.794 | 26.040 | 8.361 | 1.00 | 16.07 | C |
| ATOM | 1370 | CB | ALA | A | 98 | 23.615 | 25.387 | 9.738 | 1.00 | 15.36 | C |
| ATOM | 1374 | C | ALA | A | 98 | 23.657 | 24.997 | 7.256 | 1.00 | 15.80 | C |
| ATOM | 1375 | O | ALA | A | 98 | 22.610 | 24.906 | 6.610 | 1.00 | 18.34 | O |
| ATOM | 1376 | N | LYS | A | 99 | 24.683 | 24.195 | 7.082 | 1.00 | 16.19 | N |
| ATOM | 1378 | CA | LYS | A | 99 | 24.670 | 23.108 | 6.118 | 1.00 | 15.45 | C |
| ATOM | 1380 | CB | LYS | A | 99 | 25.882 | 23.152 | 5.268 | 1.00 | 16.64 | C |
| ATOM | 1383 | CG | LYS | A | 99 | 25.789 | 24.264 | 4.222 | 1.00 | 17.86 | C |
| ATOM | 1386 | CD | LYS | A | 99 | 24.616 | 24.101 | 3.322 | 1.00 | 22.94 | C |
| ATOM | 1389 | CE | LYS | A | 99 | 24.844 | 25.062 | 2.185 | 1.00 | 28.36 | C |
| ATOM | 1392 | NZ | LYS | A | 99 | 23.614 | 25.181 | 1.383 | 1.00 | 28.94 | N |
| ATOM | 1396 | C | LYS | A | 99 | 24.604 | 21.759 | 6.887 | 1.00 | 15.54 | C |
| ATOM | 1397 | O | LYS | A | 99 | 25.012 | 21.684 | 8.019 | 1.00 | 15.10 | O |
| ATOM | 1398 | N | LEU | A | 100 | 24.136 | 20.742 | 6.185 | 1.00 | 14.73 | N |
| ATOM | 1400 | CA | LEU | A | 100 | 23.801 | 19.460 | 6.791 | 1.00 | 15.28 | C |
| ATOM | 1402 | CB | LEU | A | 100 | 22.361 | 19.131 | 6.489 | 1.00 | 14.80 | C |
| ATOM | 1405 | CG | LEU | A | 100 | 21.852 | 17.724 | 6.719 | 1.00 | 16.65 | C |
| ATOM | 1407 | CD1 | LEU | A | 100 | 21.751 | 17.484 | 8.242 | 1.00 | 17.43 | C |
| ATOM | 1411 | CD2 | LEU | A | 100 | 20.500 | 17.473 | 6.155 | 1.00 | 17.01 | C |
| ATOM | 1415 | C | LEU | A | 100 | 24.743 | 18.373 | 6.336 | 1.00 | 15.64 | C |
| ATOM | 1416 | O | LEU | A | 100 | 25.114 | 18.290 | 5.154 | 1.00 | 17.60 | O |
| ATOM | 1417 | N | TRP | A | 101 | 25.206 | 17.566 | 7.298 | 1.00 | 15.09 | N |

APPENDIX 1-continued

| ATOM | 1419 | CA | TRP | A | 101 | 25.895 | 16.350 | 6.942 | 1.00 | 15.10 | C |
|---|---|---|---|---|---|---|---|---|---|---|---|
| ATOM | 1421 | CB | TRP | A | 101 | 27.265 | 16.234 | 7.534 | 1.00 | 14.66 | C |
| ATOM | 1424 | CG | TRP | A | 101 | 28.408 | 17.171 | 7.076 | 1.00 | 13.68 | C |
| ATOM | 1425 | CD1 | TRP | A | 101 | 28.342 | 18.164 | 6.137 | 1.00 | 14.24 | C |
| ATOM | 1427 | NE1 | TRP | A | 101 | 29.575 | 18.741 | 5.956 | 1.00 | 14.73 | N |
| ATOM | 1429 | CE2 | TRP | A | 101 | 30.465 | 18.110 | 6.770 | 1.00 | 14.20 | C |
| ATOM | 1430 | CD2 | TRP | A | 101 | 29.751 | 17.123 | 7.498 | 1.00 | 15.01 | C |
| ATOM | 1431 | CE3 | TRP | A | 101 | 30.470 | 16.329 | 8.413 | 1.00 | 15.44 | C |
| ATOM | 1433 | CZ3 | TRP | A | 101 | 31.791 | 16.598 | 8.605 | 1.00 | 14.31 | C |
| ATOM | 1435 | CH2 | TRP | A | 101 | 32.451 | 17.587 | 7.845 | 1.00 | 15.17 | C |
| ATOM | 1437 | CZ2 | TRP | A | 101 | 31.780 | 18.363 | 6.977 | 1.00 | 14.09 | C |
| ATOM | 1439 | C | TRP | A | 101 | 24.932 | 15.267 | 7.451 | 1.00 | 16.46 | C |
| ATOM | 1440 | O | TRP | A | 101 | 24.830 | 15.022 | 8.675 | 1.00 | 14.81 | O |
| ATOM | 1441 | N | ALA | A | 102 | 24.250 | 14.579 | 6.534 | 1.00 | 14.78 | N |
| ATOM | 1443 | CA | ALA | A | 102 | 23.255 | 13.610 | 6.910 | 1.00 | 15.54 | C |
| ATOM | 1445 | CB | ALA | A | 102 | 22.086 | 13.639 | 5.973 | 1.00 | 16.18 | C |
| ATOM | 1449 | C | ALA | A | 102 | 23.897 | 12.221 | 6.941 | 1.00 | 15.83 | C |
| ATOM | 1450 | O | ALA | A | 102 | 24.187 | 11.661 | 5.898 | 1.00 | 15.17 | O |
| ATOM | 1451 | N | TYR | A | 103 | 24.148 | 11.692 | 8.140 | 1.00 | 14.35 | N |
| ATOM | 1453 | CA | TYR | A | 103 | 24.797 | 10.400 | 8.290 | 1.00 | 14.35 | C |
| ATOM | 1455 | CB | TYR | A | 103 | 25.985 | 10.493 | 9.225 | 1.00 | 13.92 | C |
| ATOM | 1458 | CG | TYR | A | 103 | 27.247 | 11.147 | 8.697 | 1.00 | 13.29 | C |
| ATOM | 1459 | CD1 | TYR | A | 103 | 27.275 | 11.938 | 7.550 | 1.00 | 14.70 | C |
| ATOM | 1461 | CE1 | TYR | A | 103 | 28.455 | 12.512 | 7.113 | 1.00 | 14.99 | C |
| ATOM | 1463 | CZ | TYR | A | 103 | 29.587 | 12.335 | 7.783 | 1.00 | 13.42 | C |
| ATOM | 1464 | OH | TYR | A | 103 | 30.820 | 12.886 | 7.417 | 1.00 | 17.55 | O |
| ATOM | 1466 | CE2 | TYR | A | 103 | 29.608 | 11.561 | 8.961 | 1.00 | 11.55 | C |
| ATOM | 1468 | CD2 | TYR | A | 103 | 28.445 | 10.996 | 9.399 | 1.00 | 12.45 | C |
| ATOM | 1470 | C | TYR | A | 103 | 23.813 | 9.419 | 8.860 | 1.00 | 13.70 | C |
| ATOM | 1471 | O | TYR | A | 103 | 23.336 | 9.583 | 9.966 | 1.00 | 13.01 | O |
| ATOM | 1472 | N | LYS | A | 104 | 23.490 | 8.383 | 8.101 | 1.00 | 13.67 | N |
| ATOM | 1474 | CA | LYS | A | 104 | 22.524 | 7.385 | 8.564 | 1.00 | 12.46 | C |
| ATOM | 1476 | CB | LYS | A | 104 | 21.773 | 6.738 | 7.407 | 1.00 | 14.90 | C |
| ATOM | 1479 | CG | LYS | A | 104 | 20.789 | 5.718 | 7.815 | 1.00 | 15.07 | C |
| ATOM | 1482 | CD | LYS | A | 104 | 19.991 | 5.144 | 6.616 | 1.00 | 14.19 | C |
| ATOM | 1485 | CE | LYS | A | 104 | 18.751 | 4.402 | 7.036 | 1.00 | 17.35 | C |
| ATOM | 1488 | NZ | LYS | A | 104 | 18.027 | 3.784 | 5.831 | 1.00 | 15.18 | N |
| ATOM | 1492 | C | LYS | A | 104 | 23.249 | 6.327 | 9.362 | 1.00 | 14.29 | C |
| ATOM | 1493 | O | LYS | A | 104 | 24.138 | 5.652 | 8.836 | 1.00 | 14.08 | O |
| ATOM | 1494 | N | VAL | A | 105 | 22.893 | 6.215 | 10.645 | 1.00 | 12.75 | N |
| ATOM | 1496 | CA | VAL | A | 105 | 23.513 | 5.287 | 11.592 | 1.00 | 13.70 | C |
| ATOM | 1498 | CB | VAL | A | 105 | 24.301 | 6.043 | 12.684 | 1.00 | 13.12 | C |
| ATOM | 1500 | CG1 | VAL | A | 105 | 25.244 | 6.961 | 12.010 | 1.00 | 14.29 | C |
| ATOM | 1504 | CG2 | VAL | A | 105 | 23.388 | 6.804 | 13.578 | 1.00 | 12.47 | C |
| ATOM | 1508 | C | VAL | A | 105 | 22.491 | 4.405 | 12.292 | 1.00 | 13.35 | C |
| ATOM | 1509 | O | VAL | A | 105 | 22.851 | 3.501 | 13.036 | 1.00 | 14.40 | O |
| ATOM | 1510 | N | LEU | A | 106 | 21.218 | 4.733 | 12.140 | 1.00 | 13.80 | N |
| ATOM | 1512 | CA | LEU | A | 106 | 20.133 | 3.912 | 12.678 | 1.00 | 15.31 | C |
| ATOM | 1514 | CB | LEU | A | 106 | 19.165 | 4.715 | 13.533 | 1.00 | 14.78 | C |
| ATOM | 1517 | CG | LEU | A | 106 | 19.820 | 5.395 | 14.752 | 1.00 | 14.84 | C |
| ATOM | 1519 | CD1 | LEU | A | 106 | 18.745 | 6.216 | 15.434 | 1.00 | 13.44 | C |
| ATOM | 1523 | CD2 | LEU | A | 106 | 20.365 | 4.281 | 15.645 | 1.00 | 13.80 | C |
| ATOM | 1527 | C | LEU | A | 106 | 19.328 | 3.395 | 11.488 | 1.00 | 16.71 | C |
| ATOM | 1528 | O | LEU | A | 106 | 19.217 | 4.083 | 10.457 | 1.00 | 14.73 | O |
| ATOM | 1529 | N | GLY | A | 107 | 18.812 | 2.184 | 11.617 | 1.00 | 18.94 | N |
| ATOM | 1531 | CA | GLY | A | 107 | 17.950 | 1.629 | 10.581 | 1.00 | 20.89 | C |
| ATOM | 1534 | C | GLY | A | 107 | 16.534 | 2.176 | 10.597 | 1.00 | 22.18 | C |
| ATOM | 1535 | O | GLY | A | 107 | 16.136 | 3.087 | 11.335 | 1.00 | 21.65 | O |
| ATOM | 1536 | N | ASP | A | 108 | 15.714 | 1.570 | 9.755 | 1.00 | 24.79 | N |
| ATOM | 1538 | CA | ASP | A | 108 | 14.419 | 2.139 | 9.442 | 1.00 | 25.79 | C |
| ATOM | 1540 | CB | ASP | A | 108 | 13.946 | 1.584 | 8.117 | 1.00 | 26.09 | C |
| ATOM | 1543 | CG | ASP | A | 108 | 14.971 | 1.774 | 7.022 | 1.00 | 28.51 | C |
| ATOM | 1544 | OD1 | ASP | A | 108 | 15.795 | 2.721 | 7.082 | 1.00 | 27.80 | O |
| ATOM | 1545 | OD2 | ASP | A | 108 | 15.020 | 1.038 | 6.025 | 1.00 | 30.77 | O |
| ATOM | 1546 | C | ASP | A | 108 | 13.331 | 1.997 | 10.489 | 1.00 | 26.41 | C |
| ATOM | 1547 | O | ASP | A | 108 | 12.229 | 2.535 | 10.294 | 1.00 | 26.78 | O |
| ATOM | 1548 | N | ASN | A | 109 | 13.629 | 1.262 | 11.566 | 1.00 | 26.19 | N |
| ATOM | 1550 | CA | ASN | A | 109 | 12.751 | 1.172 | 12.719 | 1.00 | 25.53 | C |
| ATOM | 1552 | CB | ASN | A | 109 | 12.399 | −0.264 | 13.022 | 1.00 | 26.84 | C |
| ATOM | 1555 | CG | ASN | A | 109 | 11.599 | −0.920 | 11.863 | 1.00 | 30.82 | C |
| ATOM | 1556 | OD1 | ASN | A | 109 | 10.606 | −0.338 | 11.353 | 1.00 | 35.24 | O |
| ATOM | 1557 | ND2 | ASN | A | 109 | 12.038 | −2.093 | 11.429 | 1.00 | 36.51 | N |
| ATOM | 1560 | C | ASN | A | 109 | 13.340 | 1.943 | 13.933 | 1.00 | 24.23 | C |
| ATOM | 1561 | O | ASN | A | 109 | 12.941 | 1.773 | 15.071 | 1.00 | 23.68 | O |
| ATOM | 1562 | N | GLY | A | 110 | 14.325 | 2.774 | 13.652 | 1.00 | 22.01 | N |
| ATOM | 1564 | CA | GLY | A | 110 | 14.823 | 3.684 | 14.685 | 1.00 | 20.58 | C |
| ATOM | 1567 | C | GLY | A | 110 | 15.783 | 3.001 | 15.656 | 1.00 | 18.79 | C |
| ATOM | 1568 | O | GLY | A | 110 | 15.989 | 3.492 | 16.797 | 1.00 | 18.63 | O |
| ATOM | 1569 | N | SER | A | 111 | 16.373 | 1.885 | 15.208 | 1.00 | 16.52 | N |
| ATOM | 1571 | CA | SER | A | 111 | 17.377 | 1.225 | 16.057 | 1.00 | 17.48 | C |

APPENDIX 1-continued

| | | | | | | | | | | | |
|---|---|---|---|---|---|---|---|---|---|---|---|
| ATOM | 1573 | CB | SER | A | 111 | 16.805 | 0.002 | 16.752 | 1.00 | 18.93 | C |
| ATOM | 1576 | OG | SER | A | 111 | 16.663 | −1.046 | 15.856 | 1.00 | 20.57 | O |
| ATOM | 1578 | C | SER | A | 111 | 18.625 | 0.916 | 15.250 | 1.00 | 15.84 | C |
| ATOM | 1579 | O | SER | A | 111 | 18.585 | 0.814 | 14.022 | 1.00 | 15.08 | O |
| ATOM | 1580 | N | GLY | A | 112 | 19.767 | 0.761 | 15.913 | 1.00 | 15.46 | N |
| ATOM | 1582 | CA | GLY | A | 112 | 20.991 | 0.537 | 15.198 | 1.00 | 14.74 | C |
| ATOM | 1585 | C | GLY | A | 112 | 22.080 | −0.033 | 16.063 | 1.00 | 13.99 | C |
| ATOM | 1586 | O | GLY | A | 112 | 21.852 | −0.365 | 17.219 | 1.00 | 12.44 | O |
| ATOM | 1587 | N | TYR | A | 113 | 23.229 | −0.171 | 15.431 | 1.00 | 13.65 | N |
| ATOM | 1589 | CA | TYR | A | 113 | 24.372 | −0.836 | 16.000 | 1.00 | 14.69 | C |
| ATOM | 1591 | CB | TYR | A | 113 | 24.992 | −1.754 | 14.982 | 1.00 | 14.83 | C |
| ATOM | 1594 | CG | TYR | A | 113 | 24.139 | −2.928 | 14.627 | 1.00 | 16.70 | C |
| ATOM | 1595 | CD1 | TYR | A | 113 | 24.217 | −4.098 | 15.339 | 1.00 | 18.38 | C |
| ATOM | 1597 | CE1 | TYR | A | 113 | 23.392 | −5.213 | 14.997 | 1.00 | 18.28 | C |
| ATOM | 1599 | CZ | TYR | A | 113 | 22.516 | −5.121 | 13.926 | 1.00 | 19.64 | C |
| ATOM | 1600 | OH | TYR | A | 113 | 21.730 | −6.214 | 13.573 | 1.00 | 20.11 | O |
| ATOM | 1602 | CE2 | TYR | A | 113 | 22.465 | −3.958 | 13.189 | 1.00 | 19.66 | C |
| ATOM | 1604 | CD2 | TYR | A | 113 | 23.269 | −2.871 | 13.557 | 1.00 | 15.59 | C |
| ATOM | 1606 | C | TYR | A | 113 | 25.441 | 0.094 | 16.471 | 1.00 | 13.86 | C |
| ATOM | 1607 | O | TYR | A | 113 | 25.825 | 1.019 | 15.758 | 1.00 | 14.60 | O |
| ATOM | 1608 | N | SER | A | 114 | 25.880 | −0.113 | 17.706 | 1.00 | 13.30 | N |
| ATOM | 1610 | CA | SER | A | 114 | 26.958 | 0.655 | 18.290 | 1.00 | 13.35 | C |
| ATOM | 1612 | CB | SER | A | 114 | 27.507 | −0.213 | 19.432 | 1.00 | 15.78 | C |
| ATOM | 1615 | OG | SER | A | 114 | 28.722 | 0.270 | 19.995 | 1.00 | 14.15 | O |
| ATOM | 1617 | C | SER | A | 114 | 28.125 | 0.916 | 17.339 | 1.00 | 14.05 | C |
| ATOM | 1618 | O | SER | A | 114 | 28.615 | 2.023 | 17.226 | 1.00 | 13.89 | O |
| ATOM | 1619 | N | ASP | A | 115 | 28.581 | −0.139 | 16.665 | 1.00 | 13.29 | N |
| ATOM | 1621 | CA | ASP | A | 115 | 29.724 | 0.014 | 15.754 | 1.00 | 14.72 | C |
| ATOM | 1623 | CB | AASP | A | 115 | 30.159 | −1.299 | 15.125 | 0.50 | 16.85 | C |
| ATOM | 1624 | CB | BASP | A | 115 | 29.949 | −1.288 | 14.969 | 0.50 | 15.71 | C |
| ATOM | 1629 | CG | AASP | A | 115 | 29.100 | −1.900 | 14.308 | 0.50 | 20.25 | C |
| ATOM | 1630 | CG | BASP | A | 115 | 30.701 | −2.324 | 15.752 | 0.50 | 16.91 | C |
| ATOM | 1631 | OD1 | AASP | A | 115 | 28.555 | −1.177 | 13.460 | 0.50 | 32.11 | O |
| ATOM | 1632 | OD1 | BASP | A | 115 | 31.693 | −1.951 | 16.379 | 0.50 | 24.07 | O |
| ATOM | 1633 | OD2 | AASP | A | 115 | 28.717 | −3.057 | 14.477 | 0.50 | 33.25 | O |
| ATOM | 1634 | OD2 | BASP | A | 115 | 30.401 | −3.501 | 15.764 | 0.50 | 20.69 | O |
| ATOM | 1635 | C | ASP | A | 115 | 29.511 | 1.034 | 14.682 | 1.00 | 13.31 | C |
| ATOM | 1636 | O | ASP | A | 115 | 30.488 | 1.671 | 14.268 | 1.00 | 13.00 | O |
| ATOM | 1637 | N | ASP | A | 116 | 28.292 | 1.098 | 14.156 | 1.00 | 12.95 | N |
| ATOM | 1639 | CA | ASP | A | 116 | 27.982 | 1.996 | 13.046 | 1.00 | 13.15 | C |
| ATOM | 1641 | CB | ASP | A | 116 | 26.618 | 1.685 | 12.446 | 1.00 | 14.36 | C |
| ATOM | 1644 | CG | ASP | A | 116 | 26.506 | 0.299 | 11.819 | 1.00 | 14.39 | C |
| ATOM | 1645 | OD1 | ASP | A | 116 | 27.509 | −0.378 | 11.592 | 1.00 | 13.15 | O |
| ATOM | 1646 | OD2 | ASP | A | 116 | 25.408 | −0.179 | 11.584 | 1.00 | 13.28 | O |
| ATOM | 1647 | C | ASP | A | 116 | 28.001 | 3.437 | 13.581 | 1.00 | 13.01 | C |
| ATOM | 1648 | O | ASP | A | 116 | 28.529 | 4.354 | 12.937 | 1.00 | 13.99 | O |
| ATOM | 1649 | N | ILE | A | 117 | 27.409 | 3.644 | 14.748 | 1.00 | 13.05 | N |
| ATOM | 1651 | CA | ILE | A | 117 | 27.404 | 4.952 | 15.339 | 1.00 | 12.04 | C |
| ATOM | 1653 | CB | ILE | A | 117 | 26.518 | 4.961 | 16.572 | 1.00 | 12.89 | C |
| ATOM | 1655 | CG1 | ILE | A | 117 | 25.034 | 4.744 | 16.168 | 1.00 | 17.41 | C |
| ATOM | 1658 | CD1 | ILE | A | 117 | 24.279 | 3.948 | 17.085 | 1.00 | 21.55 | C |
| ATOM | 1662 | CG2 | ILE | A | 117 | 26.715 | 6.288 | 17.378 | 1.00 | 15.14 | C |
| ATOM | 1666 | C | ILE | A | 117 | 28.813 | 5.403 | 15.623 | 1.00 | 11.86 | C |
| ATOM | 1667 | O | ILE | A | 117 | 29.195 | 6.548 | 15.321 | 1.00 | 12.61 | O |
| ATOM | 1668 | N | ALA | A | 118 | 29.609 | 4.532 | 16.227 | 1.00 | 10.45 | N |
| ATOM | 1670 | CA | ALA | A | 118 | 30.981 | 4.891 | 16.519 | 1.00 | 11.56 | C |
| ATOM | 1672 | CB | ALA | A | 118 | 31.649 | 3.800 | 17.353 | 1.00 | 11.97 | C |
| ATOM | 1676 | C | ALA | A | 118 | 31.786 | 5.248 | 15.273 | 1.00 | 11.35 | C |
| ATOM | 1677 | O | ALA | A | 118 | 32.511 | 6.241 | 15.232 | 1.00 | 10.56 | O |
| ATOM | 1678 | N | ALA | A | 119 | 31.597 | 4.459 | 14.253 | 1.00 | 11.09 | N |
| ATOM | 1680 | CA | ALA | A | 119 | 32.298 | 4.693 | 13.010 | 1.00 | 10.91 | C |
| ATOM | 1682 | CB | ALA | A | 119 | 32.030 | 3.600 | 12.104 | 1.00 | 11.91 | C |
| ATOM | 1686 | C | ALA | A | 119 | 31.875 | 6.029 | 12.430 | 1.00 | 10.50 | C |
| ATOM | 1687 | O | ALA | A | 119 | 32.721 | 6.808 | 11.942 | 1.00 | 12.46 | O |
| ATOM | 1688 | N | ALA | A | 120 | 30.589 | 6.342 | 12.539 | 1.00 | 11.95 | N |
| ATOM | 1690 | CA | ALA | A | 120 | 30.079 | 7.579 | 12.001 | 1.00 | 11.18 | C |
| ATOM | 1692 | CB | ALA | A | 120 | 28.626 | 7.575 | 12.034 | 1.00 | 11.63 | C |
| ATOM | 1696 | C | ALA | A | 120 | 30.643 | 8.813 | 12.743 | 1.00 | 11.63 | C |
| ATOM | 1697 | O | ALA | A | 120 | 31.033 | 9.799 | 12.104 | 1.00 | 11.85 | O |
| ATOM | 1698 | N | ILE | A | 121 | 30.708 | 8.753 | 14.070 | 1.00 | 10.33 | N |
| ATOM | 1700 | CA | ILE | A | 121 | 31.291 | 9.848 | 14.892 | 1.00 | 10.58 | C |
| ATOM | 1702 | CB | ILE | A | 121 | 31.215 | 9.481 | 16.379 | 1.00 | 11.12 | C |
| ATOM | 1704 | CG1 | ILE | A | 121 | 29.768 | 9.320 | 16.750 | 1.00 | 11.01 | C |
| ATOM | 1707 | CD1 | ILE | A | 121 | 29.566 | 8.668 | 18.128 | 1.00 | 11.36 | C |
| ATOM | 1711 | CG2 | ILE | A | 121 | 31.860 | 10.543 | 17.229 | 1.00 | 12.83 | C |
| ATOM | 1715 | C | ILE | A | 121 | 32.749 | 10.129 | 14.510 | 1.00 | 11.68 | C |
| ATOM | 1716 | O | ILE | A | 121 | 33.158 | 11.259 | 14.287 | 1.00 | 12.00 | O |
| ATOM | 1717 | N | ARG | A | 122 | 33.536 | 9.055 | 14.448 | 1.00 | 11.70 | N |
| ATOM | 1719 | CA | ARG | A | 122 | 34.929 | 9.171 | 14.046 | 1.00 | 13.86 | C |
| ATOM | 1721 | CB | ARG | A | 122 | 35.603 | 7.810 | 14.114 | 1.00 | 14.57 | C |

APPENDIX 1-continued

| ATOM | 1724 | CG | ARG | A | 122 | 35.715 | 7.320 | 15.531 | 1.00 | 14.77 | C |
|---|---|---|---|---|---|---|---|---|---|---|---|
| ATOM | 1727 | CD | ARG | A | 122 | 36.384 | 5.975 | 15.679 | 1.00 | 18.79 | C |
| ATOM | 1730 | NE | ARG | A | 122 | 36.784 | 5.757 | 17.048 | 1.00 | 21.92 | N |
| ATOM | 1732 | CZ | ARG | A | 122 | 37.945 | 6.112 | 17.577 | 1.00 | 22.62 | C |
| ATOM | 1733 | NH1 | ARG | A | 122 | 38.894 | 6.640 | 16.838 | 1.00 | 20.73 | N |
| ATOM | 1736 | NH2 | ARG | A | 122 | 38.178 | 5.850 | 18.857 | 1.00 | 29.11 | N |
| ATOM | 1739 | C | ARG | A | 122 | 35.088 | 9.760 | 12.636 | 1.00 | 14.45 | C |
| ATOM | 1740 | O | ARG | A | 122 | 35.992 | 10.563 | 12.389 | 1.00 | 13.33 | O |
| ATOM | 1741 | N | HIS | A | 123 | 34.198 | 9.348 | 11.743 | 1.00 | 12.96 | N |
| ATOM | 1743 | CA | HIS | A | 123 | 34.231 | 9.828 | 10.385 | 1.00 | 14.40 | C |
| ATOM | 1745 | CB | HIS | A | 123 | 33.324 | 9.001 | 9.522 | 1.00 | 14.46 | C |
| ATOM | 1748 | CG | HIS | A | 123 | 33.390 | 9.347 | 8.065 | 1.00 | 17.57 | C |
| ATOM | 1749 | ND1 | HIS | A | 123 | 34.358 | 8.843 | 7.224 | 1.00 | 26.34 | N |
| ATOM | 1751 | CE1 | HIS | A | 123 | 34.183 | 9.333 | 6.005 | 1.00 | 26.65 | C |
| ATOM | 1753 | NE2 | HIS | A | 123 | 33.120 | 10.115 | 6.015 | 1.00 | 23.02 | N |
| ATOM | 1755 | CD2 | HIS | A | 123 | 32.596 | 10.125 | 7.299 | 1.00 | 22.31 | C |
| ATOM | 1757 | C | HIS | A | 123 | 33.913 | 11.345 | 10.332 | 1.00 | 15.58 | C |
| ATOM | 1758 | O | HIS | A | 123 | 34.587 | 12.095 | 9.658 | 1.00 | 14.13 | O |
| ATOM | 1759 | N | VAL | A | 124 | 32.914 | 11.801 | 11.081 | 1.00 | 13.58 | N |
| ATOM | 1761 | CA | VAL | A | 124 | 32.701 | 13.233 | 11.195 | 1.00 | 13.94 | C |
| ATOM | 1763 | CB | VAL | A | 124 | 31.583 | 13.598 | 12.235 | 1.00 | 13.67 | C |
| ATOM | 1765 | CG1 | VAL | A | 124 | 31.476 | 15.111 | 12.408 | 1.00 | 11.98 | C |
| ATOM | 1769 | CG2 | VAL | A | 124 | 30.258 | 13.019 | 11.847 | 1.00 | 14.52 | C |
| ATOM | 1773 | C | VAL | A | 124 | 33.980 | 13.971 | 11.580 | 1.00 | 12.11 | C |
| ATOM | 1774 | O | VAL | A | 124 | 34.323 | 14.973 | 10.938 | 1.00 | 13.19 | O |
| ATOM | 1775 | N | ALA | A | 125 | 34.672 | 13.495 | 12.604 | 1.00 | 12.61 | N |
| ATOM | 1777 | CA | ALA | A | 125 | 35.875 | 14.123 | 13.121 | 1.00 | 12.03 | C |
| ATOM | 1779 | CB | ALA | A | 125 | 36.351 | 13.398 | 14.322 | 1.00 | 11.98 | C |
| ATOM | 1783 | C | ALA | A | 125 | 36.972 | 14.158 | 12.062 | 1.00 | 13.52 | C |
| ATOM | 1784 | O | ALA | A | 125 | 37.610 | 15.186 | 11.838 | 1.00 | 13.20 | O |
| ATOM | 1785 | N | ASP | A | 126 | 37.081 | 13.059 | 11.312 | 1.00 | 13.79 | N |
| ATOM | 1787 | CA | ASP | A | 126 | 38.087 | 12.980 | 10.268 | 1.00 | 15.94 | C |
| ATOM | 1789 | CB | ASP | A | 126 | 38.180 | 11.566 | 9.743 | 1.00 | 16.11 | C |
| ATOM | 1792 | CG | ASP | A | 126 | 38.895 | 10.635 | 10.677 | 1.00 | 16.70 | C |
| ATOM | 1793 | OD1 | ASP | A | 126 | 39.620 | 11.075 | 11.580 | 1.00 | 17.85 | O |
| ATOM | 1794 | OD2 | ASP | A | 126 | 38.795 | 9.393 | 10.586 | 1.00 | 17.09 | O |
| ATOM | 1795 | C | ASP | A | 126 | 37.736 | 13.933 | 9.133 | 1.00 | 16.71 | C |
| ATOM | 1796 | O | ASP | A | 126 | 38.604 | 14.612 | 8.602 | 1.00 | 17.22 | O |
| ATOM | 1797 | N | GLU | A | 127 | 36.465 | 14.027 | 8.798 | 1.00 | 16.48 | N |
| ATOM | 1799 | CA | GLU | A | 127 | 36.033 | 14.934 | 7.759 | 1.00 | 17.08 | C |
| ATOM | 1801 | CB | GLU | A | 127 | 34.580 | 14.723 | 7.386 | 1.00 | 17.14 | C |
| ATOM | 1804 | CG | GLU | A | 127 | 34.319 | 13.431 | 6.618 | 1.00 | 18.23 | C |
| ATOM | 1807 | CD | GLU | A | 127 | 34.875 | 13.485 | 5.205 | 1.00 | 23.17 | C |
| ATOM | 1808 | OE1 | GLU | A | 127 | 34.333 | 14.250 | 4.412 | 1.00 | 22.57 | O |
| ATOM | 1809 | OE2 | GLU | A | 127 | 35.887 | 12.809 | 4.967 | 1.00 | 25.80 | O |
| ATOM | 1810 | C | GLU | A | 127 | 36.256 | 16.370 | 8.204 | 1.00 | 18.24 | C |
| ATOM | 1811 | O | GLU | A | 127 | 36.634 | 17.255 | 7.393 | 1.00 | 17.10 | O |
| ATOM | 1812 | N | ALA | A | 128 | 35.969 | 16.626 | 9.465 | 1.00 | 16.20 | N |
| ATOM | 1814 | CA | ALA | A | 128 | 36.165 | 17.979 | 10.000 | 1.00 | 17.01 | C |
| ATOM | 1816 | CB | ALA | A | 128 | 35.582 | 18.100 | 11.469 | 1.00 | 18.11 | C |
| ATOM | 1820 | C | ALA | A | 128 | 37.607 | 18.403 | 9.959 | 1.00 | 17.06 | C |
| ATOM | 1821 | O | ALA | A | 128 | 37.923 | 19.537 | 9.561 | 1.00 | 18.46 | O |
| ATOM | 1822 | N | SER | A | 129 | 38.496 | 17.519 | 10.360 | 1.00 | 17.73 | N |
| ATOM | 1824 | CA | SER | A | 129 | 39.896 | 17.869 | 10.334 | 1.00 | 19.04 | C |
| ATOM | 1826 | CB | SER | A | 129 | 40.735 | 16.796 | 10.996 | 1.00 | 19.88 | C |
| ATOM | 1829 | OG | SER | A | 129 | 40.289 | 15.493 | 10.649 | 1.00 | 28.54 | O |
| ATOM | 1831 | C | SER | A | 129 | 40.367 | 18.063 | 8.907 | 1.00 | 18.31 | C |
| ATOM | 1832 | O | SER | A | 129 | 41.158 | 18.968 | 8.641 | 1.00 | 19.92 | O |
| ATOM | 1833 | N | ARG | A | 130 | 39.927 | 17.209 | 8.003 | 1.00 | 17.50 | N |
| ATOM | 1835 | CA | ARG | A | 130 | 40.418 | 17.258 | 6.611 | 1.00 | 17.79 | C |
| ATOM | 1837 | CB | ARG | A | 130 | 39.938 | 16.052 | 5.802 | 1.00 | 17.78 | C |
| ATOM | 1840 | CG | ARG | A | 130 | 40.573 | 15.989 | 4.406 | 1.00 | 17.70 | C |
| ATOM | 1843 | CD | ARG | A | 130 | 40.048 | 14.864 | 3.632 | 1.00 | 18.82 | C |
| ATOM | 1846 | NE | ARG | A | 130 | 38.768 | 15.271 | 3.064 | 1.00 | 25.15 | N |
| ATOM | 1848 | CZ | ARG | A | 130 | 37.641 | 14.760 | 3.393 | 1.00 | 25.02 | C |
| ATOM | 1849 | NH1 | ARG | A | 130 | 37.620 | 13.808 | 4.337 | 1.00 | 26.77 | N |
| ATOM | 1852 | NH2 | ARG | A | 130 | 36.524 | 15.209 | 2.775 | 1.00 | 23.08 | N |
| ATOM | 1855 | C | ARG | A | 130 | 39.990 | 18.543 | 5.958 | 1.00 | 19.20 | C |
| ATOM | 1856 | O | ARG | A | 130 | 40.816 | 19.255 | 5.352 | 1.00 | 20.50 | O |
| ATOM | 1857 | N | THR | A | 131 | 38.740 | 18.915 | 6.155 | 1.00 | 18.72 | N |
| ATOM | 1859 | CA | THR | A | 131 | 38.127 | 20.089 | 5.461 | 1.00 | 19.43 | C |
| ATOM | 1861 | CB | THR | A | 131 | 36.673 | 19.866 | 5.244 | 1.00 | 20.43 | C |
| ATOM | 1863 | OG1 | THR | A | 131 | 35.973 | 19.754 | 6.517 | 1.00 | 18.62 | O |
| ATOM | 1865 | CG2 | THR | A | 131 | 36.421 | 18.548 | 4.449 | 1.00 | 22.94 | C |
| ATOM | 1869 | C | THR | A | 131 | 38.262 | 21.415 | 6.203 | 1.00 | 20.40 | C |
| ATOM | 1870 | O | THR | A | 131 | 37.906 | 22.461 | 5.657 | 1.00 | 20.95 | O |
| ATOM | 1871 | N | GLY | A | 132 | 38.758 | 21.356 | 7.431 | 1.00 | 18.57 | N |
| ATOM | 1873 | CA | GLY | A | 132 | 38.841 | 22.513 | 8.289 | 1.00 | 19.51 | C |
| ATOM | 1876 | C | GLY | A | 132 | 37.464 | 23.129 | 8.581 | 1.00 | 20.63 | C |
| ATOM | 1877 | O | GLY | A | 132 | 37.313 | 24.336 | 8.829 | 1.00 | 23.12 | O |

APPENDIX 1-continued

| ATOM | 1878 | N | SER | A | 133 | 36.442 | 22.287 | 8.646 | 1.00 | 18.55 | N |
|---|---|---|---|---|---|---|---|---|---|---|---|
| ATOM | 1880 | CA | SER | A | 133 | 35.094 | 22.754 | 8.904 | 1.00 | 18.11 | C |
| ATOM | 1882 | CB | SER | A | 133 | 34.080 | 21.819 | 8.260 | 1.00 | 18.42 | C |
| ATOM | 1885 | OG | SER | A | 133 | 34.242 | 21.666 | 6.844 | 1.00 | 21.03 | O |
| ATOM | 1887 | C | SER | A | 133 | 34.768 | 22.836 | 10.427 | 1.00 | 16.26 | C |
| ATOM | 1888 | O | SER | A | 133 | 35.348 | 22.145 | 11.284 | 1.00 | 15.54 | O |
| ATOM | 1889 | N | LYS | A | 134 | 33.798 | 23.687 | 10.720 | 1.00 | 16.27 | N |
| ATOM | 1891 | CA | LYS | A | 134 | 33.275 | 23.830 | 12.096 | 1.00 | 15.54 | C |
| ATOM | 1893 | CB | LYS | A | 134 | 32.921 | 25.274 | 12.419 | 1.00 | 15.50 | C |
| ATOM | 1896 | CG | LYS | A | 134 | 34.154 | 26.176 | 12.525 | 1.00 | 18.18 | C |
| ATOM | 1899 | CD | LYS | A | 134 | 33.819 | 27.647 | 12.502 | 1.00 | 25.94 | C |
| ATOM | 1902 | CE | LYS | A | 134 | 35.064 | 28.567 | 12.191 | 1.00 | 30.57 | C |
| ATOM | 1905 | NZ | LYS | A | 134 | 36.391 | 28.051 | 12.564 | 1.00 | 34.14 | N |
| ATOM | 1909 | C | LYS | A | 134 | 32.032 | 22.951 | 12.094 | 1.00 | 13.21 | C |
| ATOM | 1910 | O | LYS | A | 134 | 31.121 | 23.177 | 11.349 | 1.00 | 14.18 | O |
| ATOM | 1911 | N | VAL | A | 135 | 32.015 | 21.919 | 12.921 | 1.00 | 12.06 | N |
| ATOM | 1913 | CA | VAL | A | 135 | 30.964 | 20.957 | 12.863 | 1.00 | 12.02 | C |
| ATOM | 1915 | CB | VAL | A | 135 | 31.487 | 19.632 | 12.321 | 1.00 | 13.28 | C |
| ATOM | 1917 | CG1 | VAL | A | 135 | 30.363 | 18.596 | 12.114 | 1.00 | 14.27 | C |
| ATOM | 1921 | CG2 | VAL | A | 135 | 32.322 | 19.867 | 11.006 | 1.00 | 14.42 | C |
| ATOM | 1925 | C | VAL | A | 135 | 30.383 | 20.673 | 14.241 | 1.00 | 11.74 | C |
| ATOM | 1926 | O | VAL | A | 135 | 31.097 | 20.566 | 15.220 | 1.00 | 11.76 | O |
| ATOM | 1927 | N | VAL | A | 136 | 29.071 | 20.604 | 14.286 | 1.00 | 11.28 | N |
| ATOM | 1929 | CA | VAL | A | 136 | 28.389 | 20.206 | 15.478 | 1.00 | 10.73 | C |
| ATOM | 1931 | CB | VAL | A | 136 | 27.285 | 21.177 | 15.819 | 1.00 | 11.25 | C |
| ATOM | 1933 | CG1 | VAL | A | 136 | 26.576 | 20.755 | 17.127 | 1.00 | 13.78 | C |
| ATOM | 1937 | CG2 | VAL | A | 136 | 27.897 | 22.594 | 16.013 | 1.00 | 12.65 | C |
| ATOM | 1941 | C | VAL | A | 136 | 27.702 | 18.852 | 15.159 | 1.00 | 11.22 | C |
| ATOM | 1942 | O | VAL | A | 136 | 26.973 | 18.747 | 14.178 | 1.00 | 11.53 | O |
| ATOM | 1943 | N | ILE | A | 137 | 27.928 | 17.850 | 15.993 | 1.00 | 9.65 | N |
| ATOM | 1945 | CA | ILE | A | 137 | 27.255 | 16.573 | 15.854 | 1.00 | 10.61 | C |
| ATOM | 1947 | CB | ILE | A | 137 | 28.113 | 15.459 | 16.381 | 1.00 | 9.23 | C |
| ATOM | 1949 | CG1 | ILE | A | 137 | 29.215 | 15.121 | 15.395 | 1.00 | 11.83 | C |
| ATOM | 1952 | CD1 | ILE | A | 137 | 30.266 | 14.104 | 15.930 | 1.00 | 11.56 | C |
| ATOM | 1956 | CG2 | ILE | A | 137 | 27.238 | 14.230 | 16.611 | 1.00 | 10.38 | C |
| ATOM | 1960 | C | ILE | A | 137 | 25.993 | 16.610 | 16.690 | 1.00 | 10.44 | C |
| ATOM | 1961 | O | ILE | A | 137 | 26.031 | 17.014 | 17.869 | 1.00 | 11.92 | O |
| ATOM | 1962 | N | ASN | A | 138 | 24.899 | 16.203 | 16.096 | 1.00 | 9.00 | N |
| ATOM | 1964 | CA | ASN | A | 138 | 23.654 | 15.942 | 16.764 | 1.00 | 10.52 | C |
| ATOM | 1966 | CB | ASN | A | 138 | 22.494 | 16.601 | 15.996 | 1.00 | 8.55 | C |
| ATOM | 1969 | CG | ASN | A | 138 | 21.146 | 16.503 | 16.715 | 1.00 | 12.38 | C |
| ATOM | 1970 | OD1 | ASN | A | 138 | 20.648 | 17.515 | 17.236 | 1.00 | 10.74 | O |
| ATOM | 1971 | ND2 | ASN | A | 138 | 20.519 | 15.297 | 16.722 | 1.00 | 9.55 | N |
| ATOM | 1974 | C | ASN | A | 138 | 23.376 | 14.477 | 16.861 | 1.00 | 10.74 | C |
| ATOM | 1975 | O | ASN | A | 138 | 23.256 | 13.799 | 15.833 | 1.00 | 9.80 | O |
| ATOM | 1976 | N | MET | A | 139 | 23.208 | 13.987 | 18.091 | 1.00 | 9.89 | N |
| ATOM | 1978 | CA | MET | A | 139 | 22.830 | 12.585 | 18.304 | 1.00 | 10.28 | C |
| ATOM | 1980 | CB | MET | A | 139 | 23.975 | 11.764 | 18.906 | 1.00 | 9.62 | C |
| ATOM | 1983 | CG | MET | A | 139 | 24.984 | 11.345 | 17.895 | 1.00 | 8.67 | C |
| ATOM | 1986 | SD | MET | A | 139 | 26.240 | 10.206 | 18.525 | 1.00 | 11.34 | S |
| ATOM | 1987 | CE | MET | A | 139 | 27.161 | 11.324 | 19.556 | 1.00 | 13.56 | C |
| ATOM | 1991 | C | MET | A | 139 | 21.581 | 12.474 | 19.162 | 1.00 | 10.20 | C |
| ATOM | 1992 | O | MET | A | 139 | 21.587 | 12.497 | 20.413 | 1.00 | 9.22 | O |
| ATOM | 1993 | N | SER | A | 140 | 20.467 | 12.424 | 18.458 | 1.00 | 10.57 | N |
| ATOM | 1995 | CA | SER | A | 140 | 19.166 | 12.207 | 19.083 | 1.00 | 10.10 | C |
| ATOM | 1997 | CB | SER | A | 140 | 18.082 | 12.817 | 18.201 | 1.00 | 10.22 | C |
| ATOM | 2000 | OG | SER | A | 140 | 18.142 | 14.229 | 18.264 | 1.00 | 11.42 | O |
| ATOM | 2002 | C | SER | A | 140 | 18.959 | 10.705 | 19.255 | 1.00 | 11.04 | C |
| ATOM | 2003 | O | SER | A | 140 | 18.006 | 10.119 | 18.716 | 1.00 | 10.43 | O |
| ATOM | 2004 | N | LEU | A | 141 | 19.844 | 10.063 | 20.011 | 1.00 | 10.62 | N |
| ATOM | 2006 | CA | LEU | A | 141 | 19.890 | 8.627 | 20.116 | 1.00 | 10.50 | C |
| ATOM | 2008 | CB | LEU | A | 141 | 20.446 | 8.014 | 18.833 | 1.00 | 10.74 | C |
| ATOM | 2011 | CG | LEU | A | 141 | 21.881 | 8.483 | 18.439 | 1.00 | 11.49 | C |
| ATOM | 2013 | CD1 | LEU | A | 141 | 22.939 | 7.897 | 19.316 | 1.00 | 11.20 | C |
| ATOM | 2017 | CD2 | LEU | A | 141 | 22.119 | 8.057 | 17.001 | 1.00 | 12.54 | C |
| ATOM | 2021 | C | LEU | A | 141 | 20.748 | 8.223 | 21.297 | 1.00 | 9.69 | C |
| ATOM | 2022 | O | LEU | A | 141 | 21.402 | 9.060 | 21.892 | 1.00 | 9.38 | O |
| ATOM | 2023 | N | GLY | A | 142 | 20.640 | 6.975 | 21.689 | 1.00 | 11.48 | N |
| ATOM | 2025 | CA | GLY | A | 142 | 21.450 | 6.472 | 22.789 | 1.00 | 10.69 | C |
| ATOM | 2028 | C | GLY | A | 142 | 21.046 | 5.146 | 23.335 | 1.00 | 9.74 | C |
| ATOM | 2029 | O | GLY | A | 142 | 20.283 | 4.413 | 22.660 | 1.00 | 12.20 | O |
| ATOM | 2030 | N | SER | A | 143 | 21.517 | 4.850 | 24.562 | 1.00 | 11.68 | N |
| ATOM | 2032 | CA | SER | A | 143 | 21.200 | 3.610 | 25.308 | 1.00 | 11.10 | C |
| ATOM | 2034 | CB | SER | A | 143 | 22.187 | 2.489 | 25.050 | 1.00 | 11.52 | C |
| ATOM | 2037 | OG | SER | A | 143 | 23.517 | 2.918 | 25.316 | 1.00 | 11.14 | O |
| ATOM | 2039 | C | SER | A | 143 | 21.272 | 3.995 | 26.777 | 1.00 | 12.09 | C |
| ATOM | 2040 | O | SER | A | 143 | 21.941 | 4.966 | 27.161 | 1.00 | 11.62 | O |
| ATOM | 2041 | N | SER | A | 144 | 20.523 | 3.292 | 27.587 | 1.00 | 11.90 | N |
| ATOM | 2043 | CA | SER | A | 144 | 20.527 | 3.552 | 28.992 | 1.00 | 11.92 | C |
| ATOM | 2045 | CB | SER | A | 144 | 19.513 | 2.623 | 29.653 | 1.00 | 13.61 | C |

APPENDIX 1-continued

| | | | | | | | | | | | |
|---|---|---|---|---|---|---|---|---|---|---|---|
| ATOM | 2048 | OG | SER | A | 144 | 19.521 | 2.848 | 31.017 | 1.00 | 18.36 | O |
| ATOM | 2050 | C | SER | A | 144 | 21.903 | 3.362 | 29.593 | 1.00 | 13.78 | C |
| ATOM | 2051 | O | SER | A | 144 | 22.341 | 4.161 | 30.401 | 1.00 | 14.05 | O |
| ATOM | 2052 | N | ALA | A | 145 | 22.551 | 2.278 | 29.189 | 1.00 | 12.68 | N |
| ATOM | 2054 | CA | ALA | A | 145 | 23.892 | 1.972 | 29.678 | 1.00 | 11.54 | C |
| ATOM | 2056 | CB | ALA | A | 145 | 24.135 | 0.503 | 29.488 | 1.00 | 12.43 | C |
| ATOM | 2060 | C | ALA | A | 145 | 24.956 | 2.745 | 28.886 | 1.00 | 12.26 | C |
| ATOM | 2061 | O | ALA | A | 145 | 24.814 | 3.001 | 27.712 | 1.00 | 12.18 | O |
| ATOM | 2062 | N | LYS | A | 146 | 26.067 | 3.066 | 29.521 | 1.00 | 10.71 | N |
| ATOM | 2064 | CA | LYS | A | 146 | 27.184 | 3.640 | 28.760 | 1.00 | 11.08 | C |
| ATOM | 2066 | CB | LYS | A | 146 | 28.219 | 4.095 | 29.754 | 1.00 | 10.62 | C |
| ATOM | 2069 | CG | LYS | A | 146 | 29.563 | 4.535 | 29.197 | 1.00 | 13.37 | C |
| ATOM | 2072 | CD | LYS | A | 146 | 30.506 | 5.206 | 30.245 | 1.00 | 14.55 | C |
| ATOM | 2075 | CE | LYS | A | 146 | 31.796 | 5.638 | 29.643 | 1.00 | 17.59 | C |
| ATOM | 2078 | NZ | LYS | A | 146 | 32.732 | 6.238 | 30.665 | 1.00 | 17.20 | N |
| ATOM | 2082 | C | LYS | A | 146 | 27.767 | 2.559 | 27.834 | 1.00 | 8.93 | C |
| ATOM | 2083 | O | LYS | A | 146 | 27.978 | 1.383 | 28.241 | 1.00 | 11.42 | O |
| ATOM | 2084 | N | ASP | A | 147 | 28.075 | 2.956 | 26.621 | 1.00 | 10.15 | N |
| ATOM | 2086 | CA | ASP | A | 147 | 28.694 | 2.129 | 25.575 | 1.00 | 10.08 | C |
| ATOM | 2088 | CB | ASP | A | 147 | 27.843 | 2.189 | 24.296 | 1.00 | 10.84 | C |
| ATOM | 2091 | CG | ASP | A | 147 | 28.460 | 1.509 | 23.117 | 1.00 | 11.61 | C |
| ATOM | 2092 | OD1 | ASP | A | 147 | 29.701 | 1.630 | 22.895 | 1.00 | 11.69 | O |
| ATOM | 2093 | OD2 | ASP | A | 147 | 27.753 | 0.879 | 22.305 | 1.00 | 10.96 | O |
| ATOM | 2094 | C | ASP | A | 147 | 30.057 | 2.784 | 25.353 | 1.00 | 10.79 | C |
| ATOM | 2095 | O | ASP | A | 147 | 30.163 | 3.902 | 24.859 | 1.00 | 9.34 | O |
| ATOM | 2096 | N | SER | A | 148 | 31.104 | 2.055 | 25.717 | 1.00 | 9.95 | N |
| ATOM | 2098 | CA | SER | A | 148 | 32.450 | 2.588 | 25.641 | 1.00 | 11.43 | C |
| ATOM | 2100 | CB | SER | A | 148 | 33.431 | 1.838 | 26.533 | 1.00 | 11.86 | C |
| ATOM | 2103 | OG | SER | A | 148 | 33.164 | 2.051 | 27.904 | 1.00 | 13.07 | O |
| ATOM | 2105 | C | SER | A | 148 | 32.999 | 2.765 | 24.221 | 1.00 | 12.17 | C |
| ATOM | 2106 | O | SER | A | 148 | 33.958 | 3.537 | 24.021 | 1.00 | 10.72 | O |
| ATOM | 2107 | N | LEU | A | 149 | 32.471 | 1.997 | 23.269 | 1.00 | 9.59 | N |
| ATOM | 2109 | CA | LEU | A | 149 | 32.936 | 2.120 | 21.909 | 1.00 | 10.95 | C |
| ATOM | 2111 | CB | LEU | A | 149 | 32.374 | 1.029 | 21.030 | 1.00 | 11.13 | C |
| ATOM | 2114 | CG | LEU | A | 149 | 32.863 | 1.087 | 19.569 | 1.00 | 13.82 | C |
| ATOM | 2116 | CD1 | LEU | A | 149 | 34.404 | 0.961 | 19.536 | 1.00 | 14.72 | C |
| ATOM | 2120 | CD2 | LEU | A | 149 | 32.162 | 0.036 | 18.699 | 1.00 | 15.05 | C |
| ATOM | 2124 | C | LEU | A | 149 | 32.474 | 3.511 | 21.419 | 1.00 | 10.85 | C |
| ATOM | 2125 | O | LEU | A | 149 | 33.201 | 4.268 | 20.807 | 1.00 | 10.58 | O |
| ATOM | 2126 | N | ILE | A | 150 | 31.223 | 3.823 | 21.649 | 1.00 | 9.24 | N |
| ATOM | 2128 | CA | ILE | A | 150 | 30.671 | 5.127 | 21.255 | 1.00 | 9.06 | C |
| ATOM | 2130 | CB | ILE | A | 150 | 29.145 | 5.136 | 21.471 | 1.00 | 8.95 | C |
| ATOM | 2132 | CG1 | ILE | A | 150 | 28.499 | 4.376 | 20.337 | 1.00 | 9.94 | C |
| ATOM | 2135 | CD1 | ILE | A | 150 | 27.038 | 4.154 | 20.508 | 1.00 | 11.53 | C |
| ATOM | 2139 | CG2 | ILE | A | 150 | 28.601 | 6.553 | 21.538 | 1.00 | 11.45 | C |
| ATOM | 2143 | C | ILE | A | 150 | 31.433 | 6.226 | 22.052 | 1.00 | 7.79 | C |
| ATOM | 2144 | O | ILE | A | 150 | 31.793 | 7.297 | 21.500 | 1.00 | 8.15 | O |
| ATOM | 2145 | N | ALA | A | 151 | 31.724 | 5.956 | 23.300 | 1.00 | 8.34 | N |
| ATOM | 2147 | CA | ALA | A | 151 | 32.396 | 6.930 | 24.152 | 1.00 | 9.35 | C |
| ATOM | 2149 | CB | ALA | A | 151 | 32.479 | 6.402 | 25.577 | 1.00 | 10.22 | C |
| ATOM | 2153 | C | ALA | A | 151 | 33.796 | 7.240 | 23.629 | 1.00 | 9.49 | C |
| ATOM | 2154 | O | ALA | A | 151 | 34.215 | 8.422 | 23.583 | 1.00 | 9.45 | O |
| ATOM | 2155 | N | SER | A | 152 | 34.508 | 6.177 | 23.181 | 1.00 | 10.40 | N |
| ATOM | 2157 | CA | SER | A | 152 | 35.823 | 6.371 | 22.613 | 1.00 | 11.13 | C |
| ATOM | 2159 | CB | SER | A | 152 | 36.466 | 5.047 | 22.278 | 1.00 | 10.46 | C |
| ATOM | 2162 | OG | SER | A | 152 | 37.628 | 5.216 | 21.460 | 1.00 | 13.86 | O |
| ATOM | 2164 | C | SER | A | 152 | 35.737 | 7.285 | 21.349 | 1.00 | 11.17 | C |
| ATOM | 2165 | O | SER | A | 152 | 36.585 | 8.207 | 21.144 | 1.00 | 11.47 | O |
| ATOM | 2166 | N | ALA | A | 153 | 34.688 | 7.103 | 20.578 | 1.00 | 11.26 | N |
| ATOM | 2168 | CA | ALA | A | 153 | 34.476 | 7.917 | 19.358 | 1.00 | 11.23 | C |
| ATOM | 2170 | CB | ALA | A | 153 | 33.413 | 7.295 | 18.527 | 1.00 | 12.05 | C |
| ATOM | 2174 | C | ALA | A | 153 | 34.143 | 9.349 | 19.699 | 1.00 | 11.53 | C |
| ATOM | 2175 | O | ALA | A | 153 | 34.699 | 10.314 | 19.103 | 1.00 | 11.12 | O |
| ATOM | 2176 | N | VAL | A | 154 | 33.285 | 9.529 | 20.695 | 1.00 | 9.67 | N |
| ATOM | 2178 | CA | VAL | A | 154 | 32.941 | 10.878 | 21.104 | 1.00 | 9.77 | C |
| ATOM | 2180 | CB | VAL | A | 154 | 31.908 | 10.810 | 22.223 | 1.00 | 10.26 | C |
| ATOM | 2182 | CG1 | VAL | A | 154 | 31.833 | 12.136 | 22.988 | 1.00 | 12.19 | C |
| ATOM | 2186 | CG2 | VAL | A | 154 | 30.583 | 10.402 | 21.661 | 1.00 | 11.04 | C |
| ATOM | 2190 | C | VAL | A | 154 | 34.229 | 11.606 | 21.565 | 1.00 | 11.02 | C |
| ATOM | 2191 | O | VAL | A | 154 | 34.449 | 12.779 | 21.212 | 1.00 | 11.61 | O |
| ATOM | 2192 | N | ASP | A | 155 | 35.069 | 10.954 | 22.367 | 1.00 | 10.47 | N |
| ATOM | 2194 | CA | ASP | A | 155 | 36.309 | 11.603 | 22.838 | 1.00 | 12.38 | C |
| ATOM | 2196 | CB | ASP | A | 155 | 37.040 | 10.744 | 23.859 | 1.00 | 13.32 | C |
| ATOM | 2199 | CG | ASP | A | 155 | 36.328 | 10.668 | 25.183 | 1.00 | 19.66 | C |
| ATOM | 2200 | OD1 | ASP | A | 155 | 35.449 | 11.508 | 25.455 | 1.00 | 21.98 | O |
| ATOM | 2201 | OD2 | ASP | A | 155 | 36.604 | 9.813 | 26.030 | 1.00 | 21.73 | O |
| ATOM | 2202 | C | ASP | A | 155 | 37.242 | 11.932 | 21.674 | 1.00 | 13.46 | C |
| ATOM | 2203 | O | ASP | A | 155 | 37.928 | 12.926 | 21.695 | 1.00 | 12.65 | O |
| ATOM | 2204 | N | TYR | A | 156 | 37.308 | 11.034 | 20.694 | 1.00 | 12.30 | N |
| ATOM | 2206 | CA | TYR | A | 156 | 38.119 | 11.263 | 19.510 | 1.00 | 11.91 | C |

APPENDIX 1-continued

| | | | | | | | | | | |
|---|---|---|---|---|---|---|---|---|---|---|
| ATOM | 2208 | CB | TYR | A | 156 | 37.992 | 10.073 | 18.607 | 1.00 | 12.85 | C |
| ATOM | 2211 | CG | TYR | A | 156 | 38.753 | 10.140 | 17.309 | 1.00 | 13.57 | C |
| ATOM | 2212 | CD1 | TYR | A | 156 | 40.154 | 9.965 | 17.286 | 1.00 | 16.30 | C |
| ATOM | 2214 | CE1 | TYR | A | 156 | 40.822 | 9.989 | 16.093 | 1.00 | 15.71 | C |
| ATOM | 2216 | CZ | TYR | A | 156 | 40.136 | 10.172 | 14.899 | 1.00 | 20.85 | C |
| ATOM | 2217 | OH | TYR | A | 156 | 40.795 | 10.142 | 13.677 | 1.00 | 19.47 | O |
| ATOM | 2219 | CE2 | TYR | A | 156 | 38.771 | 10.352 | 14.883 | 1.00 | 14.75 | C |
| ATOM | 2221 | CD2 | TYR | A | 156 | 38.096 | 10.349 | 16.111 | 1.00 | 14.20 | C |
| ATOM | 2223 | C | TYR | A | 156 | 37.653 | 12.497 | 18.764 | 1.00 | 11.70 | C |
| ATOM | 2224 | O | TYR | A | 156 | 38.463 | 13.343 | 18.408 | 1.00 | 12.40 | O |
| ATOM | 2225 | N | ALA | A | 157 | 36.332 | 12.649 | 18.630 | 1.00 | 11.59 | N |
| ATOM | 2227 | CA | ALA | A | 157 | 35.773 | 13.776 | 17.895 | 1.00 | 10.92 | C |
| ATOM | 2229 | CB | ALA | A | 157 | 34.319 | 13.493 | 17.547 | 1.00 | 11.98 | C |
| ATOM | 2233 | C | ALA | A | 157 | 35.926 | 15.058 | 18.670 | 1.00 | 11.69 | C |
| ATOM | 2234 | O | ALA | A | 157 | 36.214 | 16.117 | 18.072 | 1.00 | 11.27 | O |
| ATOM | 2235 | N | TYR | A | 158 | 35.740 | 14.996 | 19.983 | 1.00 | 11.31 | N |
| ATOM | 2237 | CA | TYR | A | 158 | 35.855 | 16.210 | 20.809 | 1.00 | 12.56 | C |
| ATOM | 2239 | CB | TYR | A | 158 | 35.410 | 15.940 | 22.243 | 1.00 | 12.28 | C |
| ATOM | 2242 | CG | TYR | A | 158 | 35.147 | 17.188 | 23.090 | 1.00 | 9.96 | C |
| ATOM | 2243 | CD1 | TYR | A | 158 | 34.015 | 17.937 | 22.878 | 1.00 | 11.56 | C |
| ATOM | 2245 | CE1 | TYR | A | 158 | 33.754 | 19.051 | 23.629 | 1.00 | 13.20 | C |
| ATOM | 2247 | CZ | TYR | A | 158 | 34.635 | 19.477 | 24.580 | 1.00 | 13.62 | C |
| ATOM | 2248 | OH | TYR | A | 158 | 34.370 | 20.612 | 25.295 | 1.00 | 12.22 | O |
| ATOM | 2250 | CE2 | TYR | A | 158 | 35.813 | 18.809 | 24.787 | 1.00 | 13.48 | C |
| ATOM | 2252 | CD2 | TYR | A | 158 | 36.078 | 17.647 | 24.028 | 1.00 | 12.56 | C |
| ATOM | 2254 | C | TYR | A | 158 | 37.308 | 16.655 | 20.783 | 1.00 | 12.48 | C |
| ATOM | 2255 | O | TYR | A | 158 | 37.591 | 17.853 | 20.822 | 1.00 | 12.68 | O |
| ATOM | 2256 | N | GLY | A | 159 | 38.207 | 15.683 | 20.642 | 1.00 | 12.38 | N |
| ATOM | 2258 | CA | GLY | A | 159 | 39.628 | 15.978 | 20.651 | 1.00 | 13.17 | C |
| ATOM | 2261 | C | GLY | A | 159 | 40.055 | 16.611 | 19.371 | 1.00 | 13.46 | C |
| ATOM | 2262 | O | GLY | A | 159 | 41.161 | 17.165 | 19.297 | 1.00 | 14.28 | O |
| ATOM | 2263 | N | LYS | A | 160 | 39.238 | 16.495 | 18.350 | 1.00 | 12.48 | N |
| ATOM | 2265 | CA | LYS | A | 160 | 39.486 | 17.099 | 17.035 | 1.00 | 14.66 | C |
| ATOM | 2267 | CB | LYS | A | 160 | 39.324 | 16.046 | 15.953 | 1.00 | 15.36 | C |
| ATOM | 2270 | CG | LYS | A | 160 | 40.421 | 14.964 | 15.992 | 1.00 | 20.16 | C |
| ATOM | 2273 | CD | LYS | A | 160 | 40.057 | 13.848 | 15.058 | 1.00 | 25.00 | C |
| ATOM | 2276 | CE | LYS | A | 160 | 41.183 | 13.408 | 14.161 | 1.00 | 31.38 | C |
| ATOM | 2279 | NZ | LYS | A | 160 | 41.602 | 14.404 | 13.204 | 1.00 | 30.54 | N |
| ATOM | 2283 | C | LYS | A | 160 | 38.603 | 18.344 | 16.761 | 1.00 | 14.03 | C |
| ATOM | 2284 | O | LYS | A | 160 | 38.469 | 18.786 | 15.621 | 1.00 | 12.37 | O |
| ATOM | 2285 | N | GLY | A | 161 | 38.076 | 18.954 | 17.829 | 1.00 | 13.97 | N |
| ATOM | 2287 | CA | GLY | A | 161 | 37.363 | 20.230 | 17.751 | 1.00 | 13.11 | C |
| ATOM | 2290 | C | GLY | A | 161 | 35.928 | 20.180 | 17.281 | 1.00 | 12.99 | C |
| ATOM | 2291 | O | GLY | A | 161 | 35.434 | 21.185 | 16.743 | 1.00 | 14.25 | O |
| ATOM | 2292 | N | VAL | A | 162 | 35.269 | 19.020 | 17.395 | 1.00 | 11.44 | N |
| ATOM | 2294 | CA | VAL | A | 162 | 33.858 | 18.848 | 16.972 | 1.00 | 10.32 | C |
| ATOM | 2296 | CB | VAL | A | 162 | 33.621 | 17.492 | 16.309 | 1.00 | 11.03 | C |
| ATOM | 2298 | CG1 | VAL | A | 162 | 32.146 | 17.268 | 15.950 | 1.00 | 11.59 | C |
| ATOM | 2302 | CG2 | VAL | A | 162 | 34.438 | 17.378 | 15.034 | 1.00 | 13.60 | C |
| ATOM | 2306 | C | VAL | A | 162 | 32.991 | 18.918 | 18.219 | 1.00 | 10.43 | C |
| ATOM | 2307 | O | VAL | A | 162 | 33.306 | 18.259 | 19.222 | 1.00 | 11.54 | O |
| ATOM | 2308 | N | LEU | A | 163 | 31.965 | 19.748 | 18.217 | 1.00 | 9.11 | N |
| ATOM | 2310 | CA | LEU | A | 163 | 31.075 | 19.817 | 19.382 | 1.00 | 10.40 | C |
| ATOM | 2312 | CB | LEU | A | 163 | 30.278 | 21.105 | 19.344 | 1.00 | 11.53 | C |
| ATOM | 2315 | CG | LEU | A | 163 | 29.336 | 21.334 | 20.515 | 1.00 | 10.22 | C |
| ATOM | 2317 | CD1 | LEU | A | 163 | 30.163 | 21.561 | 21.748 | 1.00 | 12.89 | C |
| ATOM | 2321 | CD2 | LEU | A | 163 | 28.486 | 22.497 | 20.248 | 1.00 | 13.67 | C |
| ATOM | 2325 | C | LEU | A | 163 | 30.118 | 18.647 | 19.257 | 1.00 | 10.89 | C |
| ATOM | 2326 | O | LEU | A | 163 | 29.620 | 18.367 | 18.176 | 1.00 | 13.34 | O |
| ATOM | 2327 | N | ILE | A | 164 | 29.832 | 17.975 | 20.347 | 1.00 | 11.01 | N |
| ATOM | 2329 | CA | ILE | A | 164 | 28.860 | 16.890 | 20.383 | 1.00 | 9.92 | C |
| ATOM | 2331 | CB | ILE | A | 164 | 29.500 | 15.573 | 20.908 | 1.00 | 10.24 | C |
| ATOM | 2333 | CG1 | ILE | A | 164 | 30.616 | 15.070 | 19.976 | 1.00 | 13.39 | C |
| ATOM | 2336 | CD1 | ILE | A | 164 | 31.893 | 15.389 | 20.491 | 1.00 | 16.69 | C |
| ATOM | 2340 | CG2 | ILE | A | 164 | 28.496 | 14.458 | 20.907 | 1.00 | 12.88 | C |
| ATOM | 2344 | C | ILE | A | 164 | 27.673 | 17.259 | 21.275 | 1.00 | 10.29 | C |
| ATOM | 2345 | O | ILE | A | 164 | 27.851 | 17.505 | 22.479 | 1.00 | 10.17 | O |
| ATOM | 2346 | N | VAL | A | 165 | 26.489 | 17.191 | 20.694 | 1.00 | 9.19 | N |
| ATOM | 2348 | CA | VAL | A | 165 | 25.257 | 17.479 | 21.391 | 1.00 | 9.03 | C |
| ATOM | 2350 | CB | VAL | A | 165 | 24.576 | 18.708 | 20.753 | 1.00 | 10.21 | C |
| ATOM | 2352 | CG1 | VAL | A | 165 | 23.300 | 19.053 | 21.542 | 1.00 | 9.33 | C |
| ATOM | 2356 | CG2 | VAL | A | 165 | 25.483 | 19.888 | 20.715 | 1.00 | 11.01 | C |
| ATOM | 2360 | C | VAL | A | 165 | 24.360 | 16.245 | 21.311 | 1.00 | 8.47 | C |
| ATOM | 2361 | O | VAL | A | 165 | 24.193 | 15.681 | 20.222 | 1.00 | 10.40 | O |
| ATOM | 2362 | N | ALA | A | 166 | 23.833 | 15.747 | 22.452 | 1.00 | 9.28 | N |
| ATOM | 2364 | CA | ALA | A | 166 | 23.163 | 14.469 | 22.484 | 1.00 | 8.57 | C |
| ATOM | 2366 | CB | ALA | A | 166 | 24.104 | 13.327 | 22.794 | 1.00 | 9.70 | C |
| ATOM | 2370 | C | ALA | A | 166 | 22.011 | 14.454 | 23.489 | 1.00 | 9.40 | C |
| ATOM | 2371 | O | ALA | A | 166 | 22.028 | 15.186 | 24.476 | 1.00 | 9.37 | O |
| ATOM | 2372 | N | ALA | A | 167 | 21.000 | 13.646 | 23.186 | 1.00 | 10.21 | N |

APPENDIX 1-continued

| | | | | | | | | | | | |
|---|---|---|---|---|---|---|---|---|---|---|---|
| ATOM | 2374 | CA | ALA | A | 167 | 19.794 | 13.637 | 23.965 | 1.00 | 10.10 | C |
| ATOM | 2376 | CB | ALA | A | 167 | 18.747 | 12.726 | 23.251 | 1.00 | 11.66 | C |
| ATOM | 2380 | C | ALA | A | 167 | 20.086 | 13.087 | 25.329 | 1.00 | 10.38 | C |
| ATOM | 2381 | O | ALA | A | 167 | 20.787 | 12.038 | 25.431 | 1.00 | 8.93 | O |
| ATOM | 2382 | N | ALA | A | 168 | 19.424 | 13.572 | 26.360 | 1.00 | 10.36 | N |
| ATOM | 2384 | CA | ALA | A | 168 | 19.623 | 13.036 | 27.685 | 1.00 | 10.56 | C |
| ATOM | 2386 | CB | ALA | A | 168 | 19.014 | 13.978 | 28.698 | 1.00 | 11.45 | C |
| ATOM | 2390 | C | ALA | A | 168 | 19.026 | 11.631 | 27.894 | 1.00 | 10.08 | C |
| ATOM | 2391 | O | ALA | A | 168 | 19.441 | 10.860 | 28.771 | 1.00 | 10.97 | O |
| ATOM | 2392 | N | GLY | A | 169 | 18.020 | 11.315 | 27.108 | 1.00 | 9.80 | N |
| ATOM | 2394 | CA | GLY | A | 169 | 17.216 | 10.125 | 27.318 | 1.00 | 9.88 | C |
| ATOM | 2397 | C | GLY | A | 169 | 15.777 | 10.485 | 27.780 | 1.00 | 11.11 | C |
| ATOM | 2398 | O | GLY | A | 169 | 15.483 | 11.623 | 28.208 | 1.00 | 10.34 | O |
| ATOM | 2399 | N | ASN | A | 170 | 14.882 | 9.492 | 27.676 | 1.00 | 11.54 | N |
| ATOM | 2401 | CA | ASN | A | 170 | 13.483 | 9.636 | 28.090 | 1.00 | 11.53 | C |
| ATOM | 2403 | CB | ASN | A | 170 | 12.579 | 9.382 | 26.872 | 1.00 | 11.78 | C |
| ATOM | 2406 | CG | ASN | A | 170 | 12.911 | 10.285 | 25.682 | 1.00 | 13.65 | C |
| ATOM | 2407 | OD1 | ASN | A | 170 | 13.358 | 11.427 | 25.856 | 1.00 | 14.26 | O |
| ATOM | 2408 | ND2 | ASN | A | 170 | 12.666 | 9.791 | 24.465 | 1.00 | 10.92 | N |
| ATOM | 2411 | C | ASN | A | 170 | 13.116 | 8.658 | 29.184 | 1.00 | 12.69 | C |
| ATOM | 2412 | O | ASN | A | 170 | 12.046 | 8.036 | 29.123 | 1.00 | 12.66 | O |
| ATOM | 2413 | N | SER | A | 171 | 13.989 | 8.483 | 30.170 | 1.00 | 12.61 | N |
| ATOM | 2415 | CA | SER | A | 171 | 13.754 | 7.487 | 31.223 | 1.00 | 13.48 | C |
| ATOM | 2417 | CB | SER | A | 171 | 15.025 | 6.692 | 31.423 | 1.00 | 14.78 | C |
| ATOM | 2420 | OG | SER | A | 171 | 15.277 | 5.967 | 30.233 | 1.00 | 13.11 | O |
| ATOM | 2422 | C | SER | A | 171 | 13.308 | 8.147 | 32.538 | 1.00 | 13.22 | C |
| ATOM | 2423 | O | SER | A | 171 | 13.429 | 7.526 | 33.583 | 1.00 | 14.40 | O |
| ATOM | 2424 | N | GLY | A | 172 | 12.811 | 9.371 | 32.496 | 1.00 | 14.32 | N |
| ATOM | 2426 | CA | GLY | A | 172 | 12.428 | 10.098 | 33.710 | 1.00 | 14.13 | C |
| ATOM | 2429 | C | GLY | A | 172 | 11.127 | 9.606 | 34.292 | 1.00 | 15.66 | C |
| ATOM | 2430 | O | GLY | A | 172 | 10.473 | 8.814 | 33.614 | 1.00 | 15.22 | O |
| ATOM | 2431 | N | SER | A | 173 | 10.681 | 10.134 | 35.424 | 1.00 | 14.94 | N |
| ATOM | 2433 | CA | SER | A | 173 | 11.269 | 11.278 | 36.134 | 1.00 | 16.57 | C |
| ATOM | 2435 | CB | SER | A | 173 | 10.144 | 12.174 | 36.639 | 1.00 | 17.91 | C |
| ATOM | 2438 | OG | SER | A | 173 | 9.384 | 11.435 | 37.607 | 1.00 | 18.04 | O |
| ATOM | 2440 | C | SER | A | 173 | 12.196 | 10.908 | 37.265 | 1.00 | 16.47 | C |
| ATOM | 2441 | O | SER | A | 173 | 12.751 | 11.790 | 37.970 | 1.00 | 15.55 | O |
| ATOM | 2442 | N | GLY | A | 174 | 12.476 | 9.615 | 37.359 | 1.00 | 15.06 | N |
| ATOM | 2444 | CA | GLY | A | 174 | 13.318 | 9.075 | 38.400 | 1.00 | 16.35 | C |
| ATOM | 2447 | C | GLY | A | 174 | 14.715 | 9.629 | 38.233 | 1.00 | 17.64 | C |
| ATOM | 2448 | O | GLY | A | 174 | 15.159 | 9.906 | 37.086 | 1.00 | 17.46 | O |
| ATOM | 2449 | N | SER | A | 175 | 15.404 | 9.827 | 39.351 | 1.00 | 17.08 | N |
| ATOM | 2451 | CA | SER | A | 175 | 16.752 | 10.404 | 39.336 | 1.00 | 18.22 | C |
| ATOM | 2453 | CB | SER | A | 175 | 17.129 | 10.794 | 40.759 | 1.00 | 19.80 | C |
| ATOM | 2456 | OG | SER | A | 175 | 16.121 | 11.654 | 41.308 | 1.00 | 21.20 | O |
| ATOM | 2458 | C | SER | A | 175 | 17.783 | 9.457 | 38.777 | 1.00 | 16.85 | C |
| ATOM | 2459 | O | SER | A | 175 | 17.638 | 8.238 | 38.884 | 1.00 | 15.37 | O |
| ATOM | 2460 | N | ASN | A | 176 | 18.838 | 10.010 | 38.168 | 1.00 | 16.57 | N |
| ATOM | 2462 | CA | ASN | A | 176 | 19.966 | 9.230 | 37.675 | 1.00 | 15.32 | C |
| ATOM | 2464 | CB | ASN | A | 176 | 20.679 | 8.475 | 38.817 | 1.00 | 17.33 | C |
| ATOM | 2467 | CG | ASN | A | 176 | 22.174 | 8.352 | 38.565 | 1.00 | 20.64 | C |
| ATOM | 2468 | OD1 | ASN | A | 176 | 22.676 | 9.003 | 37.649 | 1.00 | 19.65 | O |
| ATOM | 2469 | ND2 | ASN | A | 176 | 22.881 | 7.508 | 39.336 | 1.00 | 23.68 | N |
| ATOM | 2472 | C | ASN | A | 176 | 19.634 | 8.250 | 36.592 | 1.00 | 15.22 | C |
| ATOM | 2473 | O | ASN | A | 176 | 20.208 | 7.146 | 36.528 | 1.00 | 16.86 | O |
| ATOM | 2474 | N | THR | A | 177 | 18.718 | 8.639 | 35.723 | 1.00 | 14.53 | N |
| ATOM | 2476 | CA | THR | A | 177 | 18.299 | 7.815 | 34.612 | 1.00 | 14.30 | C |
| ATOM | 2478 | CB | THR | A | 177 | 16.768 | 7.831 | 34.488 | 1.00 | 13.61 | C |
| ATOM | 2480 | OG1 | THR | A | 177 | 16.255 | 9.161 | 34.632 | 1.00 | 12.76 | O |
| ATOM | 2482 | CG2 | THR | A | 177 | 16.053 | 7.001 | 35.629 | 1.00 | 14.89 | C |
| ATOM | 2486 | C | THR | A | 177 | 18.907 | 8.265 | 33.267 | 1.00 | 13.62 | C |
| ATOM | 2487 | O | THR | A | 177 | 18.555 | 7.704 | 32.213 | 1.00 | 14.34 | O |
| ATOM | 2488 | N | ILE | A | 178 | 19.736 | 9.305 | 33.324 | 1.00 | 12.33 | N |
| ATOM | 2490 | CA | ILE | A | 178 | 20.436 | 9.809 | 32.125 | 1.00 | 10.85 | C |
| ATOM | 2492 | CB | ILE | A | 178 | 21.473 | 10.886 | 32.543 | 1.00 | 11.28 | C |
| ATOM | 2494 | CG1 | ILE | A | 178 | 22.118 | 11.576 | 31.337 | 1.00 | 11.95 | C |
| ATOM | 2497 | CD1 | ILE | A | 178 | 22.981 | 12.833 | 31.722 | 1.00 | 12.82 | C |
| ATOM | 2501 | CG2 | ILE | A | 178 | 22.550 | 10.300 | 33.406 | 1.00 | 11.10 | C |
| ATOM | 2505 | C | ILE | A | 178 | 21.057 | 8.663 | 31.350 | 1.00 | 10.78 | C |
| ATOM | 2506 | O | ILE | A | 178 | 21.582 | 7.715 | 31.950 | 1.00 | 10.96 | O |
| ATOM | 2507 | N | GLY | A | 179 | 20.973 | 8.706 | 30.032 | 1.00 | 9.07 | N |
| ATOM | 2509 | CA | GLY | A | 179 | 21.658 | 7.732 | 29.200 | 1.00 | 10.43 | C |
| ATOM | 2512 | C | GLY | A | 179 | 22.842 | 8.334 | 28.433 | 1.00 | 10.17 | C |
| ATOM | 2513 | O | GLY | A | 179 | 23.302 | 9.423 | 28.716 | 1.00 | 9.05 | O |
| ATOM | 2514 | N | PHE | A | 180 | 23.302 | 7.579 | 27.474 | 1.00 | 10.42 | N |
| ATOM | 2516 | CA | PHE | A | 180 | 24.566 | 7.766 | 26.771 | 1.00 | 9.90 | C |
| ATOM | 2518 | CB | PHE | A | 180 | 25.597 | 6.710 | 27.248 | 1.00 | 11.20 | C |
| ATOM | 2521 | CG | PHE | A | 180 | 25.926 | 6.868 | 28.691 | 1.00 | 10.40 | C |
| ATOM | 2522 | CD1 | PHE | A | 180 | 25.089 | 6.304 | 29.673 | 1.00 | 12.43 | C |
| ATOM | 2524 | CE1 | PHE | A | 180 | 25.346 | 6.539 | 31.013 | 1.00 | 13.80 | C |

APPENDIX 1-continued

| | | | | | | | | | | |
|---|---|---|---|---|---|---|---|---|---|---|
| ATOM | 2526 | CZ | PHE | A | 180 | 26.377 | 7.353 | 31.379 | 1.00 | 14.77 | C |
| ATOM | 2528 | CE2 | PHE | A | 180 | 27.195 | 7.936 | 30.428 | 1.00 | 14.15 | C |
| ATOM | 2530 | CD2 | PHE | A | 180 | 26.951 | 7.710 | 29.086 | 1.00 | 12.50 | C |
| ATOM | 2532 | C | PHE | A | 180 | 24.307 | 7.663 | 25.268 | 1.00 | 10.49 | C |
| ATOM | 2533 | O | PHE | A | 180 | 23.545 | 6.804 | 24.833 | 1.00 | 11.55 | O |
| ATOM | 2534 | N | PRO | A | 181 | 25.023 | 8.448 | 24.458 | 1.00 | 9.50 | N |
| ATOM | 2535 | CA | PRO | A | 181 | 26.196 | 9.246 | 24.890 | 1.00 | 9.13 | C |
| ATOM | 2537 | CB | PRO | A | 181 | 26.937 | 9.496 | 23.524 | 1.00 | 9.24 | C |
| ATOM | 2540 | CG | PRO | A | 181 | 25.855 | 9.591 | 22.649 | 1.00 | 11.31 | C |
| ATOM | 2543 | CD | PRO | A | 181 | 24.874 | 8.496 | 23.002 | 1.00 | 10.03 | C |
| ATOM | 2546 | C | PRO | A | 181 | 25.983 | 10.570 | 25.610 | 1.00 | 10.79 | C |
| ATOM | 2547 | O | PRO | A | 181 | 26.959 | 11.251 | 25.986 | 1.00 | 9.76 | O |
| ATOM | 2548 | N | GLY | A | 182 | 24.743 | 11.019 | 25.752 | 1.00 | 10.07 | N |
| ATOM | 2550 | CA | GLY | A | 182 | 24.480 | 12.260 | 26.450 | 1.00 | 10.91 | C |
| ATOM | 2553 | C | GLY | A | 182 | 25.260 | 12.460 | 27.748 | 1.00 | 10.65 | C |
| ATOM | 2554 | O | GLY | A | 182 | 25.843 | 13.532 | 27.983 | 1.00 | 10.24 | O |
| ATOM | 2555 | N | GLY | A | 183 | 25.246 | 11.400 | 28.570 | 1.00 | 10.23 | N |
| ATOM | 2557 | CA | GLY | A | 183 | 25.860 | 11.370 | 29.888 | 1.00 | 11.34 | C |
| ATOM | 2560 | C | GLY | A | 183 | 27.370 | 11.393 | 29.929 | 1.00 | 11.75 | C |
| ATOM | 2561 | O | GLY | A | 183 | 27.957 | 11.394 | 31.025 | 1.00 | 10.33 | O |
| ATOM | 2562 | N | LEU | A | 184 | 28.007 | 11.351 | 28.761 | 1.00 | 11.62 | N |
| ATOM | 2564 | CA | LEU | A | 184 | 29.474 | 11.436 | 28.718 | 1.00 | 11.77 | C |
| ATOM | 2566 | CB | LEU | A | 184 | 30.022 | 11.038 | 27.369 | 1.00 | 10.76 | C |
| ATOM | 2569 | CG | LEU | A | 184 | 29.612 | 9.640 | 26.946 | 1.00 | 13.28 | C |
| ATOM | 2571 | CD1 | LEU | A | 184 | 29.958 | 9.447 | 25.484 | 1.00 | 13.01 | C |
| ATOM | 2575 | CD2 | LEU | A | 184 | 30.306 | 8.563 | 27.839 | 1.00 | 15.87 | C |
| ATOM | 2579 | C | LEU | A | 184 | 29.966 | 12.827 | 29.034 | 1.00 | 11.00 | C |
| ATOM | 2580 | O | LEU | A | 184 | 29.321 | 13.827 | 28.682 | 1.00 | 10.77 | O |
| ATOM | 2581 | N | VAL | A | 185 | 31.180 | 12.922 | 29.584 | 1.00 | 11.17 | N |
| ATOM | 2583 | CA | VAL | A | 185 | 31.673 | 14.225 | 29.979 | 1.00 | 10.77 | C |
| ATOM | 2585 | CB | VAL | A | 185 | 32.994 | 14.115 | 30.811 | 1.00 | 13.00 | C |
| ATOM | 2587 | CG1 | VAL | A | 185 | 33.978 | 13.569 | 30.013 | 1.00 | 16.83 | C |
| ATOM | 2591 | CG2 | VAL | A | 185 | 33.500 | 15.504 | 31.144 | 1.00 | 16.03 | C |
| ATOM | 2595 | C | VAL | A | 185 | 31.868 | 15.172 | 28.842 | 1.00 | 9.95 | C |
| ATOM | 2596 | O | VAL | A | 185 | 31.683 | 16.370 | 28.972 | 1.00 | 10.97 | O |
| ATOM | 2597 | N | ASN | A | 186 | 32.181 | 14.614 | 27.684 | 1.00 | 10.43 | N |
| ATOM | 2599 | CA | ASN | A | 186 | 32.483 | 15.376 | 26.517 | 1.00 | 11.79 | C |
| ATOM | 2601 | CB | ASN | A | 186 | 33.763 | 14.865 | 25.836 | 1.00 | 13.55 | C |
| ATOM | 2604 | CG | ASN | A | 186 | 35.029 | 15.152 | 26.660 | 1.00 | 14.82 | C |
| ATOM | 2605 | OD1 | ASN | A | 186 | 35.093 | 16.110 | 27.370 | 1.00 | 19.19 | O |
| ATOM | 2606 | ND2 | ASN | A | 186 | 36.021 | 14.326 | 26.517 | 1.00 | 21.64 | N |
| ATOM | 2609 | C | ASN | A | 186 | 31.305 | 15.525 | 25.536 | 1.00 | 11.85 | C |
| ATOM | 2610 | O | ASN | A | 186 | 31.485 | 15.915 | 24.384 | 1.00 | 11.39 | O |
| ATOM | 2611 | N | ALA | A | 187 | 30.108 | 15.138 | 25.977 | 1.00 | 10.51 | N |
| ATOM | 2613 | CA | ALA | A | 187 | 28.904 | 15.382 | 25.179 | 1.00 | 11.08 | C |
| ATOM | 2615 | CB | ALA | A | 187 | 28.189 | 14.150 | 24.848 | 1.00 | 11.19 | C |
| ATOM | 2619 | C | ALA | A | 187 | 27.984 | 16.317 | 25.975 | 1.00 | 10.66 | C |
| ATOM | 2620 | O | ALA | A | 187 | 27.878 | 16.147 | 27.186 | 1.00 | 11.05 | O |
| ATOM | 2621 | N | VAL | A | 188 | 27.318 | 17.248 | 25.288 | 1.00 | 9.26 | N |
| ATOM | 2623 | CA | VAL | A | 188 | 26.326 | 18.148 | 25.895 | 1.00 | 9.21 | C |
| ATOM | 2625 | CB | VAL | A | 188 | 26.120 | 19.418 | 25.046 | 1.00 | 9.41 | C |
| ATOM | 2627 | CG1 | VAL | A | 188 | 25.035 | 20.249 | 25.661 | 1.00 | 7.57 | C |
| ATOM | 2631 | CG2 | VAL | A | 188 | 27.448 | 20.164 | 24.893 | 1.00 | 10.01 | C |
| ATOM | 2635 | C | VAL | A | 188 | 24.996 | 17.346 | 25.984 | 1.00 | 9.78 | C |
| ATOM | 2636 | O | VAL | A | 188 | 24.349 | 17.137 | 24.959 | 1.00 | 10.45 | O |
| ATOM | 2637 | N | ALA | A | 189 | 24.572 | 16.989 | 27.200 | 1.00 | 8.67 | N |
| ATOM | 2639 | CA | ALA | A | 189 | 23.325 | 16.236 | 27.430 | 1.00 | 9.35 | C |
| ATOM | 2641 | CB | ALA | A | 189 | 23.379 | 15.510 | 28.763 | 1.00 | 10.27 | C |
| ATOM | 2645 | C | ALA | A | 189 | 22.197 | 17.214 | 27.451 | 1.00 | 8.43 | C |
| ATOM | 2646 | O | ALA | A | 189 | 22.179 | 18.183 | 28.238 | 1.00 | 9.35 | O |
| ATOM | 2647 | N | VAL | A | 190 | 21.182 | 16.948 | 26.651 | 1.00 | 9.14 | N |
| ATOM | 2649 | CA | VAL | A | 190 | 20.084 | 17.882 | 26.554 | 1.00 | 8.32 | C |
| ATOM | 2651 | CB | VAL | A | 190 | 19.843 | 18.296 | 25.119 | 1.00 | 8.58 | C |
| ATOM | 2653 | CG1 | VAL | A | 190 | 18.731 | 19.309 | 25.052 | 1.00 | 11.50 | C |
| ATOM | 2657 | CG2 | VAL | A | 190 | 21.084 | 18.873 | 24.482 | 1.00 | 9.20 | C |
| ATOM | 2661 | C | VAL | A | 190 | 18.791 | 17.317 | 27.087 | 1.00 | 9.51 | C |
| ATOM | 2662 | O | VAL | A | 190 | 18.340 | 16.256 | 26.625 | 1.00 | 9.51 | O |
| ATOM | 2663 | N | ALA | A | 191 | 18.236 | 17.973 | 28.093 | 1.00 | 9.50 | N |
| ATOM | 2665 | CA | ALA | A | 191 | 16.934 | 17.559 | 28.685 | 1.00 | 10.18 | C |
| ATOM | 2667 | CB | ALA | A | 191 | 16.868 | 18.057 | 30.134 | 1.00 | 8.69 | C |
| ATOM | 2671 | C | ALA | A | 191 | 15.800 | 18.184 | 27.900 | 1.00 | 10.24 | C |
| ATOM | 2672 | O | ALA | A | 191 | 16.007 | 19.182 | 27.249 | 1.00 | 10.28 | O |
| ATOM | 2673 | N | ALA | A | 192 | 14.570 | 17.659 | 28.021 | 1.00 | 11.22 | N |
| ATOM | 2675 | CA | ALA | A | 192 | 13.428 | 18.171 | 27.272 | 1.00 | 11.79 | C |
| ATOM | 2677 | CB | ALA | A | 192 | 12.593 | 17.012 | 26.728 | 1.00 | 13.73 | C |
| ATOM | 2681 | C | ALA | A | 192 | 12.499 | 19.027 | 28.134 | 1.00 | 11.54 | C |
| ATOM | 2682 | O | ALA | A | 192 | 12.048 | 18.549 | 29.179 | 1.00 | 11.30 | O |
| ATOM | 2683 | N | LEU | A | 193 | 12.222 | 20.238 | 27.673 | 1.00 | 11.58 | N |
| ATOM | 2685 | CA | LEU | A | 193 | 11.194 | 21.103 | 28.258 | 1.00 | 11.55 | C |
| ATOM | 2687 | CB | LEU | A | 193 | 11.519 | 22.561 | 28.037 | 1.00 | 12.06 | C |

APPENDIX 1-continued

| ATOM | 2690 | CG | LEU | A | 193 | 12.844 | 23.095 | 28.613 | 1.00 | 10.40 | C |
|---|---|---|---|---|---|---|---|---|---|---|---|
| ATOM | 2692 | CD1 | LEU | A | 193 | 13.137 | 24.484 | 28.211 | 1.00 | 9.32 | C |
| ATOM | 2696 | CD2 | LEU | A | 193 | 12.752 | 22.903 | 30.081 | 1.00 | 13.29 | C |
| ATOM | 2700 | C | LEU | A | 193 | 9.852 | 20.802 | 27.577 | 1.00 | 14.05 | C |
| ATOM | 2701 | O | LEU | A | 193 | 9.814 | 20.460 | 26.414 | 1.00 | 13.73 | O |
| ATOM | 2702 | N | GLU | A | 194 | 8.755 | 21.004 | 28.305 | 1.00 | 13.56 | N |
| ATOM | 2704 | CA | GLU | A | 194 | 7.422 | 21.049 | 27.647 | 1.00 | 13.63 | C |
| ATOM | 2706 | CB | GLU | A | 194 | 6.472 | 20.125 | 28.359 | 1.00 | 12.74 | C |
| ATOM | 2709 | CG | GLU | A | 194 | 6.320 | 20.410 | 29.837 | 1.00 | 16.62 | C |
| ATOM | 2712 | CD | GLU | A | 194 | 5.490 | 19.404 | 30.603 | 1.00 | 19.10 | C |
| ATOM | 2713 | OE1 | GLU | A | 194 | 5.288 | 18.280 | 30.118 | 1.00 | 20.53 | O |
| ATOM | 2714 | OE2 | GLU | A | 194 | 5.153 | 19.744 | 31.765 | 1.00 | 17.20 | O |
| ATOM | 2715 | C | GLU | A | 194 | 6.934 | 22.460 | 27.699 | 1.00 | 14.48 | C |
| ATOM | 2716 | O | GLU | A | 194 | 7.502 | 23.275 | 28.431 | 1.00 | 13.32 | O |
| ATOM | 2717 | N | ASN | A | 195 | 5.862 | 22.778 | 26.954 | 1.00 | 14.74 | N |
| ATOM | 2719 | CA | ASN | A | 195 | 5.416 | 24.169 | 26.857 | 1.00 | 15.00 | C |
| ATOM | 2721 | CB | ASN | A | 195 | 4.773 | 24.467 | 25.479 | 1.00 | 16.14 | C |
| ATOM | 2724 | CG | ASN | A | 195 | 4.612 | 25.970 | 25.198 | 1.00 | 16.46 | C |
| ATOM | 2725 | OD1 | ASN | A | 195 | 5.236 | 26.803 | 25.855 | 1.00 | 14.84 | O |
| ATOM | 2726 | ND2 | ASN | A | 195 | 3.775 | 26.318 | 24.208 | 1.00 | 13.91 | N |
| ATOM | 2729 | C | ASN | A | 195 | 4.439 | 24.440 | 27.945 | 1.00 | 16.03 | C |
| ATOM | 2730 | O | ASN | A | 195 | 3.256 | 24.692 | 27.662 | 1.00 | 15.98 | O |
| ATOM | 2731 | N | VAL | A | 196 | 4.904 | 24.381 | 29.170 | 1.00 | 16.13 | N |
| ATOM | 2733 | CA | VAL | A | 196 | 4.106 | 24.623 | 30.344 | 1.00 | 16.89 | C |
| ATOM | 2735 | CB | VAL | A | 196 | 3.739 | 23.348 | 31.019 | 1.00 | 18.38 | C |
| ATOM | 2737 | CG1 | VAL | A | 196 | 3.058 | 23.613 | 32.326 | 1.00 | 20.19 | C |
| ATOM | 2741 | CG2 | VAL | A | 196 | 2.922 | 22.415 | 30.070 | 1.00 | 18.32 | C |
| ATOM | 2745 | C | VAL | A | 196 | 4.991 | 25.380 | 31.307 | 1.00 | 17.79 | C |
| ATOM | 2746 | O | VAL | A | 196 | 6.215 | 25.147 | 31.344 | 1.00 | 17.15 | O |
| ATOM | 2747 | N | GLN | A | 197 | 4.410 | 26.305 | 32.055 | 1.00 | 17.34 | N |
| ATOM | 2749 | CA | GLN | A | 197 | 5.171 | 27.048 | 33.060 | 1.00 | 16.33 | C |
| ATOM | 2751 | CB | GLN | A | 197 | 4.838 | 28.518 | 33.012 | 1.00 | 16.74 | C |
| ATOM | 2754 | CG | GLN | A | 197 | 4.987 | 29.169 | 31.720 | 1.00 | 16.89 | C |
| ATOM | 2757 | CD | GLN | A | 197 | 6.455 | 29.357 | 31.343 | 1.00 | 18.48 | C |
| ATOM | 2758 | OE1 | GLN | A | 197 | 7.216 | 30.009 | 32.096 | 1.00 | 14.66 | O |
| ATOM | 2759 | NE2 | GLN | A | 197 | 6.850 | 28.769 | 30.223 | 1.00 | 15.37 | N |
| ATOM | 2762 | C | GLN | A | 197 | 4.907 | 26.538 | 34.467 | 1.00 | 17.79 | C |
| ATOM | 2763 | O | GLN | A | 197 | 3.778 | 26.114 | 34.825 | 1.00 | 18.50 | O |
| ATOM | 2764 | N | GLN | A | 198 | 5.977 | 26.409 | 35.232 | 1.00 | 17.07 | N |
| ATOM | 2766 | CA | GLN | A | 198 | 5.879 | 25.977 | 36.627 | 1.00 | 17.39 | C |
| ATOM | 2768 | CB | GLN | A | 198 | 5.865 | 24.485 | 36.778 | 1.00 | 17.84 | C |
| ATOM | 2771 | CG | GLN | A | 198 | 5.744 | 24.058 | 38.164 | 1.00 | 18.38 | C |
| ATOM | 2774 | CD | GLN | A | 198 | 5.797 | 22.558 | 38.413 | 1.00 | 25.24 | C |
| ATOM | 2775 | OE1 | GLN | A | 198 | 6.612 | 21.813 | 37.815 | 1.00 | 26.03 | O |
| ATOM | 2776 | NE2 | GLN | A | 198 | 4.927 | 22.090 | 39.323 | 1.00 | 29.00 | N |
| ATOM | 2779 | C | GLN | A | 198 | 6.998 | 26.623 | 37.362 | 1.00 | 17.51 | C |
| ATOM | 2780 | O | GLN | A | 198 | 8.156 | 26.681 | 36.904 | 1.00 | 16.23 | O |
| ATOM | 2781 | N | ASN | A | 199 | 6.655 | 27.147 | 38.520 | 1.00 | 18.31 | N |
| ATOM | 2783 | CA | ASN | A | 199 | 7.612 | 27.890 | 39.321 | 1.00 | 19.42 | C |
| ATOM | 2785 | CB | ASN | A | 199 | 8.676 | 26.953 | 39.915 | 1.00 | 19.53 | C |
| ATOM | 2788 | CG | ASN | A | 199 | 8.107 | 25.949 | 40.861 | 1.00 | 24.01 | C |
| ATOM | 2789 | OD1 | ASN | A | 199 | 7.226 | 26.254 | 41.691 | 1.00 | 23.71 | O |
| ATOM | 2790 | ND2 | ASN | A | 199 | 8.598 | 24.738 | 40.769 | 1.00 | 25.09 | N |
| ATOM | 2793 | C | ASN | A | 199 | 8.285 | 29.018 | 38.592 | 1.00 | 20.51 | C |
| ATOM | 2794 | O | ASN | A | 199 | 9.491 | 29.356 | 38.863 | 1.00 | 20.07 | O |
| ATOM | 2795 | N | GLY | A | 200 | 7.533 | 29.653 | 37.712 | 1.00 | 19.65 | N |
| ATOM | 2797 | CA | GLY | A | 200 | 8.005 | 30.820 | 36.991 | 1.00 | 20.16 | C |
| ATOM | 2800 | C | GLY | A | 200 | 8.883 | 30.609 | 35.774 | 1.00 | 19.26 | C |
| ATOM | 2801 | O | GLY | A | 200 | 9.347 | 31.577 | 35.177 | 1.00 | 18.58 | O |
| ATOM | 2802 | N | THR | A | 201 | 9.091 | 29.348 | 35.384 | 1.00 | 17.29 | N |
| ATOM | 2804 | CA | THR | A | 201 | 9.876 | 29.045 | 34.196 | 1.00 | 16.82 | C |
| ATOM | 2806 | CB | THR | A | 201 | 11.327 | 28.563 | 34.596 | 1.00 | 16.41 | C |
| ATOM | 2808 | OG1 | THR | A | 201 | 11.309 | 27.246 | 35.174 | 1.00 | 17.63 | O |
| ATOM | 2810 | CG2 | THR | A | 201 | 11.954 | 29.437 | 35.622 | 1.00 | 17.27 | C |
| ATOM | 2814 | C | THR | A | 201 | 9.248 | 27.935 | 33.389 | 1.00 | 15.50 | C |
| ATOM | 2815 | O | THR | A | 201 | 8.267 | 27.356 | 33.817 | 1.00 | 14.83 | O |
| ATOM | 2816 | N | TYR | A | 202 | 9.845 | 27.608 | 32.230 | 1.00 | 15.66 | N |
| ATOM | 2818 | CA | TYR | A | 202 | 9.469 | 26.407 | 31.571 | 1.00 | 14.51 | C |
| ATOM | 2820 | CB | TYR | A | 202 | 10.308 | 26.183 | 30.300 | 1.00 | 15.38 | C |
| ATOM | 2823 | CG | TYR | A | 202 | 9.853 | 27.053 | 29.177 | 1.00 | 12.00 | C |
| ATOM | 2824 | CD1 | TYR | A | 202 | 8.775 | 26.682 | 28.359 | 1.00 | 12.96 | C |
| ATOM | 2826 | CE1 | TYR | A | 202 | 8.344 | 27.510 | 27.364 | 1.00 | 13.55 | C |
| ATOM | 2828 | CZ | TYR | A | 202 | 8.995 | 28.682 | 27.157 | 1.00 | 12.70 | C |
| ATOM | 2829 | OH | TYR | A | 202 | 8.586 | 29.559 | 26.172 | 1.00 | 14.68 | O |
| ATOM | 2831 | CE2 | TYR | A | 202 | 10.027 | 29.063 | 27.961 | 1.00 | 14.77 | C |
| ATOM | 2833 | CD2 | TYR | A | 202 | 10.441 | 28.245 | 28.957 | 1.00 | 13.26 | C |
| ATOM | 2835 | C | TYR | A | 202 | 9.637 | 25.229 | 32.488 | 1.00 | 14.45 | C |
| ATOM | 2836 | O | TYR | A | 202 | 10.442 | 25.231 | 33.415 | 1.00 | 14.03 | O |
| ATOM | 2837 | N | ARG | A | 203 | 8.894 | 24.168 | 32.206 | 1.00 | 14.53 | N |
| ATOM | 2839 | CA | ARG | A | 203 | 8.939 | 22.971 | 32.988 | 1.00 | 13.25 | C |

APPENDIX 1-continued

| | | | | | | | | | | |
|---|---|---|---|---|---|---|---|---|---|---|
| ATOM | 2841 | CB | ARG | A | 203 | 7.454 | 22.543 | 33.262 | 1.00 | 14.52 | C |
| ATOM | 2844 | CG | ARG | A | 203 | 7.315 | 21.347 | 34.102 | 1.00 | 14.19 | C |
| ATOM | 2847 | CD | ARG | A | 203 | 5.795 | 21.083 | 34.523 | 1.00 | 15.99 | C |
| ATOM | 2850 | NE | ARG | A | 203 | 5.730 | 20.106 | 35.572 | 1.00 | 17.45 | N |
| ATOM | 2852 | CZ | ARG | A | 203 | 5.729 | 18.806 | 35.402 | 1.00 | 17.33 | C |
| ATOM | 2853 | NH1 | ARG | A | 203 | 5.762 | 18.306 | 34.191 | 1.00 | 15.77 | N |
| ATOM | 2856 | NH2 | ARG | A | 203 | 5.741 | 17.996 | 36.447 | 1.00 | 18.53 | N |
| ATOM | 2859 | C | ARG | A | 203 | 9.595 | 21.805 | 32.251 | 1.00 | 12.75 | C |
| ATOM | 2860 | O | ARG | A | 203 | 9.285 | 21.570 | 31.076 | 1.00 | 12.82 | O |
| ATOM | 2861 | N | VAL | A | 204 | 10.505 | 21.090 | 32.907 | 1.00 | 12.18 | N |
| ATOM | 2863 | CA | VAL | A | 204 | 11.043 | 19.877 | 32.378 | 1.00 | 11.32 | C |
| ATOM | 2865 | CB | VAL | A | 204 | 12.141 | 19.338 | 33.296 | 1.00 | 11.73 | C |
| ATOM | 2867 | CG1 | VAL | A | 204 | 12.765 | 18.035 | 32.735 | 1.00 | 11.27 | C |
| ATOM | 2871 | CG2 | VAL | A | 204 | 13.229 | 20.373 | 33.437 | 1.00 | 12.71 | C |
| ATOM | 2875 | C | VAL | A | 204 | 9.925 | 18.831 | 32.221 | 1.00 | 12.28 | C |
| ATOM | 2876 | O | VAL | A | 204 | 9.172 | 18.549 | 33.185 | 1.00 | 12.08 | O |
| ATOM | 2877 | N | ALA | A | 205 | 9.855 | 18.166 | 31.063 | 1.00 | 12.11 | N |
| ATOM | 2879 | CA | ALA | A | 205 | 8.882 | 17.061 | 30.935 | 1.00 | 12.63 | C |
| ATOM | 2881 | CB | ALA | A | 205 | 8.725 | 16.612 | 29.473 | 1.00 | 14.20 | C |
| ATOM | 2885 | C | ALA | A | 205 | 9.205 | 15.894 | 31.835 | 1.00 | 14.44 | C |
| ATOM | 2886 | O | ALA | A | 205 | 10.338 | 15.546 | 32.067 | 1.00 | 12.72 | O |
| ATOM | 2887 | N | ASP | A | 206 | 8.160 | 15.251 | 32.353 | 1.00 | 12.46 | N |
| ATOM | 2889 | CA | ASP | A | 206 | 8.351 | 14.138 | 33.226 | 1.00 | 14.42 | C |
| ATOM | 2891 | CB | ASP | A | 206 | 7.015 | 13.579 | 33.660 | 1.00 | 15.15 | C |
| ATOM | 2894 | CG | ASP | A | 206 | 6.273 | 14.456 | 34.620 | 1.00 | 20.28 | C |
| ATOM | 2895 | OD1 | ASP | A | 206 | 6.717 | 15.552 | 35.015 | 1.00 | 16.78 | O |
| ATOM | 2896 | OD2 | ASP | A | 206 | 5.164 | 14.025 | 35.032 | 1.00 | 21.17 | O |
| ATOM | 2897 | C | ASP | A | 206 | 9.161 | 13.020 | 32.556 | 1.00 | 13.89 | C |
| ATOM | 2898 | O | ASP | A | 206 | 9.920 | 12.348 | 33.229 | 1.00 | 15.04 | O |
| ATOM | 2899 | N | PHE | A | 207 | 9.016 | 12.821 | 31.246 | 1.00 | 11.78 | N |
| ATOM | 2901 | CA | PHE | A | 207 | 9.710 | 11.721 | 30.612 | 1.00 | 13.96 | C |
| ATOM | 2903 | CB | PHE | A | 207 | 9.163 | 11.360 | 29.213 | 1.00 | 13.87 | C |
| ATOM | 2906 | CG | PHE | A | 207 | 9.290 | 12.439 | 28.191 | 1.00 | 14.05 | C |
| ATOM | 2907 | CD1 | PHE | A | 207 | 10.521 | 12.704 | 27.630 | 1.00 | 13.46 | C |
| ATOM | 2909 | CE1 | PHE | A | 207 | 10.677 | 13.677 | 26.709 | 1.00 | 14.99 | C |
| ATOM | 2911 | CZ | PHE | A | 207 | 9.577 | 14.463 | 26.305 | 1.00 | 12.88 | C |
| ATOM | 2913 | CE2 | PHE | A | 207 | 8.325 | 14.173 | 26.841 | 1.00 | 15.57 | C |
| ATOM | 2915 | CD2 | PHE | A | 207 | 8.199 | 13.191 | 27.787 | 1.00 | 14.48 | C |
| ATOM | 2917 | C | PHE | A | 207 | 11.220 | 11.917 | 30.546 | 1.00 | 12.81 | C |
| ATOM | 2918 | O | PHE | A | 207 | 11.950 | 10.945 | 30.339 | 1.00 | 12.43 | O |
| ATOM | 2919 | N | SER | A | 208 | 11.670 | 13.163 | 30.626 | 1.00 | 13.24 | N |
| ATOM | 2921 | CA | SER | A | 208 | 13.099 | 13.459 | 30.389 | 1.00 | 12.69 | C |
| ATOM | 2923 | CB | SER | A | 208 | 13.277 | 14.980 | 30.333 | 1.00 | 13.69 | C |
| ATOM | 2926 | OG | SER | A | 208 | 14.593 | 15.399 | 30.016 | 1.00 | 11.00 | O |
| ATOM | 2928 | C | SER | A | 208 | 13.997 | 12.799 | 31.432 | 1.00 | 11.85 | C |
| ATOM | 2929 | O | SER | A | 208 | 13.726 | 12.841 | 32.612 | 1.00 | 12.56 | O |
| ATOM | 2930 | N | SER | A | 209 | 15.095 | 12.168 | 31.001 | 1.00 | 11.34 | N |
| ATOM | 2932 | CA | SER | A | 209 | 15.961 | 11.503 | 31.941 | 1.00 | 12.26 | C |
| ATOM | 2934 | CB | SER | A | 209 | 17.003 | 10.655 | 31.240 | 1.00 | 10.68 | C |
| ATOM | 2937 | OG | SER | A | 209 | 16.442 | 9.566 | 30.515 | 1.00 | 11.25 | O |
| ATOM | 2939 | C | SER | A | 209 | 16.666 | 12.506 | 32.852 | 1.00 | 11.42 | C |
| ATOM | 2940 | O | SER | A | 209 | 17.108 | 13.568 | 32.420 | 1.00 | 12.21 | O |
| ATOM | 2941 | N | ARG | A | 210 | 16.797 | 12.128 | 34.107 | 1.00 | 13.04 | N |
| ATOM | 2943 | CA | ARG | A | 210 | 17.480 | 12.973 | 35.089 | 1.00 | 12.02 | C |
| ATOM | 2945 | CB | ARG | A | 210 | 16.783 | 12.925 | 36.439 | 1.00 | 11.62 | C |
| ATOM | 2948 | CG | ARG | A | 210 | 15.644 | 13.914 | 36.659 | 1.00 | 10.95 | C |
| ATOM | 2951 | CD | ARG | A | 210 | 14.531 | 13.936 | 35.593 | 1.00 | 12.61 | C |
| ATOM | 2954 | NE | ARG | A | 210 | 13.496 | 14.936 | 35.948 | 1.00 | 13.59 | N |
| ATOM | 2956 | CZ | ARG | A | 210 | 12.450 | 15.250 | 35.214 | 1.00 | 14.23 | C |
| ATOM | 2957 | NH1 | ARG | A | 210 | 12.267 | 14.655 | 34.035 | 1.00 | 14.26 | N |
| ATOM | 2960 | NH2 | ARG | A | 210 | 11.550 | 16.168 | 35.652 | 1.00 | 13.18 | N |
| ATOM | 2963 | C | ARG | A | 210 | 18.906 | 12.544 | 35.328 | 1.00 | 11.40 | C |
| ATOM | 2964 | O | ARG | A | 210 | 19.201 | 11.401 | 35.281 | 1.00 | 12.42 | O |
| ATOM | 2965 | N | GLY | A | 211 | 19.756 | 13.520 | 35.625 | 1.00 | 13.31 | N |
| ATOM | 2967 | CA | GLY | A | 211 | 21.140 | 13.289 | 35.977 | 1.00 | 11.79 | C |
| ATOM | 2970 | C | GLY | A | 211 | 21.263 | 12.757 | 37.395 | 1.00 | 13.79 | C |
| ATOM | 2971 | O | GLY | A | 211 | 20.286 | 12.467 | 38.054 | 1.00 | 13.33 | O |
| ATOM | 2972 | N | ASN | A | 212 | 22.508 | 12.644 | 37.831 | 1.00 | 12.68 | N |
| ATOM | 2974 | CA | ASN | A | 212 | 22.852 | 12.132 | 39.139 | 1.00 | 13.86 | C |
| ATOM | 2976 | CB | ASN | A | 212 | 24.300 | 11.647 | 39.062 | 1.00 | 14.05 | C |
| ATOM | 2979 | CG | ASN | A | 212 | 24.801 | 11.076 | 40.380 | 1.00 | 15.77 | C |
| ATOM | 2980 | OD1 | ASN | A | 212 | 24.034 | 10.961 | 41.330 | 1.00 | 20.22 | O |
| ATOM | 2981 | ND2 | ASN | A | 212 | 26.057 | 10.638 | 40.402 | 1.00 | 21.14 | N |
| ATOM | 2984 | C | ASN | A | 212 | 22.711 | 13.289 | 40.154 | 1.00 | 13.72 | C |
| ATOM | 2985 | O | ASN | A | 212 | 23.466 | 14.254 | 40.141 | 1.00 | 13.40 | O |
| ATOM | 2986 | N | PRO | A | 213 | 21.803 | 13.173 | 41.121 | 1.00 | 14.98 | N |
| ATOM | 2987 | CA | PRO | A | 213 | 21.672 | 14.248 | 42.125 | 1.00 | 16.29 | C |
| ATOM | 2989 | CB | PRO | A | 213 | 20.586 | 13.722 | 43.065 | 1.00 | 17.58 | C |
| ATOM | 2992 | CG | PRO | A | 213 | 19.803 | 12.803 | 42.224 | 1.00 | 16.96 | C |
| ATOM | 2995 | CD | PRO | A | 213 | 20.863 | 12.072 | 41.386 | 1.00 | 15.73 | C |

APPENDIX 1-continued

| | | | | | | | | | | | |
|---|---|---|---|---|---|---|---|---|---|---|---|
| ATOM | 2998 | C | PRO | A | 213 | 22.966 | 14.577 | 42.864 | 1.00 | 16.46 | C |
| ATOM | 2999 | O | PRO | A | 213 | 23.194 | 15.766 | 43.089 | 1.00 | 18.16 | O |
| ATOM | 3000 | N | ALA | A | 214 | 23.809 | 13.573 | 43.084 | 1.00 | 17.81 | N |
| ATOM | 3002 | CA | ALA | A | 214 | 25.058 | 13.706 | 43.843 | 1.00 | 18.79 | C |
| ATOM | 3004 | CB | ALA | A | 214 | 25.746 | 12.336 | 44.004 | 1.00 | 19.37 | C |
| ATOM | 3008 | C | ALA | A | 214 | 26.022 | 14.653 | 43.188 | 1.00 | 18.92 | C |
| ATOM | 3009 | O | ALA | A | 214 | 26.872 | 15.225 | 43.890 | 1.00 | 17.86 | O |
| ATOM | 3010 | N | THR | A | 215 | 25.899 | 14.879 | 41.869 | 1.00 | 17.03 | N |
| ATOM | 3012 | CA | THR | A | 215 | 26.868 | 15.751 | 41.205 | 1.00 | 16.66 | C |
| ATOM | 3014 | CB | THR | A | 215 | 27.741 | 14.942 | 40.212 | 1.00 | 18.38 | C |
| ATOM | 3016 | OG1 | THR | A | 215 | 26.907 | 14.218 | 39.271 | 1.00 | 15.43 | O |
| ATOM | 3018 | CG2 | THR | A | 215 | 28.532 | 13.928 | 40.970 | 1.00 | 18.05 | C |
| ATOM | 3022 | C | THR | A | 215 | 26.278 | 16.952 | 40.479 | 1.00 | 16.40 | C |
| ATOM | 3023 | O | THR | A | 215 | 26.955 | 17.636 | 39.745 | 1.00 | 16.41 | O |
| ATOM | 3024 | N | ALA | A | 216 | 25.035 | 17.244 | 40.773 | 1.00 | 14.91 | N |
| ATOM | 3026 | CA | ALA | A | 216 | 24.408 | 18.446 | 40.249 | 1.00 | 16.14 | C |
| ATOM | 3028 | CB | ALA | A | 216 | 22.944 | 18.182 | 39.938 | 1.00 | 16.49 | C |
| ATOM | 3032 | C | ALA | A | 216 | 24.479 | 19.548 | 41.271 | 1.00 | 17.73 | C |
| ATOM | 3033 | O | ALA | A | 216 | 24.240 | 19.279 | 42.445 | 1.00 | 21.27 | O |
| ATOM | 3034 | N | GLY | A | 217 | 24.699 | 20.763 | 40.840 | 1.00 | 16.83 | N |
| ATOM | 3036 | CA | GLY | A | 217 | 24.701 | 21.920 | 41.725 | 1.00 | 17.35 | C |
| ATOM | 3039 | C | GLY | A | 217 | 25.994 | 22.704 | 41.603 | 1.00 | 18.14 | C |
| ATOM | 3040 | O | GLY | A | 217 | 26.068 | 23.906 | 41.983 | 1.00 | 19.91 | O |
| ATOM | 3041 | N | ASP | A | 218 | 27.007 | 22.103 | 41.001 | 1.00 | 17.40 | N |
| ATOM | 3043 | CA | ASP | A | 218 | 28.294 | 22.767 | 40.941 | 1.00 | 16.68 | C |
| ATOM | 3045 | CB | ASP | A | 218 | 29.346 | 21.732 | 41.259 | 1.00 | 17.36 | C |
| ATOM | 3048 | CG | ASP | A | 218 | 29.393 | 20.585 | 40.244 | 1.00 | 20.24 | C |
| ATOM | 3049 | OD1 | ASP | A | 218 | 28.520 | 20.437 | 39.333 | 1.00 | 17.05 | O |
| ATOM | 3050 | OD2 | ASP | A | 218 | 30.286 | 19.734 | 40.356 | 1.00 | 20.78 | O |
| ATOM | 3051 | C | ASP | A | 218 | 28.648 | 23.526 | 39.664 | 1.00 | 15.65 | C |
| ATOM | 3052 | O | ASP | A | 218 | 29.638 | 24.231 | 39.613 | 1.00 | 15.75 | O |
| ATOM | 3053 | N | TYR | A | 219 | 27.756 | 23.522 | 38.689 | 1.00 | 15.41 | N |
| ATOM | 3055 | CA | TYR | A | 219 | 28.003 | 24.099 | 37.380 | 1.00 | 13.99 | C |
| ATOM | 3057 | CB | TYR | A | 219 | 27.987 | 25.607 | 37.463 | 1.00 | 14.94 | C |
| ATOM | 3060 | CG | TYR | A | 219 | 26.611 | 26.197 | 37.674 | 1.00 | 15.83 | C |
| ATOM | 3061 | CD1 | TYR | A | 219 | 25.642 | 26.086 | 36.702 | 1.00 | 12.98 | C |
| ATOM | 3063 | CE1 | TYR | A | 219 | 24.385 | 26.648 | 36.871 | 1.00 | 12.57 | C |
| ATOM | 3065 | CZ | TYR | A | 219 | 24.125 | 27.301 | 38.052 | 1.00 | 18.74 | C |
| ATOM | 3066 | OH | TYR | A | 219 | 22.947 | 27.921 | 38.286 | 1.00 | 18.11 | O |
| ATOM | 3068 | CE2 | TYR | A | 219 | 25.090 | 27.438 | 39.021 | 1.00 | 19.74 | C |
| ATOM | 3070 | CD2 | TYR | A | 219 | 26.309 | 26.869 | 38.843 | 1.00 | 19.78 | C |
| ATOM | 3072 | C | TYR | A | 219 | 29.346 | 23.584 | 36.756 | 1.00 | 14.17 | C |
| ATOM | 3073 | O | TYR | A | 219 | 29.978 | 24.283 | 35.984 | 1.00 | 14.67 | O |
| ATOM | 3074 | N | ILE | A | 220 | 29.676 | 22.330 | 37.031 | 1.00 | 13.56 | N |
| ATOM | 3076 | CA | ILE | A | 220 | 30.775 | 21.624 | 36.414 | 1.00 | 15.58 | C |
| ATOM | 3078 | CB | ILE | A | 220 | 31.961 | 21.438 | 37.355 | 1.00 | 15.45 | C |
| ATOM | 3080 | CG1 | ILE | A | 220 | 32.502 | 22.809 | 37.761 | 1.00 | 20.96 | C |
| ATOM | 3083 | CD1 | ILE | A | 220 | 33.397 | 22.711 | 39.015 | 1.00 | 23.15 | C |
| ATOM | 3087 | CG2 | ILE | A | 220 | 33.087 | 20.625 | 36.671 | 1.00 | 18.47 | C |
| ATOM | 3091 | C | ILE | A | 220 | 30.227 | 20.278 | 35.956 | 1.00 | 13.00 | C |
| ATOM | 3092 | O | ILE | A | 220 | 29.633 | 19.505 | 36.691 | 1.00 | 12.94 | O |
| ATOM | 3093 | N | ILE | A | 221 | 30.482 | 19.995 | 34.684 | 1.00 | 15.43 | N |
| ATOM | 3095 | CA | ILE | A | 221 | 29.934 | 18.782 | 34.088 | 1.00 | 13.93 | C |
| ATOM | 3097 | CB | ILE | A | 221 | 29.793 | 18.960 | 32.541 | 1.00 | 12.79 | C |
| ATOM | 3099 | CG1 | ILE | A | 221 | 28.733 | 19.979 | 32.164 | 1.00 | 12.82 | C |
| ATOM | 3102 | CD1 | ILE | A | 221 | 27.361 | 19.711 | 32.673 | 1.00 | 12.70 | C |
| ATOM | 3106 | CG2 | ILE | A | 221 | 29.513 | 17.651 | 31.889 | 1.00 | 14.76 | C |
| ATOM | 3110 | C | ILE | A | 221 | 30.836 | 17.584 | 34.406 | 1.00 | 14.63 | C |
| ATOM | 3111 | O | ILE | A | 221 | 32.059 | 17.583 | 34.006 | 1.00 | 14.50 | O |
| ATOM | 3112 | N | GLN | A | 222 | 30.246 | 16.602 | 35.097 | 1.00 | 13.31 | N |
| ATOM | 3114 | CA | GLN | A | 222 | 30.786 | 15.267 | 35.285 | 1.00 | 14.28 | C |
| ATOM | 3116 | CB | GLN | A | 222 | 30.772 | 14.858 | 36.759 | 1.00 | 16.33 | C |
| ATOM | 3119 | CG | GLN | A | 222 | 31.775 | 15.669 | 37.602 | 1.00 | 18.83 | C |
| ATOM | 3122 | CD | GLN | A | 222 | 31.204 | 16.936 | 38.223 | 1.00 | 21.01 | C |
| ATOM | 3123 | OE1 | GLN | A | 222 | 29.998 | 17.058 | 38.469 | 1.00 | 22.83 | O |
| ATOM | 3124 | NE2 | GLN | A | 222 | 32.089 | 17.874 | 38.517 | 1.00 | 23.39 | N |
| ATOM | 3127 | C | GLN | A | 222 | 29.935 | 14.289 | 34.460 | 1.00 | 14.17 | C |
| ATOM | 3128 | O | GLN | A | 222 | 28.921 | 14.664 | 33.874 | 1.00 | 12.09 | O |
| ATOM | 3129 | N | GLU | A | 223 | 30.438 | 13.079 | 34.313 | 1.00 | 13.56 | N |
| ATOM | 3131 | CA | GLU | A | 223 | 29.646 | 12.052 | 33.675 | 1.00 | 14.32 | C |
| ATOM | 3133 | CB | GLU | A | 223 | 30.455 | 10.767 | 33.682 | 1.00 | 14.62 | C |
| ATOM | 3136 | CG | GLU | A | 223 | 29.787 | 9.618 | 32.984 | 1.00 | 15.34 | C |
| ATOM | 3139 | CD | GLU | A | 223 | 30.759 | 8.474 | 32.706 | 1.00 | 16.41 | C |
| ATOM | 3140 | OE1 | GLU | A | 223 | 31.400 | 8.407 | 31.648 | 1.00 | 19.83 | O |
| ATOM | 3141 | OE2 | GLU | A | 223 | 30.808 | 7.645 | 33.564 | 1.00 | 19.76 | O |
| ATOM | 3142 | C | GLU | A | 223 | 28.315 | 11.911 | 34.451 | 1.00 | 12.77 | C |
| ATOM | 3143 | O | GLU | A | 223 | 28.294 | 11.981 | 35.679 | 1.00 | 13.97 | O |
| ATOM | 3144 | N | ARG | A | 224 | 27.210 | 11.785 | 33.700 | 1.00 | 11.67 | N |
| ATOM | 3146 | CA | ARG | A | 224 | 25.834 | 11.585 | 34.178 | 1.00 | 11.39 | C |
| ATOM | 3148 | CB | ARG | A | 224 | 25.730 | 10.549 | 35.305 | 1.00 | 12.52 | C |

APPENDIX 1-continued

| | | | | | | | | | | | |
|---|---|---|---|---|---|---|---|---|---|---|---|
| ATOM | 3151 | CG | ARG | A | 224 | 26.269 | 9.156 | 34.960 | 1.00 | 16.20 | C |
| ATOM | 3154 | CD | ARG | A | 224 | 25.988 | 8.116 | 36.088 | 1.00 | 19.39 | C |
| ATOM | 3157 | NE | ARG | A | 224 | 24.589 | 7.737 | 36.052 | 1.00 | 19.97 | N |
| ATOM | 3159 | CZ | ARG | A | 224 | 24.123 | 6.785 | 35.271 | 1.00 | 23.20 | C |
| ATOM | 3160 | NH1 | ARG | A | 224 | 24.939 | 6.070 | 34.516 | 1.00 | 22.67 | N |
| ATOM | 3163 | NH2 | ARG | A | 224 | 22.835 | 6.530 | 35.234 | 1.00 | 20.20 | N |
| ATOM | 3166 | C | ARG | A | 224 | 25.199 | 12.934 | 34.600 | 1.00 | 11.27 | C |
| ATOM | 3167 | O | ARG | A | 224 | 24.137 | 12.954 | 35.247 | 1.00 | 12.76 | O |
| ATOM | 3168 | N | ASP | A | 225 | 25.779 | 14.065 | 34.167 | 1.00 | 10.64 | N |
| ATOM | 3170 | CA | ASP | A | 225 | 25.141 | 15.322 | 34.440 | 1.00 | 11.57 | C |
| ATOM | 3172 | CB | ASP | A | 225 | 26.137 | 16.421 | 34.763 | 1.00 | 12.18 | C |
| ATOM | 3175 | CG | ASP | A | 225 | 26.783 | 16.290 | 36.115 | 1.00 | 11.47 | C |
| ATOM | 3176 | OD1 | ASP | A | 225 | 26.396 | 15.431 | 36.930 | 1.00 | 12.63 | O |
| ATOM | 3177 | OD2 | ASP | A | 225 | 27.738 | 17.024 | 36.366 | 1.00 | 12.98 | O |
| ATOM | 3178 | C | ASP | A | 225 | 24.386 | 15.833 | 33.187 | 1.00 | 11.72 | C |
| ATOM | 3179 | O | ASP | A | 225 | 24.880 | 15.761 | 32.028 | 1.00 | 10.65 | O |
| ATOM | 3180 | N | ILE | A | 226 | 23.195 | 16.366 | 33.428 | 1.00 | 10.89 | N |
| ATOM | 3182 | CA | ILE | A | 226 | 22.449 | 17.089 | 32.399 | 1.00 | 10.95 | C |
| ATOM | 3184 | CB | ILE | A | 226 | 20.988 | 17.379 | 32.826 | 1.00 | 10.97 | C |
| ATOM | 3186 | CG1 | ILE | A | 226 | 20.296 | 16.066 | 33.224 | 1.00 | 8.65 | C |
| ATOM | 3189 | CD1 | ILE | A | 226 | 20.064 | 15.192 | 32.004 | 1.00 | 12.39 | C |
| ATOM | 3193 | CG2 | ILE | A | 226 | 20.260 | 18.217 | 31.828 | 1.00 | 12.31 | C |
| ATOM | 3197 | C | ILE | A | 226 | 23.117 | 18.428 | 32.195 | 1.00 | 8.74 | C |
| ATOM | 3198 | O | ILE | A | 226 | 23.561 | 19.076 | 33.123 | 1.00 | 10.81 | O |
| ATOM | 3199 | N | GLU | A | 227 | 23.254 | 18.849 | 30.971 | 1.00 | 9.24 | N |
| ATOM | 3201 | CA | GLU | A | 227 | 23.902 | 20.150 | 30.715 | 1.00 | 9.53 | C |
| ATOM | 3203 | CB | GLU | A | 227 | 24.905 | 19.979 | 29.553 | 1.00 | 8.94 | C |
| ATOM | 3206 | CG | GLU | A | 227 | 25.869 | 21.131 | 29.345 | 1.00 | 9.79 | C |
| ATOM | 3209 | CD | GLU | A | 227 | 27.217 | 20.634 | 28.789 | 1.00 | 11.40 | C |
| ATOM | 3210 | OE1 | GLU | A | 227 | 27.527 | 19.431 | 28.857 | 1.00 | 8.56 | O |
| ATOM | 3211 | OE2 | GLU | A | 227 | 27.953 | 21.441 | 28.255 | 1.00 | 11.05 | O |
| ATOM | 3212 | C | GLU | A | 227 | 22.936 | 21.331 | 30.450 | 1.00 | 9.10 | C |
| ATOM | 3213 | O | GLU | A | 227 | 23.053 | 22.402 | 31.074 | 1.00 | 10.35 | O |
| ATOM | 3214 | N | VAL | A | 228 | 21.984 | 21.152 | 29.553 | 1.00 | 8.61 | N |
| ATOM | 3216 | CA | VAL | A | 228 | 21.094 | 22.222 | 29.176 | 1.00 | 7.54 | C |
| ATOM | 3218 | CB | VAL | A | 228 | 21.567 | 23.010 | 27.946 | 1.00 | 5.96 | C |
| ATOM | 3220 | CG1 | VAL | A | 228 | 22.834 | 23.726 | 28.263 | 1.00 | 8.28 | C |
| ATOM | 3224 | CG2 | VAL | A | 228 | 21.680 | 22.127 | 26.740 | 1.00 | 8.08 | C |
| ATOM | 3228 | C | VAL | A | 228 | 19.727 | 21.575 | 28.904 | 1.00 | 7.83 | C |
| ATOM | 3229 | O | VAL | A | 228 | 19.663 | 20.362 | 28.747 | 1.00 | 9.43 | O |
| ATOM | 3230 | N | SER | A | 229 | 18.716 | 22.426 | 28.809 | 1.00 | 10.13 | N |
| ATOM | 3232 | CA | SER | A | 229 | 17.369 | 22.024 | 28.520 | 1.00 | 9.88 | C |
| ATOM | 3234 | CB | SER | A | 229 | 16.457 | 22.371 | 29.674 | 1.00 | 10.86 | C |
| ATOM | 3237 | OG | SER | A | 229 | 16.811 | 21.670 | 30.827 | 1.00 | 11.90 | O |
| ATOM | 3239 | C | SER | A | 229 | 16.865 | 22.806 | 27.305 | 1.00 | 11.07 | C |
| ATOM | 3240 | O | SER | A | 229 | 17.290 | 23.949 | 27.065 | 1.00 | 11.59 | O |
| ATOM | 3241 | N | ALA | A | 230 | 15.964 | 22.167 | 26.536 | 1.00 | 10.22 | N |
| ATOM | 3243 | CA | ALA | A | 230 | 15.337 | 22.824 | 25.379 | 1.00 | 9.98 | C |
| ATOM | 3245 | CB | ALA | A | 230 | 16.245 | 22.786 | 24.202 | 1.00 | 11.98 | C |
| ATOM | 3249 | C | ALA | A | 230 | 14.001 | 22.181 | 25.011 | 1.00 | 10.40 | C |
| ATOM | 3250 | O | ALA | A | 230 | 13.639 | 21.143 | 25.539 | 1.00 | 11.74 | O |
| ATOM | 3251 | N | PRO | A | 231 | 13.241 | 22.873 | 24.162 | 1.00 | 12.52 | N |
| ATOM | 3252 | CA | PRO | A | 231 | 11.915 | 22.369 | 23.794 | 1.00 | 11.45 | C |
| ATOM | 3254 | CB | PRO | A | 231 | 11.440 | 23.308 | 22.676 | 1.00 | 12.82 | C |
| ATOM | 3257 | CG | PRO | A | 231 | 12.076 | 24.609 | 23.005 | 1.00 | 12.47 | C |
| ATOM | 3260 | CD | PRO | A | 231 | 13.518 | 24.184 | 23.540 | 1.00 | 12.90 | C |
| ATOM | 3263 | C | PRO | A | 231 | 11.967 | 20.969 | 23.241 | 1.00 | 10.90 | C |
| ATOM | 3264 | O | PRO | A | 231 | 12.689 | 20.713 | 22.238 | 1.00 | 11.39 | O |
| ATOM | 3265 | N | GLY | A | 232 | 11.194 | 20.071 | 23.863 | 1.00 | 11.69 | N |
| ATOM | 3267 | CA | GLY | A | 232 | 11.218 | 18.675 | 23.478 | 1.00 | 12.12 | C |
| ATOM | 3270 | C | GLY | A | 232 | 9.857 | 17.972 | 23.431 | 1.00 | 14.63 | C |
| ATOM | 3271 | O | GLY | A | 232 | 9.814 | 16.852 | 22.976 | 1.00 | 17.38 | O |
| ATOM | 3272 | N | ALA | A | 233 | 8.775 | 18.641 | 23.807 | 1.00 | 13.80 | N |
| ATOM | 3274 | CA | ALA | A | 233 | 7.441 | 17.975 | 23.841 | 1.00 | 15.69 | C |
| ATOM | 3276 | CB | ALA | A | 233 | 6.812 | 18.002 | 25.228 | 1.00 | 15.50 | C |
| ATOM | 3280 | C | ALA | A | 233 | 6.565 | 18.649 | 22.794 | 1.00 | 15.70 | C |
| ATOM | 3281 | O | ALA | A | 233 | 6.479 | 19.892 | 22.725 | 1.00 | 15.71 | O |
| ATOM | 3282 | N | SER | A | 234 | 6.008 | 17.837 | 21.901 | 1.00 | 15.70 | N |
| ATOM | 3284 | CA | SER | A | 234 | 5.123 | 18.323 | 20.820 | 1.00 | 17.34 | C |
| ATOM | 3286 | CB | SER | A | 234 | 3.816 | 18.866 | 21.396 | 1.00 | 19.34 | C |
| ATOM | 3289 | OG | SER | A | 234 | 3.151 | 17.862 | 22.071 | 1.00 | 24.09 | O |
| ATOM | 3291 | C | SER | A | 234 | 5.746 | 19.302 | 19.869 | 1.00 | 16.08 | C |
| ATOM | 3292 | O | SER | A | 234 | 5.311 | 20.419 | 19.727 | 1.00 | 16.37 | O |
| ATOM | 3293 | N | VAL | A | 235 | 6.816 | 18.859 | 19.244 | 1.00 | 13.70 | N |
| ATOM | 3295 | CA | VAL | A | 235 | 7.597 | 19.607 | 18.309 | 1.00 | 13.30 | C |
| ATOM | 3297 | CB | VAL | A | 235 | 9.124 | 19.358 | 18.536 | 1.00 | 11.29 | C |
| ATOM | 3299 | CG1 | VAL | A | 235 | 9.948 | 19.994 | 17.533 | 1.00 | 11.79 | C |
| ATOM | 3303 | CG2 | VAL | A | 235 | 9.475 | 19.925 | 19.919 | 1.00 | 13.78 | C |
| ATOM | 3307 | C | VAL | A | 235 | 7.284 | 19.242 | 16.876 | 1.00 | 14.46 | C |
| ATOM | 3308 | O | VAL | A | 235 | 7.529 | 18.141 | 16.413 | 1.00 | 15.04 | O |

APPENDIX 1-continued

| | | | | | | | | | | | |
|---|---|---|---|---|---|---|---|---|---|---|---|
| ATOM | 3309 | N | GLU | A | 236 | 6.773 | 20.208 | 16.151 | 1.00 | 15.81 | N |
| ATOM | 3311 | CA | GLU | A | 236 | 6.539 | 20.075 | 14.717 | 1.00 | 15.96 | C |
| ATOM | 3313 | CB | GLU | A | 236 | 5.419 | 21.059 | 14.323 | 1.00 | 16.03 | C |
| ATOM | 3316 | CG | GLU | A | 236 | 5.033 | 21.028 | 12.863 | 1.00 | 18.99 | C |
| ATOM | 3319 | CD | GLU | A | 236 | 3.833 | 21.939 | 12.549 | 1.00 | 22.94 | C |
| ATOM | 3320 | OE1 | GLU | A | 236 | 3.422 | 22.715 | 13.457 | 1.00 | 20.60 | O |
| ATOM | 3321 | OE2 | GLU | A | 236 | 3.255 | 21.772 | 11.420 | 1.00 | 20.10 | O |
| ATOM | 3322 | C | GLU | A | 236 | 7.751 | 20.349 | 13.881 | 1.00 | 16.01 | C |
| ATOM | 3323 | O | GLU | A | 236 | 8.534 | 21.272 | 14.139 | 1.00 | 17.39 | O |
| ATOM | 3324 | N | SER | A | 237 | 8.023 | 19.462 | 12.905 | 1.00 | 14.14 | N |
| ATOM | 3326 | CA | SER | A | 237 | 9.105 | 19.655 | 12.025 | 1.00 | 14.47 | C |
| ATOM | 3328 | CB | SER | A | 237 | 10.410 | 19.109 | 12.632 | 1.00 | 11.88 | C |
| ATOM | 3331 | OG | SER | A | 237 | 11.513 | 19.504 | 11.921 | 1.00 | 11.55 | O |
| ATOM | 3333 | C | SER | A | 237 | 8.819 | 18.900 | 10.715 | 1.00 | 14.97 | C |
| ATOM | 3334 | O | SER | A | 237 | 7.699 | 18.345 | 10.543 | 1.00 | 16.60 | O |
| ATOM | 3335 | N | THR | A | 238 | 9.838 | 18.892 | 9.886 | 1.00 | 15.64 | N |
| ATOM | 3337 | CA | THR | A | 238 | 9.851 | 18.230 | 8.581 | 1.00 | 17.00 | C |
| ATOM | 3339 | CB | THR | A | 238 | 11.090 | 18.559 | 7.844 | 1.00 | 18.10 | C |
| ATOM | 3341 | OG1 | THR | A | 238 | 12.267 | 18.454 | 8.677 | 1.00 | 16.55 | O |
| ATOM | 3343 | CG2 | THR | A | 238 | 11.152 | 19.996 | 7.339 | 1.00 | 16.33 | C |
| ATOM | 3347 | C | THR | A | 238 | 9.752 | 16.703 | 8.759 | 1.00 | 19.28 | C |
| ATOM | 3348 | O | THR | A | 238 | 10.213 | 16.169 | 9.768 | 1.00 | 18.16 | O |
| ATOM | 3349 | N | TRP | A | 239 | 9.203 | 16.032 | 7.739 | 1.00 | 19.48 | N |
| ATOM | 3351 | CA | TRP | A | 239 | 8.933 | 14.587 | 7.765 | 1.00 | 18.83 | C |
| ATOM | 3353 | CB | TRP | A | 239 | 7.503 | 14.322 | 8.122 | 1.00 | 19.25 | C |
| ATOM | 3356 | CG | TRP | A | 239 | 7.182 | 12.954 | 8.642 | 1.00 | 19.71 | C |
| ATOM | 3357 | CD1 | TRP | A | 239 | 6.343 | 12.009 | 8.085 | 1.00 | 23.51 | C |
| ATOM | 3359 | NE1 | TRP | A | 239 | 6.263 | 10.907 | 8.899 | 1.00 | 22.49 | N |
| ATOM | 3361 | CE2 | TRP | A | 239 | 7.081 | 11.114 | 9.985 | 1.00 | 21.32 | C |
| ATOM | 3362 | CD2 | TRP | A | 239 | 7.651 | 12.400 | 9.853 | 1.00 | 20.74 | C |
| ATOM | 3363 | CE3 | TRP | A | 239 | 8.529 | 12.864 | 10.851 | 1.00 | 18.32 | C |
| ATOM | 3365 | CZ3 | TRP | A | 239 | 8.751 | 12.055 | 11.962 | 1.00 | 21.08 | C |
| ATOM | 3367 | CH2 | TRP | A | 239 | 8.166 | 10.788 | 12.061 | 1.00 | 20.53 | C |
| ATOM | 3369 | CZ2 | TRP | A | 239 | 7.349 | 10.289 | 11.079 | 1.00 | 22.21 | C |
| ATOM | 3371 | C | TRP | A | 239 | 9.325 | 13.931 | 6.461 | 1.00 | 17.68 | C |
| ATOM | 3372 | O | TRP | A | 239 | 9.417 | 14.577 | 5.423 | 1.00 | 19.48 | O |
| ATOM | 3373 | N | TYR | A | 240 | 9.679 | 12.642 | 6.550 | 1.00 | 17.80 | N |
| ATOM | 3375 | CA | TYR | A | 240 | 10.332 | 11.947 | 5.485 | 1.00 | 17.76 | C |
| ATOM | 3377 | CB | TYR | A | 240 | 10.862 | 10.568 | 5.938 | 1.00 | 20.08 | C |
| ATOM | 3380 | CG | TYR | A | 240 | 9.864 | 9.469 | 6.036 | 1.00 | 17.92 | C |
| ATOM | 3381 | CD1 | TYR | A | 240 | 8.997 | 9.367 | 7.097 | 1.00 | 20.96 | C |
| ATOM | 3383 | CE1 | TYR | A | 240 | 8.113 | 8.325 | 7.179 | 1.00 | 22.25 | C |
| ATOM | 3385 | CZ | TYR | A | 240 | 8.150 | 7.317 | 6.171 | 1.00 | 27.67 | C |
| ATOM | 3386 | OH | TYR | A | 240 | 7.269 | 6.247 | 6.207 | 1.00 | 28.63 | O |
| ATOM | 3388 | CE2 | TYR | A | 240 | 9.034 | 7.397 | 5.159 | 1.00 | 25.36 | C |
| ATOM | 3390 | CD2 | TYR | A | 240 | 9.884 | 8.442 | 5.084 | 1.00 | 24.19 | C |
| ATOM | 3392 | C | TYR | A | 240 | 9.453 | 11.746 | 4.253 | 1.00 | 19.14 | C |
| ATOM | 3393 | O | TYR | A | 240 | 9.992 | 11.532 | 3.199 | 1.00 | 19.72 | O |
| ATOM | 3394 | N | THR | A | 241 | 8.172 | 11.873 | 4.401 | 1.00 | 21.32 | N |
| ATOM | 3396 | CA | THR | A | 241 | 7.309 | 11.777 | 3.214 | 1.00 | 24.31 | C |
| ATOM | 3398 | CB | THR | A | 241 | 6.015 | 11.129 | 3.549 | 1.00 | 24.08 | C |
| ATOM | 3400 | OG1 | THR | A | 241 | 5.443 | 11.711 | 4.720 | 1.00 | 25.38 | O |
| ATOM | 3402 | CG2 | THR | A | 241 | 6.238 | 9.670 | 3.924 | 1.00 | 28.14 | C |
| ATOM | 3406 | C | THR | A | 241 | 7.020 | 13.113 | 2.587 | 1.00 | 26.01 | C |
| ATOM | 3407 | O | THR | A | 241 | 6.175 | 13.200 | 1.682 | 1.00 | 27.85 | O |
| ATOM | 3408 | N | GLY | A | 242 | 7.684 | 14.159 | 3.041 | 1.00 | 26.13 | N |
| ATOM | 3410 | CA | GLY | A | 242 | 7.445 | 15.480 | 2.484 | 1.00 | 26.65 | C |
| ATOM | 3413 | C | GLY | A | 242 | 6.544 | 16.381 | 3.303 | 1.00 | 25.41 | C |
| ATOM | 3414 | O | GLY | A | 242 | 6.524 | 17.583 | 3.068 | 1.00 | 29.27 | O |
| ATOM | 3415 | N | GLY | A | 243 | 5.786 | 15.891 | 4.246 | 1.00 | 23.67 | N |
| ATOM | 3417 | CA | GLY | A | 243 | 5.002 | 16.882 | 4.959 | 1.00 | 23.78 | C |
| ATOM | 3420 | C | GLY | A | 243 | 5.719 | 17.300 | 6.239 | 1.00 | 21.57 | C |
| ATOM | 3421 | O | GLY | A | 243 | 6.944 | 17.532 | 6.218 | 1.00 | 20.45 | O |
| ATOM | 3422 | N | TYR | A | 244 | 4.939 | 17.380 | 7.296 | 1.00 | 22.18 | N |
| ATOM | 3424 | CA | TYR | A | 244 | 5.404 | 17.745 | 8.651 | 1.00 | 21.26 | C |
| ATOM | 3426 | CB | TYR | A | 244 | 4.991 | 19.201 | 8.963 | 1.00 | 20.92 | C |
| ATOM | 3429 | CG | TYR | A | 244 | 5.467 | 20.078 | 7.877 | 1.00 | 20.48 | C |
| ATOM | 3430 | CD1 | TYR | A | 244 | 4.696 | 20.312 | 6.749 | 1.00 | 20.98 | C |
| ATOM | 3432 | CE1 | TYR | A | 244 | 5.167 | 21.082 | 5.733 | 1.00 | 21.20 | C |
| ATOM | 3434 | CZ | TYR | A | 244 | 6.396 | 21.604 | 5.785 | 1.00 | 20.81 | C |
| ATOM | 3435 | OH | TYR | A | 244 | 6.852 | 22.332 | 4.745 | 1.00 | 23.64 | O |
| ATOM | 3437 | CE2 | TYR | A | 244 | 7.201 | 21.392 | 6.929 | 1.00 | 17.10 | C |
| ATOM | 3439 | CD2 | TYR | A | 244 | 6.714 | 20.660 | 7.920 | 1.00 | 14.54 | C |
| ATOM | 3441 | C | TYR | A | 244 | 4.789 | 16.816 | 9.621 | 1.00 | 21.28 | C |
| ATOM | 3442 | O | TYR | A | 244 | 3.778 | 16.224 | 9.353 | 1.00 | 23.43 | O |
| ATOM | 3443 | N | ASN | A | 245 | 5.381 | 16.692 | 10.800 | 1.00 | 19.64 | N |
| ATOM | 3445 | CA | ASN | A | 245 | 4.866 | 15.855 | 11.825 | 1.00 | 18.70 | C |
| ATOM | 3447 | CB | ASN | A | 245 | 5.322 | 14.418 | 11.590 | 1.00 | 18.51 | C |
| ATOM | 3450 | CG | ASN | A | 245 | 4.644 | 13.438 | 12.450 | 1.00 | 18.67 | C |
| ATOM | 3451 | OD1 | ASN | A | 245 | 3.509 | 13.611 | 12.925 | 1.00 | 21.26 | O |

APPENDIX 1-continued

| ATOM | 3452 | ND2 | ASN | A | 245 | 5.350 | 12.323 | 12.689 | 1.00 | 22.00 | N |
|------|------|-----|-----|---|-----|-------|--------|--------|------|-------|---|
| ATOM | 3455 | C | ASN | A | 245 | 5.304 | 16.401 | 13.154 | 1.00 | 16.91 | C |
| ATOM | 3456 | O | ASN | A | 245 | 6.289 | 17.194 | 13.212 | 1.00 | 17.80 | O |
| ATOM | 3457 | N | THR | A | 246 | 4.533 | 16.035 | 14.141 | 1.00 | 17.22 | N |
| ATOM | 3459 | CA | THR | A | 246 | 4.696 | 16.445 | 15.504 | 1.00 | 17.23 | C |
| ATOM | 3461 | CB | THR | A | 246 | 3.454 | 17.242 | 15.971 | 1.00 | 17.67 | C |
| ATOM | 3463 | OG1 | THR | A | 246 | 3.368 | 18.458 | 15.223 | 1.00 | 18.24 | O |
| ATOM | 3465 | CG2 | THR | A | 246 | 3.534 | 17.710 | 17.400 | 1.00 | 20.37 | C |
| ATOM | 3469 | C | THR | A | 246 | 4.993 | 15.244 | 16.374 | 1.00 | 17.33 | C |
| ATOM | 3470 | O | THR | A | 246 | 4.123 | 14.398 | 16.664 | 1.00 | 16.60 | O |
| ATOM | 3471 | N | ILE | A | 247 | 6.221 | 15.237 | 16.902 | 1.00 | 16.92 | N |
| ATOM | 3473 | CA | ILE | A | 247 | 6.655 | 14.201 | 17.813 | 1.00 | 16.77 | C |
| ATOM | 3475 | CB | ILE | A | 247 | 7.536 | 13.106 | 17.091 | 1.00 | 16.85 | C |
| ATOM | 3477 | CG1 | ILE | A | 247 | 8.722 | 13.699 | 16.372 | 1.00 | 16.22 | C |
| ATOM | 3480 | CD1 | ILE | A | 247 | 9.721 | 12.674 | 15.892 | 1.00 | 14.19 | C |
| ATOM | 3484 | CG2 | ILE | A | 247 | 6.620 | 12.272 | 16.155 | 1.00 | 18.78 | C |
| ATOM | 3488 | C | ILE | A | 247 | 7.394 | 14.839 | 19.045 | 1.00 | 14.93 | C |
| ATOM | 3489 | O | ILE | A | 247 | 7.628 | 16.050 | 19.098 | 1.00 | 15.83 | O |
| ATOM | 3490 | N | SER | A | 248 | 7.659 | 14.020 | 20.030 | 1.00 | 14.46 | N |
| ATOM | 3492 | CA | SER | A | 248 | 8.268 | 14.443 | 21.285 | 1.00 | 14.38 | C |
| ATOM | 3494 | CB | SER | A | 248 | 7.262 | 14.230 | 22.426 | 1.00 | 14.68 | C |
| ATOM | 3497 | OG | SER | A | 248 | 6.080 | 14.988 | 22.271 | 1.00 | 16.96 | O |
| ATOM | 3499 | C | SER | A | 248 | 9.470 | 13.594 | 21.672 | 1.00 | 13.40 | C |
| ATOM | 3500 | O | SER | A | 248 | 9.626 | 12.448 | 21.227 | 1.00 | 12.06 | O |
| ATOM | 3501 | N | GLY | A | 249 | 10.306 | 14.151 | 22.557 | 1.00 | 11.90 | N |
| ATOM | 3503 | CA | GLY | A | 249 | 11.402 | 13.420 | 23.140 | 1.00 | 12.25 | C |
| ATOM | 3506 | C | GLY | A | 249 | 12.615 | 14.294 | 23.393 | 1.00 | 11.45 | C |
| ATOM | 3507 | O | GLY | A | 249 | 12.672 | 15.399 | 22.898 | 1.00 | 12.12 | O |
| ATOM | 3508 | N | THR | A | 250 | 13.607 | 13.759 | 24.103 | 1.00 | 10.99 | N |
| ATOM | 3510 | CA | THR | A | 250 | 14.898 | 14.476 | 24.200 | 1.00 | 9.84 | C |
| ATOM | 3512 | CB | THR | A | 250 | 15.835 | 13.937 | 25.257 | 1.00 | 9.57 | C |
| ATOM | 3514 | OG1 | THR | A | 250 | 15.885 | 12.543 | 25.195 | 1.00 | 10.83 | O |
| ATOM | 3516 | CG2 | THR | A | 250 | 15.260 | 14.258 | 26.612 | 1.00 | 11.12 | C |
| ATOM | 3520 | C | THR | A | 250 | 15.506 | 14.531 | 22.800 | 1.00 | 9.75 | C |
| ATOM | 3521 | O | THR | A | 250 | 16.312 | 15.393 | 22.517 | 1.00 | 11.31 | O |
| ATOM | 3522 | N | SER | A | 251 | 15.101 | 13.616 | 21.938 | 1.00 | 9.71 | N |
| ATOM | 3524 | CA | SER | A | 251 | 15.396 | 13.711 | 20.513 | 1.00 | 10.29 | C |
| ATOM | 3526 | CB | SER | A | 251 | 14.647 | 12.660 | 19.691 | 1.00 | 10.44 | C |
| ATOM | 3529 | OG | SER | A | 251 | 15.278 | 11.374 | 19.720 | 1.00 | 11.64 | O |
| ATOM | 3531 | C | SER | A | 251 | 15.132 | 15.058 | 19.850 | 1.00 | 10.60 | C |
| ATOM | 3532 | O | SER | A | 251 | 15.871 | 15.475 | 18.968 | 1.00 | 12.05 | O |
| ATOM | 3533 | N | MET | A | 252 | 14.023 | 15.698 | 20.246 | 1.00 | 11.35 | N |
| ATOM | 3535 | CA | MET | A | 252 | 13.598 | 16.937 | 19.649 | 1.00 | 12.05 | C |
| ATOM | 3537 | CB | MET | A | 252 | 12.081 | 17.000 | 19.803 | 1.00 | 10.74 | C |
| ATOM | 3540 | CG | MET | A | 252 | 11.275 | 16.163 | 18.811 | 1.00 | 16.05 | C |
| ATOM | 3543 | SD | MET | A | 252 | 11.445 | 14.393 | 18.855 | 1.00 | 12.67 | S |
| ATOM | 3544 | CE | MET | A | 252 | 12.360 | 14.105 | 17.508 | 1.00 | 14.70 | C |
| ATOM | 3548 | C | MET | A | 252 | 14.248 | 18.146 | 20.363 | 1.00 | 11.00 | C |
| ATOM | 3549 | O | MET | A | 252 | 14.372 | 19.200 | 19.805 | 1.00 | 10.97 | O |
| ATOM | 3550 | N | ALA | A | 253 | 14.615 | 17.978 | 21.628 | 1.00 | 11.44 | N |
| ATOM | 3552 | CA | ALA | A | 253 | 15.300 | 19.023 | 22.361 | 1.00 | 9.30 | C |
| ATOM | 3554 | CB | ALA | A | 253 | 15.282 | 18.677 | 23.852 | 1.00 | 8.63 | C |
| ATOM | 3558 | C | ALA | A | 253 | 16.733 | 19.234 | 21.842 | 1.00 | 9.29 | C |
| ATOM | 3559 | O | ALA | A | 253 | 17.173 | 20.367 | 21.599 | 1.00 | 10.72 | O |
| ATOM | 3560 | N | THR | A | 254 | 17.388 | 18.107 | 21.578 | 1.00 | 9.20 | N |
| ATOM | 3562 | CA | THR | A | 254 | 18.776 | 18.047 | 21.127 | 1.00 | 9.63 | C |
| ATOM | 3564 | CB | THR | A | 254 | 19.131 | 16.592 | 20.838 | 1.00 | 11.67 | C |
| ATOM | 3566 | OG1 | THR | A | 254 | 19.001 | 15.823 | 22.036 | 1.00 | 9.34 | O |
| ATOM | 3568 | CG2 | THR | A | 254 | 20.504 | 16.467 | 20.434 | 1.00 | 9.85 | C |
| ATOM | 3572 | C | THR | A | 254 | 19.041 | 18.957 | 19.927 | 1.00 | 9.01 | C |
| ATOM | 3573 | O | THR | A | 254 | 19.932 | 19.782 | 19.958 | 1.00 | 9.02 | O |
| ATOM | 3574 | N | PRO | A | 255 | 18.255 | 18.848 | 18.856 | 1.00 | 10.43 | N |
| ATOM | 3575 | CA | PRO | A | 255 | 18.491 | 19.725 | 17.711 | 1.00 | 9.72 | C |
| ATOM | 3577 | CB | PRO | A | 255 | 17.607 | 19.149 | 16.621 | 1.00 | 11.04 | C |
| ATOM | 3580 | CG | PRO | A | 255 | 16.511 | 18.430 | 17.368 | 1.00 | 11.23 | C |
| ATOM | 3583 | CD | PRO | A | 255 | 17.253 | 17.817 | 18.535 | 1.00 | 11.38 | C |
| ATOM | 3586 | C | PRO | A | 255 | 18.195 | 21.185 | 17.941 | 1.00 | 10.12 | C |
| ATOM | 3587 | O | PRO | A | 255 | 18.724 | 22.018 | 17.171 | 1.00 | 9.83 | O |
| ATOM | 3588 | N | HIS | A | 256 | 17.398 | 21.535 | 18.943 | 1.00 | 10.53 | N |
| ATOM | 3590 | CA | HIS | A | 256 | 17.233 | 22.947 | 19.219 | 1.00 | 10.79 | C |
| ATOM | 3592 | CB | HIS | A | 256 | 16.192 | 23.258 | 20.298 | 1.00 | 11.66 | C |
| ATOM | 3595 | CG | HIS | A | 256 | 14.748 | 23.136 | 19.820 | 1.00 | 12.48 | C |
| ATOM | 3596 | ND1 | HIS | A | 256 | 14.086 | 21.930 | 19.732 | 1.00 | 11.32 | N |
| ATOM | 3598 | CE1 | HIS | A | 256 | 12.849 | 22.144 | 19.296 | 1.00 | 14.50 | C |
| ATOM | 3600 | NE2 | HIS | A | 256 | 12.709 | 23.434 | 19.040 | 1.00 | 12.79 | N |
| ATOM | 3602 | CD2 | HIS | A | 256 | 13.889 | 24.074 | 19.348 | 1.00 | 12.20 | C |
| ATOM | 3604 | C | HIS | A | 256 | 18.572 | 23.451 | 19.658 | 1.00 | 11.12 | C |
| ATOM | 3605 | O | HIS | A | 256 | 18.977 | 24.554 | 19.302 | 1.00 | 12.50 | O |
| ATOM | 3606 | N | VAL | A | 257 | 19.264 | 22.660 | 20.474 | 1.00 | 10.13 | N |
| ATOM | 3608 | CA | VAL | A | 257 | 20.558 | 23.078 | 20.969 | 1.00 | 9.71 | C |

APPENDIX 1-continued

| ATOM | 3610 | CB  | VAL | A | 257 | 20.966 | 22.264 | 22.219 | 1.00 | 10.12 | C |
| ATOM | 3612 | CG1 | VAL | A | 257 | 22.407 | 22.589 | 22.653 | 1.00 | 10.84 | C |
| ATOM | 3616 | CG2 | VAL | A | 257 | 19.951 | 22.451 | 23.324 | 1.00 | 11.41 | C |
| ATOM | 3620 | C   | VAL | A | 257 | 21.632 | 22.993 | 19.871 | 1.00 | 10.99 | C |
| ATOM | 3621 | O   | VAL | A | 257 | 22.483 | 23.871 | 19.782 | 1.00 | 11.55 | O |
| ATOM | 3622 | N   | ALA | A | 258 | 21.664 | 21.933 | 19.070 | 1.00 | 10.95 | N |
| ATOM | 3624 | CA  | ALA | A | 258 | 22.625 | 21.857 | 17.985 | 1.00 | 10.24 | C |
| ATOM | 3626 | CB  | ALA | A | 258 | 22.459 | 20.568 | 17.233 | 1.00 | 9.96  | C |
| ATOM | 3630 | C   | ALA | A | 258 | 22.446 | 23.027 | 17.061 | 1.00 | 11.33 | C |
| ATOM | 3631 | O   | ALA | A | 258 | 23.426 | 23.621 | 16.598 | 1.00 | 10.81 | O |
| ATOM | 3632 | N   | GLY | A | 259 | 21.191 | 23.351 | 16.799 | 1.00 | 11.66 | N |
| ATOM | 3634 | CA  | GLY | A | 259 | 20.929 | 24.467 | 15.916 | 1.00 | 12.69 | C |
| ATOM | 3637 | C   | GLY | A | 259 | 21.378 | 25.792 | 16.529 | 1.00 | 11.32 | C |
| ATOM | 3638 | O   | GLY | A | 259 | 21.928 | 26.653 | 15.830 | 1.00 | 12.25 | O |
| ATOM | 3639 | N   | LEU | A | 260 | 21.044 | 25.991 | 17.781 | 1.00 | 10.90 | N |
| ATOM | 3641 | CA  | LEU | A | 260 | 21.453 | 27.191 | 18.479 | 1.00 | 11.40 | C |
| ATOM | 3643 | CB  | LEU | A | 260 | 20.945 | 27.240 | 19.877 | 1.00 | 10.96 | C |
| ATOM | 3646 | CG  | LEU | A | 260 | 21.372 | 28.483 | 20.678 | 1.00 | 11.84 | C |
| ATOM | 3648 | CD1 | LEU | A | 260 | 20.781 | 29.683 | 20.099 | 1.00 | 16.22 | C |
| ATOM | 3652 | CD2 | LEU | A | 260 | 20.948 | 28.349 | 22.174 | 1.00 | 12.84 | C |
| ATOM | 3656 | C   | LEU | A | 260 | 22.984 | 27.291 | 18.477 | 1.00 | 12.53 | C |
| ATOM | 3657 | O   | LEU | A | 260 | 23.558 | 28.384 | 18.205 | 1.00 | 11.28 | O |
| ATOM | 3658 | N   | ALA | A | 261 | 23.644 | 26.153 | 18.745 | 1.00 | 11.39 | N |
| ATOM | 3660 | CA  | ALA | A | 261 | 25.093 | 26.133 | 18.661 | 1.00 | 11.97 | C |
| ATOM | 3662 | CB  | ALA | A | 261 | 25.604 | 24.716 | 18.889 | 1.00 | 13.65 | C |
| ATOM | 3666 | C   | ALA | A | 261 | 25.607 | 26.638 | 17.292 | 1.00 | 12.95 | C |
| ATOM | 3667 | O   | ALA | A | 261 | 26.563 | 27.413 | 17.203 | 1.00 | 12.12 | O |
| ATOM | 3668 | N   | ALA | A | 262 | 24.998 | 26.144 | 16.229 | 1.00 | 11.02 | N |
| ATOM | 3670 | CA  | ALA | A | 262 | 25.435 | 26.520 | 14.869 | 1.00 | 12.24 | C |
| ATOM | 3672 | CB  | ALA | A | 262 | 24.731 | 25.669 | 13.828 | 1.00 | 12.25 | C |
| ATOM | 3676 | C   | ALA | A | 262 | 25.200 | 28.002 | 14.619 | 1.00 | 13.52 | C |
| ATOM | 3677 | O   | ALA | A | 262 | 26.045 | 28.684 | 13.996 | 1.00 | 13.55 | O |
| ATOM | 3678 | N   | LYS | A | 263 | 24.091 | 28.505 | 15.135 | 1.00 | 13.42 | N |
| ATOM | 3680 | CA  | LYS | A | 263 | 23.730 | 29.913 | 15.021 | 1.00 | 13.54 | C |
| ATOM | 3682 | CB  | LYS | A | 263 | 22.319 | 30.164 | 15.511 | 1.00 | 14.20 | C |
| ATOM | 3685 | CG  | LYS | A | 263 | 21.797 | 31.603 | 15.356 | 1.00 | 13.78 | C |
| ATOM | 3688 | CD  | LYS | A | 263 | 20.412 | 31.725 | 15.984 | 1.00 | 15.37 | C |
| ATOM | 3691 | CE  | LYS | A | 263 | 19.936 | 33.158 | 16.011 | 1.00 | 17.70 | C |
| ATOM | 3694 | NZ  | LYS | A | 263 | 19.671 | 33.740 | 14.618 | 1.00 | 14.92 | N |
| ATOM | 3698 | C   | LYS | A | 263 | 24.754 | 30.774 | 15.736 | 1.00 | 12.81 | C |
| ATOM | 3699 | O   | LYS | A | 263 | 25.225 | 31.781 | 15.148 | 1.00 | 13.25 | O |
| ATOM | 3700 | N   | ILE | A | 264 | 25.133 | 30.393 | 16.961 | 1.00 | 12.96 | N |
| ATOM | 3702 | CA  | ILE | A | 264 | 26.107 | 31.136 | 17.723 | 1.00 | 12.47 | C |
| ATOM | 3704 | CB  | ILE | A | 264 | 26.209 | 30.579 | 19.150 | 1.00 | 12.83 | C |
| ATOM | 3706 | CG1 | ILE | A | 264 | 24.895 | 30.799 | 19.927 | 1.00 | 12.96 | C |
| ATOM | 3709 | CD1 | ILE | A | 264 | 24.829 | 30.017 | 21.259 | 1.00 | 13.94 | C |
| ATOM | 3713 | CG2 | ILE | A | 264 | 27.382 | 31.146 | 19.925 | 1.00 | 12.54 | C |
| ATOM | 3717 | C   | ILE | A | 264 | 27.478 | 31.081 | 17.018 | 1.00 | 12.78 | C |
| ATOM | 3718 | O   | ILE | A | 264 | 28.147 | 32.110 | 16.835 | 1.00 | 12.72 | O |
| ATOM | 3719 | N   | TRP | A | 265 | 27.843 | 29.890 | 16.527 | 1.00 | 12.74 | N |
| ATOM | 3721 | CA  | TRP | A | 265 | 29.194 | 29.711 | 15.984 | 1.00 | 13.37 | C |
| ATOM | 3723 | CB  | TRP | A | 265 | 29.445 | 28.252 | 15.665 | 1.00 | 13.60 | C |
| ATOM | 3726 | CG  | TRP | A | 265 | 30.859 | 27.836 | 15.758 | 1.00 | 12.37 | C |
| ATOM | 3727 | CD1 | TRP | A | 265 | 31.987 | 28.624 | 15.964 | 1.00 | 12.89 | C |
| ATOM | 3729 | NE1 | TRP | A | 265 | 33.101 | 27.823 | 16.063 | 1.00 | 14.49 | N |
| ATOM | 3731 | CE2 | TRP | A | 265 | 32.705 | 26.514 | 15.998 | 1.00 | 16.16 | C |
| ATOM | 3732 | CD2 | TRP | A | 265 | 31.313 | 26.493 | 15.796 | 1.00 | 12.95 | C |
| ATOM | 3733 | CE3 | TRP | A | 265 | 30.679 | 25.254 | 15.657 | 1.00 | 14.36 | C |
| ATOM | 3735 | CZ3 | TRP | A | 265 | 31.472 | 24.110 | 15.707 | 1.00 | 12.68 | C |
| ATOM | 3737 | CH2 | TRP | A | 265 | 32.809 | 24.180 | 15.941 | 1.00 | 12.39 | C |
| ATOM | 3739 | CZ2 | TRP | A | 265 | 33.462 | 25.359 | 16.069 | 1.00 | 15.97 | C |
| ATOM | 3741 | C   | TRP | A | 265 | 29.378 | 30.560 | 14.732 | 1.00 | 13.71 | C |
| ATOM | 3742 | O   | TRP | A | 265 | 30.423 | 31.117 | 14.530 | 1.00 | 17.12 | O |
| ATOM | 3743 | N   | SER | A | 266 | 28.330 | 30.599 | 13.922 | 1.00 | 15.25 | N |
| ATOM | 3745 | CA  | SER | A | 266 | 28.307 | 31.345 | 12.676 | 1.00 | 14.75 | C |
| ATOM | 3747 | CB  | SER | A | 266 | 27.000 | 31.130 | 11.945 | 1.00 | 15.47 | C |
| ATOM | 3750 | OG  | SER | A | 266 | 26.987 | 31.917 | 10.741 | 1.00 | 18.19 | O |
| ATOM | 3752 | C   | SER | A | 266 | 28.498 | 32.835 | 12.962 | 1.00 | 16.77 | C |
| ATOM | 3753 | O   | SER | A | 266 | 29.218 | 33.537 | 12.227 | 1.00 | 16.07 | O |
| ATOM | 3754 | N   | ALA | A | 267 | 27.903 | 33.307 | 14.053 | 1.00 | 15.63 | N |
| ATOM | 3756 | CA  | ALA | A | 267 | 28.046 | 34.711 | 14.450 | 1.00 | 17.65 | C |
| ATOM | 3758 | CB  | ALA | A | 267 | 26.911 | 35.093 | 15.318 | 1.00 | 19.01 | C |
| ATOM | 3762 | C   | ALA | A | 267 | 29.405 | 35.056 | 15.092 | 1.00 | 19.17 | C |
| ATOM | 3763 | O   | ALA | A | 267 | 29.744 | 36.249 | 15.277 | 1.00 | 18.66 | O |
| ATOM | 3764 | N   | ASN | A | 268 | 30.188 | 34.053 | 15.465 | 1.00 | 17.88 | N |
| ATOM | 3766 | CA  | ASN | A | 268 | 31.557 | 34.318 | 15.886 | 1.00 | 20.05 | C |
| ATOM | 3768 | CB  | ASN | A | 268 | 31.688 | 34.603 | 17.324 | 1.00 | 20.47 | C |
| ATOM | 3771 | CG  | ASN | A | 268 | 33.120 | 35.029 | 17.701 | 1.00 | 23.58 | C |
| ATOM | 3772 | OD1 | ASN | A | 268 | 34.017 | 35.076 | 16.860 | 1.00 | 24.59 | O |
| ATOM | 3773 | ND2 | ASN | A | 268 | 33.327 | 35.286 | 18.961 | 1.00 | 27.93 | N |

APPENDIX 1-continued

| ATOM | 3776 | C | ASN | A | 268 | 32.437 | 33.156 | 15.520 | 1.00 | 18.98 | C |
|---|---|---|---|---|---|---|---|---|---|---|---|
| ATOM | 3777 | O | ASN | A | 268 | 32.651 | 32.264 | 16.321 | 1.00 | 17.09 | O |
| ATOM | 3778 | N | THR | A | 269 | 32.915 | 33.169 | 14.289 | 1.00 | 19.21 | N |
| ATOM | 3780 | CA | THR | A | 269 | 33.696 | 32.076 | 13.772 | 1.00 | 19.25 | C |
| ATOM | 3782 | CB | THR | A | 269 | 33.838 | 32.153 | 12.207 | 1.00 | 21.27 | C |
| ATOM | 3784 | OG1 | THR | A | 269 | 34.379 | 33.443 | 11.889 | 1.00 | 21.88 | O |
| ATOM | 3786 | CG2 | THR | A | 269 | 32.479 | 32.127 | 11.565 | 1.00 | 23.50 | C |
| ATOM | 3790 | C | THR | A | 269 | 35.055 | 32.025 | 14.380 | 1.00 | 19.11 | C |
| ATOM | 3791 | O | THR | A | 269 | 35.761 | 31.117 | 14.072 | 1.00 | 19.77 | O |
| ATOM | 3792 | N | SER | A | 270 | 35.435 | 32.929 | 15.297 | 1.00 | 19.17 | N |
| ATOM | 3794 | CA | SER | A | 270 | 36.732 | 32.774 | 15.936 | 1.00 | 19.54 | C |
| ATOM | 3796 | CB | ASER | A | 270 | 37.231 | 34.105 | 16.454 | 0.50 | 19.48 | C |
| ATOM | 3797 | CB | BSER | A | 270 | 37.264 | 34.116 | 16.400 | 0.50 | 19.66 | C |
| ATOM | 3802 | OG | ASER | A | 270 | 36.235 | 34.749 | 17.225 | 0.50 | 21.34 | O |
| ATOM | 3803 | OG | BSER | A | 270 | 37.628 | 34.922 | 15.280 | 0.50 | 22.88 | O |
| ATOM | 3806 | C | SER | A | 270 | 36.679 | 31.795 | 17.100 | 1.00 | 17.42 | C |
| ATOM | 3807 | O | SER | A | 270 | 37.688 | 31.382 | 17.637 | 1.00 | 19.69 | O |
| ATOM | 3808 | N | LEU | A | 271 | 35.493 | 31.392 | 17.484 | 1.00 | 15.84 | N |
| ATOM | 3810 | CA | LEU | A | 271 | 35.364 | 30.456 | 18.595 | 1.00 | 13.46 | C |
| ATOM | 3812 | CB | LEU | A | 271 | 33.910 | 30.345 | 19.026 | 1.00 | 14.65 | C |
| ATOM | 3815 | CG | LEU | A | 271 | 33.146 | 31.575 | 19.466 | 1.00 | 15.68 | C |
| ATOM | 3817 | CD1 | LEU | A | 271 | 31.659 | 31.196 | 19.782 | 1.00 | 18.69 | C |
| ATOM | 3821 | CD2 | LEU | A | 271 | 33.807 | 32.216 | 20.685 | 1.00 | 21.20 | C |
| ATOM | 3825 | C | LEU | A | 271 | 35.806 | 29.028 | 18.220 | 1.00 | 12.04 | C |
| ATOM | 3826 | O | LEU | A | 271 | 35.573 | 28.546 | 17.091 | 1.00 | 11.86 | O |
| ATOM | 3827 | N | SER | A | 272 | 36.323 | 28.335 | 19.220 | 1.00 | 12.57 | N |
| ATOM | 3829 | CA | SER | A | 272 | 36.545 | 26.919 | 19.145 | 1.00 | 11.98 | C |
| ATOM | 3831 | CB | SER | A | 272 | 37.710 | 26.489 | 20.040 | 1.00 | 12.49 | C |
| ATOM | 3834 | OG | SER | A | 272 | 37.433 | 26.778 | 21.421 | 1.00 | 12.53 | O |
| ATOM | 3836 | C | SER | A | 272 | 35.275 | 26.244 | 19.663 | 1.00 | 11.47 | C |
| ATOM | 3837 | O | SER | A | 272 | 34.372 | 26.889 | 20.269 | 1.00 | 9.92 | O |
| ATOM | 3838 | N | HIS | A | 273 | 35.225 | 24.937 | 19.454 | 1.00 | 11.48 | N |
| ATOM | 3840 | CA | HIS | A | 273 | 34.074 | 24.187 | 19.920 | 1.00 | 11.75 | C |
| ATOM | 3842 | CB | HIS | A | 273 | 34.187 | 22.750 | 19.445 | 1.00 | 13.59 | C |
| ATOM | 3845 | CG | HIS | A | 273 | 35.160 | 21.921 | 20.197 | 1.00 | 13.01 | C |
| ATOM | 3846 | ND1 | HIS | A | 273 | 36.456 | 22.312 | 20.379 | 1.00 | 11.73 | N |
| ATOM | 3848 | CE1 | HIS | A | 273 | 37.072 | 21.402 | 21.124 | 1.00 | 13.52 | C |
| ATOM | 3850 | NE2 | HIS | A | 273 | 36.243 | 20.394 | 21.343 | 1.00 | 12.58 | N |
| ATOM | 3852 | CD2 | HIS | A | 273 | 35.039 | 20.708 | 20.787 | 1.00 | 14.38 | C |
| ATOM | 3854 | C | HIS | A | 273 | 33.887 | 24.268 | 21.427 | 1.00 | 11.79 | C |
| ATOM | 3855 | O | HIS | A | 273 | 32.723 | 24.252 | 21.930 | 1.00 | 10.83 | O |
| ATOM | 3856 | N | SER | A | 274 | 34.975 | 24.276 | 22.191 | 1.00 | 10.50 | N |
| ATOM | 3858 | CA | SER | A | 274 | 34.813 | 24.319 | 23.643 | 1.00 | 10.49 | C |
| ATOM | 3860 | CB | SER | A | 274 | 36.035 | 23.803 | 24.397 | 1.00 | 13.18 | C |
| ATOM | 3863 | OG | SER | A | 274 | 37.161 | 24.639 | 24.166 | 1.00 | 12.23 | O |
| ATOM | 3865 | C | SER | A | 274 | 34.478 | 25.702 | 24.113 | 1.00 | 12.50 | C |
| ATOM | 3866 | O | SER | A | 274 | 33.783 | 25.849 | 25.123 | 1.00 | 11.08 | O |
| ATOM | 3867 | N | GLN | A | 275 | 34.919 | 26.739 | 23.418 | 1.00 | 11.42 | N |
| ATOM | 3869 | CA | GLN | A | 275 | 34.425 | 28.072 | 23.784 | 1.00 | 11.21 | C |
| ATOM | 3871 | CB | GLN | A | 275 | 35.132 | 29.188 | 22.999 | 1.00 | 11.23 | C |
| ATOM | 3874 | CG | GLN | A | 275 | 36.608 | 29.464 | 23.375 | 1.00 | 13.15 | C |
| ATOM | 3877 | CD | GLN | A | 275 | 37.192 | 30.473 | 22.413 | 1.00 | 13.10 | C |
| ATOM | 3878 | OE1 | GLN | A | 275 | 37.323 | 30.182 | 21.228 | 1.00 | 15.35 | O |
| ATOM | 3879 | NE2 | GLN | A | 275 | 37.555 | 31.677 | 22.923 | 1.00 | 11.91 | N |
| ATOM | 3882 | C | GLN | A | 275 | 32.898 | 28.177 | 23.457 | 1.00 | 11.10 | C |
| ATOM | 3883 | O | GLN | A | 275 | 32.150 | 28.776 | 24.217 | 1.00 | 10.23 | O |
| ATOM | 3884 | N | LEU | A | 276 | 32.492 | 27.556 | 22.340 | 1.00 | 10.08 | N |
| ATOM | 3886 | CA | LEU | A | 276 | 31.067 | 27.521 | 21.932 | 1.00 | 10.49 | C |
| ATOM | 3888 | CB | LEU | A | 276 | 30.909 | 26.866 | 20.582 | 1.00 | 10.65 | C |
| ATOM | 3891 | CG | LEU | A | 276 | 29.466 | 26.606 | 20.164 | 1.00 | 8.36 | C |
| ATOM | 3893 | CD1 | LEU | A | 276 | 28.715 | 27.856 | 20.038 | 1.00 | 9.01 | C |
| ATOM | 3897 | CD2 | LEU | A | 276 | 29.489 | 25.869 | 18.849 | 1.00 | 11.63 | C |
| ATOM | 3901 | C | LEU | A | 276 | 30.272 | 26.790 | 23.041 | 1.00 | 11.06 | C |
| ATOM | 3902 | O | LEU | A | 276 | 29.226 | 27.252 | 23.494 | 1.00 | 10.87 | O |
| ATOM | 3903 | N | ARG | A | 277 | 30.783 | 25.671 | 23.524 | 1.00 | 9.13 | N |
| ATOM | 3905 | CA | ARG | A | 277 | 30.104 | 24.934 | 24.560 | 1.00 | 11.95 | C |
| ATOM | 3907 | CB | ARG | A | 277 | 30.915 | 23.671 | 24.913 | 1.00 | 10.95 | C |
| ATOM | 3910 | CG | ARG | A | 277 | 30.335 | 22.793 | 26.018 | 1.00 | 13.22 | C |
| ATOM | 3913 | CD | ARG | A | 277 | 31.103 | 21.490 | 26.229 | 1.00 | 13.28 | C |
| ATOM | 3916 | NE | ARG | A | 277 | 30.415 | 20.601 | 27.149 | 1.00 | 13.25 | N |
| ATOM | 3918 | CZ | ARG | A | 277 | 30.892 | 19.416 | 27.518 | 1.00 | 14.34 | C |
| ATOM | 3919 | NH1 | ARG | A | 277 | 32.089 | 19.014 | 27.110 | 1.00 | 14.38 | N |
| ATOM | 3922 | NH2 | ARG | A | 277 | 30.190 | 18.660 | 28.345 | 1.00 | 13.28 | N |
| ATOM | 3925 | C | ARG | A | 277 | 29.974 | 25.722 | 25.858 | 1.00 | 12.12 | C |
| ATOM | 3926 | O | ARG | A | 277 | 28.949 | 25.722 | 26.538 | 1.00 | 12.16 | O |
| ATOM | 3927 | N | THR | A | 278 | 31.023 | 26.469 | 26.175 | 1.00 | 12.13 | N |
| ATOM | 3929 | CA | THR | A | 278 | 31.049 | 27.295 | 27.359 | 1.00 | 11.62 | C |
| ATOM | 3931 | CB | THR | A | 278 | 32.461 | 27.918 | 27.485 | 1.00 | 12.51 | C |
| ATOM | 3933 | OG1 | THR | A | 278 | 33.379 | 26.892 | 27.846 | 1.00 | 15.78 | O |
| ATOM | 3935 | CG2 | THR | A | 278 | 32.551 | 28.829 | 28.624 | 1.00 | 17.34 | C |

APPENDIX 1-continued

| | | | | | | | | | | | |
|---|---|---|---|---|---|---|---|---|---|---|---|
| ATOM | 3939 | C | THR | A | 278 | 29.990 | 28.388 | 27.287 | 1.00 | 10.34 | C |
| ATOM | 3940 | O | THR | A | 278 | 29.372 | 28.715 | 28.294 | 1.00 | 11.22 | O |
| ATOM | 3941 | N | GLU | A | 279 | 29.775 | 28.943 | 26.101 | 1.00 | 10.24 | N |
| ATOM | 3943 | CA | GLU | A | 279 | 28.804 | 30.034 | 25.920 | 1.00 | 10.36 | C |
| ATOM | 3945 | CB | GLU | A | 279 | 29.090 | 30.744 | 24.607 | 1.00 | 13.04 | C |
| ATOM | 3948 | CG | GLU | A | 279 | 28.155 | 31.799 | 24.172 | 1.00 | 13.67 | C |
| ATOM | 3951 | CD | GLU | A | 279 | 27.827 | 32.923 | 25.148 | 1.00 | 11.41 | C |
| ATOM | 3952 | OE1 | GLU | A | 279 | 28.413 | 33.084 | 26.245 | 1.00 | 12.14 | O |
| ATOM | 3953 | OE2 | GLU | A | 279 | 26.928 | 33.691 | 24.766 | 1.00 | 13.94 | O |
| ATOM | 3954 | C | GLU | A | 279 | 27.387 | 29.439 | 25.978 | 1.00 | 10.50 | C |
| ATOM | 3955 | O | GLU | A | 279 | 26.477 | 30.093 | 26.462 | 1.00 | 10.16 | O |
| ATOM | 3956 | N | LEU | A | 280 | 27.198 | 28.205 | 25.499 | 1.00 | 10.73 | N |
| ATOM | 3958 | CA | LEU | A | 280 | 25.898 | 27.507 | 25.652 | 1.00 | 10.31 | C |
| ATOM | 3960 | CB | LEU | A | 280 | 25.846 | 26.124 | 24.973 | 1.00 | 12.52 | C |
| ATOM | 3963 | CG | LEU | A | 280 | 25.772 | 26.107 | 23.451 | 1.00 | 13.85 | C |
| ATOM | 3965 | CD1 | LEU | A | 280 | 25.964 | 24.631 | 22.911 | 1.00 | 17.63 | C |
| ATOM | 3969 | CD2 | LEU | A | 280 | 24.435 | 26.669 | 22.957 | 1.00 | 15.10 | C |
| ATOM | 3973 | C | LEU | A | 280 | 25.613 | 27.411 | 27.150 | 1.00 | 10.89 | C |
| ATOM | 3974 | O | LEU | A | 280 | 24.492 | 27.626 | 27.606 | 1.00 | 12.00 | O |
| ATOM | 3975 | N | GLN | A | 281 | 26.630 | 27.040 | 27.907 | 1.00 | 9.57 | N |
| ATOM | 3977 | CA | GLN | A | 281 | 26.479 | 26.931 | 29.322 | 1.00 | 11.52 | C |
| ATOM | 3979 | CB | GLN | A | 281 | 27.755 | 26.360 | 29.925 | 1.00 | 11.03 | C |
| ATOM | 3982 | CG | GLN | A | 281 | 28.028 | 24.891 | 29.487 | 1.00 | 12.22 | C |
| ATOM | 3985 | CD | GLN | A | 281 | 29.376 | 24.377 | 29.981 | 1.00 | 14.98 | C |
| ATOM | 3986 | OE1 | GLN | A | 281 | 30.115 | 25.172 | 30.555 | 1.00 | 15.61 | O |
| ATOM | 3987 | NE2 | GLN | A | 281 | 29.731 | 23.103 | 29.697 | 1.00 | 9.95 | N |
| ATOM | 3990 | C | GLN | A | 281 | 26.161 | 28.313 | 29.924 | 1.00 | 10.71 | C |
| ATOM | 3991 | O | GLN | A | 281 | 25.309 | 28.409 | 30.815 | 1.00 | 11.77 | O |
| ATOM | 3992 | N | ASN | A | 282 | 26.883 | 29.367 | 29.484 | 1.00 | 10.78 | N |
| ATOM | 3994 | CA | ASN | A | 282 | 26.722 | 30.715 | 30.090 | 1.00 | 10.24 | C |
| ATOM | 3996 | CB | ASN | A | 282 | 27.683 | 31.745 | 29.504 | 1.00 | 10.08 | C |
| ATOM | 3999 | CG | ASN | A | 282 | 29.136 | 31.482 | 29.812 | 1.00 | 13.02 | C |
| ATOM | 4000 | OD1 | ASN | A | 282 | 29.471 | 30.830 | 30.809 | 1.00 | 14.49 | O |
| ATOM | 4001 | ND2 | ASN | A | 282 | 30.003 | 32.000 | 28.973 | 1.00 | 12.29 | N |
| ATOM | 4004 | C | ASN | A | 282 | 25.275 | 31.172 | 29.788 | 1.00 | 11.08 | C |
| ATOM | 4005 | O | ASN | A | 282 | 24.588 | 31.667 | 30.681 | 1.00 | 12.10 | O |
| ATOM | 4006 | N | ARG | A | 283 | 24.829 | 30.902 | 28.575 | 1.00 | 9.30 | N |
| ATOM | 4008 | CA | ARG | A | 283 | 23.484 | 31.298 | 28.160 | 1.00 | 10.89 | C |
| ATOM | 4010 | CB | ARG | A | 283 | 23.305 | 31.055 | 26.697 | 1.00 | 10.96 | C |
| ATOM | 4013 | CG | ARG | A | 283 | 23.894 | 32.191 | 25.842 | 1.00 | 13.15 | C |
| ATOM | 4016 | CD | ARG | A | 283 | 23.768 | 31.880 | 24.383 | 1.00 | 11.91 | C |
| ATOM | 4019 | NE | ARG | A | 283 | 24.469 | 32.831 | 23.466 | 1.00 | 12.89 | N |
| ATOM | 4021 | CZ | ARG | A | 283 | 23.985 | 33.290 | 22.311 | 1.00 | 15.41 | C |
| ATOM | 4022 | NH1 | ARG | A | 283 | 22.780 | 33.006 | 21.903 | 1.00 | 15.22 | N |
| ATOM | 4025 | NH2 | ARG | A | 283 | 24.722 | 34.053 | 21.528 | 1.00 | 14.46 | N |
| ATOM | 4028 | C | ARG | A | 283 | 22.450 | 30.528 | 28.963 | 1.00 | 10.28 | C |
| ATOM | 4029 | O | ARG | A | 283 | 21.390 | 31.063 | 29.298 | 1.00 | 11.49 | O |
| ATOM | 4030 | N | ALA | A | 284 | 22.741 | 29.263 | 29.220 | 1.00 | 10.27 | N |
| ATOM | 4032 | CA | ALA | A | 284 | 21.789 | 28.438 | 29.957 | 1.00 | 10.07 | C |
| ATOM | 4034 | CB | ALA | A | 284 | 22.358 | 27.011 | 30.158 | 1.00 | 11.06 | C |
| ATOM | 4038 | C | ALA | A | 284 | 21.493 | 29.093 | 31.306 | 1.00 | 10.53 | C |
| ATOM | 4039 | O | ALA | A | 284 | 20.349 | 29.096 | 31.809 | 1.00 | 11.23 | O |
| ATOM | 4040 | N | LYS | A | 285 | 22.539 | 29.620 | 31.899 | 1.00 | 10.42 | N |
| ATOM | 4042 | CA | LYS | A | 285 | 22.446 | 30.158 | 33.238 | 1.00 | 10.99 | C |
| ATOM | 4044 | CB | LYS | A | 285 | 23.846 | 30.372 | 33.821 | 1.00 | 11.62 | C |
| ATOM | 4047 | CG | LYS | A | 285 | 24.664 | 29.120 | 34.054 | 1.00 | 12.18 | C |
| ATOM | 4050 | CD | LYS | A | 285 | 26.057 | 29.529 | 34.477 | 1.00 | 16.21 | C |
| ATOM | 4053 | CE | LYS | A | 285 | 27.062 | 28.492 | 34.451 | 1.00 | 15.01 | C |
| ATOM | 4056 | NZ | LYS | A | 285 | 28.349 | 29.067 | 35.077 | 1.00 | 17.35 | N |
| ATOM | 4060 | C | LYS | A | 285 | 21.566 | 31.386 | 33.281 | 1.00 | 11.59 | C |
| ATOM | 4061 | O | LYS | A | 285 | 21.120 | 31.753 | 34.363 | 1.00 | 12.70 | O |
| ATOM | 4062 | N | VAL | A | 286 | 21.419 | 32.094 | 32.168 | 1.00 | 10.88 | N |
| ATOM | 4064 | CA | VAL | A | 286 | 20.604 | 33.255 | 32.110 | 1.00 | 12.69 | C |
| ATOM | 4066 | CB | VAL | A | 286 | 20.719 | 33.961 | 30.788 | 1.00 | 12.21 | C |
| ATOM | 4068 | CG1 | VAL | A | 286 | 19.838 | 35.220 | 30.746 | 1.00 | 15.12 | C |
| ATOM | 4072 | CG2 | VAL | A | 286 | 22.221 | 34.402 | 30.612 | 1.00 | 13.05 | C |
| ATOM | 4076 | C | VAL | A | 286 | 19.153 | 32.850 | 32.362 | 1.00 | 13.03 | C |
| ATOM | 4077 | O | VAL | A | 286 | 18.399 | 33.651 | 32.960 | 1.00 | 13.04 | O |
| ATOM | 4078 | N | TYR | A | 287 | 18.788 | 31.649 | 31.885 | 1.00 | 11.44 | N |
| ATOM | 4080 | CA | TYR | A | 287 | 17.427 | 31.124 | 32.057 | 1.00 | 12.02 | C |
| ATOM | 4082 | CB | TYR | A | 287 | 16.740 | 30.949 | 30.718 | 1.00 | 12.84 | C |
| ATOM | 4085 | CG | TYR | A | 287 | 16.587 | 32.235 | 29.976 | 1.00 | 12.74 | C |
| ATOM | 4086 | CD1 | TYR | A | 287 | 15.615 | 33.157 | 30.344 | 1.00 | 14.60 | C |
| ATOM | 4088 | CE1 | TYR | A | 287 | 15.490 | 34.343 | 29.748 | 1.00 | 14.77 | C |
| ATOM | 4090 | CZ | TYR | A | 287 | 16.343 | 34.709 | 28.753 | 1.00 | 15.62 | C |
| ATOM | 4091 | OH | TYR | A | 287 | 16.139 | 35.938 | 28.183 | 1.00 | 18.73 | O |
| ATOM | 4093 | CE2 | TYR | A | 287 | 17.372 | 33.852 | 28.377 | 1.00 | 13.12 | C |
| ATOM | 4095 | CD2 | TYR | A | 287 | 17.521 | 32.646 | 28.995 | 1.00 | 11.74 | C |
| ATOM | 4097 | C | TYR | A | 287 | 17.427 | 29.860 | 32.905 | 1.00 | 12.13 | C |
| ATOM | 4098 | O | TYR | A | 287 | 17.303 | 28.740 | 32.452 | 1.00 | 13.99 | O |

APPENDIX 1-continued

| ATOM | 4099 | N | ASP | A | 288 | 17.631 | 30.057 | 34.208 | 1.00 | 12.75 | N |
|---|---|---|---|---|---|---|---|---|---|---|---|
| ATOM | 4101 | CA | ASP | A | 288 | 17.553 | 29.009 | 35.170 | 1.00 | 11.58 | C |
| ATOM | 4103 | CB | ASP | A | 288 | 17.721 | 29.636 | 36.551 | 1.00 | 11.65 | C |
| ATOM | 4106 | CG | ASP | A | 288 | 17.912 | 28.612 | 37.687 | 1.00 | 15.60 | C |
| ATOM | 4107 | OD1 | ASP | A | 288 | 18.065 | 27.373 | 37.473 | 1.00 | 17.35 | O |
| ATOM | 4108 | OD2 | ASP | A | 288 | 17.934 | 29.001 | 38.898 | 1.00 | 15.75 | O |
| ATOM | 4109 | C | ASP | A | 288 | 16.174 | 28.337 | 35.056 | 1.00 | 12.45 | C |
| ATOM | 4110 | O | ASP | A | 288 | 15.186 | 29.032 | 34.950 | 1.00 | 13.43 | O |
| ATOM | 4111 | N | ILE | A | 289 | 16.112 | 27.026 | 34.986 | 1.00 | 10.72 | N |
| ATOM | 4113 | CA | ILE | A | 289 | 14.812 | 26.271 | 34.969 | 1.00 | 12.80 | C |
| ATOM | 4115 | CB | ILE | A | 289 | 14.860 | 25.168 | 33.912 | 1.00 | 12.78 | C |
| ATOM | 4117 | CG1 | ILE | A | 289 | 15.042 | 25.785 | 32.535 | 1.00 | 13.67 | C |
| ATOM | 4120 | CD1 | ILE | A | 289 | 13.745 | 26.474 | 31.867 | 1.00 | 13.36 | C |
| ATOM | 4124 | CG2 | ILE | A | 289 | 13.659 | 24.220 | 33.989 | 1.00 | 14.37 | C |
| ATOM | 4128 | C | ILE | A | 289 | 14.517 | 25.742 | 36.352 | 1.00 | 13.79 | C |
| ATOM | 4129 | O | ILE | A | 289 | 15.376 | 25.140 | 37.045 | 1.00 | 12.95 | O |
| ATOM | 4130 | N | LYS | A | 290 | 13.299 | 26.006 | 36.825 | 1.00 | 14.91 | N |
| ATOM | 4132 | CA | LYS | A | 290 | 12.904 | 25.675 | 38.185 | 1.00 | 16.59 | C |
| ATOM | 4134 | CB | LYS | A | 290 | 12.600 | 26.955 | 38.930 | 1.00 | 17.67 | C |
| ATOM | 4137 | CG | LYS | A | 290 | 13.878 | 27.786 | 39.143 | 1.00 | 21.86 | C |
| ATOM | 4140 | CD | LYS | A | 290 | 13.627 | 28.893 | 40.134 | 1.00 | 28.07 | C |
| ATOM | 4143 | CE | LYS | A | 290 | 13.554 | 30.215 | 39.470 | 1.00 | 34.10 | C |
| ATOM | 4146 | NZ | LYS | A | 290 | 13.272 | 31.317 | 40.512 | 1.00 | 39.60 | N |
| ATOM | 4150 | C | LYS | A | 290 | 11.648 | 24.807 | 38.235 | 1.00 | 16.71 | C |
| ATOM | 4151 | O | LYS | A | 290 | 11.200 | 24.444 | 39.330 | 1.00 | 18.64 | O |
| ATOM | 4152 | N | GLY | A | 291 | 11.119 | 24.507 | 37.071 | 1.00 | 15.39 | N |
| ATOM | 4154 | CA | GLY | A | 291 | 9.895 | 23.740 | 36.907 | 1.00 | 14.24 | C |
| ATOM | 4157 | C | GLY | A | 291 | 10.134 | 22.294 | 36.570 | 1.00 | 14.85 | C |
| ATOM | 4158 | O | GLY | A | 291 | 10.997 | 21.990 | 35.707 | 1.00 | 15.05 | O |
| ATOM | 4159 | N | GLY | A | 292 | 9.376 | 21.387 | 37.185 | 1.00 | 15.54 | N |
| ATOM | 4161 | CA | GLY | A | 292 | 9.524 | 19.984 | 36.896 | 1.00 | 14.12 | C |
| ATOM | 4164 | C | GLY | A | 292 | 10.116 | 19.187 | 38.030 | 1.00 | 15.07 | C |
| ATOM | 4165 | O | GLY | A | 292 | 10.717 | 19.734 | 38.959 | 1.00 | 15.42 | O |
| ATOM | 4166 | N | ILE | A | 293 | 9.932 | 17.878 | 37.980 | 1.00 | 14.74 | N |
| ATOM | 4168 | CA | ILE | A | 293 | 10.363 | 17.018 | 39.044 | 1.00 | 15.41 | C |
| ATOM | 4170 | CB | ILE | A | 293 | 9.881 | 15.599 | 38.776 | 1.00 | 15.32 | C |
| ATOM | 4172 | CG1 | ILE | A | 293 | 8.342 | 15.549 | 38.894 | 1.00 | 18.82 | C |
| ATOM | 4175 | CD1 | ILE | A | 293 | 7.731 | 14.260 | 38.471 | 1.00 | 21.20 | C |
| ATOM | 4179 | CG2 | ILE | A | 293 | 10.526 | 14.610 | 39.740 | 1.00 | 15.00 | C |
| ATOM | 4183 | C | ILE | A | 293 | 11.885 | 17.052 | 39.176 | 1.00 | 16.26 | C |
| ATOM | 4184 | O | ILE | A | 293 | 12.586 | 16.688 | 38.214 | 1.00 | 14.62 | O |
| ATOM | 4185 | N | GLY | A | 294 | 12.367 | 17.439 | 40.346 | 1.00 | 14.72 | N |
| ATOM | 4187 | CA | GLY | A | 294 | 13.810 | 17.581 | 40.559 | 1.00 | 15.36 | C |
| ATOM | 4190 | C | GLY | A | 294 | 14.449 | 18.897 | 40.107 | 1.00 | 13.63 | C |
| ATOM | 4191 | O | GLY | A | 294 | 15.660 | 19.095 | 40.315 | 1.00 | 15.06 | O |
| ATOM | 4192 | N | ALA | A | 295 | 13.688 | 19.803 | 39.516 | 1.00 | 14.00 | N |
| ATOM | 4194 | CA | ALA | A | 295 | 14.220 | 21.064 | 39.058 | 1.00 | 13.92 | C |
| ATOM | 4196 | CB | ALA | A | 295 | 13.381 | 21.661 | 37.869 | 1.00 | 14.66 | C |
| ATOM | 4200 | C | ALA | A | 295 | 14.226 | 21.990 | 40.236 | 1.00 | 16.73 | C |
| ATOM | 4201 | O | ALA | A | 295 | 13.451 | 21.811 | 41.178 | 1.00 | 16.12 | O |
| ATOM | 4202 | N | GLY | A | 296 | 15.094 | 22.986 | 40.227 | 1.00 | 16.79 | N |
| ATOM | 4204 | CA | GLY | A | 296 | 15.114 | 23.941 | 41.340 | 1.00 | 18.72 | C |
| ATOM | 4207 | C | GLY | A | 296 | 16.052 | 25.058 | 41.052 | 1.00 | 17.66 | C |
| ATOM | 4208 | O | GLY | A | 296 | 16.601 | 25.160 | 39.963 | 1.00 | 16.21 | O |
| ATOM | 4209 | N | THR | A | 297 | 16.240 | 25.979 | 41.992 | 1.00 | 17.88 | N |
| ATOM | 4211 | CA | THR | A | 297 | 17.144 | 27.068 | 41.712 | 1.00 | 17.28 | C |
| ATOM | 4213 | CB | THR | A | 297 | 17.117 | 27.981 | 42.941 | 1.00 | 19.91 | C |
| ATOM | 4215 | OG1 | THR | A | 297 | 15.763 | 28.455 | 43.102 | 1.00 | 19.89 | O |
| ATOM | 4217 | CG2 | THR | A | 297 | 17.981 | 29.177 | 42.689 | 1.00 | 19.92 | C |
| ATOM | 4221 | C | THR | A | 297 | 18.563 | 26.600 | 41.472 | 1.00 | 17.13 | C |
| ATOM | 4222 | O | THR | A | 297 | 19.104 | 25.832 | 42.248 | 1.00 | 18.37 | O |
| ATOM | 4223 | N | GLY | A | 298 | 19.193 | 27.074 | 40.410 | 1.00 | 14.91 | N |
| ATOM | 4225 | CA | GLY | A | 298 | 20.569 | 26.702 | 40.153 | 1.00 | 15.10 | C |
| ATOM | 4228 | C | GLY | A | 298 | 20.684 | 25.492 | 39.273 | 1.00 | 14.01 | C |
| ATOM | 4229 | O | GLY | A | 298 | 19.717 | 25.039 | 38.656 | 1.00 | 12.62 | O |
| ATOM | 4230 | N | ASP | A | 299 | 21.882 | 24.932 | 39.243 | 1.00 | 13.64 | N |
| ATOM | 4232 | CA | ASP | A | 299 | 22.189 | 23.741 | 38.460 | 1.00 | 13.68 | C |
| ATOM | 4234 | CB | ASP | A | 299 | 23.689 | 23.623 | 38.447 | 1.00 | 14.28 | C |
| ATOM | 4237 | CG | ASP | A | 299 | 24.229 | 22.342 | 37.843 | 1.00 | 15.32 | C |
| ATOM | 4238 | OD1 | ASP | A | 299 | 23.578 | 21.787 | 36.970 | 1.00 | 13.87 | O |
| ATOM | 4239 | OD2 | ASP | A | 299 | 25.330 | 21.885 | 38.238 | 1.00 | 13.70 | O |
| ATOM | 4240 | C | ASP | A | 299 | 21.507 | 22.602 | 39.092 | 1.00 | 14.87 | C |
| ATOM | 4241 | O | ASP | A | 299 | 21.657 | 22.381 | 40.306 | 1.00 | 16.32 | O |
| ATOM | 4242 | N | ASP | A | 300 | 20.664 | 21.901 | 38.348 | 1.00 | 12.69 | N |
| ATOM | 4244 | CA | ASP | A | 300 | 19.921 | 20.812 | 38.953 | 1.00 | 12.30 | C |
| ATOM | 4246 | CB | ASP | A | 300 | 18.489 | 21.282 | 39.369 | 1.00 | 12.84 | C |
| ATOM | 4249 | CG | ASP | A | 300 | 17.615 | 21.597 | 38.192 | 1.00 | 11.72 | C |
| ATOM | 4250 | OD1 | ASP | A | 300 | 17.330 | 20.687 | 37.428 | 1.00 | 13.65 | O |
| ATOM | 4251 | OD2 | ASP | A | 300 | 17.079 | 22.691 | 38.018 | 1.00 | 14.33 | O |
| ATOM | 4252 | C | ASP | A | 300 | 19.928 | 19.603 | 38.011 | 1.00 | 13.91 | C |

APPENDIX 1-continued

| ATOM | 4253 | O | ASP | A | 300 | 20.278 | 19.699 | 36.822 | 1.00 | 13.63 | O |
| ATOM | 4254 | N | TYR | A | 301 | 19.514 | 18.462 | 38.539 | 1.00 | 13.49 | N |
| ATOM | 4256 | CA | TYR | A | 301 | 19.627 | 17.220 | 37.803 | 1.00 | 12.93 | C |
| ATOM | 4258 | CB | TYR | A | 301 | 19.868 | 16.046 | 38.777 | 1.00 | 11.22 | C |
| ATOM | 4261 | CG | TYR | A | 301 | 18.804 | 15.846 | 39.823 | 1.00 | 13.88 | C |
| ATOM | 4262 | CD1 | TYR | A | 301 | 17.648 | 15.225 | 39.523 | 1.00 | 14.91 | C |
| ATOM | 4264 | CE1 | TYR | A | 301 | 16.621 | 15.079 | 40.531 | 1.00 | 17.24 | C |
| ATOM | 4266 | CZ | TYR | A | 301 | 16.809 | 15.580 | 41.788 | 1.00 | 19.26 | C |
| ATOM | 4267 | OH | TYR | A | 301 | 15.803 | 15.394 | 42.776 | 1.00 | 20.79 | O |
| ATOM | 4269 | CE2 | TYR | A | 301 | 17.977 | 16.242 | 42.081 | 1.00 | 16.95 | C |
| ATOM | 4271 | CD2 | TYR | A | 301 | 18.948 | 16.384 | 41.095 | 1.00 | 13.89 | C |
| ATOM | 4273 | C | TYR | A | 301 | 18.421 | 16.951 | 36.875 | 1.00 | 11.64 | C |
| ATOM | 4274 | O | TYR | A | 301 | 18.419 | 15.954 | 36.154 | 1.00 | 11.11 | O |
| ATOM | 4275 | N | ALA | A | 302 | 17.435 | 17.846 | 36.832 | 1.00 | 11.29 | N |
| ATOM | 4277 | CA | ALA | A | 302 | 16.389 | 17.756 | 35.829 | 1.00 | 10.84 | C |
| ATOM | 4279 | CB | ALA | A | 302 | 15.006 | 18.227 | 36.391 | 1.00 | 12.99 | C |
| ATOM | 4283 | C | ALA | A | 302 | 16.684 | 18.574 | 34.581 | 1.00 | 10.79 | C |
| ATOM | 4284 | O | ALA | A | 302 | 16.424 | 18.146 | 33.444 | 1.00 | 11.72 | O |
| ATOM | 4285 | N | SER | A | 303 | 17.194 | 19.774 | 34.790 | 1.00 | 10.48 | N |
| ATOM | 4287 | CA | SER | A | 303 | 17.364 | 20.706 | 33.697 | 1.00 | 9.41 | C |
| ATOM | 4289 | CB | SER | A | 303 | 16.512 | 21.934 | 33.969 | 1.00 | 9.70 | C |
| ATOM | 4292 | OG | SER | A | 303 | 16.992 | 22.660 | 35.130 | 1.00 | 12.05 | O |
| ATOM | 4294 | C | SER | A | 303 | 18.819 | 21.172 | 33.468 | 1.00 | 10.16 | C |
| ATOM | 4295 | O | SER | A | 303 | 19.049 | 21.949 | 32.566 | 1.00 | 10.53 | O |
| ATOM | 4296 | N | GLY | A | 304 | 19.742 | 20.739 | 34.303 | 1.00 | 8.73 | N |
| ATOM | 4298 | CA | GLY | A | 304 | 21.132 | 21.139 | 34.201 | 1.00 | 10.18 | C |
| ATOM | 4301 | C | GLY | A | 304 | 21.273 | 22.616 | 34.479 | 1.00 | 10.17 | C |
| ATOM | 4302 | O | GLY | A | 304 | 20.710 | 23.138 | 35.422 | 1.00 | 10.02 | O |
| ATOM | 4303 | N | PHE | A | 305 | 22.102 | 23.286 | 33.664 | 1.00 | 11.73 | N |
| ATOM | 4305 | CA | PHE | A | 305 | 22.452 | 24.644 | 33.880 | 1.00 | 10.68 | C |
| ATOM | 4307 | CB | PHE | A | 305 | 23.661 | 25.048 | 33.036 | 1.00 | 10.84 | C |
| ATOM | 4310 | CG | PHE | A | 305 | 24.977 | 24.418 | 33.419 | 1.00 | 11.70 | C |
| ATOM | 4311 | CD1 | PHE | A | 305 | 25.070 | 23.280 | 34.195 | 1.00 | 12.20 | C |
| ATOM | 4313 | CE1 | PHE | A | 305 | 26.316 | 22.689 | 34.511 | 1.00 | 12.74 | C |
| ATOM | 4315 | CZ | PHE | A | 305 | 27.499 | 23.265 | 33.973 | 1.00 | 11.93 | C |
| ATOM | 4317 | CE2 | PHE | A | 305 | 27.380 | 24.372 | 33.184 | 1.00 | 11.62 | C |
| ATOM | 4319 | CD2 | PHE | A | 305 | 26.157 | 24.941 | 32.891 | 1.00 | 12.26 | C |
| ATOM | 4321 | C | PHE | A | 305 | 21.349 | 25.614 | 33.554 | 1.00 | 11.33 | C |
| ATOM | 4322 | O | PHE | A | 305 | 21.368 | 26.748 | 34.022 | 1.00 | 11.39 | O |
| ATOM | 4323 | N | GLY | A | 306 | 20.364 | 25.161 | 32.811 | 1.00 | 10.40 | N |
| ATOM | 4325 | CA | GLY | A | 306 | 19.276 | 26.018 | 32.414 | 1.00 | 10.88 | C |
| ATOM | 4328 | C | GLY | A | 306 | 18.926 | 25.834 | 30.963 | 1.00 | 11.20 | C |
| ATOM | 4329 | O | GLY | A | 306 | 19.208 | 24.812 | 30.318 | 1.00 | 9.40 | O |
| ATOM | 4330 | N | TYR | A | 307 | 18.291 | 26.863 | 30.443 | 1.00 | 10.29 | N |
| ATOM | 4332 | CA | TYR | A | 307 | 17.803 | 26.905 | 29.077 | 1.00 | 11.10 | C |
| ATOM | 4334 | CB | TYR | A | 307 | 16.311 | 27.194 | 29.162 | 1.00 | 10.85 | C |
| ATOM | 4337 | CG | TYR | A | 307 | 15.557 | 27.309 | 27.870 | 1.00 | 10.79 | C |
| ATOM | 4338 | CD1 | TYR | A | 307 | 16.087 | 26.885 | 26.660 | 1.00 | 10.35 | C |
| ATOM | 4340 | CE1 | TYR | A | 307 | 15.374 | 27.001 | 25.479 | 1.00 | 10.97 | C |
| ATOM | 4342 | CZ | TYR | A | 307 | 14.086 | 27.458 | 25.503 | 1.00 | 13.85 | C |
| ATOM | 4343 | OH | TYR | A | 307 | 13.388 | 27.607 | 24.308 | 1.00 | 13.18 | O |
| ATOM | 4345 | CE2 | TYR | A | 307 | 13.531 | 27.912 | 26.705 | 1.00 | 13.38 | C |
| ATOM | 4347 | CD2 | TYR | A | 307 | 14.260 | 27.849 | 27.860 | 1.00 | 11.68 | C |
| ATOM | 4349 | C | TYR | A | 307 | 18.479 | 27.939 | 28.217 | 1.00 | 12.67 | C |
| ATOM | 4350 | O | TYR | A | 307 | 18.140 | 29.113 | 28.271 | 1.00 | 13.67 | O |
| ATOM | 4351 | N | PRO | A | 308 | 19.440 | 27.555 | 27.389 | 1.00 | 11.31 | N |
| ATOM | 4352 | CA | PRO | A | 308 | 20.118 | 28.547 | 26.531 | 1.00 | 11.31 | C |
| ATOM | 4354 | CB | PRO | A | 308 | 21.315 | 27.780 | 25.971 | 1.00 | 10.82 | C |
| ATOM | 4357 | CG | PRO | A | 308 | 20.941 | 26.293 | 26.070 | 1.00 | 11.80 | C |
| ATOM | 4360 | CD | PRO | A | 308 | 19.833 | 26.179 | 27.077 | 1.00 | 12.92 | C |
| ATOM | 4363 | C | PRO | A | 308 | 19.245 | 29.003 | 25.361 | 1.00 | 11.34 | C |
| ATOM | 4364 | O | PRO | A | 308 | 18.604 | 28.159 | 24.689 | 1.00 | 10.74 | O |
| ATOM | 4365 | N | ARG | A | 309 | 19.314 | 30.266 | 25.051 | 1.00 | 12.86 | N |
| ATOM | 4367 | CA | ARG | A | 309 | 18.427 | 30.864 | 24.076 | 1.00 | 13.91 | C |
| ATOM | 4369 | CB | ARG | A | 309 | 17.252 | 31.527 | 24.844 | 1.00 | 13.02 | C |
| ATOM | 4372 | CG | ARG | A | 309 | 16.469 | 30.638 | 25.781 | 1.00 | 13.54 | C |
| ATOM | 4375 | CD | ARG | A | 309 | 15.375 | 31.251 | 26.661 | 1.00 | 14.50 | C |
| ATOM | 4378 | NE | ARG | A | 309 | 14.099 | 31.449 | 25.978 | 1.00 | 15.52 | N |
| ATOM | 4380 | CZ | ARG | A | 309 | 13.022 | 31.993 | 26.525 | 1.00 | 16.18 | C |
| ATOM | 4381 | NH1 | ARG | A | 309 | 13.055 | 32.423 | 27.777 | 1.00 | 12.53 | N |
| ATOM | 4384 | NH2 | ARG | A | 309 | 11.891 | 32.006 | 25.832 | 1.00 | 15.18 | N |
| ATOM | 4387 | C | ARG | A | 309 | 19.139 | 31.870 | 23.213 | 1.00 | 14.57 | C |
| ATOM | 4388 | O | ARG | A | 309 | 20.288 | 32.256 | 23.468 | 1.00 | 13.36 | O |
| ATOM | 4389 | N | VAL | A | 310 | 18.455 | 32.367 | 22.180 | 1.00 | 13.70 | N |
| ATOM | 4391 | CA | VAL | A | 310 | 19.053 | 33.390 | 21.325 | 1.00 | 15.05 | C |
| ATOM | 4393 | CB | VAL | A | 310 | 18.134 | 33.596 | 20.101 | 1.00 | 14.71 | C |
| ATOM | 4395 | CG1 | VAL | A | 310 | 18.580 | 34.793 | 19.258 | 1.00 | 18.54 | C |
| ATOM | 4399 | CG2 | VAL | A | 310 | 18.121 | 32.368 | 19.265 | 1.00 | 14.81 | C |
| ATOM | 4403 | C | VAL | A | 310 | 19.272 | 34.671 | 22.112 | 1.00 | 16.45 | C |
| ATOM | 4404 | O | VAL | A | 310 | 20.251 | 35.382 | 21.905 | 1.00 | 15.49 | O |

APPENDIX 1-continued

| | | | | | | | | | | |
|---|---|---|---|---|---|---|---|---|---|---|
| ATOM | 4405 | N | LYS | A | 311 | 18.316 | 34.979 | 22.979 | 1.00 | 17.77 | N |
| ATOM | 4407 | CA | LYS | A | 311 | 18.415 | 36.106 | 23.940 | 1.00 | 18.52 | C |
| ATOM | 4409 | CB | LYS | A | 311 | 17.942 | 37.380 | 23.244 | 1.00 | 18.11 | C |
| ATOM | 4412 | CG | LYS | A | 311 | 16.677 | 37.137 | 22.440 | 1.00 | 23.20 | C |
| ATOM | 4415 | CD | LYS | A | 311 | 15.574 | 38.112 | 22.630 | 1.00 | 33.02 | C |
| ATOM | 4418 | CE | LYS | A | 311 | 15.667 | 39.252 | 21.732 | 1.00 | 34.63 | C |
| ATOM | 4421 | NZ | LYS | A | 311 | 14.289 | 39.716 | 21.277 | 1.00 | 36.21 | N |
| ATOM | 4425 | C | LYS | A | 311 | 17.532 | 35.897 | 25.178 | 1.00 | 17.62 | C |
| ATOM | 4426 | O | LYS | A | 311 | 16.770 | 34.912 | 25.199 | 1.00 | 16.50 | O |
| ATOM | 4427 | OXT | LYS | A | 311 | 17.534 | 36.644 | 26.172 | 1.00 | 19.57 | O |
| ATOM | 4428 | CA | CA | C | 312 | 28.232 | 18.547 | 38.069 | 1.00 | 13.89 | CA |
| ATOM | 4429 | CA | CA | C | 313 | 17.608 | 25.091 | 37.856 | 1.00 | 18.60 | CA |
| ATOM | 4430 | CA | CA | C | 314 | 27.338 | 14.925 | 29.013 | 0.60 | 10.25 | CA |
| ATOM | 4431 | N | ALA | B | 318 | 2.727 | 2.475 | 36.156 | 1.00 | 30.60 | N |
| ATOM | 4433 | CA | ALA | B | 318 | 2.319 | 3.152 | 34.902 | 1.00 | 28.10 | C |
| ATOM | 4435 | CB | ALA | B | 318 | 1.428 | 4.295 | 35.200 | 1.00 | 27.75 | C |
| ATOM | 4439 | C | ALA | B | 318 | 3.422 | 3.533 | 33.900 | 1.00 | 24.85 | C |
| ATOM | 4440 | O | ALA | B | 318 | 3.103 | 3.596 | 32.739 | 1.00 | 27.46 | O |
| ATOM | 4443 | N | THR | B | 319 | 4.625 | 3.965 | 34.273 | 1.00 | 24.93 | N |
| ATOM | 4445 | CA | THR | B | 319 | 5.658 | 4.224 | 33.231 | 1.00 | 23.26 | C |
| ATOM | 4447 | CB | THR | B | 319 | 6.154 | 5.690 | 33.296 | 1.00 | 24.03 | C |
| ATOM | 4449 | OG1 | THR | B | 319 | 6.811 | 5.953 | 34.535 | 1.00 | 27.37 | O |
| ATOM | 4451 | CG2 | THR | B | 319 | 4.960 | 6.670 | 33.258 | 1.00 | 27.35 | C |
| ATOM | 4455 | C | THR | B | 319 | 6.926 | 3.305 | 33.235 | 1.00 | 22.75 | C |
| ATOM | 4456 | O | THR | B | 319 | 7.820 | 3.498 | 32.406 | 1.00 | 21.26 | O |
| ATOM | 4457 | N | GLU | B | 320 | 7.027 | 2.401 | 34.205 | 1.00 | 21.07 | N |
| ATOM | 4459 | CA | GLU | B | 320 | 8.177 | 1.559 | 34.324 | 1.00 | 21.49 | C |
| ATOM | 4461 | CB | GLU | B | 320 | 9.328 | 2.280 | 35.014 | 1.00 | 21.67 | C |
| ATOM | 4464 | CG | GLU | B | 320 | 8.980 | 2.681 | 36.413 | 1.00 | 25.74 | C |
| ATOM | 4467 | CD | GLU | B | 320 | 10.174 | 3.130 | 37.222 | 1.00 | 34.05 | C |
| ATOM | 4468 | OE1 | GLU | B | 320 | 10.962 | 3.910 | 36.698 | 1.00 | 36.87 | O |
| ATOM | 4469 | OE2 | GLU | B | 320 | 10.295 | 2.711 | 38.394 | 1.00 | 39.11 | O |
| ATOM | 4470 | C | GLU | B | 320 | 7.818 | 0.308 | 35.082 | 1.00 | 20.20 | C |
| ATOM | 4471 | O | GLU | B | 320 | 6.914 | 0.330 | 35.945 | 1.00 | 20.85 | O |
| ATOM | 4472 | N | TRP | B | 321 | 8.526 | −0.774 | 34.748 | 1.00 | 18.06 | N |
| ATOM | 4474 | CA | TRP | B | 321 | 8.271 | −2.092 | 35.310 | 1.00 | 17.54 | C |
| ATOM | 4476 | CB | TRP | B | 321 | 7.595 | −2.961 | 34.277 | 1.00 | 15.93 | C |
| ATOM | 4479 | CG | TRP | B | 321 | 6.265 | −2.537 | 33.906 | 1.00 | 18.41 | C |
| ATOM | 4480 | CD1 | TRP | B | 321 | 5.089 | −3.007 | 34.445 | 1.00 | 16.53 | C |
| ATOM | 4482 | NE1 | TRP | B | 321 | 4.017 | −2.406 | 33.836 | 1.00 | 19.73 | N |
| ATOM | 4484 | CE2 | TRP | B | 321 | 4.470 | −1.523 | 32.886 | 1.00 | 15.64 | C |
| ATOM | 4485 | CD2 | TRP | B | 321 | 5.889 | −1.576 | 32.903 | 1.00 | 15.37 | C |
| ATOM | 4486 | CE3 | TRP | B | 321 | 6.596 | −0.772 | 31.992 | 1.00 | 14.76 | C |
| ATOM | 4488 | CZ3 | TRP | B | 321 | 5.852 | 0.097 | 31.140 | 1.00 | 17.06 | C |
| ATOM | 4490 | CH2 | TRP | B | 321 | 4.428 | 0.089 | 31.165 | 1.00 | 17.68 | C |
| ATOM | 4492 | CZ2 | TRP | B | 321 | 3.757 | −0.693 | 32.047 | 1.00 | 18.99 | C |
| ATOM | 4494 | C | TRP | B | 321 | 9.570 | −2.716 | 35.728 | 1.00 | 16.82 | C |
| ATOM | 4495 | O | TRP | B | 321 | 10.068 | −3.654 | 35.131 | 1.00 | 16.09 | O |
| ATOM | 4496 | N | PRO | B | 322 | 10.186 | −2.151 | 36.755 | 1.00 | 18.33 | N |
| ATOM | 4497 | CA | PRO | B | 322 | 11.493 | −2.628 | 37.202 | 1.00 | 19.01 | C |
| ATOM | 4499 | CB | PRO | B | 322 | 11.829 | −1.725 | 38.392 | 1.00 | 19.99 | C |
| ATOM | 4502 | CG | PRO | B | 322 | 10.556 | −1.019 | 38.744 | 1.00 | 19.55 | C |
| ATOM | 4505 | CD | PRO | B | 322 | 9.651 | −1.061 | 37.575 | 1.00 | 19.07 | C |
| ATOM | 4508 | C | PRO | B | 322 | 11.484 | −4.065 | 37.641 | 1.00 | 19.86 | C |
| ATOM | 4509 | O | PRO | B | 322 | 12.495 | −4.748 | 37.546 | 1.00 | 20.25 | O |
| ATOM | 4510 | N | GLU | B | 323 | 10.334 | −4.557 | 38.050 | 1.00 | 20.04 | N |
| ATOM | 4512 | CA | GLU | B | 323 | 10.262 | −5.906 | 38.546 | 1.00 | 20.93 | C |
| ATOM | 4514 | CB | GLU | B | 323 | 8.960 | −6.041 | 39.331 | 1.00 | 23.24 | C |
| ATOM | 4517 | CG | GLU | B | 323 | 7.708 | −5.954 | 38.441 | 1.00 | 26.81 | C |
| ATOM | 4520 | CD | GLU | B | 323 | 7.184 | −4.530 | 38.089 | 1.00 | 27.51 | C |
| ATOM | 4521 | OE1 | GLU | B | 323 | 7.879 | −3.511 | 38.275 | 1.00 | 20.70 | O |
| ATOM | 4522 | OE2 | GLU | B | 323 | 5.996 | −4.461 | 37.641 | 1.00 | 30.50 | O |
| ATOM | 4523 | C | GLU | B | 323 | 10.325 | −6.934 | 37.407 | 1.00 | 18.55 | C |
| ATOM | 4524 | O | GLU | B | 323 | 10.521 | −8.111 | 37.642 | 1.00 | 16.50 | O |
| ATOM | 4525 | N | LEU | B | 324 | 10.256 | −6.485 | 36.172 | 1.00 | 16.08 | N |
| ATOM | 4527 | CA | LEU | B | 324 | 10.357 | −7.398 | 35.050 | 1.00 | 15.61 | C |
| ATOM | 4529 | CB | LEU | B | 324 | 9.626 | −6.849 | 33.846 | 1.00 | 15.54 | C |
| ATOM | 4532 | CG | LEU | B | 324 | 8.113 | −6.779 | 34.039 | 1.00 | 16.64 | C |
| ATOM | 4534 | CD1 | LEU | B | 324 | 7.437 | −6.061 | 32.923 | 1.00 | 19.42 | C |
| ATOM | 4538 | CD2 | LEU | B | 324 | 7.648 | −8.212 | 34.152 | 1.00 | 19.22 | C |
| ATOM | 4542 | C | LEU | B | 324 | 11.815 | −7.755 | 34.643 | 1.00 | 14.32 | C |
| ATOM | 4543 | O | LEU | B | 324 | 12.017 | −8.619 | 33.836 | 1.00 | 14.01 | O |
| ATOM | 4544 | N | VAL | B | 325 | 12.792 | −7.073 | 35.189 | 1.00 | 15.66 | N |
| ATOM | 4546 | CA | VAL | B | 325 | 14.180 | −7.370 | 34.816 | 1.00 | 15.56 | C |
| ATOM | 4548 | CB | VAL | B | 325 | 15.184 | −6.410 | 35.456 | 1.00 | 15.71 | C |
| ATOM | 4550 | CG1 | VAL | B | 325 | 16.629 | −6.860 | 35.094 | 1.00 | 16.62 | C |
| ATOM | 4554 | CG2 | VAL | B | 325 | 14.953 | −4.946 | 34.988 | 1.00 | 14.67 | C |
| ATOM | 4558 | C | VAL | B | 325 | 14.478 | −8.817 | 35.197 | 1.00 | 15.70 | C |
| ATOM | 4559 | O | VAL | B | 325 | 14.181 | −9.219 | 36.316 | 1.00 | 15.01 | O |
| ATOM | 4560 | N | GLY | B | 326 | 14.985 | −9.609 | 34.247 | 1.00 | 16.26 | N |

APPENDIX 1-continued

| | | | | | | | | | | |
|---|---|---|---|---|---|---|---|---|---|---|
| ATOM | 4562 | CA | GLY | B | 326 | 15.302 | −11.008 | 34.494 | 1.00 | 15.67 | C |
| ATOM | 4565 | C | GLY | B | 326 | 14.166 | −11.958 | 34.140 | 1.00 | 16.74 | C |
| ATOM | 4566 | O | GLY | B | 326 | 14.358 | −13.159 | 34.108 | 1.00 | 16.04 | O |
| ATOM | 4567 | N | LYS | B | 327 | 12.957 | −11.432 | 33.950 | 1.00 | 16.30 | N |
| ATOM | 4569 | CA | LYS | B | 327 | 11.848 | −12.266 | 33.510 | 1.00 | 17.25 | C |
| ATOM | 4571 | CB | LYS | B | 327 | 10.514 | −11.632 | 33.958 | 1.00 | 17.70 | C |
| ATOM | 4574 | CG | LYS | B | 327 | 10.573 | −11.307 | 35.417 | 1.00 | 22.70 | C |
| ATOM | 4577 | CD | LYS | B | 327 | 9.217 | −11.378 | 36.140 | 1.00 | 30.58 | C |
| ATOM | 4580 | CE | LYS | B | 327 | 9.404 | −11.302 | 37.674 | 1.00 | 31.61 | C |
| ATOM | 4583 | NZ | LYS | B | 327 | 10.674 | −11.962 | 38.027 | 1.00 | 33.63 | N |
| ATOM | 4587 | C | LYS | B | 327 | 11.837 | −12.497 | 32.021 | 1.00 | 16.69 | C |
| ATOM | 4588 | O | LYS | B | 327 | 12.479 | −11.805 | 31.222 | 1.00 | 15.76 | O |
| ATOM | 4589 | N | SER | B | 328 | 11.055 | −13.485 | 31.601 | 1.00 | 18.24 | N |
| ATOM | 4591 | CA | SER | B | 328 | 10.972 | −13.809 | 30.188 | 1.00 | 17.59 | C |
| ATOM | 4593 | CB | SER | B | 328 | 10.280 | −15.154 | 29.994 | 1.00 | 19.45 | C |
| ATOM | 4596 | OG | SER | B | 328 | 8.887 | −15.026 | 30.192 | 1.00 | 18.39 | O |
| ATOM | 4598 | C | SER | B | 328 | 10.206 | −12.757 | 29.431 | 1.00 | 18.63 | C |
| ATOM | 4599 | O | SER | B | 328 | 9.375 | −12.020 | 30.003 | 1.00 | 17.45 | O |
| ATOM | 4600 | N | VAL | B | 329 | 10.494 | −12.653 | 28.140 | 1.00 | 18.81 | N |
| ATOM | 4602 | CA | VAL | B | 329 | 9.771 | −11.690 | 27.299 | 1.00 | 20.52 | C |
| ATOM | 4604 | CB | VAL | B | 329 | 10.317 | −11.663 | 25.852 | 1.00 | 21.15 | C |
| ATOM | 4606 | CG1 | VAL | B | 329 | 9.817 | −12.809 | 25.060 | 1.00 | 22.84 | C |
| ATOM | 4610 | CG2 | VAL | B | 329 | 9.914 | −10.411 | 25.159 | 1.00 | 25.35 | C |
| ATOM | 4614 | C | VAL | B | 329 | 8.276 | −11.962 | 27.279 | 1.00 | 20.54 | C |
| ATOM | 4615 | O | VAL | B | 329 | 7.460 | −11.049 | 27.237 | 1.00 | 19.76 | O |
| ATOM | 4616 | N | GLU | B | 330 | 7.906 | −13.228 | 27.332 | 1.00 | 21.77 | N |
| ATOM | 4618 | CA | GLU | B | 330 | 6.504 | −13.544 | 27.379 | 1.00 | 22.29 | C |
| ATOM | 4620 | CB | GLU | B | 330 | 6.331 | −15.048 | 27.153 | 1.00 | 24.60 | C |
| ATOM | 4623 | CG | GLU | B | 330 | 6.850 | −15.472 | 25.754 | 1.00 | 27.68 | C |
| ATOM | 4626 | CD | GLU | B | 330 | 8.341 | −15.854 | 25.674 | 1.00 | 35.11 | C |
| ATOM | 4627 | OE1 | GLU | B | 330 | 9.141 | −15.647 | 26.617 | 1.00 | 28.88 | O |
| ATOM | 4628 | OE2 | GLU | B | 330 | 8.722 | −16.426 | 24.632 | 1.00 | 41.94 | O |
| ATOM | 4629 | C | GLU | B | 330 | 5.809 | −13.084 | 28.642 | 1.00 | 22.11 | C |
| ATOM | 4630 | O | GLU | B | 330 | 4.676 | −12.586 | 28.584 | 1.00 | 21.27 | O |
| ATOM | 4631 | N | GLU | B | 331 | 6.452 | −13.239 | 29.790 | 1.00 | 21.03 | N |
| ATOM | 4633 | CA | GLU | B | 331 | 5.904 | −12.751 | 31.043 | 1.00 | 21.48 | C |
| ATOM | 4635 | CB | GLU | B | 331 | 6.730 | −13.205 | 32.262 | 1.00 | 22.76 | C |
| ATOM | 4638 | CG | GLU | B | 331 | 5.844 | −13.545 | 33.454 | 1.00 | 31.85 | C |
| ATOM | 4641 | CD | GLU | B | 331 | 6.490 | −13.408 | 34.816 | 1.00 | 38.17 | C |
| ATOM | 4642 | OE1 | GLU | B | 331 | 7.584 | −14.024 | 35.014 | 1.00 | 46.35 | O |
| ATOM | 4643 | OE2 | GLU | B | 331 | 5.886 | −12.712 | 35.693 | 1.00 | 37.37 | O |
| ATOM | 4644 | C | GLU | B | 331 | 5.838 | −11.243 | 31.046 | 1.00 | 19.51 | C |
| ATOM | 4645 | O | GLU | B | 331 | 4.892 | −10.668 | 31.537 | 1.00 | 18.89 | O |
| ATOM | 4646 | N | ALA | B | 332 | 6.882 | −10.609 | 30.514 | 1.00 | 18.18 | N |
| ATOM | 4648 | CA | ALA | B | 332 | 6.951 | −9.187 | 30.538 | 1.00 | 15.95 | C |
| ATOM | 4650 | CB | ALA | B | 332 | 8.254 | −8.709 | 29.931 | 1.00 | 16.83 | C |
| ATOM | 4654 | C | ALA | B | 332 | 5.801 | −8.640 | 29.757 | 1.00 | 15.42 | C |
| ATOM | 4655 | O | ALA | B | 332 | 5.163 | −7.697 | 30.182 | 1.00 | 14.99 | O |
| ATOM | 4656 | N | LYS | B | 333 | 5.580 | −9.189 | 28.589 | 1.00 | 15.39 | N |
| ATOM | 4658 | CA | LYS | B | 333 | 4.489 | −8.693 | 27.748 | 1.00 | 17.34 | C |
| ATOM | 4660 | CB | LYS | B | 333 | 4.458 | −9.450 | 26.441 | 1.00 | 17.67 | C |
| ATOM | 4663 | CG | LYS | B | 333 | 5.438 | −9.004 | 25.401 | 1.00 | 21.32 | C |
| ATOM | 4666 | CD | LYS | B | 333 | 5.200 | −9.807 | 24.128 | 1.00 | 23.42 | C |
| ATOM | 4669 | CE | LYS | B | 333 | 6.357 | −9.619 | 23.113 | 1.00 | 28.93 | C |
| ATOM | 4672 | NZ | LYS | B | 333 | 6.005 | −10.290 | 21.820 | 1.00 | 28.19 | N |
| ATOM | 4676 | C | LYS | B | 333 | 3.127 | −8.789 | 28.452 | 1.00 | 17.99 | C |
| ATOM | 4677 | O | LYS | B | 333 | 2.338 | −7.868 | 28.410 | 1.00 | 15.95 | O |
| ATOM | 4678 | N | LYS | B | 334 | 2.858 | −9.904 | 29.125 | 1.00 | 19.30 | N |
| ATOM | 4680 | CA | LYS | B | 334 | 1.595 | −10.046 | 29.842 | 1.00 | 19.86 | C |
| ATOM | 4682 | CB | LYS | B | 334 | 1.417 | −11.432 | 30.481 | 1.00 | 21.24 | C |
| ATOM | 4685 | CG | LYS | B | 334 | 0.949 | −12.476 | 29.568 | 1.00 | 28.52 | C |
| ATOM | 4688 | CD | LYS | B | 334 | 0.499 | −13.819 | 30.317 | 1.00 | 33.48 | C |
| ATOM | 4691 | CE | LYS | B | 334 | 0.650 | −15.022 | 29.319 | 1.00 | 37.14 | C |
| ATOM | 4694 | NZ | LYS | B | 334 | 0.870 | −14.604 | 27.850 | 1.00 | 36.97 | N |
| ATOM | 4698 | C | LYS | B | 334 | 1.457 | −8.983 | 30.890 | 1.00 | 18.97 | C |
| ATOM | 4699 | O | LYS | B | 334 | 0.386 | −8.343 | 31.021 | 1.00 | 16.86 | O |
| ATOM | 4700 | N | VAL | B | 335 | 2.522 | −8.754 | 31.658 | 1.00 | 16.84 | N |
| ATOM | 4702 | CA | VAL | B | 335 | 2.480 | −7.783 | 32.726 | 1.00 | 16.65 | C |
| ATOM | 4704 | CB | VAL | B | 335 | 3.743 | −7.823 | 33.591 | 1.00 | 15.76 | C |
| ATOM | 4706 | CG1 | VAL | B | 335 | 3.817 | −6.655 | 34.612 | 1.00 | 19.24 | C |
| ATOM | 4710 | CG2 | VAL | B | 335 | 3.789 | −9.108 | 34.341 | 1.00 | 17.38 | C |
| ATOM | 4714 | C | VAL | B | 335 | 2.288 | −6.382 | 32.203 | 1.00 | 15.76 | C |
| ATOM | 4715 | O | VAL | B | 335 | 1.494 | −5.615 | 32.763 | 1.00 | 16.18 | O |
| ATOM | 4716 | N | ILE | B | 336 | 3.033 | −6.023 | 31.167 | 1.00 | 15.08 | N |
| ATOM | 4718 | CA | ILE | B | 336 | 2.903 | −4.703 | 30.635 | 1.00 | 14.79 | C |
| ATOM | 4720 | CB | ILE | B | 336 | 3.967 | −4.441 | 29.592 | 1.00 | 14.82 | C |
| ATOM | 4722 | CG1 | ILE | B | 336 | 5.290 | −4.318 | 30.367 | 1.00 | 16.31 | C |
| ATOM | 4725 | CD1 | ILE | B | 336 | 6.479 | −4.602 | 29.579 | 1.00 | 19.31 | C |
| ATOM | 4729 | CG2 | ILE | B | 336 | 3.543 | −3.266 | 28.733 | 1.00 | 16.34 | C |
| ATOM | 4733 | C | ILE | B | 336 | 1.508 | −4.472 | 30.074 | 1.00 | 15.10 | C |

APPENDIX 1-continued

| | | | | | | | | | | | |
|---|---|---|---|---|---|---|---|---|---|---|---|
| ATOM | 4734 | O | ILE | B | 336 | 0.914 | −3.437 | 30.347 | 1.00 | 16.57 | O |
| ATOM | 4735 | N | LEU | B | 337 | 0.956 | −5.456 | 29.390 | 1.00 | 15.14 | N |
| ATOM | 4737 | CA | LEU | B | 337 | −0.343 | −5.235 | 28.769 | 1.00 | 15.94 | C |
| ATOM | 4739 | CB | LEU | B | 337 | −0.645 | −6.290 | 27.727 | 1.00 | 15.77 | C |
| ATOM | 4742 | CG | LEU | B | 337 | 0.121 | −6.195 | 26.404 | 1.00 | 13.58 | C |
| ATOM | 4744 | CD1 | LEU | B | 337 | 0.021 | −7.498 | 25.632 | 1.00 | 15.44 | C |
| ATOM | 4748 | CD2 | LEU | B | 337 | −0.350 | −5.049 | 25.553 | 1.00 | 17.85 | C |
| ATOM | 4752 | C | LEU | B | 337 | −1.450 | −5.146 | 29.810 | 1.00 | 17.57 | C |
| ATOM | 4753 | O | LEU | B | 337 | −2.511 | −4.531 | 29.544 | 1.00 | 17.36 | O |
| ATOM | 4754 | N | GLN | B | 338 | −1.210 | −5.702 | 30.985 | 1.00 | 18.09 | N |
| ATOM | 4756 | CA | GLN | B | 338 | −2.195 | −5.610 | 32.047 | 1.00 | 21.31 | C |
| ATOM | 4758 | CB | GLN | B | 338 | −1.830 | −6.557 | 33.205 | 1.00 | 21.97 | C |
| ATOM | 4761 | CG | GLN | B | 338 | −1.842 | −8.050 | 32.775 | 1.00 | 26.01 | C |
| ATOM | 4764 | CD | GLN | B | 338 | −1.562 | −9.127 | 33.893 | 1.00 | 29.25 | C |
| ATOM | 4765 | OE1 | GLN | B | 338 | −0.720 | −8.942 | 34.831 | 1.00 | 34.90 | O |
| ATOM | 4766 | NE2 | GLN | B | 338 | −2.211 | −10.262 | 33.738 | 1.00 | 29.07 | N |
| ATOM | 4769 | C | GLN | B | 338 | −2.398 | −4.143 | 32.469 | 1.00 | 22.67 | C |
| ATOM | 4770 | O | GLN | B | 338 | −3.530 | −3.694 | 32.741 | 1.00 | 22.11 | O |
| ATOM | 4771 | N | ASP | B | 339 | −1.318 | −3.366 | 32.465 | 1.00 | 21.30 | N |
| ATOM | 4773 | CA | ASP | B | 339 | −1.377 | −1.936 | 32.761 | 1.00 | 21.98 | C |
| ATOM | 4775 | CB | ASP | B | 339 | −0.047 | −1.478 | 33.381 | 1.00 | 22.85 | C |
| ATOM | 4778 | CG | ASP | B | 339 | 0.213 | −2.106 | 34.710 | 1.00 | 26.72 | C |
| ATOM | 4779 | OD1 | ASP | B | 339 | −0.740 | −2.105 | 35.518 | 1.00 | 33.25 | O |
| ATOM | 4780 | OD2 | ASP | B | 339 | 1.269 | −2.680 | 35.026 | 1.00 | 26.47 | O |
| ATOM | 4781 | C | ASP | B | 339 | −1.644 | −1.066 | 31.555 | 1.00 | 22.06 | C |
| ATOM | 4782 | O | ASP | B | 339 | −2.247 | 0.004 | 31.667 | 1.00 | 23.60 | O |
| ATOM | 4783 | N | LYS | B | 340 | −1.218 | −1.515 | 30.387 | 1.00 | 19.19 | N |
| ATOM | 4785 | CA | LYS | B | 340 | −1.226 | −0.722 | 29.218 | 1.00 | 18.98 | C |
| ATOM | 4787 | CB | LYS | B | 340 | 0.186 | −0.070 | 29.118 | 1.00 | 18.88 | C |
| ATOM | 4790 | CG | LYS | B | 340 | 0.345 | 0.901 | 28.024 | 1.00 | 18.59 | C |
| ATOM | 4793 | CD | LYS | B | 340 | 1.805 | 1.491 | 28.014 | 1.00 | 19.17 | C |
| ATOM | 4796 | CE | LYS | B | 340 | 1.999 | 2.462 | 26.848 | 1.00 | 20.90 | C |
| ATOM | 4799 | NZ | LYS | B | 340 | 1.137 | 3.683 | 27.041 | 1.00 | 23.19 | N |
| ATOM | 4803 | C | LYS | B | 340 | −1.611 | −1.550 | 28.035 | 1.00 | 18.75 | C |
| ATOM | 4804 | O | LYS | B | 340 | −0.822 | −1.920 | 27.224 | 1.00 | 18.54 | O |
| ATOM | 4805 | N | PRO | B | 341 | −2.906 | −1.822 | 27.892 | 1.00 | 17.67 | N |
| ATOM | 4806 | CA | PRO | B | 341 | −3.391 | −2.768 | 26.911 | 1.00 | 17.68 | C |
| ATOM | 4808 | CB | PRO | B | 341 | −4.926 | −2.753 | 27.108 | 1.00 | 18.59 | C |
| ATOM | 4811 | CG | PRO | B | 341 | −5.155 | −1.955 | 28.331 | 1.00 | 19.20 | C |
| ATOM | 4814 | CD | PRO | B | 341 | −3.919 | −1.347 | 28.825 | 1.00 | 20.06 | C |
| ATOM | 4817 | C | PRO | B | 341 | −3.101 | −2.444 | 25.491 | 1.00 | 15.31 | C |
| ATOM | 4818 | O | PRO | B | 341 | −3.022 | −3.289 | 24.614 | 1.00 | 19.02 | O |
| ATOM | 4819 | N | GLU | B | 342 | −2.986 | −1.143 | 25.254 | 1.00 | 17.33 | N |
| ATOM | 4821 | CA | GLU | B | 342 | −2.745 | −0.687 | 23.906 | 1.00 | 17.70 | C |
| ATOM | 4823 | CB | GLU | B | 342 | −3.615 | 0.545 | 23.555 | 1.00 | 20.27 | C |
| ATOM | 4826 | CG | GLU | B | 342 | −5.028 | 0.042 | 23.191 | 1.00 | 21.84 | C |
| ATOM | 4829 | CD | GLU | B | 342 | −6.029 | 1.135 | 22.803 | 1.00 | 30.03 | C |
| ATOM | 4830 | OE1 | GLU | B | 342 | −5.646 | 2.108 | 22.127 | 1.00 | 34.62 | O |
| ATOM | 4831 | OE2 | GLU | B | 342 | −7.217 | 0.982 | 23.131 | 1.00 | 29.42 | O |
| ATOM | 4832 | C | GLU | B | 342 | −1.232 | −0.491 | 23.581 | 1.00 | 17.99 | C |
| ATOM | 4833 | O | GLU | B | 342 | −0.912 | −0.071 | 22.473 | 1.00 | 17.45 | O |
| ATOM | 4834 | N | ALA | B | 343 | −0.348 | −0.902 | 24.474 | 1.00 | 18.01 | N |
| ATOM | 4836 | CA | ALA | B | 343 | 1.075 | −0.825 | 24.187 | 1.00 | 17.75 | C |
| ATOM | 4838 | CB | ALA | B | 343 | 1.886 | −1.320 | 25.374 | 1.00 | 17.76 | C |
| ATOM | 4842 | C | ALA | B | 343 | 1.501 | −1.509 | 22.934 | 1.00 | 18.41 | C |
| ATOM | 4843 | O | ALA | B | 343 | 1.018 | −2.612 | 22.539 | 1.00 | 16.39 | O |
| ATOM | 4844 | N | GLN | B | 344 | 2.398 | −0.808 | 22.223 | 1.00 | 16.93 | N |
| ATOM | 4846 | CA | GLN | B | 344 | 3.007 | −1.326 | 21.061 | 1.00 | 16.94 | C |
| ATOM | 4848 | CB | GLN | B | 344 | 3.197 | −0.264 | 19.951 | 1.00 | 18.67 | C |
| ATOM | 4851 | CG | GLN | B | 344 | 1.915 | 0.367 | 19.450 | 1.00 | 22.45 | C |
| ATOM | 4854 | CD | GLN | B | 344 | 1.041 | −0.668 | 18.836 | 1.00 | 23.74 | C |
| ATOM | 4855 | OE1 | GLN | B | 344 | 1.336 | −1.176 | 17.737 | 1.00 | 28.25 | O |
| ATOM | 4856 | NE2 | GLN | B | 344 | 0.022 | −1.076 | 19.570 | 1.00 | 24.17 | N |
| ATOM | 4859 | C | GLN | B | 344 | 4.371 | −1.804 | 21.578 | 1.00 | 16.61 | C |
| ATOM | 4860 | O | GLN | B | 344 | 5.276 | −0.987 | 21.833 | 1.00 | 15.55 | O |
| ATOM | 4861 | N | ILE | B | 345 | 4.503 | −3.109 | 21.745 | 1.00 | 14.81 | N |
| ATOM | 4863 | CA | ILE | B | 345 | 5.747 | −3.697 | 22.338 | 1.00 | 15.57 | C |
| ATOM | 4865 | CB | ILE | B | 345 | 5.426 | −4.864 | 23.229 | 1.00 | 14.52 | C |
| ATOM | 4867 | CG1 | ILE | B | 345 | 4.420 | −4.437 | 24.307 | 1.00 | 16.03 | C |
| ATOM | 4870 | CD1 | ILE | B | 345 | 4.237 | −5.385 | 25.452 | 1.00 | 21.70 | C |
| ATOM | 4874 | CG2 | ILE | B | 345 | 6.683 | −5.445 | 23.832 | 1.00 | 18.60 | C |
| ATOM | 4878 | C | ILE | B | 345 | 6.713 | −4.108 | 21.261 | 1.00 | 15.60 | C |
| ATOM | 4879 | O | ILE | B | 345 | 6.317 | −4.759 | 20.335 | 1.00 | 14.53 | O |
| ATOM | 4880 | N | ILE | B | 346 | 7.947 | −3.618 | 21.338 | 1.00 | 15.09 | N |
| ATOM | 4882 | CA | ILE | B | 346 | 9.006 | −3.853 | 20.373 | 1.00 | 17.65 | C |
| ATOM | 4884 | CB | ILE | B | 346 | 9.607 | −2.448 | 19.887 | 1.00 | 18.73 | C |
| ATOM | 4886 | CG1 | ILE | B | 346 | 8.486 | −1.515 | 19.488 | 1.00 | 25.44 | C |
| ATOM | 4889 | CD1 | ILE | B | 346 | 7.656 | −2.110 | 18.400 | 1.00 | 27.09 | C |
| ATOM | 4893 | CG2 | ILE | B | 346 | 10.538 | −2.639 | 18.736 | 1.00 | 24.66 | C |
| ATOM | 4897 | C | ILE | B | 346 | 10.126 | −4.549 | 21.136 | 1.00 | 15.44 | C |

APPENDIX 1-continued

| | | | | | | | | | | | |
|---|---|---|---|---|---|---|---|---|---|---|---|
| ATOM | 4898 | O | ILE | B | 346 | 10.515 | −4.048 | 22.174 | 1.00 | 15.03 | O |
| ATOM | 4899 | N | VAL | B | 347 | 10.621 | −5.685 | 20.637 | 1.00 | 15.30 | N |
| ATOM | 4901 | CA | VAL | B | 347 | 11.701 | −6.425 | 21.310 | 1.00 | 14.26 | C |
| ATOM | 4903 | CB | VAL | B | 347 | 11.363 | −7.916 | 21.411 | 1.00 | 13.95 | C |
| ATOM | 4905 | CG1 | VAL | B | 347 | 12.550 | −8.744 | 21.949 | 1.00 | 15.52 | C |
| ATOM | 4909 | CG2 | VAL | B | 347 | 10.056 | −8.103 | 22.171 | 1.00 | 16.01 | C |
| ATOM | 4913 | C | VAL | B | 347 | 12.980 | −6.253 | 20.518 | 1.00 | 13.34 | C |
| ATOM | 4914 | O | VAL | B | 347 | 12.999 | −6.387 | 19.275 | 1.00 | 13.71 | O |
| ATOM | 4915 | N | LEU | B | 348 | 14.025 | −5.824 | 21.225 | 1.00 | 13.58 | N |
| ATOM | 4917 | CA | LEU | B | 348 | 15.334 | −5.595 | 20.654 | 1.00 | 14.50 | C |
| ATOM | 4919 | CB | LEU | B | 348 | 15.629 | −4.101 | 20.619 | 1.00 | 14.73 | C |
| ATOM | 4922 | CG | LEU | B | 348 | 14.624 | −3.255 | 19.836 | 1.00 | 18.66 | C |
| ATOM | 4924 | CD1 | LEU | B | 348 | 14.885 | −1.758 | 20.172 | 1.00 | 20.34 | C |
| ATOM | 4928 | CD2 | LEU | B | 348 | 14.781 | −3.515 | 18.370 | 1.00 | 21.48 | C |
| ATOM | 4932 | C | LEU | B | 348 | 16.420 | −6.246 | 21.500 | 1.00 | 13.69 | C |
| ATOM | 4933 | O | LEU | B | 348 | 16.298 | −6.400 | 22.715 | 1.00 | 12.97 | O |
| ATOM | 4934 | N | PRO | B | 349 | 17.533 | −6.626 | 20.864 | 1.00 | 13.80 | N |
| ATOM | 4935 | CA | PRO | B | 349 | 18.630 | −7.173 | 21.635 | 1.00 | 12.71 | C |
| ATOM | 4937 | CB | PRO | B | 349 | 19.686 | −7.528 | 20.564 | 1.00 | 14.22 | C |
| ATOM | 4940 | CG | PRO | B | 349 | 18.940 | −7.614 | 19.288 | 1.00 | 17.12 | C |
| ATOM | 4943 | CD | PRO | B | 349 | 17.802 | −6.586 | 19.422 | 1.00 | 13.86 | C |
| ATOM | 4946 | C | PRO | B | 349 | 19.238 | −6.154 | 22.603 | 1.00 | 12.67 | C |
| ATOM | 4947 | O | PRO | B | 349 | 19.358 | −4.987 | 22.270 | 1.00 | 10.43 | O |
| ATOM | 4948 | N | VAL | B | 350 | 19.679 | −6.629 | 23.756 | 1.00 | 10.88 | N |
| ATOM | 4950 | CA | VAL | B | 350 | 20.463 | −5.844 | 24.676 | 1.00 | 11.84 | C |
| ATOM | 4952 | CB | VAL | B | 350 | 20.967 | −6.740 | 25.861 | 1.00 | 12.85 | C |
| ATOM | 4954 | CG1 | VAL | B | 350 | 21.918 | −7.822 | 25.385 | 1.00 | 14.03 | C |
| ATOM | 4958 | CG2 | VAL | B | 350 | 21.614 | −5.822 | 26.921 | 1.00 | 13.28 | C |
| ATOM | 4962 | C | VAL | B | 350 | 21.627 | −5.189 | 23.892 | 1.00 | 10.88 | C |
| ATOM | 4963 | O | VAL | B | 350 | 22.262 | −5.815 | 23.000 | 1.00 | 10.87 | O |
| ATOM | 4964 | N | GLY | B | 351 | 21.864 | −3.926 | 24.205 | 1.00 | 11.86 | N |
| ATOM | 4966 | CA | GLY | B | 351 | 22.882 | −3.099 | 23.581 | 1.00 | 11.51 | C |
| ATOM | 4969 | C | GLY | B | 351 | 22.512 | −2.331 | 22.313 | 1.00 | 12.47 | C |
| ATOM | 4970 | O | GLY | B | 351 | 23.335 | −1.618 | 21.744 | 1.00 | 10.98 | O |
| ATOM | 4971 | N | THR | B | 352 | 21.315 | −2.561 | 21.822 | 1.00 | 11.64 | N |
| ATOM | 4973 | CA | THR | B | 352 | 20.841 | −1.861 | 20.642 | 1.00 | 11.92 | C |
| ATOM | 4975 | CB | THR | B | 352 | 19.508 | −2.419 | 20.225 | 1.00 | 13.71 | C |
| ATOM | 4977 | OG1 | THR | B | 352 | 19.641 | −3.812 | 19.860 | 1.00 | 10.89 | O |
| ATOM | 4979 | CG2 | THR | B | 352 | 18.993 | −1.703 | 18.981 | 1.00 | 12.02 | C |
| ATOM | 4983 | C | THR | B | 352 | 20.720 | −0.383 | 20.920 | 1.00 | 11.24 | C |
| ATOM | 4984 | O | THR | B | 352 | 20.235 | 0.015 | 21.976 | 1.00 | 12.17 | O |
| ATOM | 4985 | N | ILE | B | 353 | 21.218 | 0.435 | 20.012 | 1.00 | 11.34 | N |
| ATOM | 4987 | CA | ILE | B | 353 | 21.125 | 1.893 | 20.166 | 1.00 | 11.58 | C |
| ATOM | 4989 | CB | ILE | B | 353 | 22.322 | 2.605 | 19.504 | 1.00 | 13.21 | C |
| ATOM | 4991 | CG1 | ILE | B | 353 | 23.642 | 2.014 | 19.992 | 1.00 | 11.55 | C |
| ATOM | 4994 | CD1 | ILE | B | 353 | 23.795 | 1.980 | 21.496 | 1.00 | 15.61 | C |
| ATOM | 4998 | CG2 | ILE | B | 353 | 22.294 | 4.098 | 19.802 | 1.00 | 13.36 | C |
| ATOM | 5002 | C | ILE | B | 353 | 19.828 | 2.332 | 19.509 | 1.00 | 11.44 | C |
| ATOM | 5003 | O | ILE | B | 353 | 19.485 | 1.827 | 18.417 | 1.00 | 11.02 | O |
| ATOM | 5004 | N | VAL | B | 354 | 19.136 | 3.268 | 20.180 | 1.00 | 10.73 | N |
| ATOM | 5006 | CA | VAL | B | 354 | 17.785 | 3.663 | 19.740 | 1.00 | 11.42 | C |
| ATOM | 5008 | CB | VAL | B | 354 | 16.693 | 3.043 | 20.663 | 1.00 | 11.30 | C |
| ATOM | 5010 | CG1 | VAL | B | 354 | 16.741 | 1.521 | 20.568 | 1.00 | 11.88 | C |
| ATOM | 5014 | CG2 | VAL | B | 354 | 16.873 | 3.542 | 22.103 | 1.00 | 12.49 | C |
| ATOM | 5018 | C | VAL | B | 354 | 17.558 | 5.152 | 19.702 | 1.00 | 10.76 | C |
| ATOM | 5019 | O | VAL | B | 354 | 18.289 | 5.918 | 20.294 | 1.00 | 11.15 | O |
| ATOM | 5020 | N | THR | B | 355 | 16.607 | 5.599 | 18.894 | 1.00 | 10.94 | N |
| ATOM | 5022 | CA | THR | B | 355 | 16.207 | 7.001 | 18.884 | 1.00 | 12.16 | C |
| ATOM | 5024 | CB | THR | B | 355 | 15.004 | 7.267 | 17.939 | 1.00 | 13.72 | C |
| ATOM | 5026 | OG1 | THR | B | 355 | 13.885 | 6.481 | 18.413 | 1.00 | 16.24 | O |
| ATOM | 5028 | CG2 | THR | B | 355 | 15.313 | 6.840 | 16.561 | 1.00 | 14.33 | C |
| ATOM | 5032 | C | THR | B | 355 | 15.684 | 7.378 | 20.254 | 1.00 | 12.37 | C |
| ATOM | 5033 | O | THR | B | 355 | 15.263 | 6.554 | 21.050 | 1.00 | 11.43 | O |
| ATOM | 5034 | N | MET | B | 356 | 15.787 | 8.659 | 20.540 | 1.00 | 12.52 | N |
| ATOM | 5036 | CA | MET | B | 356 | 15.258 | 9.222 | 21.775 | 1.00 | 11.53 | C |
| ATOM | 5038 | CB | MET | B | 356 | 16.311 | 10.075 | 22.468 | 1.00 | 11.42 | C |
| ATOM | 5041 | CG | MET | B | 356 | 17.427 | 9.202 | 23.035 | 1.00 | 12.95 | C |
| ATOM | 5044 | SD | MET | B | 356 | 16.825 | 8.040 | 24.219 | 1.00 | 15.08 | S |
| ATOM | 5045 | CE | MET | B | 356 | 17.963 | 6.799 | 24.107 | 1.00 | 20.89 | C |
| ATOM | 5049 | C | MET | B | 356 | 13.952 | 9.961 | 21.568 | 1.00 | 13.71 | C |
| ATOM | 5050 | O | MET | B | 356 | 13.675 | 11.024 | 22.215 | 1.00 | 12.74 | O |
| ATOM | 5051 | N | GLU | B | 357 | 13.148 | 9.417 | 20.659 | 1.00 | 14.50 | N |
| ATOM | 5053 | CA | GLU | B | 357 | 11.765 | 9.869 | 20.543 | 1.00 | 14.30 | C |
| ATOM | 5055 | CB | GLU | B | 357 | 11.135 | 9.357 | 19.210 | 1.00 | 15.52 | C |
| ATOM | 5058 | CG | GLU | B | 357 | 9.674 | 9.735 | 19.153 | 1.00 | 15.25 | C |
| ATOM | 5061 | CD | GLU | B | 357 | 8.947 | 9.187 | 17.960 | 1.00 | 18.46 | C |
| ATOM | 5062 | OE1 | GLU | B | 357 | 7.768 | 9.559 | 17.802 | 1.00 | 19.97 | O |
| ATOM | 5063 | OE2 | GLU | B | 357 | 9.543 | 8.377 | 17.237 | 1.00 | 20.59 | O |
| ATOM | 5064 | C | GLU | B | 357 | 11.001 | 9.282 | 21.703 | 1.00 | 14.50 | C |
| ATOM | 5065 | O | GLU | B | 357 | 11.233 | 8.123 | 22.030 | 1.00 | 14.99 | O |

APPENDIX 1-continued

| | | | | | | | | | | | |
|---|---|---|---|---|---|---|---|---|---|---|---|
| ATOM | 5066 | N | TYR | B | 358 | 10.129 | 10.074 | 22.335 | 1.00 | 13.93 | N |
| ATOM | 5068 | CA | TYR | B | 358 | 9.207 | 9.612 | 23.363 | 1.00 | 14.38 | C |
| ATOM | 5070 | CB | TYR | B | 358 | 9.026 | 10.601 | 24.499 | 1.00 | 14.43 | C |
| ATOM | 5073 | CG | TYR | B | 358 | 8.057 | 10.136 | 25.563 | 1.00 | 12.84 | C |
| ATOM | 5074 | CD1 | TYR | B | 358 | 8.436 | 9.165 | 26.487 | 1.00 | 14.52 | C |
| ATOM | 5076 | CE1 | TYR | B | 358 | 7.559 | 8.706 | 27.463 | 1.00 | 19.65 | C |
| ATOM | 5078 | CZ | TYR | B | 358 | 6.266 | 9.240 | 27.504 | 1.00 | 19.95 | C |
| ATOM | 5079 | OH | TYR | B | 358 | 5.321 | 8.903 | 28.447 | 1.00 | 26.07 | O |
| ATOM | 5081 | CE2 | TYR | B | 358 | 5.873 | 10.184 | 26.607 | 1.00 | 16.96 | C |
| ATOM | 5083 | CD2 | TYR | B | 358 | 6.767 | 10.650 | 25.643 | 1.00 | 18.09 | C |
| ATOM | 5085 | C | TYR | B | 358 | 7.867 | 9.326 | 22.712 | 1.00 | 15.23 | C |
| ATOM | 5086 | O | TYR | B | 358 | 7.142 | 10.261 | 22.340 | 1.00 | 14.02 | O |
| ATOM | 5087 | N | ARG | B | 359 | 7.551 | 8.048 | 22.606 | 1.00 | 15.15 | N |
| ATOM | 5089 | CA | ARG | B | 359 | 6.294 | 7.557 | 22.003 | 1.00 | 16.88 | C |
| ATOM | 5091 | CB | ARG | B | 359 | 6.615 | 6.465 | 20.998 | 1.00 | 18.79 | C |
| ATOM | 5094 | CG | ARG | B | 359 | 6.824 | 6.884 | 19.703 | 1.00 | 22.92 | C |
| ATOM | 5097 | CD | ARG | B | 359 | 6.435 | 5.794 | 18.692 | 1.00 | 25.80 | C |
| ATOM | 5100 | NE | ARG | B | 359 | 7.237 | 6.083 | 17.556 | 1.00 | 25.82 | N |
| ATOM | 5102 | CZ | ARG | B | 359 | 7.515 | 5.241 | 16.593 | 1.00 | 26.84 | C |
| ATOM | 5103 | NH1 | ARG | B | 359 | 7.000 | 3.996 | 16.593 | 1.00 | 26.53 | N |
| ATOM | 5106 | NH2 | ARG | B | 359 | 8.297 | 5.668 | 15.627 | 1.00 | 28.90 | N |
| ATOM | 5109 | C | ARG | B | 359 | 5.449 | 6.946 | 23.095 | 1.00 | 17.14 | C |
| ATOM | 5110 | O | ARG | B | 359 | 5.767 | 5.861 | 23.625 | 1.00 | 15.98 | O |
| ATOM | 5111 | N | ILE | B | 360 | 4.401 | 7.656 | 23.504 | 1.00 | 16.16 | N |
| ATOM | 5113 | CA | ILE | B | 360 | 3.633 | 7.262 | 24.670 | 1.00 | 17.53 | C |
| ATOM | 5115 | CB | ILE | B | 360 | 2.575 | 8.354 | 24.998 | 1.00 | 17.66 | C |
| ATOM | 5117 | CG1 | ILE | B | 360 | 1.895 | 8.067 | 26.333 | 1.00 | 24.45 | C |
| ATOM | 5120 | CD1 | ILE | B | 360 | 1.711 | 9.278 | 27.140 | 1.00 | 28.72 | C |
| ATOM | 5124 | CG2 | ILE | B | 360 | 1.506 | 8.417 | 23.930 | 1.00 | 18.76 | C |
| ATOM | 5128 | C | ILE | B | 360 | 2.947 | 5.899 | 24.595 | 1.00 | 16.17 | C |
| ATOM | 5129 | O | ILE | B | 360 | 2.649 | 5.307 | 25.629 | 1.00 | 19.59 | O |
| ATOM | 5130 | N | ASP | B | 361 | 2.692 | 5.431 | 23.402 | 1.00 | 19.19 | N |
| ATOM | 5132 | CA | ASP | B | 361 | 2.049 | 4.131 | 23.290 | 1.00 | 20.04 | C |
| ATOM | 5134 | CB | ASP | B | 361 | 1.070 | 4.141 | 22.156 | 1.00 | 22.33 | C |
| ATOM | 5137 | CG | ASP | B | 361 | −0.210 | 4.932 | 22.509 | 1.00 | 27.91 | C |
| ATOM | 5138 | OD1 | ASP | B | 361 | −0.701 | 4.823 | 23.693 | 1.00 | 33.70 | O |
| ATOM | 5139 | OD2 | ASP | B | 361 | −0.734 | 5.711 | 21.687 | 1.00 | 38.62 | O |
| ATOM | 5140 | C | ASP | B | 361 | 3.025 | 2.996 | 23.111 | 1.00 | 19.38 | C |
| ATOM | 5141 | O | ASP | B | 361 | 2.580 | 1.872 | 22.958 | 1.00 | 18.79 | O |
| ATOM | 5142 | N | ARG | B | 362 | 4.342 | 3.291 | 23.099 | 1.00 | 15.34 | N |
| ATOM | 5144 | CA | ARG | B | 362 | 5.342 | 2.241 | 22.870 | 1.00 | 15.87 | C |
| ATOM | 5146 | CB | ARG | B | 362 | 6.480 | 2.793 | 21.992 | 1.00 | 13.90 | C |
| ATOM | 5149 | CG | ARG | B | 362 | 7.657 | 1.839 | 21.867 | 1.00 | 16.63 | C |
| ATOM | 5152 | CD | ARG | B | 362 | 8.570 | 2.234 | 20.721 | 1.00 | 16.00 | C |
| ATOM | 5155 | NE | ARG | B | 362 | 9.204 | 3.494 | 21.085 | 1.00 | 15.40 | N |
| ATOM | 5157 | CZ | ARG | B | 362 | 9.808 | 4.315 | 20.234 | 1.00 | 14.22 | C |
| ATOM | 5158 | NH1 | ARG | B | 362 | 9.893 | 4.014 | 18.939 | 1.00 | 16.86 | N |
| ATOM | 5161 | NH2 | ARG | B | 362 | 10.295 | 5.449 | 20.686 | 1.00 | 14.53 | N |
| ATOM | 5164 | C | ARG | B | 362 | 5.970 | 1.737 | 24.163 | 1.00 | 14.75 | C |
| ATOM | 5165 | O | ARG | B | 362 | 6.130 | 2.504 | 25.117 | 1.00 | 13.39 | O |
| ATOM | 5166 | N | VAL | B | 363 | 6.285 | 0.467 | 24.199 | 1.00 | 13.88 | N |
| ATOM | 5168 | CA | VAL | B | 363 | 7.159 | −0.094 | 25.241 | 1.00 | 14.50 | C |
| ATOM | 5170 | CB | VAL | B | 363 | 6.448 | −0.910 | 26.349 | 1.00 | 14.42 | C |
| ATOM | 5172 | CG1 | VAL | B | 363 | 7.477 | −1.351 | 27.372 | 1.00 | 17.68 | C |
| ATOM | 5176 | CG2 | VAL | B | 363 | 5.401 | −0.069 | 27.015 | 1.00 | 16.62 | C |
| ATOM | 5180 | C | VAL | B | 363 | 8.230 | −0.943 | 24.576 | 1.00 | 14.33 | C |
| ATOM | 5181 | O | VAL | B | 363 | 7.928 | −1.989 | 23.984 | 1.00 | 14.74 | O |
| ATOM | 5182 | N | ARG | B | 364 | 9.483 | −0.510 | 24.651 | 1.00 | 13.57 | N |
| ATOM | 5184 | CA | ARG | B | 364 | 10.570 | −1.349 | 24.131 | 1.00 | 13.59 | C |
| ATOM | 5186 | CB | ARG | B | 364 | 11.753 | −0.458 | 23.713 | 1.00 | 12.88 | C |
| ATOM | 5189 | CG | ARG | B | 364 | 11.565 | 0.380 | 22.482 | 1.00 | 14.21 | C |
| ATOM | 5192 | CD | ARG | B | 364 | 12.671 | 1.411 | 22.216 | 1.00 | 18.75 | C |
| ATOM | 5195 | NE | ARG | B | 364 | 12.606 | 2.066 | 20.950 | 1.00 | 16.44 | N |
| ATOM | 5197 | CZ | ARG | B | 364 | 13.123 | 3.278 | 20.638 | 1.00 | 18.34 | C |
| ATOM | 5198 | NH1 | ARG | B | 364 | 13.591 | 4.073 | 21.531 | 1.00 | 21.95 | N |
| ATOM | 5201 | NH2 | ARG | B | 364 | 13.073 | 3.670 | 19.412 | 1.00 | 23.97 | N |
| ATOM | 5204 | C | ARG | B | 364 | 11.046 | −2.339 | 25.177 | 1.00 | 14.09 | C |
| ATOM | 5205 | O | ARG | B | 364 | 11.154 | −1.994 | 26.361 | 1.00 | 16.64 | O |
| ATOM | 5206 | N | LEU | B | 365 | 11.340 | −3.548 | 24.735 | 1.00 | 13.84 | N |
| ATOM | 5208 | CA | LEU | B | 365 | 11.904 | −4.519 | 25.617 | 1.00 | 12.64 | C |
| ATOM | 5210 | CB | LEU | B | 365 | 11.017 | −5.737 | 25.667 | 1.00 | 14.17 | C |
| ATOM | 5213 | CG | LEU | B | 365 | 9.653 | −5.571 | 26.305 | 1.00 | 14.30 | C |
| ATOM | 5215 | CD1 | LEU | B | 365 | 8.907 | −6.860 | 26.267 | 1.00 | 17.46 | C |
| ATOM | 5219 | CD2 | LEU | B | 365 | 9.813 | −5.054 | 27.714 | 1.00 | 18.97 | C |
| ATOM | 5223 | C | LEU | B | 365 | 13.235 | −4.929 | 25.065 | 1.00 | 13.48 | C |
| ATOM | 5224 | O | LEU | B | 365 | 13.307 | −5.386 | 23.919 | 1.00 | 13.99 | O |
| ATOM | 5225 | N | PHE | B | 366 | 14.271 | −4.775 | 25.887 | 1.00 | 12.70 | N |
| ATOM | 5227 | CA | PHE | B | 366 | 15.619 | −5.176 | 25.533 | 1.00 | 12.04 | C |
| ATOM | 5229 | CB | PHE | B | 366 | 16.651 | −4.148 | 25.971 | 1.00 | 12.03 | C |
| ATOM | 5232 | CG | PHE | B | 366 | 16.476 | −2.809 | 25.291 | 1.00 | 13.71 | C |

APPENDIX 1-continued

| | | | | | | | | | | |
|---|---|---|---|---|---|---|---|---|---|---|
| ATOM | 5233 | CD1 | PHE | B | 366 | 15.591 | −1.889 | 25.820 | 1.00 | 13.42 | C |
| ATOM | 5235 | CE1 | PHE | B | 366 | 15.373 | −0.702 | 25.229 | 1.00 | 16.78 | C |
| ATOM | 5237 | CZ | PHE | B | 366 | 16.025 | −0.376 | 24.078 | 1.00 | 16.52 | C |
| ATOM | 5239 | CE2 | PHE | B | 366 | 16.899 | −1.322 | 23.444 | 1.00 | 15.87 | C |
| ATOM | 5241 | CD2 | PHE | B | 366 | 17.121 | −2.554 | 24.083 | 1.00 | 15.60 | C |
| ATOM | 5243 | C | PHE | B | 366 | 15.875 | −6.502 | 26.202 | 1.00 | 13.03 | C |
| ATOM | 5244 | O | PHE | B | 366 | 15.700 | −6.682 | 27.407 | 1.00 | 13.72 | O |
| ATOM | 5245 | N | VAL | B | 367 | 16.319 | −7.448 | 25.407 | 1.00 | 13.72 | N |
| ATOM | 5247 | CA | VAL | B | 367 | 16.457 | −8.824 | 25.906 | 1.00 | 14.35 | C |
| ATOM | 5249 | CB | VAL | B | 367 | 15.408 | −9.719 | 25.263 | 1.00 | 15.42 | C |
| ATOM | 5251 | CG1 | VAL | B | 367 | 13.988 | −9.325 | 25.626 | 1.00 | 17.97 | C |
| ATOM | 5255 | CG2 | VAL | B | 367 | 15.608 | −9.853 | 23.736 | 1.00 | 13.87 | C |
| ATOM | 5259 | C | VAL | B | 367 | 17.829 | −9.418 | 25.654 | 1.00 | 14.47 | C |
| ATOM | 5260 | O | VAL | B | 367 | 18.508 | −9.099 | 24.686 | 1.00 | 13.82 | O |
| ATOM | 5261 | N | ASP | B | 368 | 18.186 | −10.385 | 26.500 | 1.00 | 15.21 | N |
| ATOM | 5263 | CA | ASP | B | 368 | 19.421 | −11.145 | 26.337 | 1.00 | 14.26 | C |
| ATOM | 5265 | CB | ASP | B | 368 | 20.020 | −11.526 | 27.668 | 1.00 | 12.83 | C |
| ATOM | 5268 | CG | ASP | B | 368 | 19.168 | −12.492 | 28.461 | 1.00 | 13.78 | C |
| ATOM | 5269 | OD1 | ASP | B | 368 | 18.383 | −13.277 | 27.864 | 1.00 | 15.03 | O |
| ATOM | 5270 | OD2 | ASP | B | 368 | 19.284 | −12.487 | 29.687 | 1.00 | 14.11 | O |
| ATOM | 5271 | C | ASP | B | 368 | 19.197 | −12.347 | 25.438 | 1.00 | 15.37 | C |
| ATOM | 5272 | O | ASP | B | 368 | 18.090 | −12.572 | 24.940 | 1.00 | 13.77 | O |
| ATOM | 5273 | N | LYS | B | 369 | 20.201 | −13.219 | 25.295 | 1.00 | 15.53 | N |
| ATOM | 5275 | CA | LYS | B | 369 | 20.096 | −14.274 | 24.320 | 1.00 | 16.17 | C |
| ATOM | 5277 | CB | LYS | B | 369 | 21.492 | −14.913 | 24.031 | 1.00 | 18.57 | C |
| ATOM | 5280 | CG | LYS | B | 369 | 22.335 | −14.040 | 23.132 | 1.00 | 23.43 | C |
| ATOM | 5283 | CD | LYS | B | 369 | 21.692 | −13.930 | 21.723 | 1.00 | 33.33 | C |
| ATOM | 5286 | CE | LYS | B | 369 | 21.825 | −15.245 | 20.863 | 1.00 | 37.24 | C |
| ATOM | 5289 | NZ | LYS | B | 369 | 20.834 | −15.304 | 19.703 | 1.00 | 39.15 | N |
| ATOM | 5293 | C | LYS | B | 369 | 19.120 | −15.342 | 24.746 | 1.00 | 17.09 | C |
| ATOM | 5294 | O | LYS | B | 369 | 18.736 | −16.166 | 23.914 | 1.00 | 16.83 | O |
| ATOM | 5295 | N | LEU | B | 370 | 18.744 | −15.352 | 26.029 | 1.00 | 15.51 | N |
| ATOM | 5297 | CA | LEU | B | 370 | 17.739 | −16.298 | 26.509 | 1.00 | 15.40 | C |
| ATOM | 5299 | CB | LEU | B | 370 | 18.053 | −16.814 | 27.899 | 1.00 | 15.53 | C |
| ATOM | 5302 | CG | LEU | B | 370 | 19.358 | −17.657 | 28.054 | 1.00 | 17.89 | C |
| ATOM | 5304 | CD1 | LEU | B | 370 | 19.624 | −17.980 | 29.490 | 1.00 | 16.28 | C |
| ATOM | 5308 | CD2 | LEU | B | 370 | 19.237 | −18.944 | 27.314 | 1.00 | 17.77 | C |
| ATOM | 5312 | C | LEU | B | 370 | 16.346 | −15.711 | 26.481 | 1.00 | 17.02 | C |
| ATOM | 5313 | O | LEU | B | 370 | 15.426 | −16.340 | 27.005 | 1.00 | 16.78 | O |
| ATOM | 5314 | N | ASP | B | 371 | 16.191 | −14.538 | 25.884 | 1.00 | 15.62 | N |
| ATOM | 5316 | CA | ASP | B | 371 | 14.909 | −13.828 | 25.822 | 1.00 | 17.82 | C |
| ATOM | 5318 | CB | ASP | B | 371 | 13.844 | −14.610 | 25.070 | 1.00 | 16.70 | C |
| ATOM | 5321 | CG | ASP | B | 371 | 13.943 | −14.455 | 23.561 | 1.00 | 26.05 | C |
| ATOM | 5322 | OD1 | ASP | B | 371 | 14.579 | −13.492 | 23.026 | 1.00 | 26.78 | O |
| ATOM | 5323 | OD2 | ASP | B | 371 | 13.333 | −15.252 | 22.835 | 1.00 | 35.44 | O |
| ATOM | 5324 | C | ASP | B | 371 | 14.392 | −13.390 | 27.197 | 1.00 | 16.31 | C |
| ATOM | 5325 | O | ASP | B | 371 | 13.179 | −13.251 | 27.432 | 1.00 | 15.98 | O |
| ATOM | 5326 | N | ASN | B | 372 | 15.334 | −13.152 | 28.115 | 1.00 | 14.12 | N |
| ATOM | 5328 | CA | ASN | B | 372 | 15.057 | −12.509 | 29.380 | 1.00 | 13.45 | C |
| ATOM | 5330 | CB | ASN | B | 372 | 15.846 | −13.137 | 30.518 | 1.00 | 14.25 | C |
| ATOM | 5333 | CG | ASN | B | 372 | 15.359 | −14.530 | 30.868 | 1.00 | 17.78 | C |
| ATOM | 5334 | OD1 | ASN | B | 372 | 14.170 | −14.830 | 30.726 | 1.00 | 15.50 | O |
| ATOM | 5335 | ND2 | ASN | B | 372 | 16.280 | −15.394 | 31.268 | 1.00 | 15.27 | N |
| ATOM | 5338 | C | ASN | B | 372 | 15.328 | −11.025 | 29.328 | 1.00 | 13.56 | C |
| ATOM | 5339 | O | ASN | B | 372 | 16.185 | −10.535 | 28.526 | 1.00 | 12.51 | O |
| ATOM | 5340 | N | ILE | B | 373 | 14.521 | −10.271 | 30.078 | 1.00 | 12.00 | N |
| ATOM | 5342 | CA | ILE | B | 373 | 14.595 | −8.793 | 30.098 | 1.00 | 12.80 | C |
| ATOM | 5344 | CB | ILE | B | 373 | 13.409 | −8.177 | 30.868 | 1.00 | 12.48 | C |
| ATOM | 5346 | CG1 | ILE | B | 373 | 12.115 | −8.624 | 30.263 | 1.00 | 14.38 | C |
| ATOM | 5349 | CD1 | ILE | B | 373 | 12.021 | −8.386 | 28.913 | 1.00 | 13.59 | C |
| ATOM | 5353 | CG2 | ILE | B | 373 | 13.467 | −6.685 | 30.862 | 1.00 | 13.18 | C |
| ATOM | 5357 | C | ILE | B | 373 | 15.888 | −8.319 | 30.716 | 1.00 | 12.70 | C |
| ATOM | 5358 | O | ILE | B | 373 | 16.217 | −8.667 | 31.872 | 1.00 | 13.25 | O |
| ATOM | 5359 | N | ALA | B | 374 | 16.619 | −7.490 | 29.940 | 1.00 | 12.49 | N |
| ATOM | 5361 | CA | ALA | B | 374 | 17.962 | −7.065 | 30.334 | 1.00 | 11.98 | C |
| ATOM | 5363 | CB | ALA | B | 374 | 18.894 | −6.974 | 29.099 | 1.00 | 11.19 | C |
| ATOM | 5367 | C | ALA | B | 374 | 18.005 | −5.723 | 31.031 | 1.00 | 12.88 | C |
| ATOM | 5368 | O | ALA | B | 374 | 19.017 | −5.394 | 31.640 | 1.00 | 13.61 | O |
| ATOM | 5369 | N | GLU | B | 375 | 16.957 | −4.922 | 30.954 | 1.00 | 12.63 | N |
| ATOM | 5371 | CA | GLU | B | 375 | 16.927 | −3.628 | 31.592 | 1.00 | 11.71 | C |
| ATOM | 5373 | CB | GLU | B | 375 | 17.669 | −2.571 | 30.740 | 1.00 | 13.04 | C |
| ATOM | 5376 | CG | GLU | B | 375 | 17.020 | −2.247 | 29.443 | 1.00 | 13.36 | C |
| ATOM | 5379 | CD | GLU | B | 375 | 17.854 | −1.238 | 28.611 | 1.00 | 16.47 | C |
| ATOM | 5380 | OE1 | GLU | B | 375 | 18.961 | −1.591 | 28.279 | 1.00 | 19.52 | O |
| ATOM | 5381 | OE2 | GLU | B | 375 | 17.355 | −0.152 | 28.242 | 1.00 | 18.89 | O |
| ATOM | 5382 | C | GLU | B | 375 | 15.464 | −3.195 | 31.858 | 1.00 | 12.84 | C |
| ATOM | 5383 | O | GLU | B | 375 | 14.563 | −3.750 | 31.276 | 1.00 | 12.27 | O |
| ATOM | 5384 | N | VAL | B | 376 | 15.277 | −2.235 | 32.747 | 1.00 | 12.90 | N |
| ATOM | 5386 | CA | VAL | B | 376 | 13.918 | −1.872 | 33.175 | 1.00 | 13.25 | C |
| ATOM | 5388 | CB | VAL | B | 376 | 13.941 | −0.719 | 34.173 | 1.00 | 13.63 | C |

APPENDIX 1-continued

| | | | | | | | | | | | |
|---|---|---|---|---|---|---|---|---|---|---|---|
| ATOM | 5390 | CG1 | VAL | B | 376 | 12.515 | −0.240 | 34.514 | 1.00 | 15.72 | C |
| ATOM | 5394 | CG2 | VAL | B | 376 | 14.681 | −1.129 | 35.424 | 1.00 | 19.49 | C |
| ATOM | 5398 | C | VAL | B | 376 | 13.110 | −1.441 | 32.018 | 1.00 | 12.36 | C |
| ATOM | 5399 | O | VAL | B | 376 | 13.458 | −0.494 | 31.358 | 1.00 | 12.35 | O |
| ATOM | 5400 | N | PRO | B | 377 | 12.016 | −2.117 | 31.700 | 1.00 | 13.27 | N |
| ATOM | 5401 | CA | PRO | B | 377 | 11.169 | −1.588 | 30.649 | 1.00 | 14.34 | C |
| ATOM | 5403 | CB | PRO | B | 377 | 10.141 | −2.697 | 30.437 | 1.00 | 15.95 | C |
| ATOM | 5406 | CG | PRO | B | 377 | 10.777 | −3.950 | 31.039 | 1.00 | 13.76 | C |
| ATOM | 5409 | CD | PRO | B | 377 | 11.585 | −3.453 | 32.170 | 1.00 | 13.52 | C |
| ATOM | 5412 | C | PRO | B | 377 | 10.472 | −0.302 | 31.046 | 1.00 | 14.46 | C |
| ATOM | 5413 | O | PRO | B | 377 | 10.078 | −0.158 | 32.190 | 1.00 | 14.50 | O |
| ATOM | 5414 | N | ARG | B | 378 | 10.291 | 0.603 | 30.087 | 1.00 | 14.99 | N |
| ATOM | 5416 | CA | ARG | B | 378 | 9.687 | 1.912 | 30.298 | 1.00 | 14.79 | C |
| ATOM | 5418 | CB | ARG | B | 378 | 10.756 | 3.004 | 30.386 | 1.00 | 14.41 | C |
| ATOM | 5421 | CG | ARG | B | 378 | 11.717 | 2.809 | 31.542 | 1.00 | 16.49 | C |
| ATOM | 5424 | CD | ARG | B | 378 | 12.848 | 3.892 | 31.600 | 1.00 | 17.97 | C |
| ATOM | 5427 | NE | ARG | B | 378 | 13.805 | 3.569 | 32.642 | 1.00 | 15.14 | N |
| ATOM | 5429 | CZ | ARG | B | 378 | 13.602 | 3.673 | 33.949 | 1.00 | 19.35 | C |
| ATOM | 5430 | NH1 | ARG | B | 378 | 12.452 | 4.173 | 34.445 | 1.00 | 21.30 | N |
| ATOM | 5433 | NH2 | ARG | B | 378 | 14.548 | 3.250 | 34.752 | 1.00 | 20.05 | N |
| ATOM | 5436 | C | ARG | B | 378 | 8.797 | 2.263 | 29.129 | 1.00 | 14.34 | C |
| ATOM | 5437 | O | ARG | B | 378 | 8.974 | 1.810 | 28.013 | 1.00 | 14.31 | O |
| ATOM | 5438 | N | VAL | B | 379 | 7.801 | 3.052 | 29.411 | 1.00 | 13.60 | N |
| ATOM | 5440 | CA | VAL | B | 379 | 7.028 | 3.650 | 28.358 | 1.00 | 14.99 | C |
| ATOM | 5442 | CB | VAL | B | 379 | 5.847 | 4.399 | 28.967 | 1.00 | 16.05 | C |
| ATOM | 5444 | CG1 | VAL | B | 379 | 5.148 | 5.163 | 27.928 | 1.00 | 17.97 | C |
| ATOM | 5448 | CG2 | VAL | B | 379 | 4.863 | 3.410 | 29.606 | 1.00 | 19.07 | C |
| ATOM | 5452 | C | VAL | B | 379 | 7.899 | 4.629 | 27.551 | 1.00 | 13.40 | C |
| ATOM | 5453 | O | VAL | B | 379 | 8.683 | 5.397 | 28.127 | 1.00 | 13.64 | O |
| ATOM | 5454 | N | GLY | B | 380 | 7.742 | 4.666 | 26.241 | 1.00 | 13.02 | N |
| ATOM | 5456 | CA | GLY | B | 380 | 8.480 | 5.637 | 25.459 | 1.00 | 14.94 | C |
| ATOM | 5459 | C | GLY | B | 380 | 8.968 | 5.181 | 24.107 | 1.00 | 13.89 | C |
| ATOM | 5460 | O | GLY | B | 380 | 8.939 | 3.974 | 23.839 | 1.00 | 13.82 | O |
| ATOM | 5461 | OXT | GLY | B | 380 | 9.391 | 6.068 | 23.366 | 1.00 | 15.44 | O |
| ATOM | 5462 | O | HOH | W | 1 | 26.337 | 16.956 | 29.710 | 1.00 | 8.65 | O |
| ATOM | 5465 | O | HOH | W | 2 | 9.939 | 2.105 | 25.538 | 1.00 | 12.99 | O |
| ATOM | 5468 | O | HOH | W | 3 | 22.328 | 10.101 | 24.400 | 1.00 | 12.55 | O |
| ATOM | 5471 | O | HOH | W | 4 | 30.572 | 18.292 | 23.118 | 1.00 | 9.33 | O |
| ATOM | 5474 | O | HOH | W | 5 | 8.147 | 23.150 | 18.782 | 1.00 | 14.00 | O |
| ATOM | 5477 | O | HOH | W | 6 | 11.956 | 29.794 | 31.575 | 1.00 | 15.66 | O |
| ATOM | 5480 | O | HOH | W | 7 | 36.742 | 23.674 | 17.265 | 1.00 | 14.06 | O |
| ATOM | 5483 | O | HOH | W | 8 | 26.462 | 19.745 | 37.226 | 1.00 | 12.03 | O |
| ATOM | 5486 | O | HOH | W | 9 | 23.101 | 0.721 | 12.656 | 1.00 | 12.19 | O |
| ATOM | 5489 | O | HOH | W | 10 | 20.065 | −2.650 | 26.156 | 1.00 | 20.32 | O |
| ATOM | 5492 | O | HOH | W | 11 | 18.435 | 36.223 | 15.049 | 1.00 | 20.55 | O |
| ATOM | 5495 | O | HOH | W | 12 | 18.961 | −14.287 | 31.415 | 1.00 | 12.28 | O |
| ATOM | 5498 | O | HOH | W | 13 | 13.655 | −3.630 | 28.503 | 1.00 | 11.25 | O |
| ATOM | 5501 | O | HOH | W | 14 | 6.772 | 28.494 | 24.564 | 1.00 | 16.02 | O |
| ATOM | 5504 | O | HOH | W | 15 | 25.827 | −0.949 | 23.096 | 1.00 | 13.13 | O |
| ATOM | 5507 | O | HOH | W | 16 | 10.548 | 23.630 | 17.206 | 1.00 | 15.05 | O |
| ATOM | 5510 | O | HOH | W | 17 | 21.366 | −0.008 | 27.896 | 1.00 | 14.00 | O |
| ATOM | 5513 | O | HOH | W | 18 | 6.571 | 29.390 | 22.100 | 1.00 | 18.38 | O |
| ATOM | 5516 | O | HOH | W | 19 | 25.418 | 4.779 | 24.010 | 1.00 | 11.22 | O |
| ATOM | 5519 | O | HOH | W | 20 | 15.446 | 15.813 | 32.417 | 1.00 | 13.39 | O |
| ATOM | 5522 | O | HOH | W | 21 | 5.625 | 22.360 | 17.718 | 1.00 | 14.91 | O |
| ATOM | 5525 | O | HOH | W | 22 | 27.953 | 5.617 | 25.060 | 1.00 | 12.69 | O |
| ATOM | 5528 | O | HOH | W | 23 | 13.200 | 17.441 | 16.128 | 1.00 | 12.98 | O |
| ATOM | 5531 | O | HOH | W | 24 | 42.359 | 19.143 | 18.719 | 1.00 | 14.71 | O |
| ATOM | 5534 | O | HOH | W | 25 | 24.537 | −2.025 | 19.216 | 1.00 | 12.97 | O |
| ATOM | 5537 | O | HOH | W | 26 | 27.926 | 25.732 | 6.249 | 1.00 | 17.25 | O |
| ATOM | 5540 | O | HOH | W | 27 | 39.025 | 23.474 | 22.653 | 1.00 | 12.82 | O |
| ATOM | 5543 | O | HOH | W | 28 | 23.815 | 15.465 | 37.744 | 1.00 | 13.10 | O |
| ATOM | 5546 | O | HOH | W | 29 | 18.367 | −9.817 | 33.092 | 1.00 | 17.61 | O |
| ATOM | 5549 | O | HOH | W | 30 | 20.380 | 12.554 | 15.652 | 1.00 | 10.66 | O |
| ATOM | 5552 | O | HOH | W | 31 | 18.651 | 1.596 | 26.271 | 1.00 | 14.85 | O |
| ATOM | 5555 | O | HOH | W | 32 | 35.209 | 6.007 | 10.838 | 1.00 | 15.93 | O |
| ATOM | 5558 | O | HOH | W | 33 | 18.465 | 24.874 | 35.632 | 1.00 | 11.70 | O |
| ATOM | 5561 | O | HOH | W | 34 | 20.815 | 27.470 | 36.539 | 1.00 | 14.90 | O |
| ATOM | 5564 | O | HOH | W | 35 | 20.733 | 10.911 | 9.565 | 1.00 | 14.64 | O |
| ATOM | 5567 | O | HOH | W | 36 | 4.788 | 27.744 | 28.587 | 1.00 | 16.40 | O |
| ATOM | 5570 | O | HOH | W | 37 | 8.972 | 17.007 | 35.207 | 1.00 | 15.88 | O |
| ATOM | 5573 | O | HOH | W | 38 | 33.433 | 11.882 | 27.279 | 1.00 | 15.71 | O |
| ATOM | 5576 | O | HOH | W | 39 | 11.974 | 0.247 | 27.662 | 1.00 | 14.69 | O |
| ATOM | 5579 | O | HOH | W | 40 | 11.026 | 22.081 | 14.883 | 1.00 | 14.23 | O |
| ATOM | 5582 | O | HOH | W | 41 | 26.884 | −0.716 | 26.776 | 1.00 | 14.35 | O |
| ATOM | 5585 | O | HOH | W | 42 | 41.266 | 13.179 | 18.993 | 1.00 | 17.71 | O |
| ATOM | 5588 | O | HOH | W | 43 | 27.981 | −2.861 | 17.044 | 1.00 | 20.05 | O |
| ATOM | 5591 | O | HOH | W | 44 | 2.212 | −4.670 | 21.196 | 1.00 | 17.41 | O |
| ATOM | 5594 | O | HOH | W | 45 | 5.416 | 16.195 | 31.844 | 1.00 | 15.02 | O |
| ATOM | 5597 | O | HOH | W | 46 | 20.229 | 32.354 | 26.988 | 1.00 | 15.42 | O |

APPENDIX 1-continued

| | | | | | | | | | | | |
|---|---|---|---|---|---|---|---|---|---|---|---|
| ATOM | 5600 | O | HOH | W | 47 | 27.214 | 14.437 | 31.277 | 1.00 | 10.24 | O |
| ATOM | 5603 | O | HOH | W | 48 | 24.332 | 32.917 | 12.832 | 1.00 | 16.80 | O |
| ATOM | 5606 | O | HOH | W | 49 | 9.986 | 5.426 | 33.075 | 1.00 | 16.06 | O |
| ATOM | 5609 | O | HOH | W | 50 | 21.134 | 30.372 | 36.728 | 1.00 | 15.50 | O |
| ATOM | 5612 | O | HOH | W | 51 | 4.815 | 20.991 | 24.941 | 1.00 | 17.09 | O |
| ATOM | 5615 | O | HOH | W | 52 | 39.195 | 8.284 | 21.866 | 1.00 | 17.72 | O |
| ATOM | 5618 | O | HOH | W | 53 | 24.661 | 0.260 | 25.378 | 1.00 | 13.02 | O |
| ATOM | 5621 | O | HOH | W | 54 | 6.599 | 11.219 | 19.732 | 1.00 | 15.01 | O |
| ATOM | 5624 | O | HOH | W | 55 | −1.402 | −3.742 | 22.540 | 1.00 | 17.94 | O |
| ATOM | 5627 | O | HOH | W | 56 | 23.967 | 19.287 | 36.011 | 1.00 | 12.16 | O |
| ATOM | 5630 | O | HOH | W | 57 | 32.403 | 10.495 | 30.395 | 1.00 | 18.72 | O |
| ATOM | 5633 | O | HOH | W | 58 | 30.411 | 20.433 | 3.925 | 1.00 | 19.29 | O |
| ATOM | 5636 | O | HOH | W | 59 | 14.110 | 5.986 | 23.754 | 1.00 | 21.44 | O |
| ATOM | 5639 | O | HOH | W | 60 | 9.502 | 31.255 | 31.238 | 1.00 | 19.33 | O |
| ATOM | 5642 | O | HOH | W | 61 | 17.881 | 7.531 | 29.614 | 1.00 | 18.16 | O |
| ATOM | 5645 | O | HOH | W | 62 | 35.920 | 21.100 | 27.416 | 1.00 | 18.14 | O |
| ATOM | 5648 | O | HOH | W | 63 | 21.184 | 17.585 | 43.689 | 1.00 | 19.63 | O |
| ATOM | 5651 | O | HOH | W | 64 | 11.422 | 6.357 | 17.386 | 1.00 | 17.47 | O |
| ATOM | 5654 | O | HOH | W | 65 | 7.568 | 24.486 | 1.717 | 1.00 | 26.99 | O |
| ATOM | 5657 | O | HOH | W | 66 | 11.835 | 23.396 | 12.551 | 1.00 | 17.33 | O |
| ATOM | 5660 | O | HOH | W | 67 | 15.674 | −0.267 | 13.102 | 1.00 | 28.14 | O |
| ATOM | 5663 | O | HOH | W | 68 | 35.246 | 4.205 | 18.695 | 1.00 | 18.92 | O |
| ATOM | 5666 | O | HOH | W | 69 | 12.071 | 7.219 | 35.891 | 1.00 | 17.95 | O |
| ATOM | 5669 | O | HOH | W | 70 | 33.151 | 1.122 | 14.747 | 1.00 | 19.80 | O |
| ATOM | 5672 | O | HOH | W | 71 | 22.406 | 17.015 | 36.075 | 1.00 | 12.42 | O |
| ATOM | 5675 | O | HOH | W | 72 | 20.744 | 5.444 | 32.336 | 1.00 | 24.35 | O |
| ATOM | 5678 | O | HOH | W | 73 | 20.988 | −0.601 | 11.337 | 1.00 | 17.02 | O |
| ATOM | 5681 | O | HOH | W | 74 | 32.168 | 21.857 | 32.986 | 1.00 | 16.30 | O |
| ATOM | 5684 | O | HOH | W | 75 | 28.340 | 34.388 | 18.531 | 1.00 | 14.67 | O |
| ATOM | 5687 | O | HOH | W | 76 | 27.395 | 34.930 | 22.269 | 1.00 | 15.72 | O |
| ATOM | 5690 | O | HOH | W | 77 | −2.881 | 1.257 | 27.203 | 1.00 | 24.36 | O |
| ATOM | 5693 | O | HOH | W | 78 | 1.320 | 22.974 | 26.514 | 1.00 | 16.10 | O |
| ATOM | 5696 | O | HOH | W | 79 | 20.014 | 2.049 | 4.590 | 1.00 | 18.49 | O |
| ATOM | 5699 | O | HOH | W | 80 | 20.131 | −10.521 | 22.803 | 1.00 | 16.67 | O |
| ATOM | 5702 | O | HOH | W | 81 | 2.801 | −12.938 | 26.738 | 1.00 | 21.33 | O |
| ATOM | 5705 | O | HOH | W | 82 | 13.524 | 14.422 | 42.122 | 1.00 | 22.70 | O |
| ATOM | 5708 | O | HOH | W | 83 | 41.288 | 13.787 | 8.384 | 1.00 | 21.34 | O |
| ATOM | 5711 | O | HOH | W | 84 | 33.383 | 31.044 | 25.382 | 1.00 | 20.83 | O |
| ATOM | 5714 | O | HOH | W | 85 | 39.402 | 29.928 | 19.487 | 1.00 | 19.25 | O |
| ATOM | 5717 | O | HOH | W | 86 | 14.181 | −0.702 | 28.733 | 1.00 | 20.17 | O |
| ATOM | 5720 | O | HOH | W | 87 | 11.217 | 5.903 | 27.361 | 1.00 | 18.74 | O |
| ATOM | 5723 | O | HOH | W | 88 | 28.627 | 31.304 | 33.345 | 1.00 | 18.56 | O |
| ATOM | 5726 | O | HOH | W | 89 | 25.546 | 35.322 | 19.001 | 1.00 | 21.03 | O |
| ATOM | 5729 | O | HOH | W | 90 | 17.693 | −0.865 | 33.818 | 1.00 | 23.45 | O |
| ATOM | 5732 | O | HOH | W | 91 | 16.853 | 2.781 | 26.050 | 1.00 | 20.34 | O |
| ATOM | 5735 | O | HOH | W | 92 | 34.612 | 21.168 | 14.066 | 1.00 | 15.33 | O |
| ATOM | 5738 | O | HOH | W | 93 | 19.619 | 19.119 | 0.936 | 1.00 | 29.35 | O |
| ATOM | 5741 | O | HOH | W | 94 | 20.721 | 21.727 | 42.621 | 1.00 | 20.03 | O |
| ATOM | 5744 | O | HOH | W | 95 | 17.040 | 19.477 | 42.629 | 1.00 | 20.78 | O |
| ATOM | 5747 | O | HOH | W | 96 | 20.111 | −0.122 | 24.735 | 1.00 | 19.14 | O |
| ATOM | 5750 | O | HOH | W | 97 | 3.609 | 25.498 | 17.596 | 1.00 | 22.36 | O |
| ATOM | 5753 | O | HOH | W | 98 | 22.201 | 34.610 | 13.464 | 1.00 | 19.68 | O |
| ATOM | 5756 | O | HOH | W | 99 | 1.306 | 27.285 | 34.611 | 1.00 | 28.89 | O |
| ATOM | 5759 | O | HOH | W | 100 | 1.618 | 26.901 | 31.789 | 1.00 | 16.56 | O |
| ATOM | 5762 | O | HOH | W | 101 | 34.765 | 7.143 | 28.884 | 1.00 | 25.03 | O |
| ATOM | 5765 | O | HOH | W | 102 | 39.459 | 5.374 | 23.644 | 1.00 | 21.05 | O |
| ATOM | 5768 | O | HOH | W | 103 | 7.666 | 6.005 | 10.390 | 1.00 | 23.68 | O |
| ATOM | 5771 | O | HOH | W | 104 | 25.629 | 6.850 | 39.327 | 1.00 | 25.93 | O |
| ATOM | 5774 | O | HOH | W | 105 | 4.516 | 10.592 | 22.714 | 1.00 | 16.32 | O |
| ATOM | 5777 | O | HOH | W | 106 | 23.065 | −8.147 | 22.078 | 1.00 | 22.91 | O |
| ATOM | 5780 | O | HOH | W | 107 | 15.215 | 5.229 | 8.027 | 1.00 | 18.64 | O |
| ATOM | 5783 | O | HOH | W | 108 | 9.120 | −7.084 | 18.432 | 1.00 | 24.86 | O |
| ATOM | 5786 | O | HOH | W | 109 | 9.059 | 32.376 | 26.670 | 1.00 | 22.20 | O |
| ATOM | 5789 | O | HOH | W | 110 | 28.414 | 12.755 | 0.995 | 1.00 | 20.29 | O |
| ATOM | 5792 | O | HOH | W | 111 | 14.310 | 19.153 | −3.544 | 1.00 | 25.42 | O |
| ATOM | 5795 | O | HOH | W | 112 | 18.007 | −11.145 | 20.744 | 1.00 | 25.31 | O |
| ATOM | 5798 | O | HOH | W | 113 | 38.102 | 21.625 | 11.695 | 1.00 | 21.89 | O |
| ATOM | 5801 | O | HOH | W | 114 | 6.120 | 13.736 | 30.142 | 1.00 | 24.46 | O |
| ATOM | 5804 | O | HOH | W | 115 | 15.906 | −18.386 | 31.627 | 1.00 | 22.15 | O |
| ATOM | 5807 | O | HOH | W | 116 | 22.389 | 33.907 | 19.142 | 1.00 | 22.92 | O |
| ATOM | 5810 | O | HOH | W | 117 | 32.200 | 35.724 | 21.334 | 1.00 | 26.32 | O |
| ATOM | 5813 | O | HOH | W | 118 | 2.190 | 17.510 | 6.678 | 1.00 | 25.22 | O |
| ATOM | 5816 | O | HOH | W | 119 | 1.118 | 4.704 | 29.359 | 1.00 | 25.72 | O |
| ATOM | 5819 | O | HOH | W | 120 | 9.611 | 1.556 | 17.312 | 1.00 | 23.94 | O |
| ATOM | 5822 | O | HOH | W | 121 | 3.629 | 23.370 | 16.136 | 1.00 | 22.93 | O |
| ATOM | 5825 | O | HOH | W | 122 | 32.907 | 25.232 | 8.564 | 1.00 | 22.34 | O |
| ATOM | 5828 | O | HOH | W | 123 | −1.806 | −9.230 | 29.885 | 1.00 | 26.14 | O |
| ATOM | 5831 | O | HOH | W | 124 | 32.230 | 21.567 | 30.291 | 1.00 | 23.29 | O |
| ATOM | 5834 | O | HOH | W | 125 | 37.450 | 14.678 | 29.329 | 1.00 | 25.24 | O |
| ATOM | 5837 | O | HOH | W | 126 | 15.339 | 36.760 | 18.883 | 1.00 | 20.61 | O |

APPENDIX 1-continued

| | | | | | | | | | | | |
|---|---|---|---|---|---|---|---|---|---|---|---|
| ATOM | 5840 | O | HOH | W | 127 | 10.235 | 7.567 | 31.063 | 1.00 | 21.51 | O |
| ATOM | 5843 | O | HOH | W | 128 | 24.897 | 37.442 | 19.549 | 1.00 | 24.86 | O |
| ATOM | 5846 | O | HOH | W | 129 | 17.030 | −13.244 | 22.390 | 1.00 | 21.48 | O |
| ATOM | 5849 | O | HOH | W | 130 | 9.040 | 8.412 | 14.673 | 1.00 | 27.72 | O |
| ATOM | 5852 | O | HOH | W | 131 | 14.720 | 31.661 | 34.320 | 1.00 | 22.71 | O |
| ATOM | 5855 | O | HOH | W | 132 | 19.535 | 8.925 | 0.482 | 1.00 | 21.18 | O |
| ATOM | 5858 | O | HOH | W | 133 | 12.077 | 0.962 | 18.542 | 1.00 | 22.23 | O |
| ATOM | 5861 | O | HOH | W | 134 | 3.441 | 12.279 | 24.403 | 1.00 | 21.97 | O |
| ATOM | 5864 | O | HOH | W | 135 | 13.235 | 21.344 | −4.722 | 1.00 | 25.46 | O |
| ATOM | 5867 | O | HOH | W | 136 | 4.989 | 14.655 | 27.582 | 1.00 | 28.75 | O |
| ATOM | 5870 | O | HOH | W | 137 | −0.388 | 24.768 | 31.623 | 1.00 | 23.62 | O |
| ATOM | 5873 | O | HOH | W | 138 | 9.733 | 10.653 | 39.989 | 1.00 | 28.29 | O |
| ATOM | 5876 | O | HOH | W | 139 | 5.022 | 2.800 | 18.295 | 1.00 | 34.14 | O |
| ATOM | 5879 | O | HOH | W | 140 | 26.430 | −3.864 | 19.091 | 1.00 | 26.57 | O |
| ATOM | 5882 | O | HOH | W | 141 | 33.127 | 12.459 | 35.197 | 1.00 | 24.55 | O |
| ATOM | 5885 | O | HOH | W | 142 | 4.529 | 14.653 | 24.602 | 1.00 | 27.79 | O |
| ATOM | 5888 | O | HOH | W | 143 | 34.889 | 3.006 | 29.679 | 1.00 | 26.45 | O |
| ATOM | 5891 | O | HOH | W | 144 | 26.472 | 27.781 | 5.265 | 1.00 | 24.30 | O |
| ATOM | 5894 | O | HOH | W | 145 | 9.844 | 1.973 | 10.352 | 1.00 | 30.48 | O |
| ATOM | 5897 | O | HOH | W | 146 | 23.113 | 35.988 | 15.667 | 1.00 | 24.26 | O |
| ATOM | 5900 | O | HOH | W | 147 | 3.506 | 18.934 | 26.329 | 1.00 | 23.36 | O |
| ATOM | 5903 | O | HOH | W | 148 | 41.932 | 12.669 | 10.942 | 1.00 | 26.60 | O |
| ATOM | 5906 | O | HOH | W | 149 | 40.619 | 12.671 | 22.354 | 1.00 | 26.08 | O |
| ATOM | 5909 | O | HOH | W | 150 | 33.062 | 38.217 | 15.479 | 1.00 | 37.76 | O |
| ATOM | 5912 | O | HOH | W | 151 | 3.554 | 31.071 | 10.635 | 1.00 | 26.96 | O |
| ATOM | 5915 | O | HOH | W | 152 | 14.084 | 8.928 | 41.767 | 1.00 | 28.97 | O |
| ATOM | 5918 | O | HOH | W | 153 | 29.827 | 1.222 | 9.591 | 1.00 | 30.85 | O |
| ATOM | 5921 | O | HOH | W | 154 | 23.088 | −1.722 | 26.918 | 1.00 | 27.80 | O |
| ATOM | 5924 | O | HOH | W | 155 | 8.435 | 8.580 | 36.298 | 1.00 | 27.72 | O |
| ATOM | 5927 | O | HOH | W | 156 | 42.926 | 15.621 | 8.285 | 1.00 | 29.85 | O |
| ATOM | 5930 | O | HOH | W | 157 | 6.654 | 11.279 | 36.797 | 1.00 | 28.44 | O |
| ATOM | 5933 | O | HOH | W | 158 | 15.300 | 6.642 | 27.237 | 1.00 | 23.08 | O |
| ATOM | 5936 | O | HOH | W | 159 | 14.085 | −11.817 | 20.799 | 1.00 | 27.86 | O |
| ATOM | 5939 | O | HOH | W | 160 | −1.521 | −6.774 | 36.408 | 1.00 | 31.93 | O |
| ATOM | 5942 | O | HOH | W | 161 | 15.519 | 1.708 | 31.201 | 1.00 | 27.02 | O |
| ATOM | 5945 | O | HOH | W | 162 | 0.621 | −5.366 | 35.349 | 1.00 | 28.46 | O |
| ATOM | 5948 | O | HOH | W | 163 | 18.036 | −12.751 | 33.648 | 1.00 | 22.09 | O |
| ATOM | 5951 | O | HOH | W | 164 | 32.843 | 18.669 | 30.344 | 1.00 | 28.48 | O |
| ATOM | 5954 | O | HOH | W | 165 | 27.765 | 11.874 | 38.295 | 1.00 | 18.10 | O |
| ATOM | 5957 | O | HOH | W | 166 | 1.781 | 17.606 | 13.084 | 1.00 | 28.85 | O |
| ATOM | 5960 | O | HOH | W | 167 | 20.211 | 0.158 | 6.249 | 1.00 | 29.98 | O |
| ATOM | 5963 | O | HOH | W | 168 | 2.759 | 19.112 | 32.488 | 1.00 | 24.07 | O |
| ATOM | 5966 | O | HOH | W | 169 | 33.968 | 18.793 | 32.524 | 1.00 | 23.54 | O |
| ATOM | 5969 | O | HOH | W | 170 | −1.571 | −13.592 | 26.165 | 1.00 | 34.45 | O |
| ATOM | 5972 | O | HOH | W | 171 | 39.370 | 28.627 | 17.071 | 1.00 | 26.29 | O |
| ATOM | 5975 | O | HOH | W | 172 | 17.376 | 32.794 | 35.436 | 1.00 | 23.98 | O |
| ATOM | 5978 | O | HOH | W | 173 | 9.391 | 6.761 | 35.029 | 1.00 | 21.74 | O |
| ATOM | 5981 | O | HOH | W | 174 | 16.352 | 11.687 | 43.877 | 1.00 | 31.51 | O |
| ATOM | 5984 | O | HOH | W | 175 | 36.018 | 4.292 | 25.853 | 1.00 | 21.19 | O |
| ATOM | 5987 | O | HOH | W | 176 | 24.899 | −2.518 | 10.289 | 1.00 | 21.66 | O |
| ATOM | 5990 | O | HOH | W | 177 | −1.286 | 2.934 | 25.647 | 1.00 | 31.88 | O |
| ATOM | 5993 | O | HOH | W | 178 | 13.449 | −16.540 | 28.665 | 1.00 | 26.26 | O |
| ATOM | 5996 | O | HOH | W | 179 | 13.301 | −0.613 | 16.357 | 1.00 | 27.05 | O |
| ATOM | 5999 | O | HOH | W | 180 | 24.842 | 17.585 | 44.930 | 1.00 | 26.85 | O |
| ATOM | 6002 | O | HOH | W | 181 | 5.856 | 18.874 | 39.008 | 1.00 | 29.19 | O |
| ATOM | 6005 | O | HOH | W | 182 | −1.630 | 2.543 | 31.697 | 1.00 | 33.70 | O |
| ATOM | 6008 | O | HOH | W | 183 | 38.130 | 17.164 | 1.491 | 1.00 | 33.90 | O |
| ATOM | 6011 | O | HOH | W | 184 | 38.533 | 33.710 | 21.252 | 1.00 | 23.89 | O |
| ATOM | 6014 | O | HOH | W | 185 | 8.687 | 18.331 | 1.042 | 1.00 | 28.46 | O |
| ATOM | 6017 | O | HOH | W | 186 | 13.162 | 5.211 | 37.558 | 1.00 | 29.88 | O |
| ATOM | 6020 | O | HOH | W | 187 | 13.148 | −16.170 | 33.001 | 1.00 | 24.01 | O |
| ATOM | 6023 | O | HOH | W | 188 | 17.877 | 11.059 | 1.344 | 1.00 | 30.31 | O |
| ATOM | 6026 | O | HOH | W | 189 | 1.036 | −11.099 | 25.828 | 1.00 | 27.54 | O |
| ATOM | 6029 | O | HOH | W | 190 | 19.608 | 24.676 | 5.693 | 1.00 | 30.78 | O |
| ATOM | 6032 | O | HOH | W | 191 | 19.946 | 19.409 | 42.111 | 1.00 | 26.14 | O |
| ATOM | 6035 | O | HOH | W | 192 | 3.476 | 10.629 | 29.248 | 1.00 | 33.62 | O |
| ATOM | 6038 | O | HOH | W | 193 | 30.257 | 27.659 | 31.979 | 1.00 | 37.42 | O |
| ATOM | 6041 | O | HOH | W | 194 | 16.442 | 32.431 | 6.611 | 1.00 | 24.66 | O |
| ATOM | 6044 | O | HOH | W | 195 | 34.073 | 12.318 | 2.203 | 1.00 | 35.07 | O |
| ATOM | 6047 | O | HOH | W | 196 | 4.395 | 17.038 | 28.248 | 1.00 | 26.36 | O |
| ATOM | 6050 | O | HOH | W | 197 | 33.318 | 3.825 | 31.828 | 1.00 | 23.35 | O |
| ATOM | 6053 | O | HOH | W | 198 | 18.983 | 33.274 | 37.816 | 1.00 | 19.94 | O |
| ATOM | 6056 | O | HOH | W | 199 | 13.726 | 12.394 | 40.361 | 1.00 | 26.01 | O |
| ATOM | 6059 | O | HOH | W | 200 | 12.010 | 7.108 | 2.281 | 1.00 | 28.49 | O |
| ATOM | 6062 | O | HOH | W | 201 | 17.870 | 4.803 | 31.837 | 1.00 | 28.97 | O |
| ATOM | 6065 | O | HOH | W | 202 | 27.323 | 19.119 | 43.497 | 1.00 | 31.89 | O |
| ATOM | 6068 | O | HOH | W | 203 | 24.085 | 33.024 | 8.818 | 1.00 | 27.59 | O |
| ATOM | 6071 | O | HOH | W | 204 | 19.302 | −7.180 | 37.095 | 1.00 | 25.01 | O |
| ATOM | 6074 | O | HOH | W | 205 | 34.921 | 3.097 | 15.744 | 1.00 | 35.90 | O |
| ATOM | 6077 | O | HOH | W | 206 | 22.046 | 36.365 | 19.883 | 1.00 | 33.71 | O |

APPENDIX 1-continued

| ATOM | 6080 | O | HOH | W | 207 | 4.178 | 27.080 | 39.663 | 1.00 | 28.68 | O |
|---|---|---|---|---|---|---|---|---|---|---|---|
| ATOM | 6083 | O | HOH | W | 208 | 21.450 | 25.719 | 2.335 | 1.00 | 29.50 | O |
| ATOM | 6086 | O | HOH | W | 209 | 7.625 | 37.543 | 22.457 | 1.00 | 27.39 | O |
| ATOM | 6089 | O | HOH | W | 210 | 27.905 | 0.363 | 30.805 | 1.00 | 27.13 | O |
| ATOM | 6092 | O | HOH | W | 211 | 29.963 | 26.817 | 34.574 | 1.00 | 28.33 | O |
| ATOM | 6095 | O | HOH | W | 212 | 37.812 | 29.413 | 15.021 | 1.00 | 35.13 | O |
| ATOM | 6098 | O | HOH | W | 213 | 31.600 | 5.299 | 33.905 | 1.00 | 30.36 | O |
| ATOM | 6101 | O | HOH | W | 214 | 0.934 | 2.893 | 30.953 | 1.00 | 26.27 | O |
| ATOM | 6104 | O | HOH | W | 215 | 15.151 | −19.091 | 27.503 | 1.00 | 36.44 | O |
| ATOM | 6107 | O | HOH | W | 216 | 31.891 | 29.580 | 32.140 | 1.00 | 23.31 | O |
| ATOM | 6110 | O | HOH | W | 217 | 13.828 | −7.788 | 38.638 | 1.00 | 33.17 | O |
| ATOM | 6113 | O | HOH | W | 218 | 37.026 | 8.221 | 8.178 | 1.00 | 43.15 | O |
| ATOM | 6116 | O | HOH | W | 219 | 12.026 | −5.374 | 16.938 | 1.00 | 29.86 | O |
| ATOM | 6119 | O | HOH | W | 220 | −1.767 | −3.163 | 19.781 | 1.00 | 23.61 | O |
| ATOM | 6122 | O | HOH | W | 221 | 5.748 | 3.990 | 37.161 | 1.00 | 34.03 | O |
| ATOM | 6125 | O | HOH | W | 222 | 15.126 | 10.026 | 2.394 | 1.00 | 29.52 | O |
| ATOM | 6128 | O | HOH | W | 223 | 28.930 | 25.732 | 2.063 | 1.00 | 32.92 | O |
| ATOM | 6131 | O | HOH | W | 224 | 17.834 | 38.165 | 18.660 | 1.00 | 32.25 | O |
| ATOM | 6134 | O | HOH | W | 225 | 15.576 | −9.633 | 19.956 | 1.00 | 29.35 | O |
| ATOM | 6137 | O | HOH | W | 226 | 21.532 | 33.500 | 36.344 | 1.00 | 30.91 | O |
| ATOM | 6140 | O | HOH | W | 227 | 37.166 | 25.308 | 14.969 | 1.00 | 30.80 | O |
| ATOM | 6143 | O | HOH | W | 228 | 4.201 | 13.978 | 20.632 | 1.00 | 29.14 | O |
| ATOM | 6146 | O | HOH | W | 229 | −8.921 | 0.073 | 20.951 | 1.00 | 29.35 | O |
| ATOM | 6149 | O | HOH | W | 230 | 30.930 | 14.280 | 0.673 | 1.00 | 42.54 | O |
| ATOM | 6152 | O | HOH | W | 231 | 0.993 | −10.363 | 23.294 | 1.00 | 35.64 | O |
| ATOM | 6155 | O | HOH | W | 232 | 19.283 | −9.456 | 35.875 | 1.00 | 21.72 | O |
| ATOM | 6158 | O | HOH | W | 233 | 29.715 | 33.139 | 9.438 | 1.00 | 28.66 | O |
| ATOM | 6161 | O | HOH | W | 234 | 2.904 | −7.322 | 21.953 | 1.00 | 29.37 | O |
| ATOM | 6164 | O | HOH | W | 235 | −0.395 | 23.877 | 34.029 | 1.00 | 37.81 | O |
| ATOM | 6167 | O | HOH | W | 236 | 15.054 | −3.907 | 38.561 | 1.00 | 26.91 | O |
| ATOM | 6170 | O | HOH | W | 237 | 25.729 | 34.682 | 11.457 | 1.00 | 29.23 | O |
| ATOM | 6173 | O | HOH | W | 238 | 9.385 | 33.323 | 24.057 | 1.00 | 36.55 | O |
| ATOM | 6176 | O | HOH | W | 239 | 24.093 | −5.021 | 21.077 | 1.00 | 26.10 | O |
| ATOM | 6179 | O | HOH | W | 240 | 34.767 | 17.185 | 37.911 | 1.00 | 29.03 | O |
| ATOM | 6182 | O | HOH | W | 241 | 18.069 | 25.299 | 24.326 | 1.00 | 23.95 | O |
| ATOM | 6185 | O | HOH | W | 242 | 25.539 | 23.840 | −0.133 | 1.00 | 27.32 | O |
| ATOM | 6188 | O | HOH | W | 243 | −8.581 | −0.882 | 24.380 | 1.00 | 32.46 | O |
| ATOM | 6191 | O | HOH | W | 244 | 37.140 | 34.955 | 20.025 | 1.00 | 39.20 | O |
| ATOM | 6194 | O | HOH | W | 245 | 25.828 | −6.464 | 17.951 | 1.00 | 35.90 | O |
| ATOM | 6197 | O | HOH | W | 246 | 20.526 | 5.042 | 2.568 | 1.00 | 23.17 | O |
| ATOM | 6200 | O | HOH | W | 247 | 16.909 | 37.789 | 30.355 | 1.00 | 24.49 | O |
| ATOM | 6203 | O | HOH | W | 248 | 4.170 | −13.753 | 24.179 | 1.00 | 34.75 | O |
| ATOM | 6206 | O | HOH | W | 249 | 4.757 | 29.554 | 36.890 | 1.00 | 27.07 | O |
| ATOM | 6209 | O | HOH | W | 250 | 14.985 | 25.383 | 44.611 | 1.00 | 36.67 | O |
| ATOM | 6212 | O | HOH | W | 251 | 21.002 | 34.942 | 26.743 | 1.00 | 24.40 | O |
| ATOM | 6215 | O | HOH | W | 252 | 35.187 | 37.614 | 16.171 | 1.00 | 41.70 | O |
| ATOM | 6218 | O | HOH | W | 253 | 9.429 | 35.849 | 24.299 | 1.00 | 29.47 | O |
| ATOM | 6221 | O | HOH | W | 254 | 22.360 | −8.508 | 14.886 | 1.00 | 39.42 | O |
| ATOM | 6224 | O | HOH | W | 255 | 27.125 | 28.229 | 2.829 | 1.00 | 36.93 | O |
| ATOM | 6227 | O | HOH | W | 256 | 7.686 | 9.225 | 33.089 | 1.00 | 35.16 | O |
| ATOM | 6230 | O | HOH | W | 257 | 4.744 | 8.641 | 8.479 | 1.00 | 31.36 | O |
| ATOM | 6233 | O | HOH | W | 258 | 43.322 | 15.064 | 19.229 | 1.00 | 34.65 | O |
| ATOM | 6236 | O | HOH | W | 259 | 12.158 | 34.202 | 31.572 | 1.00 | 22.62 | O |
| ATOM | 6239 | O | HOH | W | 260 | 40.415 | 22.262 | 16.091 | 1.00 | 26.05 | O |
| ATOM | 6242 | O | HOH | W | 261 | 7.689 | 33.643 | 34.608 | 1.00 | 27.52 | O |
| ATOM | 6245 | O | HOH | W | 262 | −2.516 | −11.500 | 29.608 | 1.00 | 27.56 | O |
| ATOM | 6248 | O | HOH | W | 263 | 23.197 | 30.603 | 38.577 | 1.00 | 30.81 | O |
| ATOM | 6251 | O | HOH | W | 264 | 1.669 | −4.135 | 18.399 | 1.00 | 34.72 | O |
| ATOM | 6254 | O | HOH | W | 265 | 31.682 | 18.313 | 2.510 | 1.00 | 27.38 | O |
| ATOM | 6257 | O | HOH | W | 266 | 21.515 | 33.588 | 40.094 | 1.00 | 30.03 | O |
| ATOM | 6260 | O | HOH | W | 267 | 16.458 | 13.271 | −0.901 | 1.00 | 38.54 | O |
| ATOM | 6263 | O | HOH | W | 268 | 40.177 | 32.128 | 16.843 | 1.00 | 41.26 | O |
| ATOM | 6266 | O | HOH | W | 269 | 12.143 | −2.734 | 15.885 | 1.00 | 27.02 | O |
| ATOM | 6269 | O | HOH | W | 270 | 27.486 | −3.196 | 12.318 | 1.00 | 30.88 | O |
| ATOM | 6272 | O | HOH | W | 271 | 15.668 | 6.307 | 39.384 | 1.00 | 31.07 | O |
| ATOM | 6275 | O | HOH | W | 272 | 7.819 | 6.715 | 30.569 | 1.00 | 22.48 | O |
| ATOM | 6278 | O | HOH | W | 273 | 29.983 | 17.529 | 41.917 | 1.00 | 33.57 | O |
| ATOM | 6281 | O | HOH | W | 274 | 2.674 | 6.648 | 20.688 | 1.00 | 34.77 | O |
| ATOM | 6284 | O | HOH | W | 275 | 16.983 | 2.502 | 33.738 | 1.00 | 29.85 | O |
| ATOM | 6287 | O | HOH | W | 276 | 18.800 | 36.320 | 34.162 | 1.00 | 30.58 | O |
| ATOM | 6290 | O | HOH | W | 277 | 12.363 | 24.605 | −1.596 | 1.00 | 34.55 | O |
| ATOM | 6293 | O | HOH | W | 278 | 14.702 | 17.110 | −5.593 | 1.00 | 27.29 | O |
| ATOM | 6296 | O | HOH | W | 279 | 40.591 | 12.389 | 6.204 | 1.00 | 33.96 | O |
| ATOM | 6299 | O | HOH | W | 280 | 31.608 | 16.687 | 1.057 | 1.00 | 38.88 | O |
| ATOM | 6302 | O | HOH | W | 281 | 23.897 | −11.952 | 20.222 | 1.00 | 34.68 | O |
| ATOM | 6305 | O | HOH | W | 282 | 11.219 | 39.478 | 21.517 | 1.00 | 33.54 | O |
| ATOM | 6308 | O | HOH | W | 283 | 2.552 | 16.703 | 24.563 | 1.00 | 35.86 | O |
| ATOM | 6311 | O | HOH | W | 284 | 27.258 | 9.495 | 42.694 | 1.00 | 30.97 | O |
| ATOM | 6314 | O | HOH | W | 285 | 5.535 | 8.881 | 16.549 | 1.00 | 28.65 | O |
| ATOM | 6317 | O | HOH | W | 286 | 2.189 | 24.192 | 36.099 | 1.00 | 31.47 | O |

APPENDIX 1-continued

| ATOM | 6320 | O | HOH | W | 287 | 19.058 | −1.798 | 12.329 | 1.00 | 34.23 | O |
|---|---|---|---|---|---|---|---|---|---|---|---|
| ATOM | 6323 | O | HOH | W | 288 | 10.635 | 34.933 | 33.408 | 1.00 | 30.86 | O |
| ATOM | 6326 | O | HOH | W | 289 | 4.333 | −0.576 | 36.893 | 1.00 | 44.65 | O |
| ATOM | 6329 | O | HOH | W | 290 | 25.069 | 21.389 | −1.195 | 1.00 | 37.85 | O |
| ATOM | 6332 | O | HOH | W | 291 | 28.073 | 7.826 | 39.103 | 1.00 | 28.63 | O |
| ATOM | 6335 | O | HOH | W | 292 | 14.225 | 35.260 | 33.101 | 1.00 | 43.65 | O |
| ATOM | 6338 | O | HOH | W | 293 | 18.965 | −2.916 | 15.137 | 1.00 | 38.32 | O |
| ATOM | 6341 | O | HOH | W | 294 | 40.370 | 19.000 | 13.716 | 1.00 | 33.50 | O |
| ATOM | 6344 | O | HOH | W | 295 | 6.261 | 32.033 | 33.639 | 1.00 | 30.04 | O |
| ATOM | 6347 | O | HOH | W | 296 | 13.696 | 37.943 | 17.160 | 1.00 | 36.07 | O |
| ATOM | 6350 | O | HOH | W | 297 | 2.518 | 21.734 | 35.950 | 1.00 | 40.41 | O |
| ATOM | 6353 | O | HOH | W | 298 | 31.821 | 26.389 | 38.109 | 1.00 | 33.84 | O |
| ATOM | 6356 | O | HOH | W | 299 | −1.406 | 2.015 | 20.824 | 1.00 | 32.14 | O |
| ATOM | 6359 | O | HOH | W | 300 | 27.841 | 5.928 | 34.623 | 1.00 | 31.37 | O |
| ATOM | 6362 | O | HOH | W | 301 | 33.128 | 25.346 | 29.949 | 1.00 | 26.11 | O |
| ATOM | 6365 | O | HOH | W | 302 | 16.952 | 35.715 | 12.956 | 1.00 | 35.08 | O |
| ATOM | 6368 | O | HOH | W | 303 | 19.607 | 39.276 | 19.928 | 1.00 | 43.31 | O |
| ATOM | 6371 | O | HOH | W | 304 | 31.667 | 24.286 | 33.803 | 1.00 | 31.06 | O |
| ATOM | 6374 | O | HOH | W | 305 | 9.682 | 34.631 | 35.657 | 1.00 | 36.70 | O |
| ATOM | 6377 | O | HOH | W | 306 | 24.913 | 37.958 | 16.991 | 1.00 | 33.31 | O |
| ATOM | 6380 | O | HOH | W | 307 | 27.526 | −1.443 | 8.577 | 1.00 | 31.08 | O |
| ATOM | 6383 | O | HOH | W | 308 | 34.923 | 14.237 | 35.665 | 1.00 | 33.29 | O |
| ATOM | 6386 | O | HOH | W | 309 | 23.480 | 3.819 | 33.037 | 1.00 | 28.70 | O |
| ATOM | 6389 | O | HOH | W | 310 | 39.917 | 30.468 | 13.351 | 1.00 | 43.99 | O |
| ATOM | 6392 | O | HOH | W | 311 | 20.005 | 30.742 | 39.713 | 1.00 | 31.34 | O |
| ATOM | 6395 | O | HOH | W | 312 | 1.762 | 19.900 | 10.728 | 1.00 | 33.53 | O |
| ATOM | 6398 | O | HOH | W | 313 | 21.282 | 35.887 | 11.600 | 1.00 | 34.66 | O |
| ATOM | 6401 | O | HOH | W | 314 | 22.512 | −2.583 | 9.740 | 1.00 | 30.42 | O |
| ATOM | 6404 | O | HOH | W | 315 | 19.079 | 3.993 | 34.105 | 1.00 | 40.61 | O |
| ATOM | 6407 | O | HOH | W | 316 | 2.068 | 20.663 | 16.198 | 1.00 | 29.05 | O |
| ATOM | 6410 | O | HOH | W | 317 | 2.691 | 6.046 | 36.126 | 1.00 | 41.50 | O |
| ATOM | 6413 | O | HOH | W | 318 | 34.645 | 5.648 | 8.339 | 1.00 | 37.23 | O |
| ATOM | 6416 | O | HOH | W | 319 | 23.607 | 9.100 | 43.132 | 1.00 | 28.98 | O |
| ATOM | 6419 | O | HOH | W | 320 | 32.041 | 25.470 | 4.056 | 1.00 | 37.21 | O |
| ATOM | 6422 | O | HOH | W | 321 | 20.362 | 8.689 | 26.048 | 1.00 | 25.83 | O |
| ATOM | 6425 | O | HOH | W | 322 | 11.708 | 6.948 | 24.652 | 1.00 | 11.83 | O |
| ATOM | 6428 | O | HOH | W | 323 | 27.069 | 1.261 | 5.299 | 1.00 | 22.09 | O |
| ATOM | 6431 | O | HOH | W | 324 | 23.654 | 25.543 | 41.612 | 1.00 | 22.43 | O |
| ATOM | 6434 | O | HOH | W | 325 | 23.776 | 33.886 | 17.441 | 1.00 | 26.34 | O |
| ATOM | 6437 | O | HOH | W | 326 | 34.498 | 18.045 | 27.924 | 1.00 | 26.83 | O |
| ATOM | 6440 | O | HOH | W | 327 | 34.129 | 9.041 | 28.001 | 1.00 | 29.40 | O |
| ATOM | 6443 | O | HOH | W | 328 | 22.398 | −4.833 | 18.306 | 1.00 | 31.97 | O |
| ATOM | 6446 | O | HOH | W | 329 | 32.650 | 36.061 | 13.569 | 1.00 | 32.16 | O |
| ATOM | 6449 | O | HOH | W | 330 | 18.875 | 6.699 | 27.476 | 1.00 | 31.00 | O |
| ATOM | 6452 | O | HOH | W | 331 | 43.627 | 18.936 | 5.210 | 1.00 | 33.15 | O |
| ATOM | 6455 | O | HOH | W | 332 | 13.390 | 23.630 | −3.991 | 1.00 | 34.31 | O |
| ATOM | 6458 | O | HOH | W | 333 | −0.102 | 6.438 | 34.964 | 1.00 | 48.55 | O |
| ATOM | 6461 | O | HOH | W | 334 | −0.118 | 6.687 | 37.269 | 1.00 | 35.34 | O |
| ATOM | 6464 | O | HOH | W | 335 | 37.771 | 7.069 | 11.352 | 1.00 | 32.60 | O |
| ATOM | 6467 | O | HOH | W | 336 | 31.257 | 24.829 | 41.652 | 1.00 | 34.05 | O |
| ATOM | 6470 | O | HOH | W | 337 | 10.129 | 21.939 | 40.735 | 1.00 | 34.24 | O |
| ATOM | 6473 | O | HOH | W | 338 | 6.286 | 34.026 | 36.723 | 1.00 | 34.35 | O |
| ATOM | 6476 | O | HOH | W | 339 | 10.691 | 33.573 | 28.674 | 1.00 | 35.22 | O |
| ATOM | 6479 | O | HOH | W | 340 | 12.399 | 2.285 | 25.575 | 1.00 | 35.31 | O |
| ATOM | 6482 | O | HOH | W | 341 | 34.307 | 9.058 | 2.642 | 1.00 | 42.37 | O |
| ATOM | 6485 | O | HOH | W | 342 | 15.597 | 2.822 | 28.675 | 1.00 | 34.26 | O |
| ATOM | 6488 | O | HOH | W | 343 | 11.007 | 37.789 | 24.517 | 1.00 | 39.01 | O |
| ATOM | 6491 | O | HOH | W | 344 | 6.436 | −13.362 | 22.903 | 1.00 | 41.47 | O |
| ATOM | 6494 | O | HOH | W | 345 | 19.680 | 17.126 | 45.857 | 1.00 | 37.81 | O |
| ATOM | 6497 | O | HOH | W | 346 | 10.533 | 36.113 | 27.412 | 1.00 | 34.50 | O |
| ATOM | 6500 | O | HOH | W | 347 | 41.809 | 19.887 | 16.869 | 1.00 | 37.61 | O |
| ATOM | 6503 | O | HOH | W | 348 | 21.611 | 15.053 | −0.998 | 1.00 | 45.55 | O |
| ATOM | 6506 | O | HOH | W | 349 | 22.337 | −9.031 | 17.861 | 1.00 | 49.31 | O |
| ATOM | 6509 | O | HOH | W | 350 | 9.303 | 25.984 | −1.560 | 1.00 | 39.69 | O |
| ATOM | 6512 | O | HOH | W | 351 | 13.153 | 3.923 | 27.389 | 1.00 | 35.74 | O |
| ATOM | 6515 | O | HOH | W | 352 | 20.365 | 4.572 | 37.533 | 1.00 | 43.93 | O |
| ATOM | 6518 | O | HOH | W | 353 | −2.246 | 27.322 | 10.724 | 1.00 | 42.74 | O |
| ATOM | 6521 | O | HOH | W | 354 | 9.435 | 33.000 | 4.908 | 1.00 | 38.59 | O |
| ATOM | 6524 | O | HOH | W | 355 | 15.473 | 17.843 | 44.371 | 1.00 | 40.00 | O |
| ATOM | 6527 | O | HOH | W | 356 | 13.009 | 31.258 | 32.197 | 1.00 | 21.10 | O |
| ATOM | 6530 | O | HOH | W | 357 | 36.838 | 8.242 | 3.607 | 1.00 | 35.04 | O |
| ATOM | 6533 | O | HOH | W | 358 | 30.674 | −0.077 | 10.899 | 1.00 | 34.69 | O |
| ATOM | 6536 | O | HOH | W | 359 | 31.146 | 37.498 | 19.980 | 1.00 | 36.95 | O |
| ATOM | 6539 | O | HOH | W | 360 | 16.880 | −0.664 | 8.461 | 1.00 | 39.07 | O |
| ATOM | 6542 | O | HOH | W | 361 | 40.707 | 6.845 | 20.023 | 1.00 | 32.40 | O |
| ATOM | 6545 | O | HOH | W | 362 | 19.502 | 25.524 | 0.606 | 1.00 | 41.49 | O |
| ATOM | 6548 | O | HOH | W | 363 | 27.574 | 22.139 | 44.653 | 1.00 | 52.17 | O |
| ATOM | 6551 | O | HOH | W | 364 | 11.308 | 11.015 | 41.537 | 1.00 | 41.08 | O |
| ATOM | 6554 | O | HOH | W | 365 | 9.385 | −15.147 | 33.423 | 1.00 | 33.24 | O |
| ATOM | 6557 | O | HOH | W | 366 | 8.340 | 36.413 | 6.953 | 1.00 | 46.38 | O |

APPENDIX 1-continued

| ATOM | 6560 | O | HOH | W | 367 | 1.749 | 16.224 | 29.518 | 1.00 | 42.28 | O |
|---|---|---|---|---|---|---|---|---|---|---|---|
| ATOM | 6563 | O | HOH | W | 368 | 21.762 | 29.936 | 41.718 | 1.00 | 39.52 | O |
| ATOM | 6566 | O | HOH | W | 369 | 5.916 | 6.084 | 8.101 | 1.00 | 42.08 | O |
| ATOM | 6569 | O | HOH | W | 370 | 22.021 | 34.841 | 24.376 | 1.00 | 41.54 | O |
| ATOM | 6572 | O | HOH | W | 371 | 21.487 | −18.393 | 21.594 | 1.00 | 38.90 | O |
| ATOM | 6575 | O | HOH | W | 372 | 39.073 | 5.237 | 9.752 | 1.00 | 40.75 | O |
| ATOM | 6578 | O | HOH | W | 373 | 23.013 | −4.111 | 6.967 | 1.00 | 39.88 | O |
| ATOM | 6581 | O | HOH | W | 374 | 14.536 | 36.281 | 12.246 | 1.00 | 37.61 | O |
| ATOM | 6584 | O | HOH | W | 375 | 29.859 | 34.515 | 20.996 | 1.00 | 28.10 | O |
| ATOM | 6587 | O | HOH | W | 376 | 28.570 | 38.564 | 14.823 | 1.00 | 51.95 | O |
| ATOM | 6590 | O | HOH | W | 377 | 33.330 | 21.383 | 4.315 | 1.00 | 36.55 | O |
| ATOM | 6593 | O | HOH | W | 378 | 44.550 | 14.418 | 11.401 | 1.00 | 45.79 | O |
| ATOM | 6596 | O | HOH | W | 379 | 20.051 | 17.411 | −1.528 | 1.00 | 37.86 | O |
| ATOM | 6599 | O | HOH | W | 380 | 0.588 | 25.706 | 15.094 | 1.00 | 42.46 | O |
| ATOM | 6602 | O | HOH | W | 381 | 4.339 | −3.887 | 18.462 | 1.00 | 42.68 | O |
| ATOM | 6605 | O | HOH | W | 382 | 15.219 | 38.779 | 25.987 | 1.00 | 45.72 | O |
| ATOM | 6608 | O | HOH | W | 383 | 26.263 | −1.807 | 0.657 | 1.00 | 35.43 | O |
| ATOM | 6611 | O | HOH | W | 384 | 43.222 | 8.889 | 13.058 | 1.00 | 39.12 | O |
| ATOM | 6614 | O | HOH | W | 385 | 3.804 | 15.072 | 37.146 | 1.00 | 35.83 | O |
| ATOM | 6617 | O | HOH | W | 386 | 13.685 | 22.152 | 44.161 | 1.00 | 46.34 | O |
| ATOM | 6620 | O | HOH | W | 387 | 39.745 | 6.714 | 14.451 | 1.00 | 43.87 | O |
| ATOM | 6623 | O | HOH | W | 388 | 4.160 | 10.246 | 14.729 | 1.00 | 40.70 | O |
| ATOM | 6626 | O | HOH | W | 389 | 8.951 | 3.749 | 5.381 | 1.00 | 35.43 | O |
| ATOM | 6629 | O | HOH | W | 390 | 12.861 | −18.451 | 24.960 | 1.00 | 37.73 | O |
| ATOM | 6632 | O | HOH | W | 391 | 2.829 | 15.459 | 20.671 | 1.00 | 39.80 | O |
| ATOM | 6635 | O | HOH | W | 392 | 13.542 | 1.619 | 37.956 | 1.00 | 42.36 | O |
| ATOM | 6638 | O | HOH | W | 393 | 16.727 | 31.361 | 39.312 | 1.00 | 38.23 | O |
| ATOM | 6641 | O | HOH | W | 394 | 36.063 | 3.510 | 12.324 | 1.00 | 41.15 | O |
| ATOM | 6644 | O | HOH | W | 395 | 5.800 | 1.387 | 38.322 | 1.00 | 38.68 | O |
| ATOM | 6647 | O | HOH | W | 396 | 12.445 | 36.715 | 28.596 | 1.00 | 36.10 | O |
| ATOM | 6650 | O | HOH | W | 397 | 2.782 | 12.760 | 27.641 | 1.00 | 47.29 | O |
| ATOM | 6653 | O | HOH | W | 398 | −1.700 | −3.625 | 37.395 | 1.00 | 36.77 | O |
| ATOM | 6656 | O | HOH | W | 399 | 41.093 | 10.367 | 21.318 | 1.00 | 46.59 | O |
| ATOM | 6659 | O | HOH | W | 400 | 21.734 | −5.069 | 9.760 | 1.00 | 48.11 | O |
| ATOM | 6662 | O | HOH | W | 401 | 14.290 | 3.253 | 24.475 | 1.00 | 36.49 | O |
| ATOM | 6665 | O | HOH | W | 402 | 22.729 | 2.974 | −0.954 | 1.00 | 40.03 | O |
| ATOM | 6668 | O | HOH | W | 403 | 4.597 | 11.469 | 0.380 | 1.00 | 42.88 | O |
| ATOM | 6671 | O | HOH | W | 404 | 17.898 | 4.552 | −0.927 | 1.00 | 39.85 | O |

SEQUENCE LISTING

<160> NUMBER OF SEQ ID NOS: 51

<210> SEQ ID NO 1
<211> LENGTH: 311
<212> TYPE: PRT
<213> ORGANISM: Bacillus sp. TY145
<220> FEATURE:
<221> NAME/KEY: PEPTIDE
<222> LOCATION: (1)..(311)
<223> OTHER INFORMATION: Protease TY145

<400> SEQUENCE: 1

```
Ala Val Pro Ser Thr Gln Thr Pro Trp Gly Ile Lys Ser Ile Tyr Asn
1               5                   10                  15

Asp Gln Ser Ile Thr Lys Thr Gly Gly Ser Gly Ile Lys Val Ala
                20                  25                  30

Val Leu Asp Thr Gly Val Tyr Thr Ser His Leu Asp Leu Ala Gly Ser
            35                  40                  45

Ala Glu Gln Cys Lys Asp Phe Thr Gln Ser Asn Pro Leu Val Asp Gly
        50                  55                  60

Ser Cys Thr Asp Arg Gln Gly His Gly Thr His Val Ala Gly Thr Val
65                  70                  75                  80

Leu Ala His Gly Gly Ser Asn Gly Gln Val Tyr Gly Val Ala Pro
                85                  90                  95

Gln Ala Lys Leu Trp Ala Tyr Lys Val Leu Gly Asp Asn Gly Ser Gly
                100                 105                 110
```

```
Tyr Ser Asp Asp Ile Ala Ala Ala Ile Arg His Val Ala Asp Glu Ala
            115                 120                 125

Ser Arg Thr Gly Ser Lys Val Val Ile Asn Met Ser Leu Gly Ser Ser
        130                 135                 140

Ala Lys Asp Ser Leu Ile Ala Ser Ala Val Asp Tyr Ala Tyr Gly Lys
145                 150                 155                 160

Gly Val Leu Ile Val Ala Ala Gly Asn Ser Gly Ser Gly Ser Asn
                165                 170                 175

Thr Ile Gly Phe Pro Gly Gly Leu Val Asn Ala Val Ala Val Ala Ala
                180                 185                 190

Leu Glu Asn Val Gln Gln Asn Gly Thr Tyr Arg Val Ala Asp Phe Ser
            195                 200                 205

Ser Arg Gly Asn Pro Ala Thr Ala Gly Asp Tyr Ile Ile Gln Glu Arg
        210                 215                 220

Asp Ile Glu Val Ser Ala Pro Gly Ala Ser Val Glu Ser Thr Trp Tyr
225                 230                 235                 240

Thr Gly Gly Tyr Asn Thr Ile Ser Gly Thr Ser Met Ala Thr Pro His
                245                 250                 255

Val Ala Gly Leu Ala Ala Lys Ile Trp Ser Ala Asn Thr Ser Leu Ser
            260                 265                 270

His Ser Gln Leu Arg Thr Glu Leu Gln Asn Arg Ala Lys Val Tyr Asp
        275                 280                 285

Ile Lys Gly Gly Ile Gly Ala Gly Thr Gly Asp Asp Tyr Ala Ser Gly
                290                 295                 300

Phe Gly Tyr Pro Arg Val Lys
305                 310

<210> SEQ ID NO 2
<211> LENGTH: 420
<212> TYPE: PRT
<213> ORGANISM: Bacillus sp. TA39
<220> FEATURE:
<221> NAME/KEY: PEPTIDE
<222> LOCATION: (1)..(420)
<223> OTHER INFORMATION: Protease BSTA39

<400> SEQUENCE: 2

Met Lys Arg Ser Gly Lys Ile Phe Thr Thr Ala Met Leu Ala Val Thr
1               5                   10                  15

Leu Met Met Pro Ala Met Gly Val Ser Ala Asn Glu Gly Asn Ala Ala
            20                  25                  30

Ala Glu Gly Asn Glu Lys Phe Arg Val Leu Val Asp Ser Val Asp Gln
        35                  40                  45

Lys Asn Leu Lys Asn Ala Lys Gln Gln Tyr Gly Val His Trp Asp Phe
50                  55                  60

Ala Gly Glu Gly Phe Thr Thr Asp Met Asn Glu Lys Gln Phe Asn Ala
65                  70                  75                  80

Leu Lys Lys Asn Lys Asn Leu Thr Val Glu Lys Val Pro Glu Leu Glu
                85                  90                  95

Ile Ala Thr Ala Thr Asp Lys Pro Glu Ala Leu Tyr Asn Ala Met Ala
            100                 105                 110

Ala Ser Gln Ser Thr Pro Trp Gly Ile Lys Ala Ile Tyr Asn Asn Ser
        115                 120                 125

Ser Ile Thr Gln Thr Ser Gly Gly Gly Ile Asn Ile Ala Val Leu
130                 135                 140

Asp Thr Gly Val Asn Thr Asn His Pro Asp Leu Arg Asn Asn Val Glu
```

```
            145                 150                 155                 160
        Gln Cys Lys Asp Phe Thr Val Gly Thr Thr Tyr Thr Asn Asn Ser Cys
                        165                 170                 175
        Thr Asp Arg Gln Gly His Gly Thr His Val Ala Gly Ser Ala Leu Ala
                        180                 185                 190
        Asp Gly Gly Thr Gly Asn Gly Val Tyr Gly Val Ala Pro Asp Ala Asp
                        195                 200                 205
        Leu Trp Ala Tyr Lys Val Leu Gly Asp Asp Ser Gly Tyr Ala Asp
            210                 215                 220
        Asp Ile Ala Ala Ile Arg His Ala Gly Asp Gln Ala Thr Ala Leu
        225                 230                 235                 240
        Asn Thr Lys Val Val Ile Asn Met Ser Leu Gly Ser Ser Gly Glu Ser
                        245                 250                 255
        Ser Leu Ile Thr Asn Ala Val Asn Tyr Ser Tyr Asn Lys Gly Val Leu
                        260                 265                 270
        Ile Ile Ala Ala Ala Gly Asn Ser Gly Pro Tyr Gln Gly Ser Ile Gly
                        275                 280                 285
        Tyr Pro Gly Ala Leu Val Asn Ala Val Ala Val Ala Ala Leu Glu Asn
                        290                 295                 300
        Lys Val Glu Asn Gly Thr Tyr Arg Val Ala Asp Phe Ser Ser Arg Gly
        305                 310                 315                 320
        Tyr Ser Trp Thr Asp Gly Asp Tyr Ala Ile Gln Lys Gly Asp Val Glu
                        325                 330                 335
        Ile Ser Ala Pro Gly Ala Ala Ile Tyr Ser Thr Trp Phe Asp Gly Gly
                        340                 345                 350
        Tyr Ala Thr Ile Ser Gly Thr Ser Met Ala Ser Pro His Ala Ala Gly
                        355                 360                 365
        Leu Ala Ala Lys Ile Trp Ala Gln Tyr Pro Ser Ala Ser Asn Val Asp
                        370                 375                 380
        Val Arg Gly Glu Leu Gln Tyr Arg Ala Tyr Glu Asn Asp Ile Leu Ser
        385                 390                 395                 400
        Gly Tyr Tyr Ala Gly Tyr Gly Asp Asp Phe Ala Ser Gly Phe Gly Phe
                        405                 410                 415
        Ala Thr Val Gln
                    420

<210> SEQ ID NO 3
<211> LENGTH: 419
<212> TYPE: PRT
<213> ORGANISM: Bacillus sp. TA41
<220> FEATURE:
<221> NAME/KEY: PEPTIDE
<222> LOCATION: (1)..(419)
<223> OTHER INFORMATION: Protease BSTA41

<400> SEQUENCE: 3

Met Lys Arg Ser Gly Lys Ile Phe Thr Thr Ala Met Leu Ala Val Thr
1               5                   10                  15

Leu Met Met Pro Ala Ile Gly Val Ser Ala Asn Arg Gly Asn Ala Ala
                20                  25                  30

Asp Gly Asn Glu Lys Phe Arg Val Leu Val Asp Ser Ala Asn Gln Asn
            35                  40                  45

Asn Leu Lys Asn Val Lys Glu Gln Tyr Gly Val His Trp Asp Phe Ala
    50                  55                  60

Gly Glu Gly Phe Thr Thr Asn Met Asn Glu Lys Gln Phe Asn Ala Leu
65                  70                  75                  80
```

-continued

Gln Asn Asn Lys Asn Leu Thr Val Glu Lys Val Pro Glu Leu Glu Ile
            85                  90                  95

Ala Thr Ala Thr Asn Lys Pro Glu Ala Leu Tyr Asn Ala Met Ala Ala
            100                 105                 110

Ser Gln Ser Thr Pro Trp Gly Ile Lys Ala Ile Tyr Asn Asn Ser Asn
            115                 120                 125

Leu Thr Ser Thr Ser Gly Gly Ala Gly Ile Asn Ile Ala Val Leu Asp
            130                 135                 140

Thr Gly Val Asn Thr Asn His Pro Asp Leu Ser Asn Asn Val Glu Gln
145                 150                 155                 160

Cys Lys Asp Phe Thr Val Gly Thr Asn Phe Thr Asp Asn Ser Cys Thr
                165                 170                 175

Asp Arg Gln Gly His Gly Thr His Val Ala Gly Ser Ala Leu Ala Asn
            180                 185                 190

Gly Gly Thr Gly Ser Gly Val Tyr Gly Val Ala Pro Glu Ala Asp Leu
            195                 200                 205

Trp Ala Tyr Lys Val Leu Gly Asp Asp Gly Ser Gly Tyr Ala Asp Asp
            210                 215                 220

Ile Ala Glu Ala Ile Arg His Ala Gly Asp Gln Ala Thr Ala Leu Asn
225                 230                 235                 240

Thr Lys Val Val Ile Asn Met Ser Leu Gly Ser Ser Gly Glu Ser Ser
                245                 250                 255

Leu Ile Thr Asn Ala Val Asp Tyr Ala Tyr Asp Lys Gly Val Leu Ile
                260                 265                 270

Ile Ala Ala Ala Gly Asn Ser Gly Pro Lys Pro Gly Ser Ile Gly Tyr
            275                 280                 285

Pro Gly Ala Leu Val Asn Ala Val Ala Val Ala Ala Leu Glu Asn Thr
290                 295                 300

Ile Gln Asn Gly Thr Tyr Arg Val Ala Asp Phe Ser Ser Arg Gly His
305                 310                 315                 320

Lys Arg Thr Ala Gly Asp Tyr Val Ile Gln Lys Gly Asp Val Glu Ile
                325                 330                 335

Ser Ala Pro Gly Ala Ala Val Tyr Ser Thr Trp Phe Asp Gly Gly Tyr
            340                 345                 350

Ala Thr Ile Ser Gly Thr Ser Met Ala Ser Pro His Ala Ala Gly Leu
            355                 360                 365

Ala Ala Lys Ile Trp Ala Gln Ser Pro Ala Ala Ser Asn Val Asp Val
            370                 375                 380

Arg Gly Glu Leu Gln Thr Arg Ala Ser Val Asn Asp Ile Leu Ser Gly
385                 390                 395                 400

Asn Ser Ala Gly Ser Gly Asp Asp Ile Ala Ser Gly Phe Gly Phe Ala
                405                 410                 415

Lys Val Gln

<210> SEQ ID NO 4
<211> LENGTH: 310
<212> TYPE: PRT
<213> ORGANISM: Bacillus sphaericus
<220> FEATURE:
<221> NAME/KEY: PEPTIDE
<222> LOCATION: (1)..(310)
<223> OTHER INFORMATION: Protease Sphericase

<400> SEQUENCE: 4

Arg Ala Ser Gln Gln Ile Pro Trp Gly Ile Lys Ala Ile Tyr Asn Asn

```
  1               5                  10                 15
Asp Thr Leu Thr Ser Thr Thr Gly Gly Ser Gly Ile Asn Ile Ala Val
                20                  25                 30

Leu Asp Thr Gly Val Asn Thr Ser His Pro Asp Leu Val Asn Asn Val
                35                  40                 45

Glu Gln Cys Lys Asp Phe Thr Gly Ala Thr Thr Pro Ile Asn Asn Ser
        50                  55                 60

Cys Thr Asp Arg Asn Gly His Gly Thr His Val Ala Gly Thr Ala Leu
 65                 70                  75                 80

Ala Asp Gly Gly Ser Asp Gln Ala Gly Ile Tyr Gly Val Ala Pro Asp
                85                  90                 95

Ala Asp Leu Trp Ala Tyr Lys Val Leu Leu Asp Ser Gly Ser Gly Tyr
                100                 105                110

Ser Asp Asp Ile Ala Ala Ile Arg His Ala Ala Asp Gln Ala Thr
                115                 120                125

Ala Thr Gly Thr Lys Thr Ile Ile Ser Met Ser Leu Gly Ser Ser Ala
                130                 135                140

Asn Asn Ser Leu Ile Ser Ser Ala Val Asn Tyr Ala Tyr Ser Lys Gly
145                 150                 155                160

Val Leu Ile Val Ala Ala Gly Asn Ser Gly Tyr Ser Gln Gly Thr
                165                 170                175

Ile Gly Tyr Pro Gly Ala Leu Pro Asn Ala Ile Ala Val Ala Ala Leu
                180                 185                190

Glu Asn Val Gln Gln Asn Gly Thr Tyr Arg Val Ala Asp Tyr Ser Ser
                195                 200                205

Arg Gly Tyr Ile Ser Thr Ala Gly Asp Tyr Val Ile Gln Glu Gly Asp
                210                 215                220

Ile Glu Ile Ser Ala Pro Gly Ser Ser Val Tyr Ser Thr Trp Tyr Asn
225                 230                 235                240

Gly Gly Tyr Asn Thr Ile Ser Gly Thr Ser Met Ala Thr Pro His Val
                245                 250                255

Ser Gly Leu Ala Ala Lys Ile Trp Ala Glu Asn Pro Ser Leu Ser Asn
                260                 265                270

Thr Gln Leu Arg Ser Asn Leu Gln Glu Arg Ala Lys Ser Val Asp Ile
                275                 280                285

Lys Gly Gly Tyr Gly Ala Ala Ile Gly Asp Asp Tyr Ala Ser Gly Phe
                290                 295                300

Gly Phe Ala Arg Val Gln
305                 310

<210> SEQ ID NO 5
<211> LENGTH: 275
<212> TYPE: PRT
<213> ORGANISM: Bacillus amyloliquefaciens
<220> FEATURE:
<221> NAME/KEY: PEPTIDE
<222> LOCATION: (1)..(275)
<223> OTHER INFORMATION: Protease BPN'

<400> SEQUENCE: 5

Ala Gln Ser Val Pro Tyr Gly Val Ser Gln Ile Lys Ala Pro Ala Leu
 1               5                  10                 15

His Ser Gln Gly Tyr Thr Gly Ser Asn Val Lys Val Ala Val Ile Asp
                20                  25                 30

Ser Gly Ile Asp Ser Ser His Pro Asp Leu Lys Val Ala Gly Gly Ala
                35                  40                 45
```

```
Ser Met Val Pro Ser Glu Thr Asn Pro Phe Gln Asp Asn Asn Ser His
         50                  55                  60

Gly Thr His Val Ala Gly Thr Val Ala Ala Leu Asn Asn Ser Ile Gly
 65                  70                  75                  80

Val Leu Gly Val Ala Pro Ser Ala Ser Leu Tyr Ala Val Lys Val Leu
                 85                  90                  95

Gly Ala Asp Gly Ser Gly Gln Tyr Ser Trp Ile Ile Asn Gly Ile Glu
                100                 105                 110

Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
                180                 185                 190

Gly Pro Glu Leu Asp Val Met Ala Pro Gly Val Ser Ile Gln Ser Thr
            195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
                260                 265                 270

Ala Ala Gln
        275

<210> SEQ ID NO 6
<211> LENGTH: 269
<212> TYPE: PRT
<213> ORGANISM: Bacillus lentus
<220> FEATURE:
<221> NAME/KEY: PEPTIDE
<222> LOCATION: (1)..(269)
<223> OTHER INFORMATION: Protease Savinase or Subtilisin 309

<400> SEQUENCE: 6

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
             35                  40                  45

Phe Val Pro Gly Glu Pro Ser Thr Gln Asp Gly Asn Gly His Gly Thr
         50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Ser Gly Ser Gly Ser Val Ser Ser Ile Ala Gln Gly Leu Glu Trp Ala
                100                 105                 110
```

-continued

```
Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 7
<211> LENGTH: 60
<212> TYPE: DNA
<213> ORGANISM: Artificial Sequence
<220> FEATURE:
<223> OTHER INFORMATION: synthetic oligopeptide
<220> FEATURE:
<221> NAME/KEY: misc_feature
<222> LOCATION: (1)..(60)
<223> OTHER INFORMATION: primer 28-35-CN

<400> SEQUENCE: 7
tagatctgga tgagtggawv yccctgtatc gaggacagcw rbttttacac cagaacctgt        60

<210> SEQ ID NO 8
<211> LENGTH: 18
<212> TYPE: DNA
<213> ORGANISM: Artificial Sequence
<220> FEATURE:
<223> OTHER INFORMATION: synthetic oligopeptide
<220> FEATURE:
<221> NAME/KEY: misc_feature
<222> LOCATION: (1)..(18)
<223> OTHER INFORMATION: primer 28-35-NC

<400> SEQUENCE: 8
tccactcatc cagatcta        18

<210> SEQ ID NO 9
<211> LENGTH: 45
<212> TYPE: DNA
<213> ORGANISM: Artificial Sequence
<220> FEATURE:
<223> OTHER INFORMATION: synthetic oligopeptide
<220> FEATURE:
<221> NAME/KEY: misc_feature
<222> LOCATION: (1)..(45)
<223> OTHER INFORMATION: primer 71-72-73-CN (I)

<400> SEQUENCE: 9
aatcgaattg tttaaagcag cwvyygwccc ggccacatgc gtgcc        45

```
<210> SEQ ID NO 10
<211> LENGTH: 45
<212> TYPE: DNA
<213> ORGANISM: Artificial Sequence
<220> FEATURE:
<223> OTHER INFORMATION: synthetic oligopeptide
<220> FEATURE:
<221> NAME/KEY: misc_feature
<222> LOCATION: (1)..(45)
<223> OTHER INFORMATION: primer 71-72-73-CN (II)

<400> SEQUENCE: 10
aatcgaattg tttaaagcaa gwvyygwccc ggccacatgc gtgcc              45

<210> SEQ ID NO 11
<211> LENGTH: 45
<212> TYPE: DNA
<213> ORGANISM: Artificial Sequence
<220> FEATURE:
<223> OTHER INFORMATION: synthetic oligopeptide
<220> FEATURE:
<221> NAME/KEY: misc_feature
<222> LOCATION: (1)..(45)
<223> OTHER INFORMATION: primer 71-72-73-CN (III)

<400> SEQUENCE: 11
aatcgaattg tttaaagcgc cwvyygwccc ggccacatgc gtgcc              45

<210> SEQ ID NO 12
<211> LENGTH: 18
<212> TYPE: DNA
<213> ORGANISM: Artificial Sequence
<220> FEATURE:
<223> OTHER INFORMATION: synthetic oligopeptide
<220> FEATURE:
<221> NAME/KEY: misc_feature
<222> LOCATION: (1)..(18)
<223> OTHER INFORMATION: primer 71-72-73-NC

<400> SEQUENCE: 12
gctttaaaca attcgatt                                            18

<210> SEQ ID NO 13
<211> LENGTH: 24
<212> TYPE: DNA
<213> ORGANISM: Artificial Sequence
<220> FEATURE:
<223> OTHER INFORMATION: synthetic oligopeptide
<220> FEATURE:
<221> NAME/KEY: misc_feature
<222> LOCATION: (1)..(24)
<223> OTHER INFORMATION: primer 139

<400> SEQUENCE: 13
gattaacgcg ttgccgcttc tgcg                                     24

<210> SEQ ID NO 14
<211> LENGTH: 39
<212> TYPE: DNA
<213> ORGANISM: Artificial Sequence
<220> FEATURE:
<223> OTHER INFORMATION: synthetic oligopeptide
<220> FEATURE:
<221> NAME/KEY: misc_feature
<222> LOCATION: (1)..(39)
<223> OTHER INFORMATION: primer 175-CN (I)

<400> SEQUENCE: 14
atcagtagct ccgactgcca ytgcgttcgc atagcgcgc                     39
```

```
<210> SEQ ID NO 15
<211> LENGTH: 39
<212> TYPE: DNA
<213> ORGANISM: Artificial Sequence
<220> FEATURE:
<223> OTHER INFORMATION: synthetic oligopeptide
<220> FEATURE:
<221> NAME/KEY: misc_feature
<222> LOCATION: (1)..(39)
<223> OTHER INFORMATION: primer 175-CN (II)

<400> SEQUENCE: 15
atcagtagct ccgactgccg ctgcgttcgc atagcgcgc                              39

<210> SEQ ID NO 16
<211> LENGTH: 18
<212> TYPE: DNA
<213> ORGANISM: Artificial Sequence
<220> FEATURE:
<223> OTHER INFORMATION: synthetic oligopeptide
<220> FEATURE:
<221> NAME/KEY: misc_feature
<222> LOCATION: (1)..(18)
<223> OTHER INFORMATION: primer 175-NC

<400> SEQUENCE: 16
gcagtcggag ctactgat                                                    18

<210> SEQ ID NO 17
<211> LENGTH: 39
<212> TYPE: DNA
<213> ORGANISM: Artificial Sequence
<220> FEATURE:
<223> OTHER INFORMATION: synthetic oligopeptide
<220> FEATURE:
<221> NAME/KEY: misc_feature
<222> LOCATION: (1)..(39)
<223> OTHER INFORMATION: primer 224-CN

<400> SEQUENCE: 17
cgcacctgca acatgaggcg hagccatcga tgtaccgtt                             39

<210> SEQ ID NO 18
<211> LENGTH: 18
<212> TYPE: DNA
<213> ORGANISM: Artificial Sequence
<220> FEATURE:
<223> OTHER INFORMATION: synthetic oligopeptide
<220> FEATURE:
<221> NAME/KEY: misc_feature
<222> LOCATION: (1)..(18)
<223> OTHER INFORMATION: primer 224-NC

<400> SEQUENCE: 18
cctcatgttg caggtgcg                                                    18

<210> SEQ ID NO 19
<211> LENGTH: 22
<212> TYPE: DNA
<213> ORGANISM: Artificial Sequence
<220> FEATURE:
<223> OTHER INFORMATION: synthetic oligopeptide
<220> FEATURE:
<221> NAME/KEY: misc_feature
<222> LOCATION: (1)..(22)
<223> OTHER INFORMATION: primer 317-CN

<400> SEQUENCE: 19
tggcgcaatc ggtaccatgg gg                                               22
```

<210> SEQ ID NO 20
<211> LENGTH: 936
<212> TYPE: DNA
<213> ORGANISM: Bacillus sp. TY145

<400> SEQUENCE: 20

| | | | | | |
|---|---|---|---|---|---|
| gcggtaccaa | gtacacaaac | cccttggggc | ataaagtcaa | tttataatga | tcaatcaatt | 60 |
| acaaaaacaa | ctggaggcag | cggaattaag | gtagctgttt | tagatacagg | ggtttataca | 120 |
| agccatttag | atttagctgg | ttctgccgag | caatgcaagg | attttaccca | atctaatcct | 180 |
| ttagtagatg | gttcatgcac | cgatcgccaa | gggcatggta | cacatgttgc | cggaactgta | 240 |
| ttggcgcatg | gaggcagtaa | tggacaaggc | gtttacgggg | tggctccgca | agcgaaacta | 300 |
| tgggcatata | aagtattagg | agataacggc | agcggatact | ctgatgatat | tgcagcagct | 360 |
| atcagacatg | tagctgatga | agcttcacgt | acaggttcca | aagtagtaat | taatatgtcg | 420 |
| ctaggttcat | ctgccaagga | ttcattgatt | gctagtgcag | tagattatgc | atatggaaaa | 480 |
| ggtgtattaa | tcgttgctgc | ggctggtaat | agtgggtcag | gcagcaatac | aatcggcttt | 540 |
| cctggcgggc | ttgtaaatgc | agtggcagta | gcggcattgg | agaatgttca | gcaaaatgga | 600 |
| acttatcgag | tagctgattt | ctcatctaga | gggaatccgg | caactgctgg | agattatatc | 660 |
| attcaagagc | gtgatattga | agtttcagct | ccggagcaa | gtgtagagtc | tacatggtac | 720 |
| actggcggtt | ataatacgat | cagcggtaca | tcaatggcta | cacctcatgt | agctgggtta | 780 |
| gctgctaaaa | tctggtcagc | gaatacttca | ttaagtcata | gccaactgcg | cacagaattg | 840 |
| caaaatcgcg | ctaaagtata | tgatattaaa | ggtggtatcg | gagccggaac | aggtgacgat | 900 |
| tatgcatcag | ggttcggata | tccaagagta | aaataa | | | 936 |

<210> SEQ ID NO 21
<211> LENGTH: 1143
<212> TYPE: DNA
<213> ORGANISM: Bacillus lentus

<400> SEQUENCE: 21

| | | | | | |
|---|---|---|---|---|---|
| atgaagaaac | cgttggggaa | aattgtcgca | agcaccgcac | tactcatttc | tgttgctttt | 60 |
| agttcatcga | tcgcatcggc | tgctgaagaa | gcaaaagaaa | aatatttaat | tggctttaat | 120 |
| gagcaggaag | ctgtcagtga | gttttgtagaa | caagtagagg | caaatgacga | ggtcgccatt | 180 |
| ctctctgagg | aagaggaagt | cgaaattgaa | ttgcttcatg | aatttgaaac | gattcctgtt | 240 |
| ttatccgttg | agttaagccc | agaagatgtg | gacgcgcttg | aactcgatcc | agcgatttct | 300 |
| tatattgaag | aggatgcaga | agtaacgaca | atggcgcaat | cggtaccatg | gggaattagc | 360 |
| cgtgtgcaag | ccccagctgc | ccataaccgt | ggattgacag | gttctggtgt | aaaagttgct | 420 |
| gtcctcgata | cagggatatc | cactcatcca | gatctaaata | ttcgtggtgg | cgcaagcttt | 480 |
| gtaccagggg | aaccgtcgac | tcaagatggg | aatgggcatg | gcacgcatgt | ggccgggacg | 540 |
| atcgctgctt | taaacaattc | gattggcgtt | cttggcgtag | cgccgagcgc | tgagctatac | 600 |
| gctgttaaag | tcctagggc | gagcggttca | ggttcggtca | gctcgattgc | ccaaggattg | 660 |
| gaatgggcag | ggaacaatgg | catgcacgtt | gctaatttga | gttaggaag | cccttcgcca | 720 |
| agtgccacac | tcgagcaagc | tgttaatagc | gcgacttcta | gaggcgttct | tgttgtagcg | 780 |
| gcatctggga | attcaggtgc | aggctcaatc | agctatccgg | cgcgctatgc | gaacgcaatg | 840 |
| gcagtcggag | ctactgatca | aaacaacaac | cgcgctagct | tttcacagta | tggcgcaggc | 900 |

```
cttgacattg tcgcacccgg ggtaaacgtg cagagcacat acccaggttc aacatatgcc    960
agcttaaacg gtacatcgat ggctactcct catgttgcag gtgcggccgc ccttgttaaa   1020
caaaagaacc catcttggtc taatgtacaa attcgaaatc atctaaagaa tacggcaact   1080
agtttaggaa gcacgaactt gtatggaagc ggacttgtta acgcagaagc ggcaacgcgt   1140
taa                                                                 1143
```

```
<210> SEQ ID NO 22
<211> LENGTH: 12
<212> TYPE: PRT
<213> ORGANISM: Artificial sequence
<220> FEATURE:
<223> OTHER INFORMATION: Highly mobile region of Savinase

<400> SEQUENCE: 22

Ser Ala Lys Asp Ser Leu Ile Ala Ser Ala Val Asp
1               5                   10

<210> SEQ ID NO 23
<211> LENGTH: 12
<212> TYPE: PRT
<213> ORGANISM: Artificial sequence
<220> FEATURE:
<223> OTHER INFORMATION: Highly mobile region of Savinase

<400> SEQUENCE: 23

Pro Ser Pro Ser Ala Thr Leu Glu Gln Ala Val Asn
1               5                   10

<210> SEQ ID NO 24
<211> LENGTH: 18
<212> TYPE: PRT
<213> ORGANISM: Artificial sequence
<220> FEATURE:
<223> OTHER INFORMATION: Highly mobile region of Savinase

<400> SEQUENCE: 24

Ala Gly Asn Ser Gly Ser Gly Ser Asn Thr Ile Gly Phe Pro Gly Gly
1               5                   10                  15

Leu Val

<210> SEQ ID NO 25
<211> LENGTH: 16
<212> TYPE: PRT
<213> ORGANISM: Artificial sequence
<220> FEATURE:
<223> OTHER INFORMATION: Highly mobile region of Savinase

<400> SEQUENCE: 25

Ser Gly Asn Ser Gly Ala Gly Ser Ile Ser Tyr Pro Ala Arg Tyr Ala
1               5                   10                  15

<210> SEQ ID NO 26
<211> LENGTH: 16
<212> TYPE: PRT
<213> ORGANISM: Artificial sequence
<220> FEATURE:
<223> OTHER INFORMATION: Highly mobile region of Savinase

<400> SEQUENCE: 26

Ala Ser Val Glu Ser Thr Trp Tyr Thr Gly Gly Tyr Asn Thr Ile Ser
1               5                   10                  15

<210> SEQ ID NO 27
```

```
<211> LENGTH: 16
<212> TYPE: PRT
<213> ORGANISM: Artificial sequence
<220> FEATURE:
<223> OTHER INFORMATION: Highly mobile region of Savinase

<400> SEQUENCE: 27

Val Asn Val Gln Ser Thr Tyr Pro Gly Ser Thr Tyr Ala Ser Leu Asn
1               5                   10                  15

<210> SEQ ID NO 28
<211> LENGTH: 7
<212> TYPE: PRT
<213> ORGANISM: Artificial sequence
<220> FEATURE:
<223> OTHER INFORMATION: Highly mobile region of Savinase

<400> SEQUENCE: 28

Met Ser Leu Gly Ser Ser Gly
1               5

<210> SEQ ID NO 29
<211> LENGTH: 7
<212> TYPE: PRT
<213> ORGANISM: Artificial sequence
<220> FEATURE:
<223> OTHER INFORMATION: Highly mobile region of Savinase

<400> SEQUENCE: 29

Leu Ser Leu Gly Ser Pro Ser
1               5

<210> SEQ ID NO 30
<211> LENGTH: 12
<212> TYPE: PRT
<213> ORGANISM: Artificial sequence
<220> FEATURE:
<223> OTHER INFORMATION: Highly mobile region of Savinase

<400> SEQUENCE: 30

Met Ser Leu Gly Ser Ser Gly Glu Ser Ser Leu Ile
1               5                   10

<210> SEQ ID NO 31
<211> LENGTH: 12
<212> TYPE: PRT
<213> ORGANISM: Artificial sequence
<220> FEATURE:
<223> OTHER INFORMATION: Highly mobile region of Savinase

<400> SEQUENCE: 31

Leu Ser Leu Gly Ser Pro Ser Pro Ser Ala Thr Leu
1               5                   10

<210> SEQ ID NO 32
<211> LENGTH: 8
<212> TYPE: PRT
<213> ORGANISM: Artificial sequence
<220> FEATURE:
<223> OTHER INFORMATION: Highly mobile region of Savinase

<400> SEQUENCE: 32

Asn Asn Ser Ser Ile Thr Gln Thr
1               5

<210> SEQ ID NO 33
<211> LENGTH: 8
```

-continued

```
<212> TYPE: PRT
<213> ORGANISM: Artificial sequence
<220> FEATURE:
<223> OTHER INFORMATION: Highly mobile region of Savinase

<400> SEQUENCE: 33

Val Gln Ala Pro Ala Ala His Asn
1               5

<210> SEQ ID NO 34
<211> LENGTH: 8
<212> TYPE: PRT
<213> ORGANISM: Artificial sequence
<220> FEATURE:
<223> OTHER INFORMATION: Highly mobile region of Savinase

<400> SEQUENCE: 34

Thr Val Gly Thr Thr Tyr Thr Asn
1               5

<210> SEQ ID NO 35
<211> LENGTH: 7
<212> TYPE: PRT
<213> ORGANISM: Artificial sequence
<220> FEATURE:
<223> OTHER INFORMATION: Highly mobile region of Savinase

<400> SEQUENCE: 35

Val Pro Gly Glu Pro Ser Thr
1               5

<210> SEQ ID NO 36
<211> LENGTH: 7
<212> TYPE: PRT
<213> ORGANISM: Artificial sequence
<220> FEATURE:
<223> OTHER INFORMATION: Highly mobile region of Savinase

<400> SEQUENCE: 36

Ser Gly Glu Ser Ser Leu Ile
1               5

<210> SEQ ID NO 37
<211> LENGTH: 7
<212> TYPE: PRT
<213> ORGANISM: Artificial sequence
<220> FEATURE:
<223> OTHER INFORMATION: Highly mobile region of Savinase

<400> SEQUENCE: 37

Pro Ser Pro Ser Ala Thr Leu
1               5

<210> SEQ ID NO 38
<211> LENGTH: 9
<212> TYPE: PRT
<213> ORGANISM: Artificial sequence
<220> FEATURE:
<223> OTHER INFORMATION: Highly mobile region of Savinase

<400> SEQUENCE: 38

Trp Phe Asp Gly Gly Tyr Ala Thr Ile
1               5

<210> SEQ ID NO 39
<211> LENGTH: 9
<212> TYPE: PRT
```

<213> ORGANISM: Artificial sequence
<220> FEATURE:
<223> OTHER INFORMATION: Highly mobile region of Savinase

<400> SEQUENCE: 39

Tyr Pro Gly Ser Thr Tyr Ala Ser Leu
1               5

<210> SEQ ID NO 40
<211> LENGTH: 8
<212> TYPE: PRT
<213> ORGANISM: Artificial sequence
<220> FEATURE:
<223> OTHER INFORMATION: Highly mobile region of Savinase

<400> SEQUENCE: 40

Thr Val Gly Thr Asn Phe Thr Asp
1               5

<210> SEQ ID NO 41
<211> LENGTH: 7
<212> TYPE: PRT
<213> ORGANISM: Artificial sequence
<220> FEATURE:
<223> OTHER INFORMATION: Highly mobile region of Savinase

<400> SEQUENCE: 41

Val Pro Gly Glu Pro Ser Thr
1               5

<210> SEQ ID NO 42
<211> LENGTH: 6
<212> TYPE: PRT
<213> ORGANISM: Artificial sequence
<220> FEATURE:
<223> OTHER INFORMATION: Highly mobile region of Savinase

<400> SEQUENCE: 42

Asn Gly Gly Thr Gly Ser
1               5

<210> SEQ ID NO 43
<211> LENGTH: 6
<212> TYPE: PRT
<213> ORGANISM: Artificial sequence
<220> FEATURE:
<223> OTHER INFORMATION: Highly mobile region of Savinase

<400> SEQUENCE: 43

Ala Leu Asn Asn Ser Ile
1               5

<210> SEQ ID NO 44
<211> LENGTH: 7
<212> TYPE: PRT
<213> ORGANISM: Artificial sequence
<220> FEATURE:
<223> OTHER INFORMATION: Highly mobile region of Savinase

<400> SEQUENCE: 44

Asp Asp Gly Ser Gly Tyr Ala
1               5

<210> SEQ ID NO 45
<211> LENGTH: 7
<212> TYPE: PRT
<213> ORGANISM: Artificial sequence

```
<220> FEATURE:
<223> OTHER INFORMATION: Highly mobile region of Savinase

<400> SEQUENCE: 45

Ala Ser Gly Ser Gly Ser Val
1               5

<210> SEQ ID NO 46
<211> LENGTH: 7
<212> TYPE: PRT
<213> ORGANISM: Artificial sequence
<220> FEATURE:
<223> OTHER INFORMATION: Highly mobile region of Savinase

<400> SEQUENCE: 46

Trp Ala Gln Ser Pro Ala Ala
1               5

<210> SEQ ID NO 47
<211> LENGTH: 7
<212> TYPE: PRT
<213> ORGANISM: Artificial sequence
<220> FEATURE:
<223> OTHER INFORMATION: Highly mobile region of Savinase

<400> SEQUENCE: 47

Lys Gln Lys Asn Pro Ser Trp
1               5

<210> SEQ ID NO 48
<211> LENGTH: 6
<212> TYPE: PRT
<213> ORGANISM: Artificial sequence
<220> FEATURE:
<223> OTHER INFORMATION: Ion binding site

<400> SEQUENCE: 48

Leu Asn Asn Ser Ile Gly
1               5

<210> SEQ ID NO 49
<211> LENGTH: 3
<212> TYPE: PRT
<213> ORGANISM: Artificial sequence
<220> FEATURE:
<223> OTHER INFORMATION: Ion binding site

<400> SEQUENCE: 49

Gly Asp Ser
1

<210> SEQ ID NO 50
<211> LENGTH: 3
<212> TYPE: PRT
<213> ORGANISM: Artificial sequence
<220> FEATURE:
<223> OTHER INFORMATION: Ion binding site

<400> SEQUENCE: 50

Asp Ser Thr
1

<210> SEQ ID NO 51
<211> LENGTH: 5
<212> TYPE: PRT
<213> ORGANISM: Artificial sequence
<220> FEATURE:
```

```
<223> OTHER INFORMATION: Ion binding site

<400> SEQUENCE: 51

Gly Gly Ser Asn Gly
1               5
```

The invention claimed is:

1. A subtilase variant which comprises an substitution at the position corresponding to position 147 of the amino acid sequence of the subtilase having the amino acid sequence of SEQ ID NO: 1, wherein the subtilase variant is at least 83% identical to the sequence of SEQ ID NO:1 and has subtilase activity.

2. The subtilase variant of claim 1, wherein the variant is at least 90% identical to the sequence of SEQ ID NO: 1.

3. A detergent composition comprising the subtilase variant of claim 1 and at least one surfactant.

4. The subtilase variant of claim 1, wherein the variant is at least 90% identical to the amino acid sequence of SEQ ID NO: 1.

5. The subtilase variant of claim 1, wherein the variant is at least 95% identical to the amino acid sequence of SEQ ID NO: 1.

6. The subtilase variant of claim 1, wherein the variant is at least 97% identical to the amino acid sequence of SEQ ID NO: 1.

7. The subtilase variant of claim 1, wherein the variant is at least 99% identical to the amino acid sequence of SEQ ID NO: 1.

* * * * *